(12) United States Patent
Ohlmeyer et al.

(10) Patent No.: US 6,919,347 B2
(45) Date of Patent: Jul. 19, 2005

(54) BRADYKININ $B_1$ RECEPTOR ANTAGONISTS

(75) Inventors: Michael H. J. Ohlmeyer, Plainsboro, NJ (US); John J. Baldwin, Gwynedd Valley, PA (US); Roland E. Dolle, III, King of Prussia, PA (US); Vidyadhar Paradkar, Somerville, NJ (US); Jorge Gabriel Quintero, Sayreville, NJ (US); Gonghua Pan, Groton, CT (US)

(73) Assignee: Pharmacopeia Drug Discovery, Inc., Princeton, NJ (US)

( * ) Notice: Subject to any disclaimer, the term of this patent is extended or adjusted under 35 U.S.C. 154(b) by 0 days.

(21) Appl. No.: 10/046,616

(22) Filed: Jan. 14, 2002

(65) Prior Publication Data

US 2003/0229092 A1 Dec. 11, 2003

Related U.S. Application Data

(63) Continuation of application No. PCT/US00/19185, filed on Jul. 14, 2000.
(60) Provisional application No. 60/143,990, filed on Jul. 15, 1999.

(51) Int. Cl.$^7$ .................... C07D 403/04; C07D 409/04; C07D 417/04; A61K 31/506; A61P 3/10
(52) U.S. Cl. .................. 514/269; 514/275; 544/310; 544/318; 544/320; 544/321; 544/324; 544/326; 544/328; 544/331
(58) Field of Search ................... 544/310, 318, 544/320, 321, 324, 326, 328, 331; 514/269, 275

(56) References Cited

U.S. PATENT DOCUMENTS

| | | | |
|---|---|---|---|
| 3,707,560 A | 12/1972 | DeAngelis | 260/256.5 |
| 6,432,947 B1 | 8/2002 | Arnaiz et al. | 514/227.8 |
| 6,670,473 B2 | 12/2003 | Arnaiz et al. | 544/118 |
| 2002/0165203 A1 | 11/2002 | Arnaiz et al. | 514/86 |
| 2002/0183323 A1 | 12/2002 | Arnaiz et al. | 514/245 |
| 2003/0004137 A1 | 1/2003 | Arnaiz et al. | 514/64 |
| 2003/0027794 A1 | 2/2003 | Arnaiz et al. | 514/79 |
| 2003/0060452 A1 | 3/2003 | Arnaiz et al. | 514/79 |
| 2003/0069210 A1 | 4/2003 | Arnaiz et al. | 514/83 |
| 2003/0073669 A1 | 4/2003 | Arnaiz et al. | 514/85 |
| 2003/0083332 A1 | 5/2003 | Arnaiz et al. | 514/242 |
| 2003/0092678 A1 | 5/2003 | Arnaiz et al. | 514/84 |

FOREIGN PATENT DOCUMENTS

| | | |
|---|---|---|
| EP | 0096657 | 12/1983 |
| EP | 0864567 | 9/1998 |
| WO | WO97/24349 | 7/1997 |
| WO | WO98/37079 | 8/1998 |
| WO | WO98/42672 | 10/1998 |
| WO | WO 01/14371 | 3/2001 |

OTHER PUBLICATIONS

Kharitonov et al. Eur. Respir. J. 14(5): 1023–1027, 1999.*
Bagate et al., Br. J. Pharmacol. 128(8) : 1643–1650.*

* cited by examiner

*Primary Examiner*—Venkataraman Balasubramanian
(74) *Attorney, Agent, or Firm*—Edward Timmer, Esq.; Heslin Rothenberg Farley & Mesiti P.C.

(57) ABSTRACT

Bradykinin $B_1$-receptor antagonists of formula $$A-\underset{(CH_2)_m}{\overset{R^1 \; R^2}{|}}-\underset{(CH_2)_n}{\overset{}{|}}-\underset{}{\overset{R^3}{|}}-N-\underset{X \quad Y}{\overset{Z \quad Q}{\diagdown \diagup}} W$$

are disclosed. The compounds are useful for treating diseases associated with inappropriate bradykinin receptor activity, such as diabetic vasculopathy, inflammation, pain, hyperalgesia, asthma, rhinitis, septic shock, atherosclerosis and multiple sclerosis. Pyrimidines, triazines, and anilines in which Q is imidazolyl or pyrrolyl are particularly preferred.

64 Claims, No Drawings

BRADYKININ B₁ RECEPTOR ANTAGONISTS

CROSS REFERENCE TO RELATED APPLICATIONS

This application is a continuation of PCT application PCT/US00/19185 filed Jul. 14, 2000, and published under PCT Article 21(2) in English as WO 01/05783 on Jan. 25, 2001. PCT/US00/19185 claimed the priority of U.S. provisional application 60/143,990, filed Jul. 15, 1999. The entire disclosures of both are incorporated herein by reference.

FIELD OF THE INVENTION

The invention relates to pyrimidines, triazines, and anilines that are bradykinin $B_1$-receptor antagonists. The compounds are useful for treating diseases associated with inappropriate or excessive bradykinin receptor activity, such as diabetic vasculopathy, inflammation, pain, hyperalgesia, asthma, rhinitis, septic shock, atherosclerosis and multiple sclerosis.

BACKGROUND OF THE INVENTION

Bradykinin receptors of two classes are known. The $B_1$ receptor ($B_1$-BK) is not present in normal cells under normal conditions. In contrast, the $B_2$-BK receptor is normally present on many cell types or tissues. Although the $B_1$ receptor ($B_1$-BK) is not present under normal conditions, its synthesis is induced in blood vessel muscular layers during inflammation.

Recent reports point to an important role of bradykinin $B_1$ receptors in physiopathology. Dray and Perkins [*Trends in Neurosci.* 16, 99–104(1993)] have reviewed the possible implication of $B_1$ receptors in various inflammatory states, in tissue reactions and in hyperalgesia. Alvarez et al. [*Clin. Sci.* 82, 513–519 (1992)] have provided evidence that $B_1$ receptors are present in spontaneously hypertensive rats (SHR), and Regoli et al. [PCT application WO 98/07746] have provided evidence that inappropriate $B_1$ receptor activity is associated with some forms of diabetes. In particular, it is known that capillary permeability is augmented in the streptozotocin diabetic rat model, and the vascular BK receptors of the portal veins of these animals have been shown to exhibit enhanced contractibility and capillary permeability in response to the $B_1$-agonist desArg⁸BK. This effect was abolished by the $B_1$-antagonist Lys[Leu] desArg⁹BK while the $B_2$-antagonist HOE140 had no effect. A similar increased sensitivity to desArg⁹BK was observed in untreated SHR animals, prior to the establishment of hypertension, which was reversed by the same $B_1$-antagonist. These results indicate that the $B_1$-receptor is a target for a drug-preventive approach to diabetic or hypertensive vasculopathy.

Peptide antagonists of bradykinin receptors are known, although most reported antagonists have activity towards $B_2$-receptors. There are to date very few small molecule $B_1$ antagonists. It would be useful to have effective antagonists of the $B_1$-BK receptor.

SUMMARY OF THE INVENTION

In one aspect, the invention relates to a genus of bradykinin $B_1$ receptor antagonists sharing the general formula I:

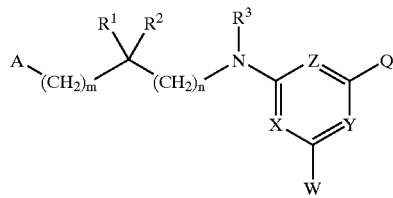

wherein:
(a) all of X, Y and Z are CH; or (b) one of X, Y and Z is N and the rest of X, Y and Z are CH; or (c) two of X, Y and Z are N and the other of X, Y and Z is CH; or (d) all of X, Y and Z are N;
A is $A^1$ or $A^2$;
$A^1$ is $R^4R^5N$—C(O)—

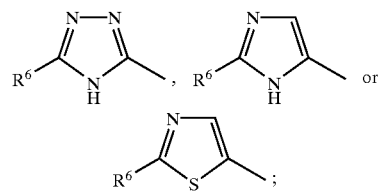

$A^2$ is chosen from $R^7C(O)NH$—, $R^7S(O)_2NH$—, $R^4NH$—, and $R^4O$—;
Q is chosen from heteroaryl, aryl, —$CH_2R^{13}$, —CH=N—OCH₃ and

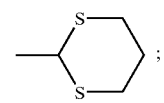

W is chosen from H, Cl, F, $R^8$, $C_1$–$C_4$-alkylaryl, —$OR^8$, —$SR^8$, —$NR^9R^{10}$ and —$NHC(O)R^{11}$;
$R^1$ is chosen from alkyl, cycloalkyl, alkenyl, $C_1$–$C_3$-alkylcycloalkyl, heterocyclyl, $C_1$–$C_3$-alkylheterocyclyl, aryl, $C_1$–$C_3$-alkylaryl, heteroaryl, $C_1$–$C_3$-alkylheteroaryl, ($C_1$–$C_3$-alkyloxy)alkyl, ($C_1$–$C_3$-alkyloxy)cycloalkyl, ($C_1$–$C_3$-alkylthio)alkyl, ($C_1$–$C_3$-alkylthio)cycloalkyl and ($C_1$–$C_3$-alkylsulfonyl)alkyl;
$R^2$ is H or $C_1$–$C_3$-alkyl, or $R^1$ and $R^2$ taken together form a 5- to 7-membered ring structure optionally containing O, S or $NR^{12}$;
$R^3$ is H or $C_1$–$C_6$-alkyl, or, when n is zero, $R^2$ and $R^3$ taken together may form a 6-membered ring, which may be fused to a six-membered saturated or aromatic carbocycle;
$R^4$ is chosen from H, aryl, heteroaryl, $C_1$–$C_4$-alkyl substituted with from one to three aryl or heteroaryl residues,

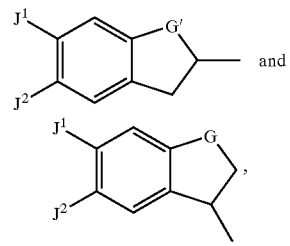

wherein $J^1$ and $J^2$ are independently chosen from H, F, Cl, CN, $NO_2$ and $CH_3$; G is chosen from —$CH_2$—, —$CH_2CH_2$—, —$CH_2CH_2CH_2$—, —$OCH_2$—, —$CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—; and G' is chosen from —$CH_2$—, —$CH_2CH_2$—, —$CH_2CH_2CH_2$—, —$OCH_2$—, —$OCH_2CH_2$—, —N(lower alkyl)$CH_2$—, —$SCH_2$—, —$SOCH_2$— and —$SO_2CH_2$—;

$R^5$ is H or $C_1$–$C_3$-alkyl, with the proviso that both $R^3$ and $R^5$ cannot be alkyl;

$R^6$ is aryl;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl; or $R^9$ and $R^{10}$ taken together may form a 5- to 7-membered ring structure optionally containing O, S, SO, $SO_2$ or $NR^{12}$, said ring optionally substituted with —OH, —CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and n is zero or one, with the proviso that when A is $A^2$, m and n cannot both be zero.

This genus may be considered to comprise subgenera of pyrimidines (IIa–IIc), triazines (III), anilines (IV) and pyridines (not shown):

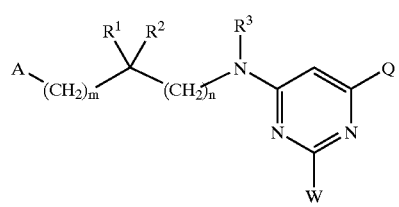

IIa

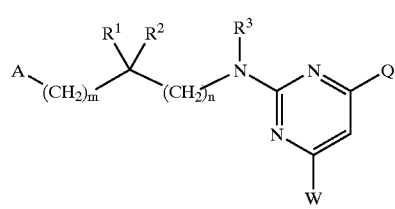

IIb

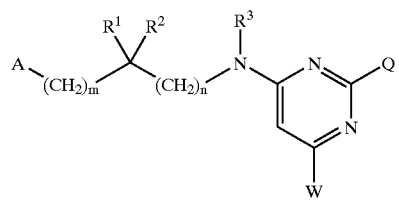

IIc

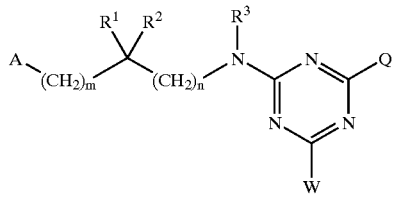

III

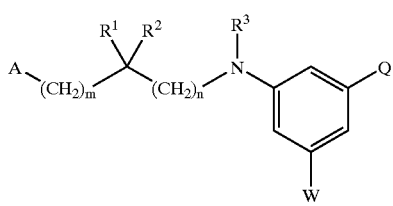

IV

In another aspect, the invention relates to a method of treating a condition resulting from inappropriate bradykinin receptor activity comprising administering to a subject in need of such treatment a therapeutically effective amount of a compound of formula I. Conditions resulting from inappropriate bradykinin receptor activity include diabetic vasculopathy, post-capillary resistance or diabetic symptoms associated with insulitis, inflammation, edema, liver disease, asthma, rhinitis, septic shock, pain, hyperalgesia, multiple sclerosis, atherosclerosis, Alzheimer's disease or closed head trauma. Of particular importance are chronic pain, pain associated with inflammation and dental pain. Diabetic symptoms associated with insulitis include hyperglycemia, diuresis, proteinuria and increased nitrite and kallikrein urinary excretion. Stimulating hair growth or preventing hair loss may also be accomplished by administering to a subject in need of such treatment a therapeutically effective amount of a compound of formula I.

In another aspect, the invention relates to pharmaceutical compositions comprising a pharmaceutically acceptable carrier and compounds of formula I. The formulations may additionally comprise steroidal or nonsteroidal anti-inflammatory drugs (NSAIDS), cyclo-oxygenase (COX) inhibitors or selective cyclooxygenase-2 (COX-2) inhibitors.

In another aspect, the invention relates to compounds, useful as intermediates in the synthesis of bradykinin inhibitors. One genus of such compounds is represented by formula

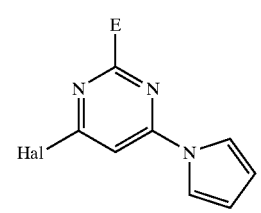 or 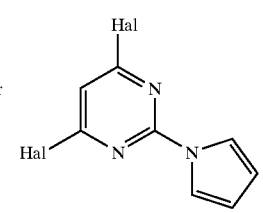

wherein E is halogen or methylthio and Hal is halogen. Another genus is represented by formulae

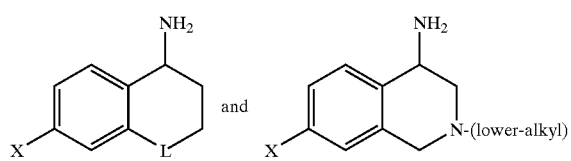

wherein X is —CN or halogen and L is —O—, —CH$_2$— or —N(CH$_3$)—.

DETAILED DESCRIPTION OF THE INVENTION

Preferred compounds of the invention are found in the class of pyrimidines of formula II

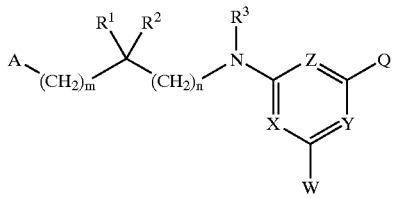

These are compounds of formula I in which two of X, Y and Z are N and the third is CH. Three classes of pyrimidines can be limned, depending on which of X, Y and Z is CH The first of these is the 4-pyrimidinamines, in which Z is CH. These have the formula IIa

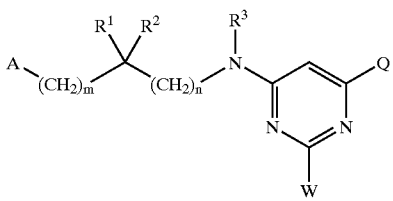

In preferred embodiments, Q is chosen from imidazolyl, methylimidazolyl, pyrrolyl, methylpyrrolyl, pyrazolyl, methylpyrazolyl, hydroxymethylimidazolyl, (dimethylaminomethyl)imidazolyl, furanyl, methylfuranyl, thienyl, oxazolyl, thiazolyl, pyridinyl, quinolinyl, 1-methylpyrimidin-2-onyl, phenyl, fluorophenyl, hydroxymethyl, tetrahydropyranyloxymethyl, imidazolylmethyl, pyrrolylmethyl, CH=N—OCH$_3$ and

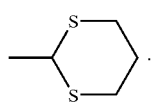

In particularly preferred embodiments Q is pyrrol-1-yl, imidazol-1-yl, furan-3-yl, 2-methylimidazol-1-yl or 4-methylimidazol-1-yl; A is R$^4$R$^5$N—C(O)—; W is Cl, NHR$^9$, N(CH$_3$)R$^9$, OR$^8$, SR$^8$, R$^8$, morpholin-4-yl,

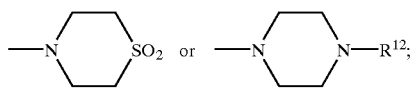

R$^1$ is chosen from alkyl, cycloalkyl, C$_1$–C$_3$-alkylaryl, C$_1$–C$_3$-alkylcycloalkyl, C$_1$–C$_3$-alkylheterocyclyl, and C$_1$–C$_3$-alkylheteroaryl; R$^2$, R$^3$ and R$^5$ are H; R$^4$ is C$_1$–C$_4$-alkylaryl or C$_1$–C$_4$-alkylheteroaryl; R$^8$ is C$_1$–C$_4$-alkylaryl; R$^9$ is chosen from hydrogen, alkyl, substituted alkyl, (C$_1$–C$_4$)-alkoxy, C$_1$–C$_4$-alkylcycloalkyl, C$_1$–C$_4$-alkylaryl, heterocyclyl, C$_1$–C$_4$-alkylheteroaryl, and C$_1$–C$_4$-alkylheterocyclyl; and m and n are zero. When W is NHR$^9$, preferred values of R$^9$ are hydrogen; methyl; ethyl; 2,2,2-trifluoroethyl; allyl; cyclopropyl; 2-cyanoethyl; propargyl; methoxy; methoxyethyl; cyclopropyl; cyclopropylmethyl; (methylthio)ethyl; 3-methoxypropyl; 3-pyridyl; 2-(3-pyridyl)ethyl; 2-(2-pyridyl)ethyl; 3-pyridylmethyl; 4-pyridylmethyl; 4-pyridylmethyl-N-oxide; 2-pyridazinylmethyl; sulfolan-3-yl; 3-tetrahydrofuranyl; 2-tetrahydrofuranylmethyl; 3-(1-imidazolyl)propyl; 1-t-butoxycarbonyl-4-piperidinyl; 1-t-butoxycarbonyl-4-piperidinylmethyl; 2-(hydroxyimino)propyl; 2-(methoxyimino)propyl; 2-oxo-1-propyl; and

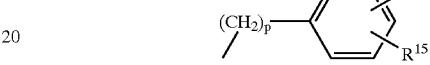

wherein R$^{14}$ is H, Cl, F, CN, NO$_2$, SO$_2$NH$_2$, CF$_3$, COOCH$_3$, OCH$_3$, OH, SO$_2$CH$_3$, N(CH$_3$)$_2$ or COOH; R$^{15}$ is chosen from H, OCH$_3$, F and Cl; and p is one or two. When W is

R$^{12}$ is preferably t-butoxycarbonyl, methoxyacetyl or phenyl.

In another preferred embodiment of formula IIa, A is

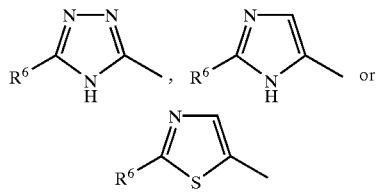

and R$^1$ is n-butyl; cyclohexylmethyl; cyclopentylmethyl; 2-methylpropyl; 3-methyl-1-butyl; cyclohexyl; 2,2-dimethylpropyl; benzyl; 2-thienylmethyl; 1-t-butoxycarbonyl-4-piperidinyl; 4-chlorobenzyl; 2-pyranylmethyl; 4-pyranylmethyl; 4-pyranyl or 1,1-dimethylethyl; R$^2$ and R$^3$ are H; Q is imidazolyl or pyrrolyl; W is NHR$^9$; and R$^9$ is alkyl, cycloalkyl or

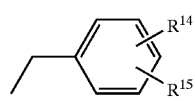

wherein R$^{14}$ is chosen from H, Cl, F, CN, NO$_2$, SO$_2$NH$_2$, CF$_3$, COOCH$_3$, OCH$_3$, SO$_2$CH$_3$, N(CH$_3$)$_2$ and COOH; and R$^{15}$ is chosen from H, OCH$_3$ and Cl.

In another preferred embodiment of formula IIa, A is R$^4$R$^5$N—C(O)—; R$^1$ is chosen from isopropyl; n-butyl; cyclohexylmethyl; cyclopentylmethyl; naphthylmethyl; cyclohexylethyl; 2-methylpropyl; 3-methyl-1-butyl; cyclohexyl; 2,2-dimethylpropyl; benzyl; 2-thienylmethyl; 1-t-butoxycarbonyl-4-piperidinyl; 4-methoxybenzyl; 4-chlorobenzyl; 3,4-dichlorobenzyl; 2-pyranylmethyl; 4-pyranylmethyl; 4-pyranyl and 1,1-dimethylethyl; R$^2$, R$^3$ and $R^5$ are H; $R^4$ is are (including substituted aryl), indanylmethyl, heteroarylmethyl, pyridinyl or

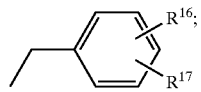

$R^{16}$ is H, F, Cl, CN, $NO_2$, $SO_2NH_2$, $CF_3$, $CH_3$, $COOCH_3$, $OCH_3$, $SO_2CH_3$, $SOCH_3$, $N(CH_3)_2$ or COOH; and $R^{17}$ is H, $OCH_3$ F or Cl. In these compounds, the carbon to which $R^1$ and $R^2$ are attached is preferably of the R absolute configuration, i.e. derivatives of D-amino acids, when m and n are zero.

In another preferred embodiment of formula IIa, which is also a preferred embodiment in other subgenera of the general formula I, $R^4$ is

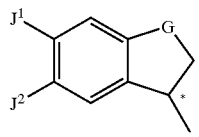

In this genus, one of $J^1$ and $J^2$ is preferably H and the other is H, Cl or CN and G is chosen from $-CH_2-$, $-CH_2CH_2-$, $-OCH_2-$, $-O-$ and $-CH_2N$(lower alkyl)-. Compounds having the R configuration at the carbon indicated with an asterisk have higher potency as bradykinin receptor antagonists.

In a second class of pyrimidines, the 2-pyrimidinamines, Y is CH. These have the formula IIb:

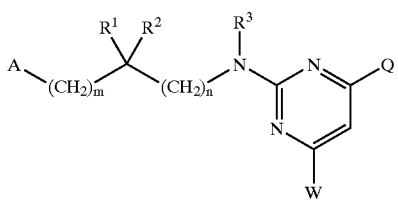

Preferred embodiments are as for IIa. Particularly preferred embodiments are those in which Q is imidazolyl, pyrrolyl, pyridinyl, fluorophenyl or 2-thienyl. In these compounds, A is preferably $R^4R^5N-C(O)-$; W is H, Cl, $NHR^9$ or $OR^8$; $R^1$ is alkyl or $C_1-C_3$-alkylcycloalkyl; $R^2$, $R^3$ and $R^5$ are H; $R^4$ is $C_1-C_4$-alkylaryl or $C_1-C_4$-alkylheteroaryl; $R^8$ is $C_1-C_4$-alkylaryl; $R^9$ is hydrogen, alkyl, fluoroalkyl, ($C_1-C_4$-alkoxy)alkyl, ($C_1-C_4$-alkylthio)alkyl, $C_1-C_4$-alkylcycloalkyl, $C_1-C_4$-alkylaryl, heterocyclyl, $C_1-C_4$-alkylheteroaryl, or $C_1-C_4$-alkylheterocyclyl; and m and n are zero. Among these, the most preferred compounds are those in which W is $NHR^9$ and $R^9$ is

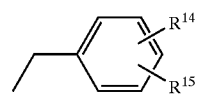

wherein $R^{14}$ is H, F, Cl, CN, $NO_2$, $SO_2NH_2$, $CF_3$, $COOCH_3$, $OCH_3$, $SO_2CH_3$, $N(CH_3)_2$ or COOH; and $R^{15}$ is H, $OCH_3$ or Cl.

In the third class of pyrimidines, a different set of 4-pyrimidinamines, X is CH. These have the formula IIc:

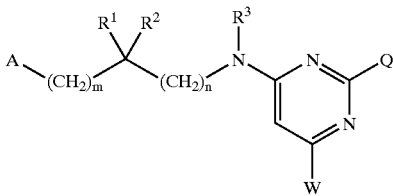

Preferred embodiments are as for IIa. Particularly preferred embodiments are those in which Q is imidazolyl or pyrrolyl and m and n are zero. In these compounds, A is preferably $R^4R^5N-C(O)-$; W is $NHR^9$; $R^1$ is cyclohexylmethyl; 2-methylpropyl or 3-methyl-1-butyl; $R^2$, $R^3$ and $R^5$ are H; and $R^4$ and $R^9$ are benzyl or substituted benzyl.

Triazines form another subgenus of the invention according to formula I; in this subgenus, all of X, Y, and Z are N. The triazines of interest have the formula III

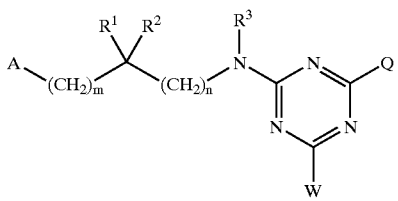

Preferred embodiments are as for the pyrimidines. Particularly preferred embodiments are those in which Q is imidazolyl or pyrrolyl. In these compounds, A is preferably $R^4R^5N-C(O)-$; W is $NHR^9$; $R^1$ is cyclohexylmethyl; 2-methylpropyl or 3-methyl-1-butyl; $R^2$, $R^3$ and $R^5$ are H; and $R^4$ and $R^9$ are benzyl or substituted benzyl.

Anilines form another subgenus of the invention according to formula I in which all of X, Y, and Z are CH. Anilines of the invention have the formula IV:

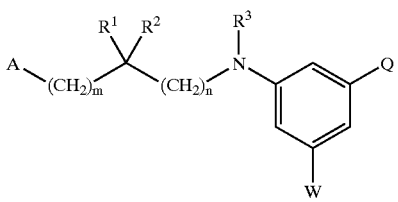

Preferred embodiments are as for the pyrimidines. Particularly preferred embodiments are those in which Q is imidazolyl or pyrrolyl. In these compounds, A is preferably $R^4R^5N-C(O)-$; W is $NHR^9$; $R^1$ is alkyl, cycloalkyl, $C_1-C_3$-alkylaryl or $C_1-C_3$-alkylcycloalkyl; $R^2$, $R^3$ and $R^5$ are H; $R^4$ is $C_1-C_4$-alkylaryl; $R^9$ is

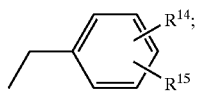

$R^{14}$ is H, Cl, CN, $NO_2$, $SO_2NH_2$, $CF_3$, $COOCH_3$, $OCH_3$, $SO_2CH_3$, $N(CH_3)_2$ or COOH; $R^{15}$ is H, $OCH_3$ or Cl; and m and n are zero.

All of the compounds falling within the foregoing parent genus and its subgenera are useful as bradykinin inhibitors, but not all the compounds are novel. In particular, certain pyrimidines in which Q is imidazolyl and W is H, Cl, F or lower alkyl are disclosed as inhibitors of nitric oxide synthetase in PCT application WO 98/37079. The specific exceptions in the claims below reflect applicants' intent to avoid claiming subject matter that, while functionally part of their invention, is not patentable to them for reasons having nothing to do with the scope of the inventive concept.

"Alkyl" is intended to include linear, or branched hydrocarbon structures and combinations thereof; hydrocarbons of 20 or fewer carbons are generally preferred. "Lower alkyl" means alkyl groups of from 1 to 6 carbon atoms. Examples of lower alkyl groups include methyl, ethyl, propyl, isopropyl, butyl, s- and t-butyl, pentyl, hexyl, and the like.

"Cycloalkyl" includes cycloalkyl groups of from 3 to 12 carbon atoms. Examples of "cycloalkyl" groups include c-propyl, c-butyl, c-pentyl, c-hexyl, 2-methylcyclopropyl, cyclopropylmethyl, cyclopentylmethyl, norbornyl, adamantyl, myrtanyl and the like.

"Alkenyl" refers to a $C_2$ to $C_{20}$ hydrocarbon of a linear, branched, or cyclic ($C_5$–$C_6$) configuration, and combinations thereof, having one or two degrees of unsaturation. $C_2$–$C_8$ Alkenes are preferred. Examples of alkenyl groups include vinyl, allyl, isopropenyl, pentenyl, hexenyl, c-hexenyl, 1-propenyl, 2-butenyl, 2-methyl-2-butenyl, 2,4-hexadienyl and the like.

Alkynyl is $C_2$–$C_8$ alkynyl of a linear or branched configuration and combinations thereof. Examples of alkynyl groups include ethyne, propyne, butyne, pentyne, 3-methyl-1-butyne, 3,3-dimethyl-1-butyne, and the like.

$C_1$ to $C_{20}$ Hydrocarbon includes alkyl, cycloalkyl, alkenyl, alkynyl, aryl and combinations thereof. Examples include phenethyl, cyclohexylmethyl and naphthylethyl.

"Alkoxy" means alkoxy groups of from 1 to 8 carbon atoms of a straight, branched, cyclic configuration and combinations thereof. Examples of alkoxy groups include methoxy, ethoxy, propoxy, isopropoxy, cyclopropyloxy, cyclohexyloxy, and the like. Lower-alkoxy refers to groups containing one to four carbons.

Halogen includes F, Cl, Br, and I, with F and Cl as the preferred groups. "Halophenyl" means phenyl substituted by 1–5 halogen atoms. Halophenyl includes pentachlorophenyl, pentafluorophenyl, and 2,4,6-trichlorophenyl. "Fluoroalkyl" refers to an alkyl residue in which one or more hydrogen atoms are replaced with F, for example: trifluoromethyl, difluoromethyl, and pentafluoroethyl, 2,2,2-trifluoroethyl.

"Aryl" and "heteroaryl" mean a 5- or 6-membered aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or tricyclic 13- or 14-membered aromatic or heteroaromatic ring system containing 0–3 heteroatoms selected from O, N, and S; each of which rings is optionally substituted with up to three substituents chosen independently from lower alkyl, =O, nitro, halogen, hydroxy, alkoxy, alkylsulfonyl; methylenedioxy, alkoxyethoxy, cyano, amino, alkylamino, dialkylamino, acylamino, aminosulfonyl, $C_1$–$C_6$-alkoxycarbonyl, carboxy, methylsulfonamido, perfluoroalkyl, phenyl, benzyl, trityl, and phenoxy. 6- to 14-Membered aryl residues include, for example, benzene and naphthalene, and the 5- to 10-membered heteroaryl residues include, for example, imidazole, pyridine, indole, oxazole, thiophene, benzopyranone, benzodioxan, benzodioxole, thiazole, furan, benzimidazole, quinoline, isoquinoline, quinoxaline, pyrimidine, pyrimidinone, pyridazine, tetrazole, and pyrazole. From the exemplary heteroaryl residues, it will be understood that heteroaryl does not imply the highest possible degree of unsaturation, only that there be at least one fully aromatic ring (e.g. benzodioxan).

"Arylalkyl" and "alkylaryl" denote an aryl residue attached to the parent structure through an alkyl residue. The alkyl need not be straight chain. Examples include benzyl, phenethyl, 2-phenylpropyl, 4-chlorobenzyl, and the like. The alkyl may also be a fused cycloalkyl such as indan (e.g. indan-2-yl), tetralin, and fluorene (e.g fluoren-9-yl) or a substituted alkyl, such as in 1-hydroxyindan-2-yl. "Heteroarylalkyl" denotes a residue comprising an alkyl attached to a heteroaryl ring such as pyridinylmethyl, pyrimidinylethyl, and the like.

"Heterocycloalkyl" means a cycloalkyl where one to three carbon atoms is replaced with a heteroatom, such as O, NR(R=H, alkyl), N→O, S, SO, $SO_2$ and the like. The term includes residues in which one or more rings is optionally substituted with up to three substituents chosen independently from lower alkyl, =O, halogen, hydroxy, alkoxy, amino, alkylamino, dialkylamino, acylamino, aminosulfonyl, $C_1$–$C_6$-alkoxycarbonyl, carboxy, methylsulfonamido, perfluoroalkyl, phenyl, benzyl, trityl, and phenoxy. When two heteroatoms are separated by a single carbon, the resulting heterocycloalkyls tend to be unstable in aqueous solutions and are therefore not preferred. Examples of heterocycloalkyls include: tetrahydrofuran, tetrahydropyran, piperidine, pyridine-N-oxide, 2-methyl-1,3-dithiane, dioxane, and the like.

"Substituted" alkyl, alkenyl, cycloalkyl, aryl, heteroaryl or heterocycloalkyl means alkyl, alkenyl, cycloalkyl, aryl, heteroaryl or heterocycloalkyl, wherein hydrogen atoms are replaced by halogen, hydroxy, hydroxyimino, alkoxyimino, nitro, alkoxy, alkoxyethoxy, amino, alkylamino, dialkylamino, aminosulfonyl, perfluoroalkyl, phenyl, benzyl, trityl, phenoxy, amidino, guanidino, ureido, alkyl, alkylenedioxy (e.g. methylenedioxy) fluoroalkyl, carboxy (—COOH), carboalkoxy (i.e. acyloxy RCOO—), carboxyalkyl (i.e. alkoxycarbonyl —COOR), carboxamido (—CONH$_2$), acylamino (RCONH—), cyano, carbonyl, alkylthio, alkylsulfinyl, alkylsulfonyl, alkylsulfonamido, arylthio, arylsulfinyl, arylsulfonyl, arylsulfonamido, heteroaryl, heterocyclyl, phenoxy, benzyloxy, or heteroaryloxy.

Most of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers are prepared as described below using chiral synthons or chiral reagents, or resolved using conventional techniques. When a specific chirality is intended, it is indicated by the conventional wedge and dash notation; a simple single bond emanating from a chiral center implies no particular stereochemistry. Usually such compositions will be mixtures of enantiomers. When the compounds described herein contain olefinic double bonds or other centers of geometric asymmetry, and unless specified otherwise, it is intended that the compounds include both E and Z geometric isomers. Likewise, all tautomeric forms are also intended to be included.

As stated above, pharmaceutical compositions comprise a pharmaceutically acceptable carrier and compounds of formula I. The formulations may additionally include steroidal or nonsteroidal anti-inflammatory drugs (NSAIDS), cyclooxygenase (COX) inhibitors or selective cyclooxygenase-2

(COX-2) inhibitors. Preferred drugs for inclusion in pharmaceutical formulations include: NSAIDs such as arylpropionic acids, arylacetic acids, arylbutyric acids, fenamic acids, arylcarboxylic acids, pyrazoles, pyrazolones, salicylic acids; and oxicams; cyclooxygenase inhibitors such as ibuprofen and salicylic acid derivatives; selective cyclooxygenase-2 inhibitors such as rofecoxib and celecoxib; steroidal antiinflammatory drugs such as finasteride, beclomethasone and hydrocortisone.

Abbreviations and Definitions

The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
PfP=pentafluorophenol
PPTS=pyridinium p-toluenesulfonate
PyBroP=bromo-tris-pyrrolidino-phosphonium hexafluorophosphate
rt or RT=room temperature
sat'd or sat.=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl The compounds of the invention are synthesized as follows.

Scheme 1 Generic Solid Phase Synthesis

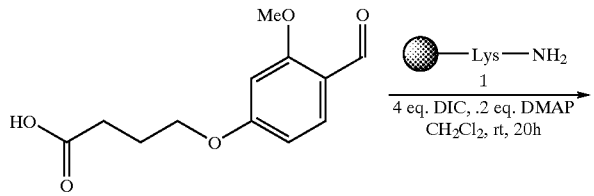

62

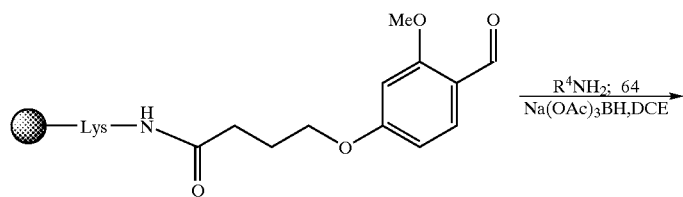

63

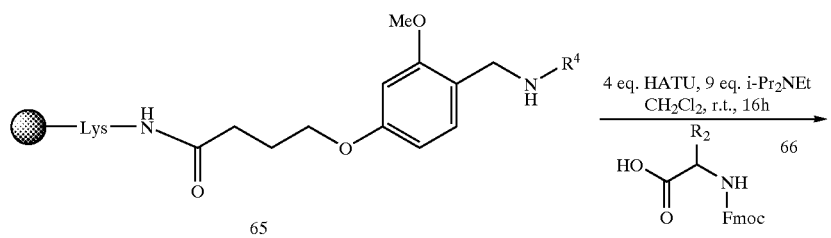

65

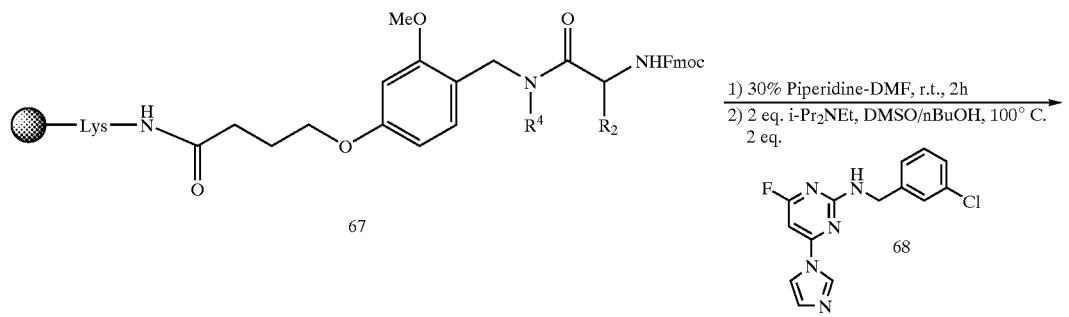

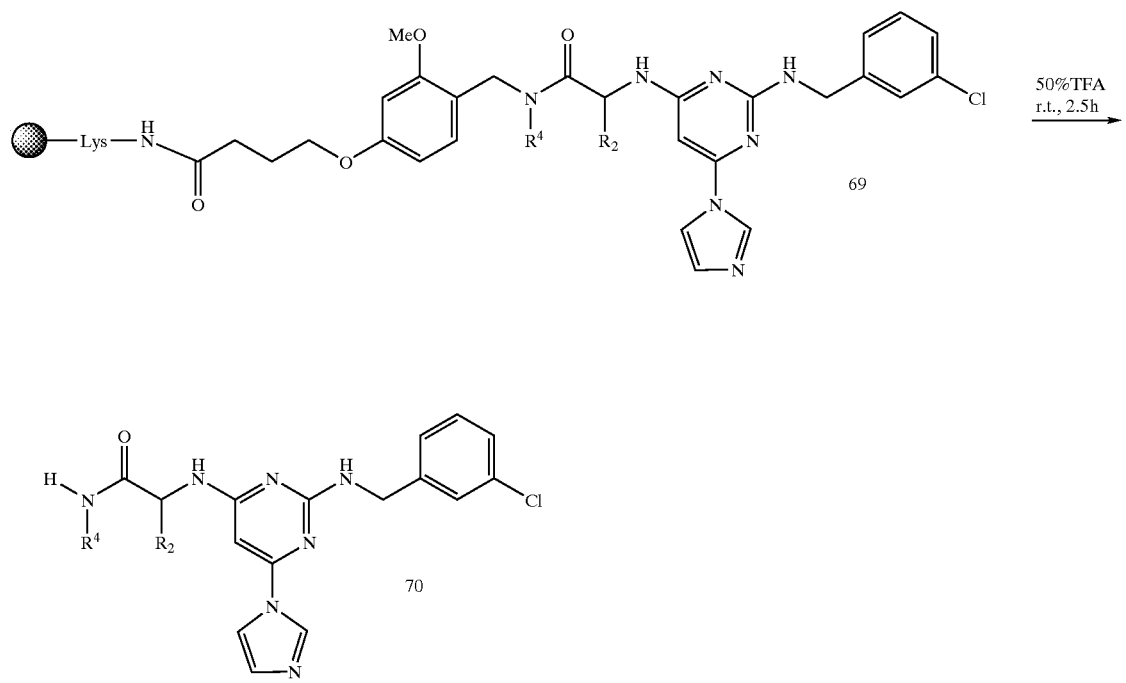

Amino functionalized TentaGel resin 1 (10 g 5.2 mmole) was suspended in 50 mL of CH₂Cl₂ and treated with 3.73 g of linker acid 62 (15.6 mmole), 3.25 mL of DIC (20.8 mmole), and 63 mg of DMAP (0.52 mmole). After 48 h at room temperature, 3.77 g of linker acid 62, 3.25 mL of DIC and 2.1 g HOBt were added. The mixture was shaken at room temperature for 17 h and then washed with DMF twice, CH₂Cl₂ ten times to give resin 63. The resins 63 was treated with amine R⁴NH₂ 64 and Na(OAc)₃BH in dichloroethane at room temperature for 36 h then washed with methanol 5 times and methylene chloride 5 times to give resin-bound amine 65. The amine was coupled with an N-Fmoc amino acid (66) by treatment with HATU and i-Pr₂NEt in methylene chloride at room temperature for 48 h to provide resin 67. Fmoc on resin 67 was removed by treatment with 30% piperidine in DMF and the resulting resin-bound amine was then reacted with fluoropyrimidine 68, i-Pr₂NEt in DMSO:nBuOH (1:1) at 100° C. for 18 h and then washed with methanol, CH₂Cl₂ to give resin bound product 69. The final product was cleaved off resin by treatment with TFA for 3 h to give product 70.

The fluoropyrimidine 68 was prepared by stirring together 315 mg 6-imidazolyl-2,4-difluoropyrimidine (1.7 mmole), 265 mg of 3-chlorobenzylamine and 0.5 mL of i-Pr₂NEt in 30 mL of THF at 50° C. for 16 h, then cooling to room temperature. The reaction was diluted with ethyl acetate and washed with saturated NH₄Cl, H₂O, brine, dried over MgSO₄ and concentrated. The crude product was purified by flash chromatography (eluted with 4:5:1 EtOAc:hexanes:MeOH) to give 160 mg of 68 (more polar product as compared the other regioisomer).

Scheme 2
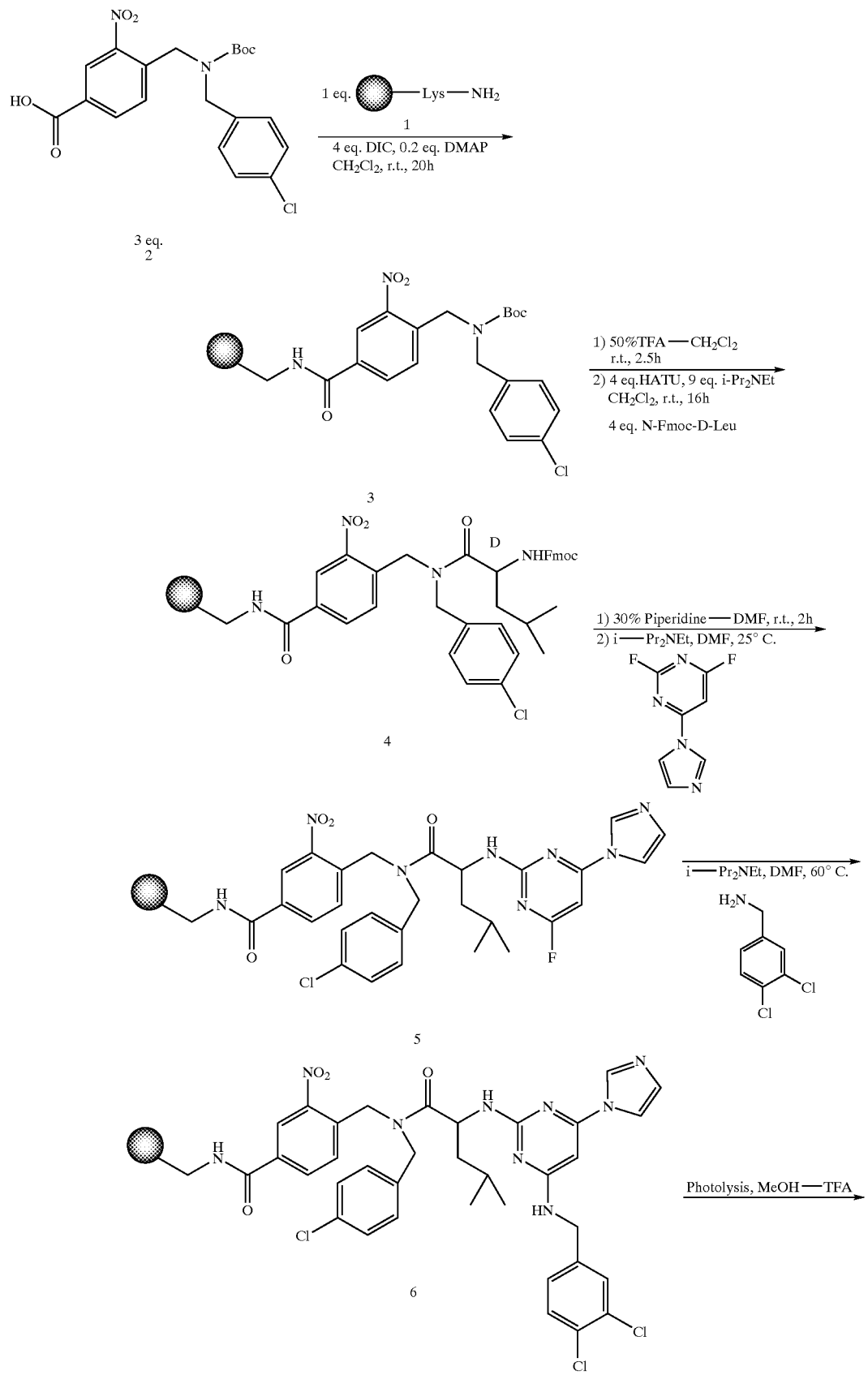

-continued

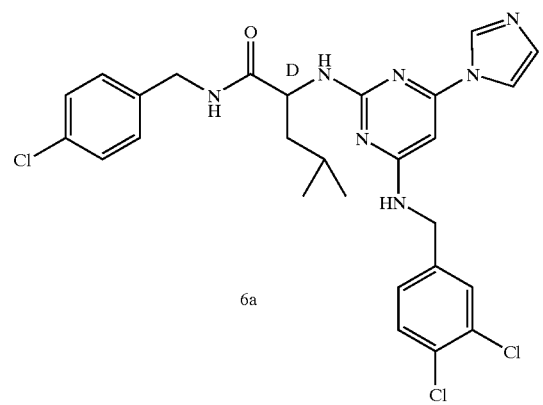

6a

Scheme 2 depicts a similar synthesis to that of Scheme 1, except the linker is photolytically cleavable instead of acid cleavable. As shown in Scheme 2, 2.5 g of amino functionalized TENTAGEL™ resin 1 (0.70 mmole) was suspended in 10 mL of $CH_2Cl_2$ and treated with 0.882 g of linker acid 2 (2.1 mmole), 0.44 mL of DIC (2.8 mmole), and 17 mg of DMAP (0.14 mmole). The mixture was shaken at room temperature for 17 h and then washed with $CH_2Cl_2$ ten times to give resin 3.

1.13 g of resin 3 was treated with 50% TFA-$CH_2Cl_2$ at room temperature for 1.5 h and then washed with $CH_2Cl_2$ ten times, 15% $Et_3N$—$CH_2Cl_2$ for 10 min, and $CH_2Cl_2$ for 5 times. The deprotected resin was then suspended in 12 mL of $CH_2Cl_2$ and treated with 449 mg of N-Fmoc-D-Leu (1.27 mmole), 483 mg of HATU (1.27 mmole), and 0.50 mL of i-$Pr_2$NEt (2.85 mmole). The mixture was shaken for 19 h at ambient temperature and then washed 5 times to give resin 4. Fmoc on resin 4 was removed by treatment with 30% piperidine in DMF and the resulting resin-bound amine (0.32 mmole) was then reacted with 182 mg of 6-imidazolyl-2,4-difluoropyrimidine (0.64 mmole), 0.34 mL of i-$Pr_2$NEt (1.92 mmole) in 10 mL of DMF at 23° C. for 17 h and then washed with DMF, $CH_2Cl_2$ to give resin 5. This reaction also produces the other regioisomer 5a,

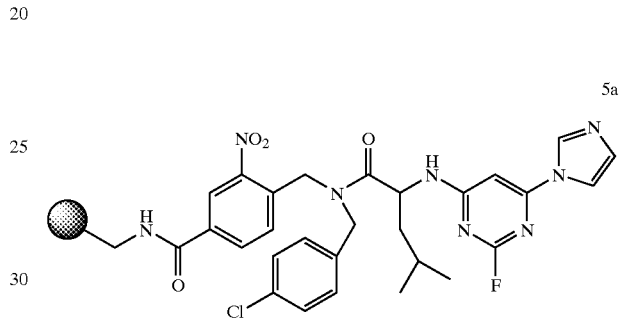

5a which provides entry into the series of pyrimidines of general formula IIa above. The two are separated after cleavage. For simplicity, only the further transformations in the IIb series are shown in Scheme 2. The resin-bound fluoride 5 was treated with 0.25 mL of 3,4-dichlorobenzylamine (1.6 mmole) in 15 mL of DMF and 0.30 mL of Hünig's base at 60° C. for 18 h and then cooled to room temperature and washed with DMF, $CH_2Cl_2$. The final product was cleaved off resin by photolysis in MeOH for 17 h to give 49.2 mg of crude product. Purification by flash chromatography (eluted with 5:5:1 EtOAc:hexanes:MeOH) gave 27.2 mg of 6a (later determined to be mixture of two regioisomers with 1:1 ratio).

Scheme 3

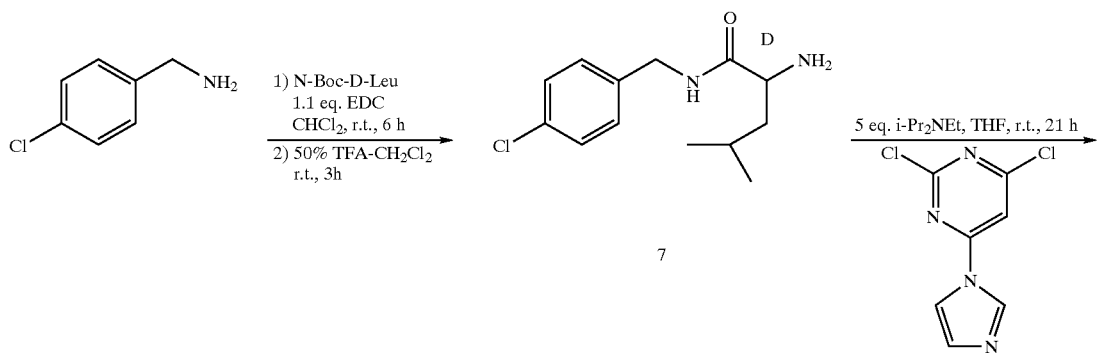

-continued
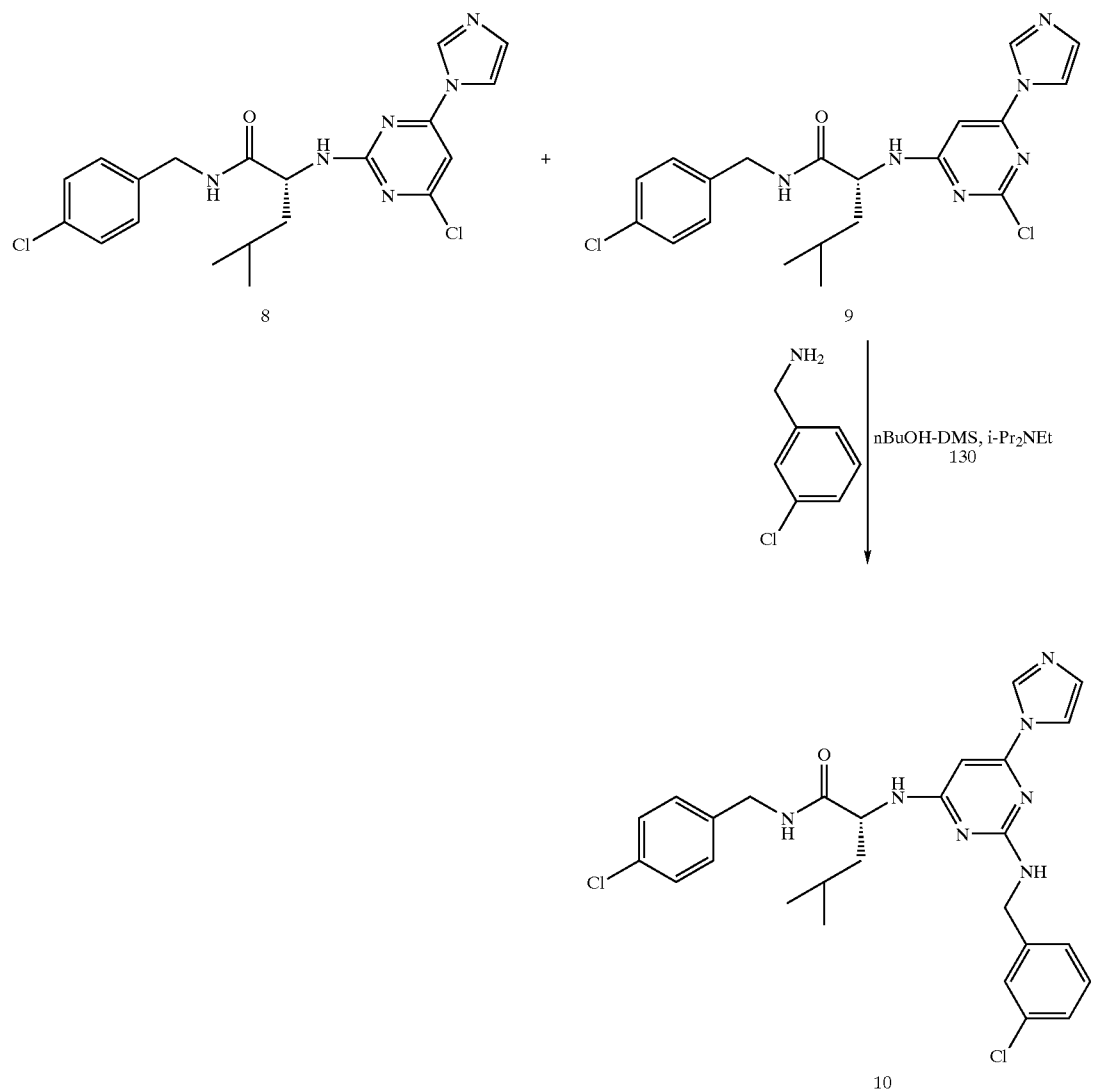
Scheme 4
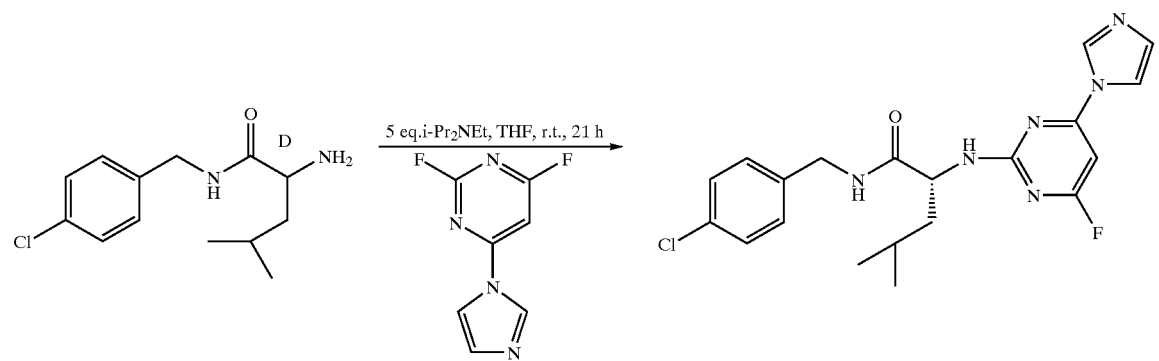
+

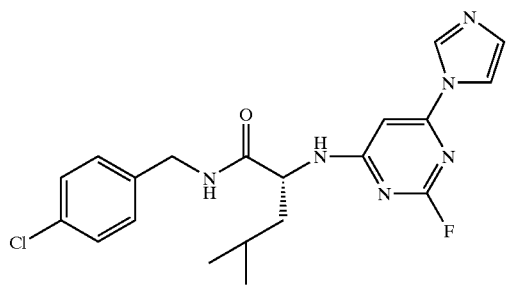

12

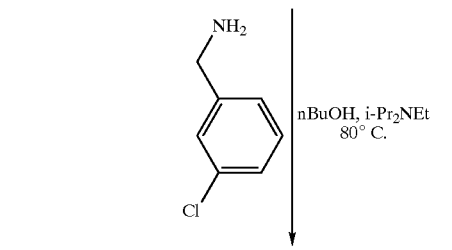

nBuOH, i-Pr₂NEt
80° C.

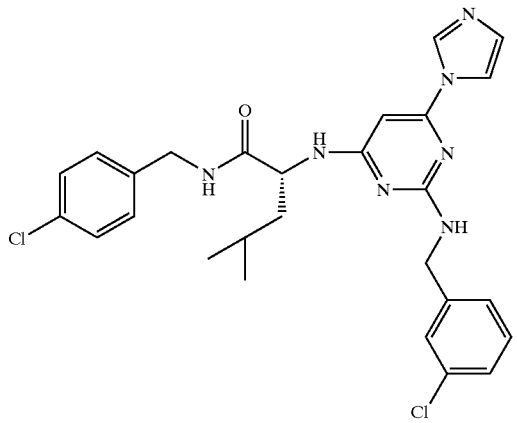

10

Scheme 3 illustrates a solution phase synthesis via chloropyrimidines and Scheme 4 illustrates a solution phase synthesis via fluoropyrimidines. As shown in Scheme 3, EDC (5.18 g, 26.47 mmole) was added into a solution of N-Boc-D-leucine (6.0 g, 24.07 mmole) in 250 mL of CH₂Cl₂, followed by 2.99 mL of 4-chlorobenzylamine (24.07 mmol). The mixture was stirred at room temperature for 4 h then diluted with ethyl acetate and washed with 1N HCl twice, saturated NaHCO₃ and brine twice, dried over MgSO₄ and concentrated to give 7.92 g of crude amide product which was treated with 50% TFA in CH₂Cl₂ at room temperature for 4 h. The solvent was removed and the residue was taken up into ethyl acetate and washed with 2 N NaOH aqueous solution, then brine, dried over MgSO₄ and concentrated to give amine product 7 quantitatively. Three hundred ninety milligrams of the free amine 7 (1.1 mmole) was treated with 0.6 mL of i-Pr₂NEt and 500 mg 6-imidazolyl-2,4-dichloropyrimidine (2.0 mmole) in DMF at 50° C. for 16 hr, then diluted with ethyl acetate and washed with saturated NH₄Cl, H₂O, brine, dried over MgSO₄ and concentrated and purification by flash chromatography (eluted with 8:10:1 EtOAc:Hexanes:MeOH) to give 200 mg of 8 and 130 mg of 9 Ninety two milligrams of 9 (0.21 mmole) in 3 mL of n-butanol was treated with 0.9 mL of 3-chlorobenzylamine and 1 mL of i-Pr₂NEt at 100° C. for 16 h, then cooled to room temperature, diluted with ethyl acetate and washed with saturated NH₄C₁, H₂O, brine, dried over MgSO₄ and concentrated. The crude product was purified by flash chromatography (eluted with 4:5:1 EtOAc:Hexanes:MeOH) o give 97.2 mg of 10.

Alternatively, as illustrated in Scheme 4, 280 mg of the free amine 7 (1.1 mmole) was treated with 0.25 mL of i-Pr₂NEt and 200 mg of 6-imidazolyl-2,4-difluoropyrimidine (1.1 mmole) in THF at room temperature for 13 hr, then diluted with ethyl acetate and washed with saturated NH₄Cl, H₂O, brine, dried over MgSO₄ and concentrated. The crude product was purified by flash chromatography (eluted with 8:10:1 EtOAc:hexanes:MeOH) to give 35 mg of 11 (less polar product) and 80 mg of 12 (more polar product). Four hundred fifty milligrams of 12 (1.08 mmole) in 50 mL of THF or n-butanol was treated with 1.7 g of 3-chlorobenzylamine and 5 mL of i-Pr₂NEt at 80° C. for 16 h then diluted with ethyl acetate and washed with saturated NH₄Cl, H₂O, brine, dried over MgSO₄ and concentrated. The crude product was purified by flash chromatography (eluted with 6:12:1 EtOAc:hexanes:MeOH) to give 350 mg of 10.

Scheme 5
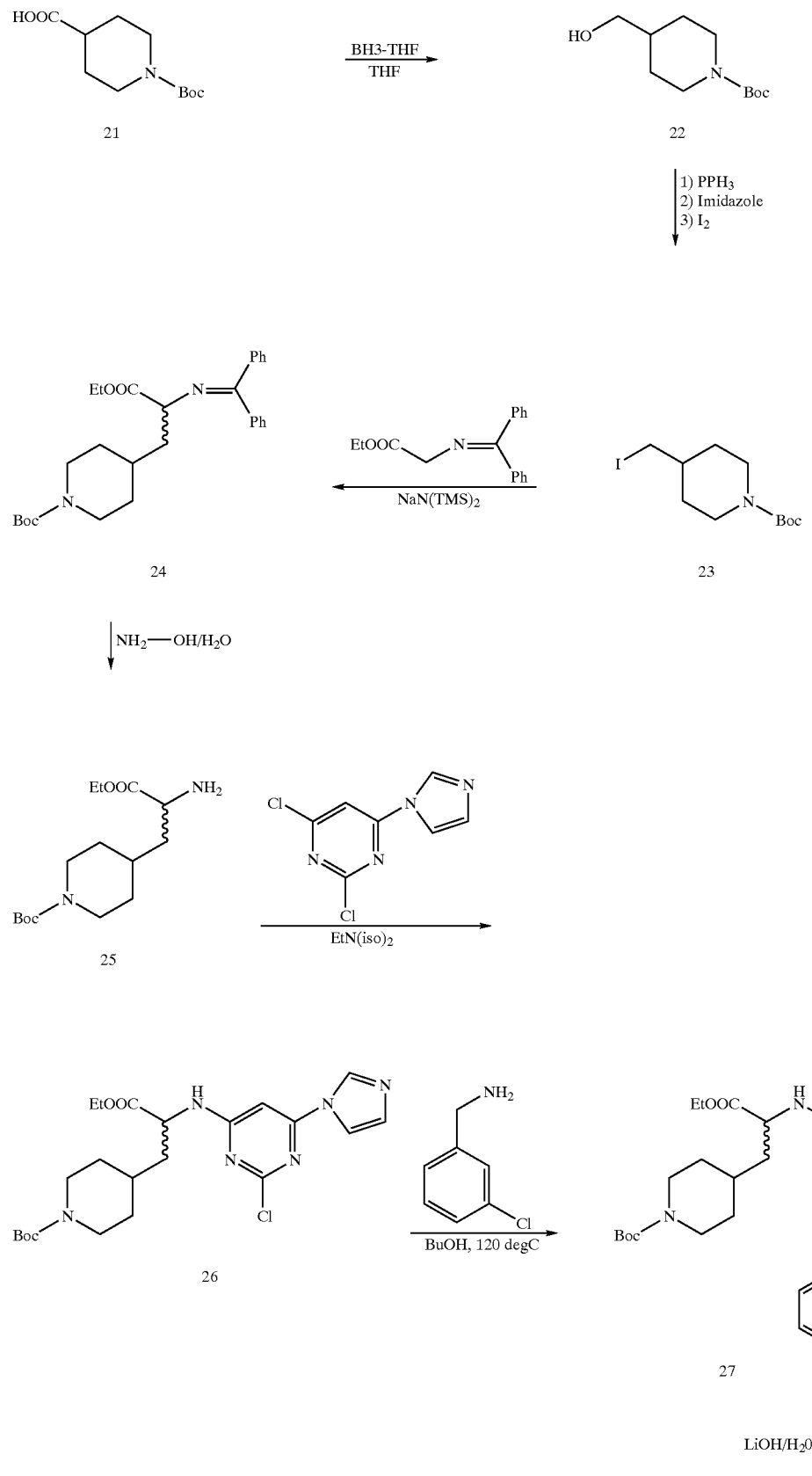

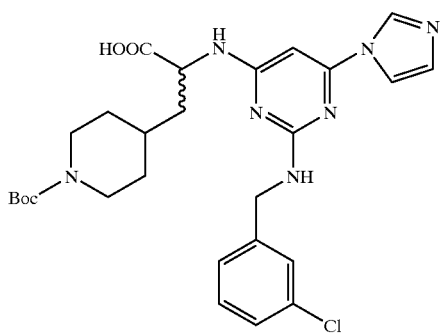

28

1)

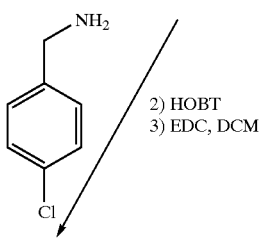

2) HOBT
3) EDC, DCM

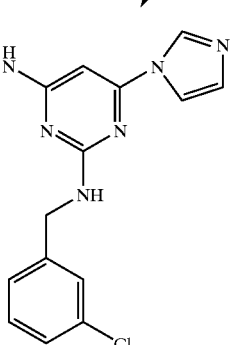

29

TFA / DCM →

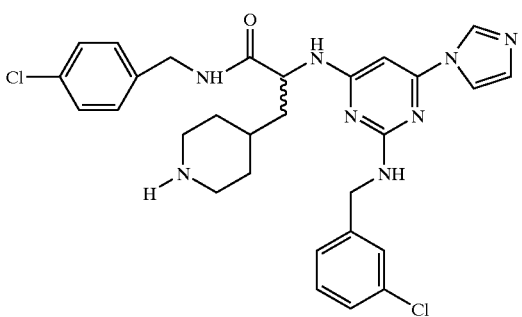

30

Scheme 5 illustrates a synthesis of a member of the subgenus in which R¹ is heterocycloalkyl. According to Scheme 5 a dry 500 mL round bottom flask (oven-heated/ argon cooled), was charged with 25 g (109.2 mmol) of Boc-isonipecotic acid (21). The flask was purged with argon, and 150 mL of dry THF were injected by syringe into the air-free system. The mixture was then stirred while being cooled to 0° C., and an oil-bubbler was attached, then 131 mL of a 1M solution of borane/THF (131 mmol) were injected into the solution slowly, and the solution was stirred for ½ hour. Methanol was dripped into the solution slowly until bubbles ceased to be evolved. The solution was washed with 200 mL of a saturated sodium bicarbonate solution, and extracted twice with ethyl acetate, and the organic layer was dried over magnesium sulfate. The yield of the reaction was 22.44 g (96%) of the 22 product as a white solid. ¹H NMR in CDCl₃: a 3H multiplet from 0.85–1.2 ppm, a 9H singlet at 1.45 ppm, a 4H multiplet 1.455–1.8 ppm, a 2H broad signal at 2.65 ppm, a 1H broad signal at 3.45 ppm, and a 1H broad signal at 3.6 ppm.

A 250 mL round bottom flask was charged with 5.8 g (27 mmol) of 22, 8.5 g (32.37 mmol) of triphenylphosphine, and 2.2 g (32.37 mmol) of imidazole. One hundred milliliters of methylene chloride were added, and the resulting solution was stirred at 0° C. for about 5 minutes. Finally, 8.2 g (32.37 mmol) of iodine were added and the solution was stirred at 0° C. for 5 minutes and at room temp for about 1 hour. The reaction mixture was diluted with 200 mL of hexane, and the triphenylphosphine oxide precipitate was filtered off (this was repeated until all precipitate was removed). The crude mixture was purified by flash chromatography using a 5%–10% ethyl acetate/hexane solvent system. A Phosphomolybdic acid stain (PMA), was used to see the product on the TLC plate. The resulting yield of pure 23 as an oil was 2.6 g (30%). $^1$H NMR in CDCl$_3$: 2H quartet at 1.1 ppm (J=12 Hz), a 9H singlet at 1.4 ppm, a 1H broad signal at 1.55 ppm, a 2H doublet at 1.75 (J=12 Hz), a 2H broad signal at 2.65 ppm, a 2H doublet at 3.05 ppm (J=6 Hz), and a 2H broad signal at 4.1 ppm. The R$_f$=0.13 using a 5% ethyl acetate/hexane solvent system.

A dry 250 mL round bottom flask (oven heated/argon cooled), was charged with 1.3 g (5.113 mmol) of N-(diphenylmethylene) glycine ethyl ester. The flask was purged with argon, and 100 mL of dry THF were injected into the air-free system. The resulting solution was cooled to −78° C. with stirring, and 6.2 mL (6.15 mmol) of a 0.1M solution of sodium hexamethyldisilazane in THF were injected into the solution. The reaction was stirred at −78° C. for ½ hr, and a solution of 2 g of 23 in dry THF was injected into the system. The solution was stirred at −78° C. for 1 hr, at 0° C. for 1 hr, and at room temp overnight. The reaction mixture was washed with a solution of 1 g (6.15 mmol) of citric acid in water, and diluted with 200 mL of ethyl acetate. The organic layer was extracted and dried over magnesium sulfate. The crude mixture was purified by flash chromatography using a 10% ethyl acetate/hexane solvent system. The yield was 1.45 g (61%) of solid product 24. $^1$H NMR in CDCl$_3$: A 3H broad multiplet from 0.8–1.15 ppm, a 4H broad signal at 1.25 ppm, a 9H singlet at 1.4 ppm, a 2H broad signal at 1.5 ppm, a 1H broad triplet at 1.85 ppm, a 2H broad quartet at 2.6 ppm, a 2H broad signal at 3.95 ppm, a 2H broad signal at 4.15 ppm, a 2H triplet at 7.15 ppm (J=3.6 Hz), a 6H multiplet from 7.25–7.5 ppm, and a 2H doublet at 7.6 ppm (J=9 Hz). The R$_f$=0.22 suing a 10% ethyl acetate/hexane solvent system. ESI MS at 465 MH+.

A 100 mL round bottom flask was charged with 0.35 g (0.75 mmol) of 24, and 20 mL of ethanol were added to the flask. With stirring, 0.5 mL of a 50% (by weight) solution of hydroxylamine was added followed by 0.5 mL of glacial acetic acid (5 minutes later). The reaction was stirred for 10 minutes, until the starting material disappeared by TLC. The reaction mixture was diluted with 100 mL ethyl acetate, 20 mL of a brine solution was added, followed by basification using 0.5 M NaOH. The organic layer was extracted, and the aqueous layer was then extracted with two 20 mL portions of methylene chloride. The combined organic layers were dried over magnesium sulfate. The crude mixture was purified by flash chromatography using a 55% ethyl acetate/hexane solvent system. A ninhydrin stain was used to see the product spot on the TLC plate. The yield of pure 25 as an oil was 0.25 g (96%). $^1$H NMR in CDCl$_3$: A 1H multiplet from 0.9–1.05 ppm, a 3H broad triplet at 1.1 ppm, a 3H triplet at 1.25 ppm (J=6 Hz), an 11H broad signal at 1.4 ppm, a 3H multiplet from 1.5–1.8 ppm, a 2H broad triplet at 2.7 ppm, a 3H quartet at 3.45 ppm (J=3.6 Hz), and a 4H multiplet from 4–4.2 ppm. The R$_f$=0.22 using a 55% ethyl acetate/hexane solvent system.

A 50 mL round bottom flask was charged with 0.310 g (1 mmol) of 25 and mL of DMF. With stirring, 0.22 g (1 mmol) of the pyrimidine/imidazole subunit, and 0.35 mL (2 mmol) of diisopropylethylamine (Hünig's base) were added. The mixture was stirred at 90° C. overnight. The reaction mixture was diluted with 200 mL of ethyl acetate, and washed with water. The organic layer was extracted and dried over magnesium sulfate. The crude mixture was purified by flash chromatography using an 80%–90% ethyl acetate/hexane solvent system. The yield of the reaction was 0.14 g of the regio-isomer with substitution of the pyrimidine at the 2-position and 0.12 g (25%) of the desired regio-isomer 36 (oil), (total yield is 54%). $^1$H NMR in CDCl$_3$: a 1H multiplet from 0.9–1.05 ppm, a 3H broad triplet at 1.15 ppm, a 2H triplet at 1.3 ppm (J=6 Hz), a 9H singlet at 1.45 ppm, a 2H broad signal at 1.7 ppm, a 2H broad signal at 1.85 ppm, a 2H broad triplet at 2.65 ppm, a 2H broad signal at 4.1 ppm, a 2H quartet at 4.2 ppm (J=2.4 Hz), a 1H broad signal at 4.9 ppm, a 1H doublet at 6.05 ppm (J=9 Hz), a 1H broad singlet at 6.3 ppm, a 1H singlet at 7.15 ppm, a 1H singlet at 7.5 ppm, and a 1H singlet at 8.3 ppm. The R$_f$ of the desired regio-isomer was about 0.22 using an 80% ethyl acetate/hexane solvent system. The pure product gave a molecular ion of 480, MH+.

A 50 mL round bottom flask was charged with 0.12 g (0.25 mmol) of 26, 0.142 g (1 mmol) of 3-chlorobenzylamine, and 5 mL of dry n-butanol. The solution was stirred at 120° C. overnight. The reaction mixture was diluted with 200 mL of ethyl acetate, and washed with water. The organic layer was extracted and dried over magnesium sulfate. The crude mixture was purified by flash chromatography using a 90%–95% ethyl acetate/hexane solvent system. The yield was 0.125 g (87%) of 27 as an oil. $^1$H NMR in CDCl$_3$: a 1H triplet at 0.9 ppm (J=6), a 2H broad signal at 1.1 ppm, a 3H triplet at 1.25 ppm (J=4.8 Hz), a 9H singlet at 1.45 ppm, a 5H broad signal at 1.65 ppm, a 2H broad signal at 2.6 ppm, a 4H broad signal at 4.1 ppm, a 2H doublet at 4.55 ppm (J=6 Hz), a 1H broad signal at 4.7 ppm, a 1H doublet at 5.4 ppm (J=9 Hz), a 1H singlet at 5.75 ppm, a 1H singlet at 7.1 ppm, a 3H singlet at 7.2 ppm, a 1H singlet at 7.35 ppm, a 1H singlet at 7.5 ppm, and a 1H singlet at 8.25 ppm. The R$_f$ of the product was about 0.28 using an 80% ethyl acetate/hexane solvent system. The pure product gave a molecular ion of 584, MH+.

A 50 mL round bottom flask was charged with 0.125 g (0.214 mmol) of 27 and 10 mL of THF. With stirring, a solution of 0.09 g (2.14 mmol) of lithium hydroxide in 10 mL of water was added. The solution was heated at 55° C. for 2 hr. The reaction mixture was diluted with 200 mL of ethyl acetate, and washed with a solution of 0.412 g (2.14 mmol) of citric acid in water to neutralize the excess base present. The organic layer was extracted and dried over magnesium sulfate. The crude mixture was purified by flash chromatography using an 95% ethyl acetate/methanol solvent system. The yield was 0.1 g (83%) of pure 28 as a white solid. $^1$H NMR in CDCl$_3$: a 1H broad signal at 0.9 ppm, a 3H broad signal at 1.1 ppm, a 2H triplet at 1.25 ppm (J=6 Hz), a 9H singlet at 1.4 ppm, a 4H broad signal at 1.65 ppm, a 2H broad signal at 2.45 ppm, a 3H broad signal at 4 ppm, a 2H broad signal at 4.3–4.8 ppm, a 1H broad signal at 5.85 ppm, a 1H singlet at 7.05 ppm, a 3H singlet at 7.15 ppm, a 1H doublet at 7.25 ppm (J=3.6), a 1H singlet at 7.5 ppm, and a 1H singlet at 8.5 ppm. The R$_f$ of the product was about 0.08 using a 95% ethyl acetate/methanol solvent system. The pure product gave a molecular ion of 556, consistent with its molecular weight of 555, MH+.

A 50 mL round bottom flask was charged with 0.099 g (0.178 mmol) of 28 and 20 mL of methylene chloride. With stirring, 0.048 g (0.356 mmol) of 1-hydroxybenzotriazole (HOBT) and 0.068 g (0.356 mmol) of 1-(3-dimethylaminopropyl)-3-ethyl-carbodiimide hydrochloride (EDC), were added to the solution, then 1 mL of DMF was added to aid in solubility, and the solution was stirred for 20 minutes, until the acid intermediate spot disappeared by TLC. Fifty milligrams (0.356 mmol) of 4-chlorobenzylamine was added to the solution and it was stirred for 2 hrs. The reaction mixture was diluted with 200 mL of ethyl acetate and washed successively with solutions of 0.5 M HCl, 0.5 M NaOH, and brine. The organic layer was extracted and dried over magnesium sulfate. The crude mixture was purified by flash chromatography using 100%–98% ethyl acetate/methanol as the solvent system. The yield was 0.085 g (71%) of pure 29 as an oil. $^1$H NMR in CDCl$_3$: a 4H multiplet from 0.9–1.3 ppm, a 9H singlet at 1.4 ppm, a 5H broad signal at 1.6 ppm, a 1H multiplet from 1.75–2.15 ppm, a 2H broad signal at 2.6 ppm, a 2H singlet evaporated twice. The product 30 was diluted with 50 mL ethyl acetate, and washed with 0.5 M NaOH. $^1$H NMR in CDCl$_3$: a 5H multiplet from 0.75–1 ppm, a 5H multiplet from 1.5–1.8 ppm, a 1H singlet at 1.95 ppm, a 2H quartet at 2.6 ppm (J=14), a 1H broad signal at 3.1 ppm, a 2H singlet at 3.65 ppm, a 4H multiplet from 4.–4.7 ppm. A 1H singlet at 5.9 ppm, a 9H multiplet from 7.05–7.15 ppm, a 1H singlet at 7.5 ppm and a 1H singlet at 8.3 ppm. The pure product gave a molecular ion of 579, consistent with its molecular weight of 578 amu.

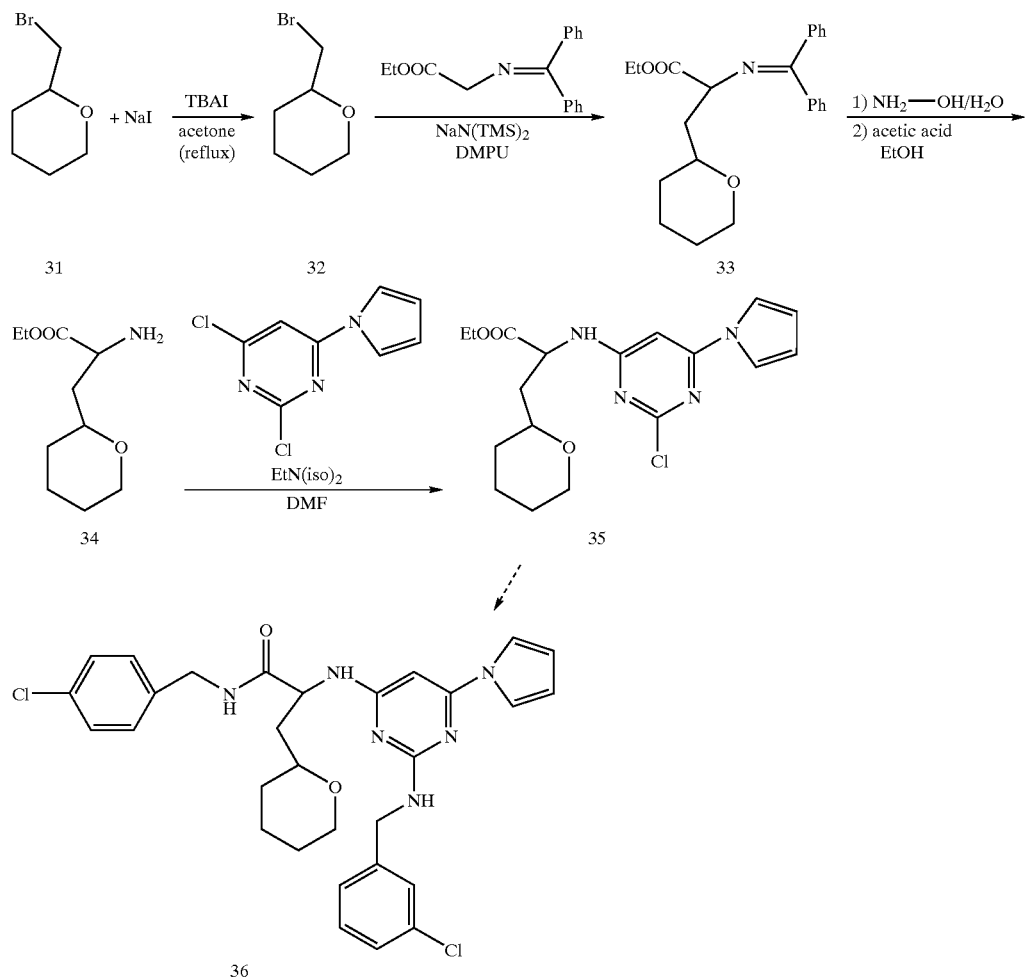

at 3.85 ppm, a 1H broad signal at 4.05 ppm, a 4H multiplet from 4.3–4.6 ppm, a 1H doublet at 5.3 ppm (J=6), a 1H singlet at 5.7 ppm, a 2H singlet at 7.1 ppm, a 7H multiplet from 7.15–7.3 ppm, a 1H singlet at 7.45 ppm, and a 1H singlet at 8.25 ppm. The R$_f$ of the product was about 0.24 using a 95% ethyl acetate/methanol solvent system. The pure product gave a molecular ion of 679, consistent with its molecular weight of 678 amu.

A 50 mL round bottom flask was charged with 0.020 g (0.03 mmol) of 29 and 3 mL of methylene chloride. With stirring, 1.5 mL (0.02 mmol) of trifluoroacetic acid was added, and the solution was stirred for about 20 minutes, until the Boc-containing intermediate disappeared by TLC. The reaction mixture was diluted with 10 mL toluene and As outlined in Scheme 6, a 500 mL round bottom flask was charged with 10 g (55.84 mmol) of 31, 84 g (558.4 mmol) of sodium iodide, 20.63 g (55.84 mmol) of t-butyl ammonium iodide, and 250 mL acetone. The mixture was stirred at reflux overnight. The reaction mixture was filtered to eliminate excess sodium iodide, and was diluted with 100 mL hexane. The mixture was filtered again to remove more of the remaining sodium iodide. This was repeated until no precipitate formed when the mixture was diluted with hexane. The reaction yield was 9.66 g (77%) of pure 2-(iodomethyl)tetrahydro-2H-pyran 32 as an oil. $^1$H NMR in CDCl$_3$ was consistent with structure. R$_f$=0.55, using a 2% ethyl acetate/hexane solvent system and a phosphomolybdic acid stain. The product did not give a mass spec signal.

A dry 100 mL round bottom flask (oven heated/argon cooled) was charged with 3.2 g (11.80 mmol) of N-(diphenylmethylene) glycine ethyl ester and purged with argon. Thirty-five milliliters of dry DMPU and 15 mL of dry THF were injected by syringe into the air-free system. The resulting solution was cooled to −78° C., and 17.70 mL (1.5 mmol) of a 0.1M solution of sodium hexamethylsilazane in THF was injected into the system, which was then stirred at −78° C. for 20 minutes. Finally, an air-free solution of 4 g (17.70 mmol) of 32 in dry THF was injected into the system, which was then stirred at −78° C. for ½ hr, 0° C. for ½ hr, and room temp overnight. The reaction mixture was diluted with 300 mL of ethyl acetate and washed 5 times with 50 mL portions of water to remove the DMPU. The organic layer was extracted and dried over magnesium sulfate. The crude mixture was purified by flash chromatography 4–11% ethyl acetate/hexane solvent system. The yield of the reaction was 1.57 g of the less polar diastereomer of 33, and 0.33 g of the more polar diastereomer of 33. The overall yield was 1.9 g (44%). $^1$H NMR in CDCl$_3$ was consistent with structures. The diastereomers have partial overlap by TLC, R$_f$=0.55 using a 5% ethyl acetate/hexane solvent system. The product gave a molecular ion of 366, consistent with its molecular weight of 365.

Note: Throughout the rest of the synthesis, the procedures involve the use of the more polar diastereomer, for the sake of clarity.

The deprotection and work-up of 33 to give 34 follows the same procedure as that for the isonipecotic analogue (see the synthesis of 25 in that sequence).

The crude mixture was purified by flash chromatography using an 80–90% ethyl acetate/hexane solvent system and a ninhydrin stain. The yield for the reaction was 68%. $^1$H NMR in CDCl$_3$ was consistent with structures. The R$_f$=0.15 using a 90% ethyl acetate/hexane solvent system. The product gave MH+@ 202.

The coupling and work-up of 34 with the dichloropyrimidine-pyrrole intermediate follows the same procedure as that for the isonipecotic analogue with the dichloropyrimidine-imidazole intermediate (see the synthesis of 26 in that sequence). The crude mixture was purified by flash chromatography using a 10–20% ethyl acetate/hexane solvent system. The yield for the reaction was 25% for the desired more polar regio-isomer, and 62% for the total yield for both regio-isomers. $^1$H NMR in CDCl$_3$ was consistent with structure. The R$_f$=0.15 using a 10% ethyl acetate/hexane solvent system. The product gave MH+@ 379.

The remaining steps from 35 to 36 follow the corresponding procedures as for the isonipecotic analogue (see Scheme 5). The crude 36 was purified by flash chromatography using a 16–25% ethyl acetate/hexane solvent system. $^1$H NMR in CDCl$_3$ was consistent with structure. The R$_f$=0.55 using a 20% ethyl acetate/hexane solvent system. The product gave MH+ at 615.

Scheme 7

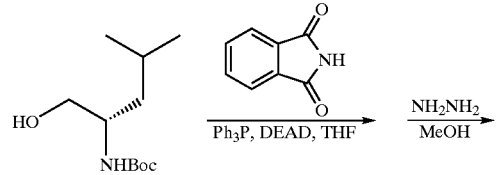

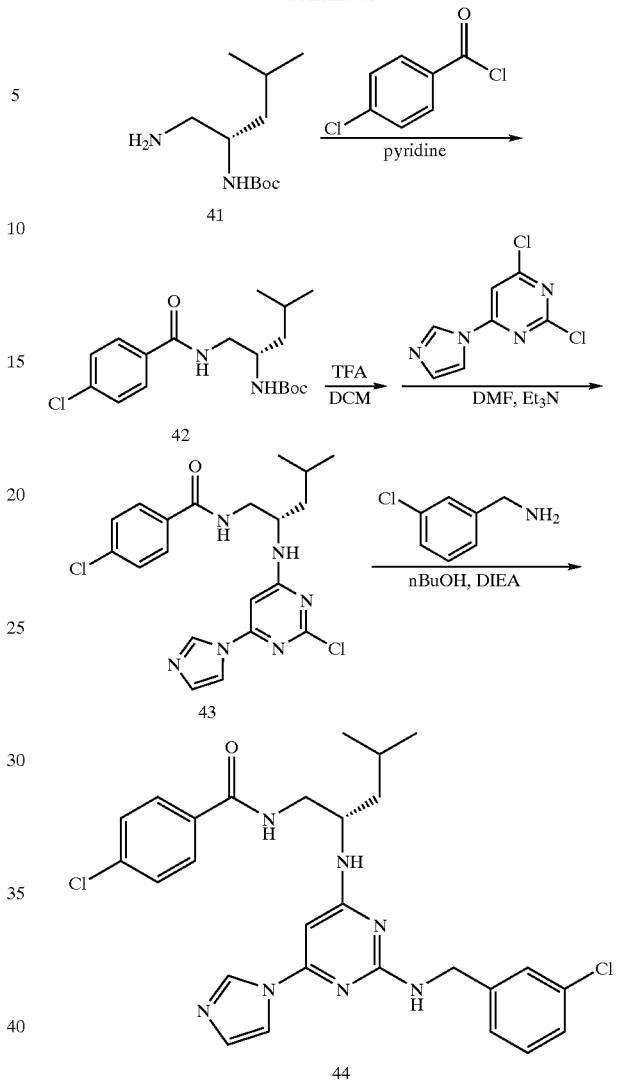

Scheme 7 depicts an exemplary synthesis wherein m> zero and A=A$^2$. To Boc-D-leucinol (2.7 g, 12.4 mmol), triphenylphosphine (3.25 g, 12.4 mmol), and phthalimide (1.82 g, 12.4 mmol) in 25 mL of dry THF was added DEAD dropwise. The solution was stirred at room temperature overnight, concentrated and taken up in MeOH. To this solution was added hydrazine (780 mL, 24.8 mmol) and heated to reflux for 2 hours. The mixture was allowed to cool to room temperature, and the white precipitate filtered. The mother liquor was concentrated, taken up in EtOAc and washed with 1N HCl. The aqueous layer was then cooled in an ice bath, basified with 3N NaOH, and extracted with EtOAc. The organic layer was dried over K$_2$CO$_3$ and concentrated to yield 41 as a clear oil. (0.75 g, 3.5 mmol, 28%).

To 41(0.3 g, 1.4 mmol) in 15 mL pyridine was added 4-chlorobenzoyl chloride (194 mL, 1.5 mmol) and the mixture was stirred at room temperature for 4 hours. The reaction was poured into 200 mL water and the precipitate filtered. The resulting solid was taken up in DCM and washed with saturated NaHCO$_3$ and 1M KHSO$_4$. The organic layer was dried over MgSO$_4$ and concentrated to yield 42 as a pale white solid. (0.30 g, 0.84 mmol, 61%).

One hundred sixty-five milligrams of 42 (0.46 mmol) was taken up in 10 mL of DCM and 5 mL TFA was added. After 30 minutes the solution was concentrated, taken up in DMF and basified with excess triethylamine. To this was added 2,4-dichloro-6-imidazolylpyrimidine (100 mg, 0.46 mmol) and the mixture stirred at room temperature overnight. The reaction mixture was concentrated and the resulting oil purified on a silica gel column, eluting with 2% MeOH/DCM to yield 43. (42 mg, 0.1 mmol, 21%).

To 43 (30 mg, 0.07 mmol) in 10 mL n-butanol was added DIEA (60 mL, 0.35 mmol) and 3-chlorobenzylamine (200 mL, 1.4 mmol), and the reaction was heated to 100° C. overnight. The solution was concentrated and the resulting oil purified on a silica gel column, eluting with 5% MeOH/DCM to yield 44 as a foam. (31 mg 0.06 mmol, 82%).

Scheme 8

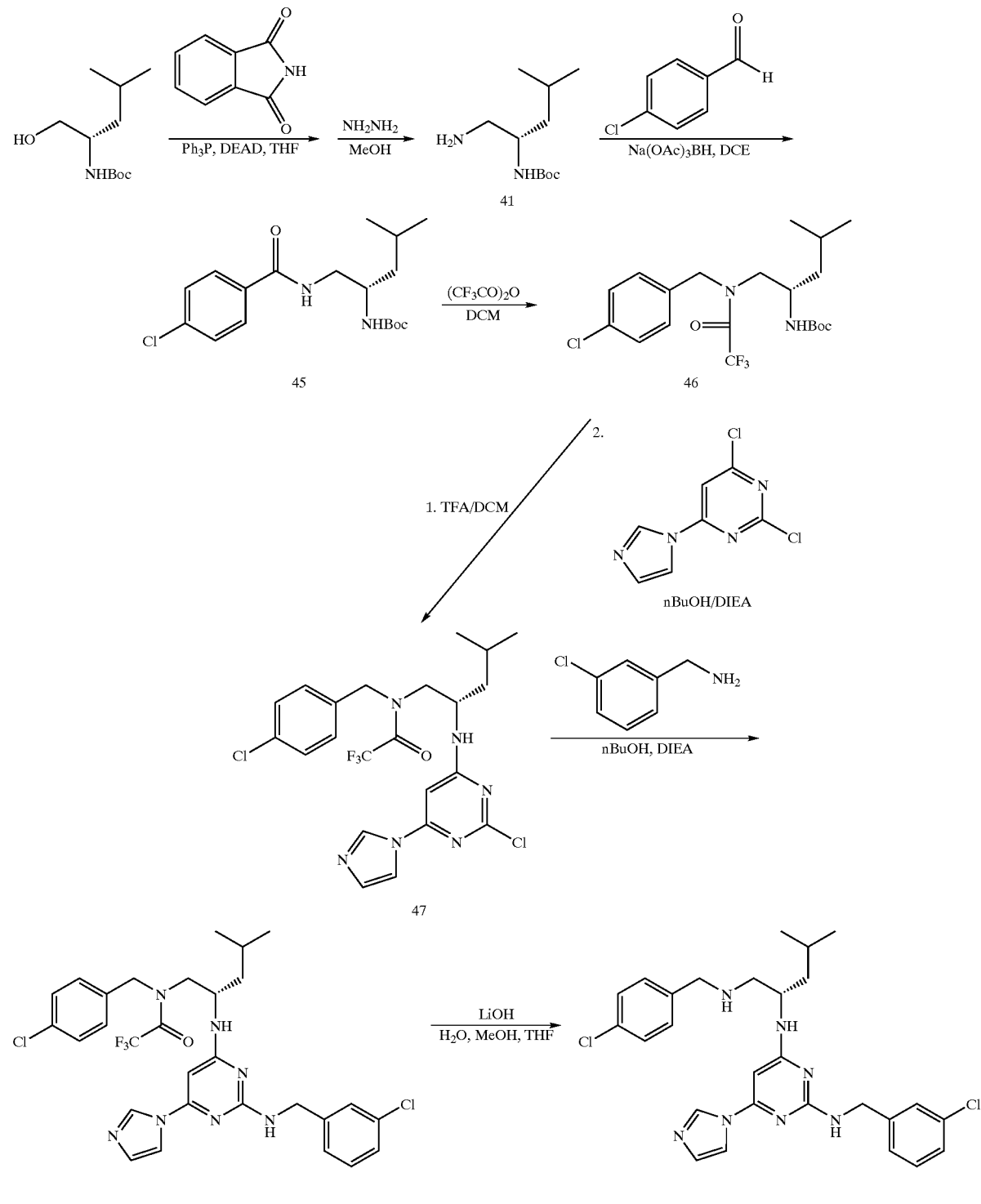

Scheme 8 illustrates a similar synthesis to that of Scheme 7 in which A is R⁴NH—.

Two hundred seventy milligrams of 41 (1.25 mmol), 4-chlorobenzaldehyde (193 mg, 1.4 mmol) and sodium triacetoxyborohydride (0.4 g, 1.9 mmol) were combined in 20 mL dichloroethane and stirred at room temperature overnight. The mixture was then concentrated, taken up in DCM and washed with saturated NaHCO$_3$, dried over MgSO$_4$ and concentrated to yield 45 which was used without further purification. (0.40 g, 1.2 mmol, 94%).

To 45 (0.35 g, 1.03 mmol) in DCM cooled in an ice bath was added trifluoroacetic anhydride (145 µl, 1.03 mmol) slowly. After 10 minutes the solution was concentrated, taken up in DCM and washed with 1M KHSO$_4$. The organic layer was dried over MgSO$_4$ and concentrated to yield 46 which was used without further purification. (0.32 g, 0.75 mmol, 75%).

Three hundred twenty milligrams of 46 (0.73 mmol) was taken up in 10 mL of DCM and 5 mL TFA was added. After 30 minutes the solution was concentrated, taken up in DMF and basified with excess triethylamine. To this was added 2,4-dichloro-6-imidazolylpyrimidine (190 mg, 0.88 mmol) and stirred at room temperature overnight. The reaction mixture was concentrated and the resulting oil purified on a silica gel column, eluting with 2% MeOH/DCM to yield 47. (100 mg, 0.19 mmol, 27%).

To 47 (100 mg, 0.19) in 5 mL of n-butanol was added DIEA (60 µl, 0.35 mmol) and 3-chlorobenzylamine (200 µL, 1.4 mmol) and heated to 100° C. overnight. The solution was concentrated and the resulting oil purified on a silica gel column, eluting with 5% MeOH/DCM to yield 48 as a foam. (10 mg 0.02 mmol, 9%).

A solution of 48 (10 mg 0.02 mmol) in 10 mL of MeOH:H$_2$O:THF (1:1:1) was refluxed for 6 hours with excess LiOH. The solution was concentrated, taken up in DCM and washed with brine. The organic layer was dried over MgSO$_4$ and concentrated to yield 49. (6 mg, 0.01 mmol, 50%).

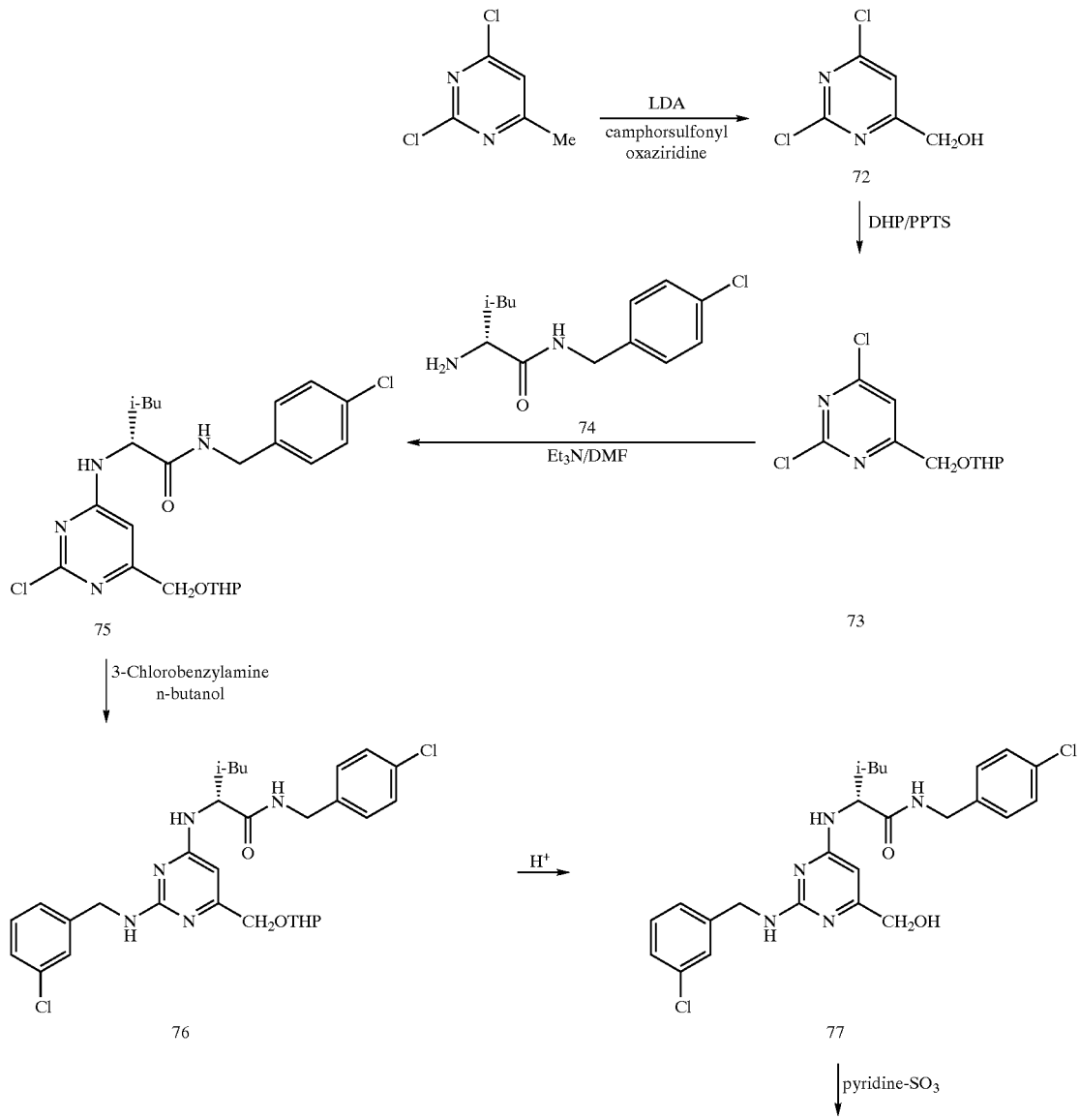

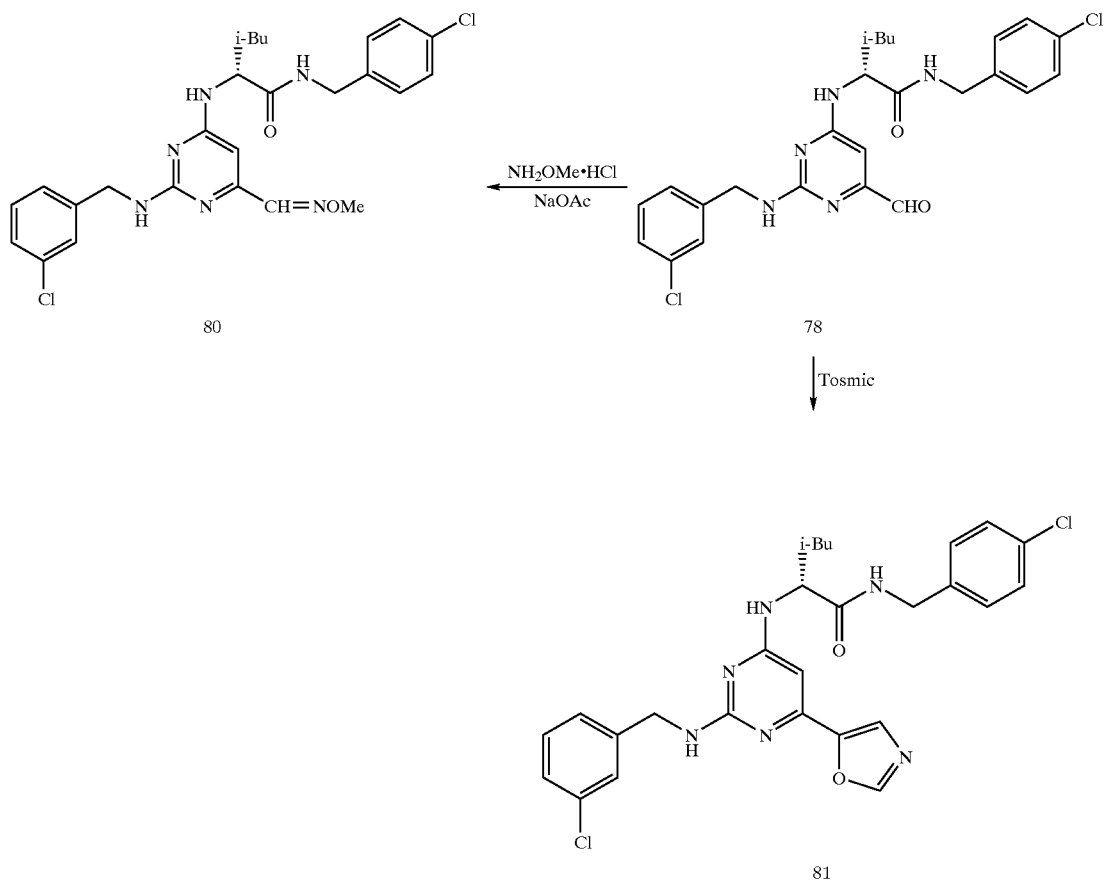

According to Scheme 9, a solution of 2,4-dichloro-6-methylpyrimidine (710 mg, 4.36 mmol) in 4.5 mL of dry THF was added dropwise to a solution of freshly prepared LDA (466 mg, 4.36 mmol) in 17.5 mL of dry THF at −78° C. After stirring for additional 15 min, the solution of the anion formed was cannulated into a solution of camphor-sulfonyloxaziridine (1.0 g, 4.36 mmol) in 11 mL of dry THF maintained at −78° C. The reaction mixture was stirred in dry ice-acetone bath for 1 h, then quenched with acetic acid and brought to room temperature. Aqueous work up and chromatography (silica gel, hexane:ethyl acetate, 4:1) gave 300 mg of 72.

A solution of 2,4-dichloro-6-hydroxymethylpyrimidine (1.8 g, 10.0 mmol), dihydropyran (1.26 g, 15 mmol) and PPTS (502 mg, 2.0 mmol) in 20 mL of dry chloroform was stirred for 1 h at RT. TLC indicated complete absence of the starting material. Aqueous work up and chromatography (silica gel, hexane:ethyl acetate, 85:15) gave 1.02 g of the THP ether 73.

A solution of leucine amide 74 (254 mg, 1.0 mmol), THP ether (263 mg, 1 mmol) and Et$_3$N (101 mg, 1 mmol) in 10 mL of dry THF was refluxed for 24 h. Evaporation of the solvent, followed by aqueous work up and chromatography (silica gel, hexane:ethyl acetate, 65:35) gave 174 mg of the desired isomer 75.

A solution of 75 (174 mg, 0.36 mmol) and 3-chlorobenzylamine (142 mg, 1.0 mmol) in 15 mL of n-butanol was refluxed overnight. The solvent was removed in vacuo and the residue was purified by chromatography (silica gel, ethyl acetate) to provide 52 mg of 6.

A solution of 76 (52 mg, 0.085 mmol) and PPTS (50 mg, 0.2 mmol) in 12 mL of 5:1 ethanol:water was refluxed overnight. Evaporation of the solvent and aqueous work up provided 33 mg of alcohol 77, which was used in the next step without purification.

A solution of alcohol 77 (140 mg, 0.28 mmol) and Et$_3$N (85 mg, 0.84 mmol) in 3 mL of dry DMSO was treated with pyridine. SO$_3$ complex (134 mg, 0.84 mmol) at RT. Aqueous work up gave the aldehyde 78 in almost quantitative yield.

A solution of aldehyde 78 (25 mg, 0.05 mmol), NH$_2$OMe.HCl (42 mg, 0.5 mmol) and anhydrous NaOAc (41 mg, 0.5 mmol) in 5 mL of ethanol was refluxed overnight. Aqueous work up and chromatography (silica gel, hexane:ethyl acetate, 3:1) gave 10 mg of oxime ether 80, (M+H)$^+$: 529.2.

A mixture of aldehyde 78 (135 mg, 0.27 mmol), toluene-sulfonylmethyl isocyanide (TOSMIC) (195 mg, 1 mmol) and K$_2$CO$_3$ (138 mg, 1 mmol) in 5 mL of methanol was refluxed for 5 h. Evaporation of the solvent and chromatography (silica gel, hexane:ethyl acetate, 1:2) gave 57 mg of oxazole 81, (M+H)$^+$: 539.2.

Scheme 10

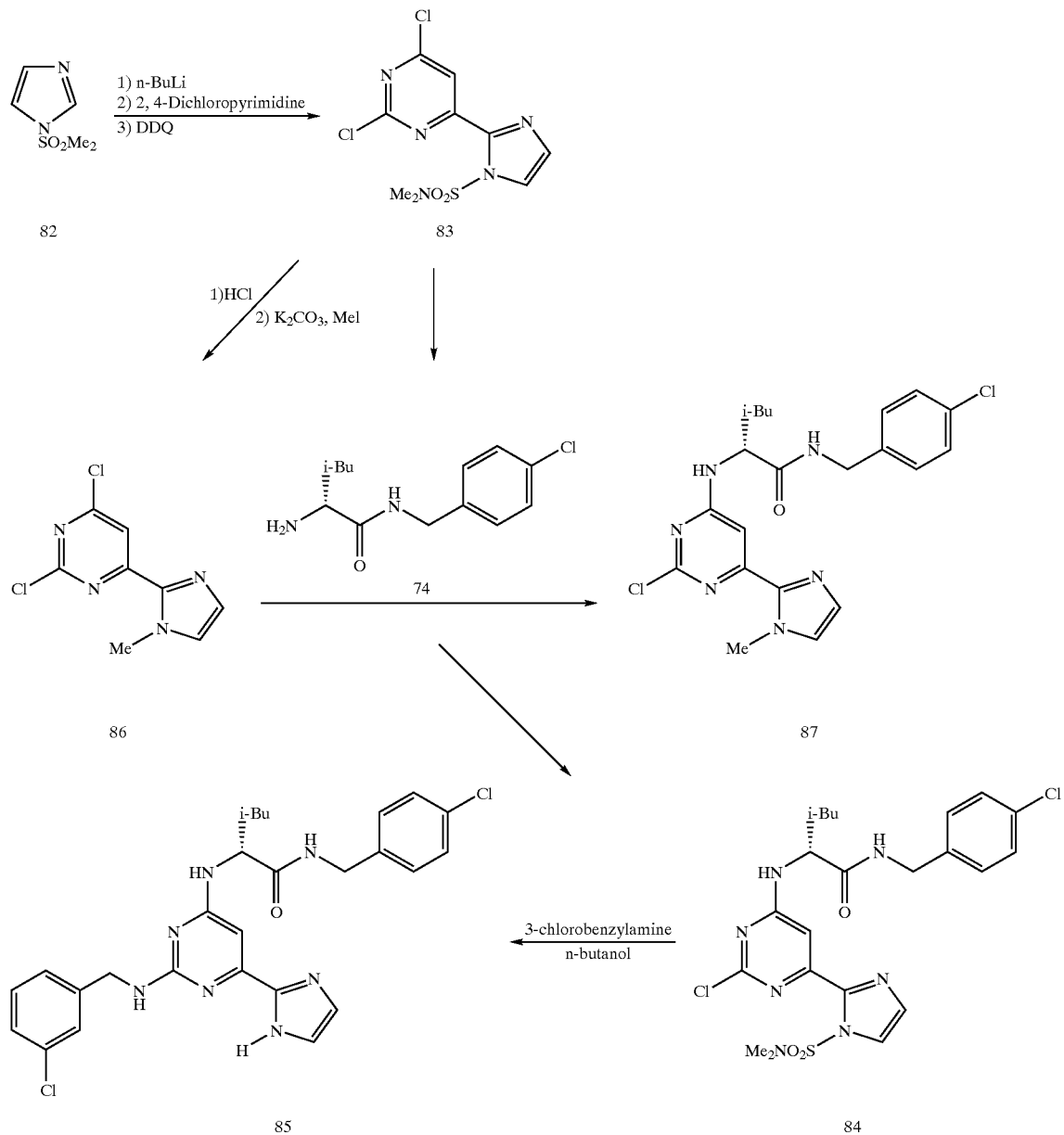

According to Scheme 10, n-BuLi (10 mmol, 4 mL of 2.5 M solution in hexane) was added at −78° C. to a solution of 1-dimethylsulfamoylimidazole (1.75 g, 10 mmol) in 50 mL of dry ether. After stirring for 1 h, the suspension of the anion formed was quickly transferred by a syringe to a suspension of 2,4-dichloropyrimidine (1.49 g, 10 mmol) in 80 mL of dry ether maintained at −30° C. After stirring at −30° C. for 30 min, the temperature was brought to 0° C. and maintained there for additional 30 min. The reaction mixture was quenched with a mixture of acetic acid (0.64 mL) water (0.1 mL) and THF (2 mL). Immediately afterwards, a solution of DDQ (2.27 g, 10 mmol) in 10 mL of THF was added and the reaction mixture was stirred overnight. After diluting with ethyl acetate (25 mL), the reaction mixture was filtered through celite and the filtrate was washed with water three times. Finally, a quick wash with ice cold 0.5% NaOH was employed to get rid of the hydroquinone. Evaporation of the solvent and chromatography (silica gel, hexane:ethyl acetate 3:1) provided 550 mg of 83.

A solution of leucine amide 74 (200 mg, 0.79 mmol), 2,4-dichloro-6-(1-dimethylsulfamoylimidazole-2-yl) pyrimidine (254 mg, 0.79 mmol) and Et$_3$N (88 mg, 0.87 mmol) in 3 mL of DMF was stirred at RT for 5 days. Aqueous work up and chromatography (silica gel, ethyl acetate) gave 200 mg of 84, (M+H)$^+$: 540.1.

A solution of chloropyrimidine 84 (200 mg, 0.37 mmol) and 3-chlorobenzylamine (568 mg, 4 mmol) in 10 mL of n-butanol was refluxed overnight. The solvent was removed in vacuo and the residue was chromatographed (silica gel, ethyl acetate:methanol, 98:2) to provide 12 mg of 85, (M+H)$^+$: 538.2.

A solution of 2,4-Dichloro-6-(1-dimethylsulfamoylimidazole-2-yl)pyrimidine 83 (246 mg, 0.76 mmol) in 10 mL of 1.5 N HCl was refluxed for 1 h.

After cooling to RT, the pH was adjusted to 8.5 with aq NaHCO$_3$ and the product was extracted into CH$_2$Cl$_2$. After drying the CH$_2$Cl$_2$ layer was evaporated to give 110 mg of 2,4-dichloro-6-(imidazole-2-yl)pyrimidine. A mixture of 2,4-dichloro-6-(imidazole-2-yl)pyrimidine (121 mg, 0.56 mmol), K$_2$CO$_3$ (100 mg, 0.72 mmol) and CH$_3$I (2.280 g, 1 mL, 16 mmol) in 15 mL of dry acetone was refluxed for 48 h. After cooling to RT, the solvent was evaporated and the residue was partitioned between water and CH$_2$Cl$_2$. The CH$_2$Cl$_2$ layer was washed successively with water and brine, and then the solvent was evaporated to give 75 mg of 2,4-dichloro-6-(1-methylimidazole-2-yl)pyrimidine 86.

A solution of 2,4-dichloro-6-(1-methylimidazole-2-yl) pyrimidine 86 (72 mg, 0.31 mmol), leucine amide 74 (100 mg, 0.39 mmol) and Et$_3$N (100 mg, 1 mmol) in 3 mL of DMF was heated to 70° C. overnight. Aqueous work up and chromatography (silica gel, hexane:ethyl acetate, 1:3) gave 67 mg of 87, (M+H)$^+$: 447.2.

3-chlorophenethyl bromide. A solution of the bromide (6.5 g, 29.6 mmol) in 50 mL of dry DMSO containing NaCN (2.17 g, 44 mmol) was heated to 100° C. overnight. The reaction mixture was diluted with water and extracted with ether. The ether layer was washed with water, dried and the solvent was removed in vacuo. Chromatography (silica gel, hexane:ethyl acetate, 4:1) provided 3.7 g of nitrile 89.

A 2 M solution of Me$_3$Al in toluene (18 mL, 36 mmol) was slowly added to a stirred suspension of NH$_4$Cl (2.07 g, 38.7 mmol) in 20 mL of dry toluene at 5° C. After the addition was over, the reaction mixture was warmed to RT and stirred for 2 h. Then, a solution of nitrile 89 (3.7 g, 22.4 mmol) in 15 mL of dry toluene was added and the solution was heated to 80° C. for 18 h. After cooling to RT, the reaction mixture was poured into a slurry of 15 g of silica gel in 50 mL of CHCl$_3$ and stirred for 5 min. The silica gel was filtered and washed with methanol. The filtrate and washings were combined and the solvent was removed. The residue obtained was partitioned between water and methylene

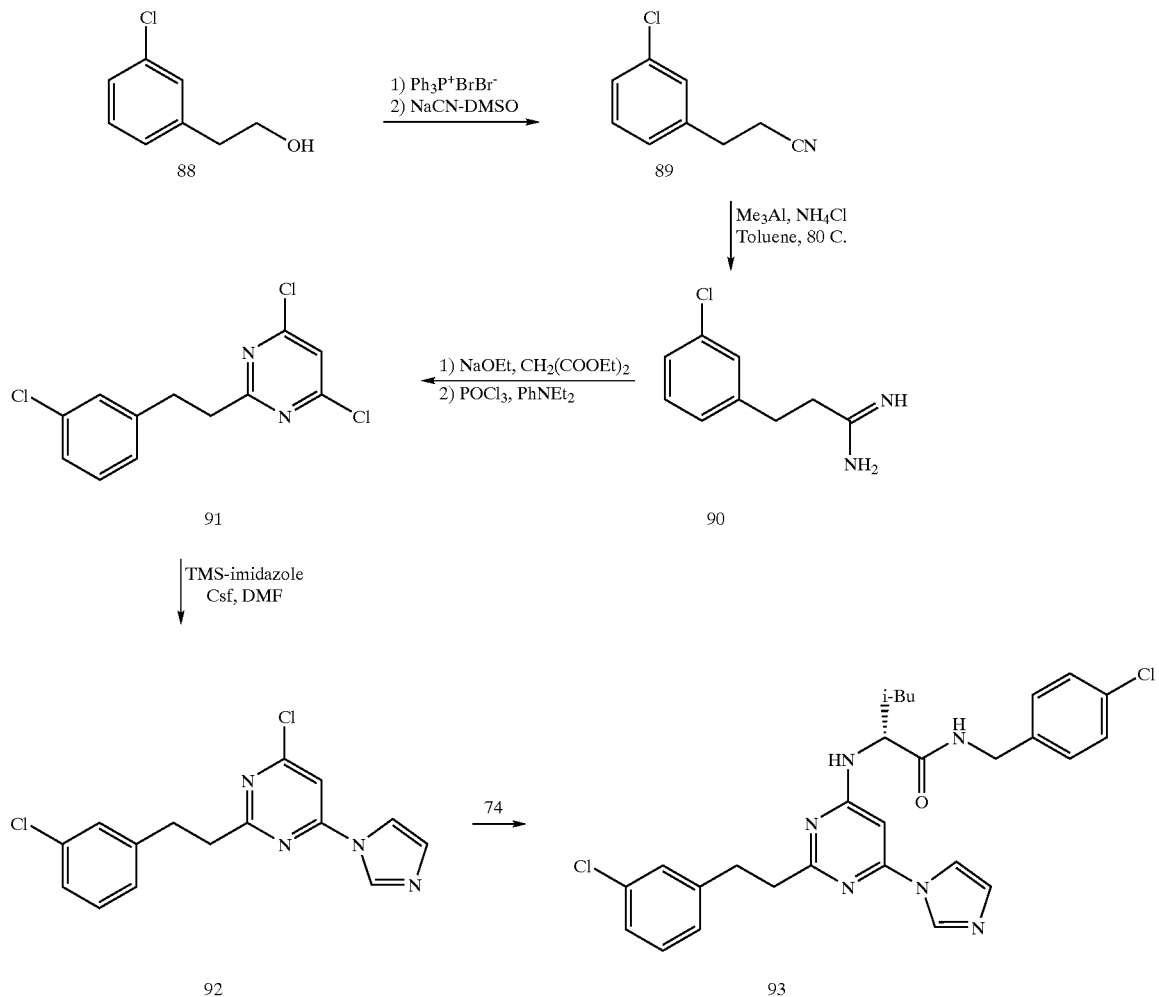

Scheme 11 chloride. Evaporation of the methylene chloride provided 2.7 g of amidine 90.

A solution of amidine 90 (2.7 g, 14.8 mmol) and diethyl malonate (2.37 g, 14.8 mmol) in 50 mL of dry ethanol containing freshly prepared NaOEt (1.0 g, 14.8 mmol) was refluxed for 15 h. Afer cooling to RT, the solvent was According to Scheme 11, a solution of 3-chlorophenethyl alcohol (5 g, 32 mmol) in 50 mL of dry MeCN was treated with dibromotriphenylphosphorane (13.54 g, 32 mmol) for 24 h. The reaction mixture was filtered and the solvent was removed in vacuo. The residue was triturated with hexane and filtered. Evaporation of the solvent provided 6.5 g of removed and the residue was dissolved in water. The pH was adjusted to 4 and the precipitated solid was filtered and dried to provide 2.6 g of 2-(3-chlorophenethyl)-4,6-dihydroxypyrimidine. A mixture of 2-(3-chlorophenethyl)-4,6-dihydroxypyrimidine (2.6 g, 10.38 mmol), POCl$_3$ (25 mL) and N,N-diethylaniline (6 mL) was refluxed overnight. After cooling to RT, the reaction mixture was poured into ice water and the product was extracted into ether. The ether layer was washed successively with water and brine and the solvent was evaporated. Chromatography (silica gel, hexane:ethyl acetate, 9:1) of the oil provided 2.6 g of the 2-(3-chlorophenethyl)-4,6-dichloropyrimidine (91).

A solution of 2-(3-chlorophenethyl)-4,6-dichloropyrimidine (286 mg, 1 mmol) 91 in 3 mL of dry DMF was treated with 1-trimethylsilylimidazole (140 mg, 1 mmol) and CsF (152 mg, 1 mmol) at RT overnight. Aqueous work up and chromatography (silica gel, hexane:ethyl acetate, 1:1) gave 200 mg of 4-chloro-2-(3-chlorophenethyl)-6-(1-imidazolyl)pyrimidine (92).

A solution of 4-chloro-2-(3-chlorophenethyl)-6-(1-imidazolyl)pyrimidine 92 (100 mg, 0.31 mmol), leucine amide 74 (95 mg, 0.372 mmol) and DIEA (129 mg, 1 mmol) in 2 mL of DMF was heated to 80° C. for 24 h. Aqueous work up and chromatography (silica gel, ethyl acetate:methanol, 98:2) gave 105 mg of 93, (M+H)$^+$: 537.4.

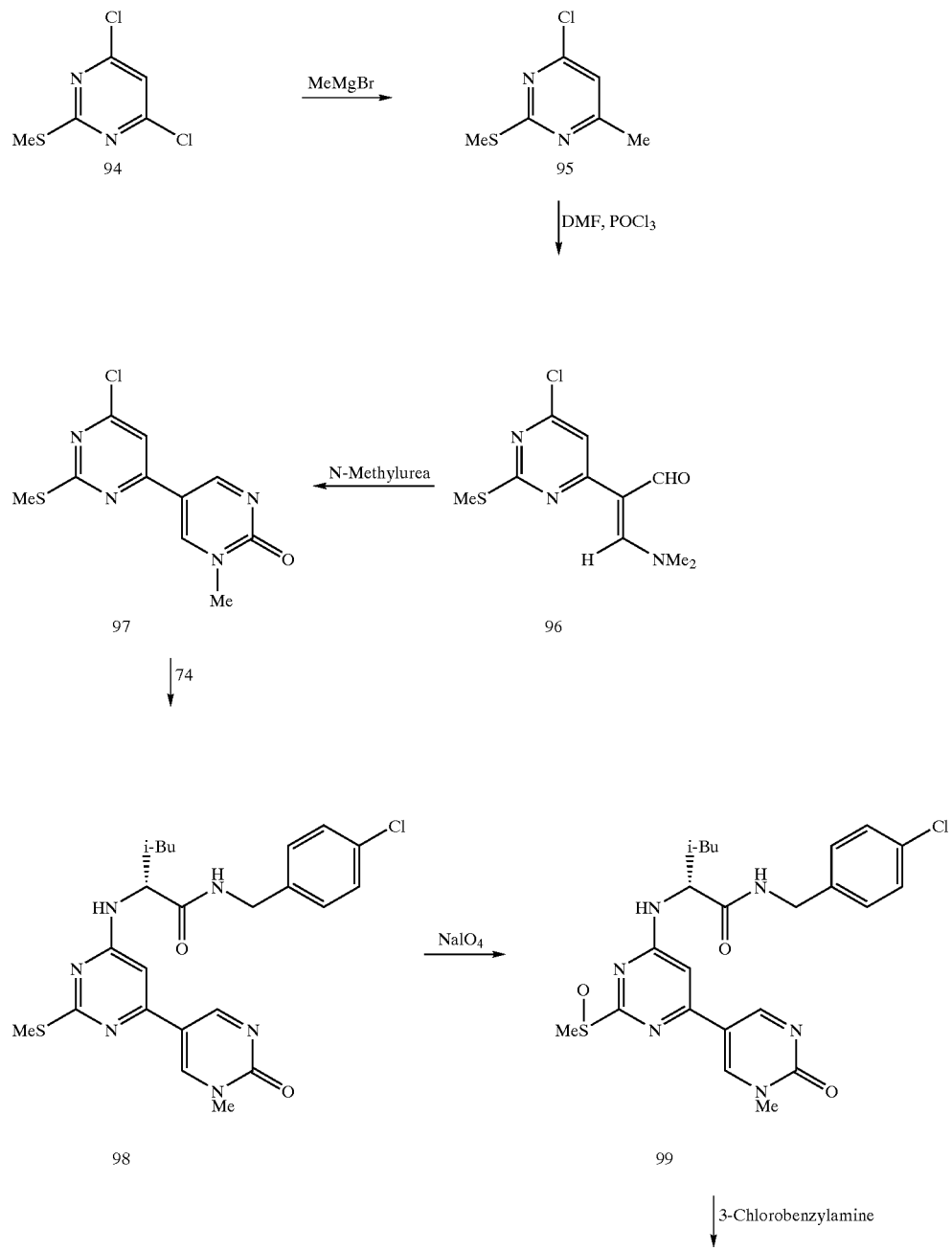

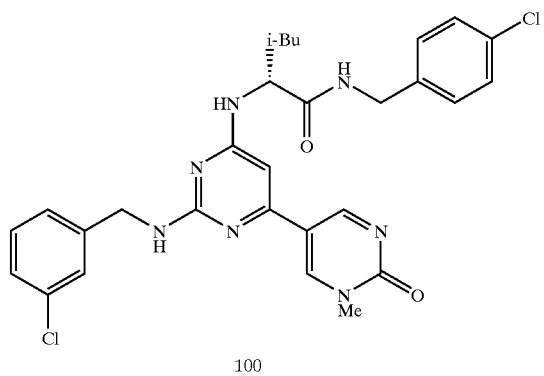

100

According to Scheme 12, a solution of 4,6-dichloro-2-methylthiopyrimidine (1.95 g, 10 mmol) in 30 mL of dry THF was cooled to 0° C. and treated with a solution of MeMgBr (14 mL of 1.4 M solution, 19.6 mmol). After overnight stirring at RT, the reaction mixture was quenched with sat. NH$_4$Cl. The organic layer washed with brine, dried and evaporated. The residue was purified by chromatography (silica gel, hexane:ethyl acetate, 9:1) to provide 1.3 g of 4-chloro-6-methyl-2-methylthiopyrimidine (95).

Dry DMF (2 mL) was cooled to −5° C. and POCl$_3$ (15.4 mmol, 2.31 g) was added dropwise. The cooling bath was removed and the reaction mixture was stirred for 15 min at RT. 4-chloro-6-methyl-2-methylthiopyrimidine (1.3 g, 7.47 mmol) was added and the contents were heated to 60° C. overnight. The reaction mixture was poured on ice, pH was adjusted to 9 and the precipitated product was filtered. The precipitate was washed with water and dried to provide 1.3 g of the enaminone 96.

A mixture of enaminone 96 (675 mg, 2.6 mmol) and N-methylurea (232 mg, 3.14 mmol) in 5 mL of acetic acid was heated to 100° C. for 2 h. Aqueous work up and chromatography (silica gel, ethyl acetate:methanol, 98:2) gave 100 mg of pyrimidinone 97.

A solution of 97 (100 mg, 0.37 mmol), leucine amide 74 (100 mg, 0.34 mmol) and DIEA (60 mg, 0.46 mmol) in 3 mL of DMF was heated to 80° C. for 2 days. Aqueous work up followed by chromatography (silica gel, ethyl acetate:methanol, 95:5) gave 30 mg of 98.

A mixture of 98 (30 mg, 0.061 mmol) and NaIO$_4$ (263 mg, 1.23 mmol) in 6 mL of 1:1 methanol:water was stirred overnight at RT. Aqueous work up gave 10 mg of the crude sulfoxide 99.

The sulfoxide 99 (10 mg, 0.002 mmol) and 3-chlorobenzylamine (27 mg, 0.2 mmol) in 2 mL of n-butanol were heated to reflux for 24 h. Aqueous work up after removal of n-butanol, followed by chromatography (silica gel, CH2Cl2:methanol, 95:5) gave 2 mg of 100, (M+H)$^+$: 580.2.

Scheme 13

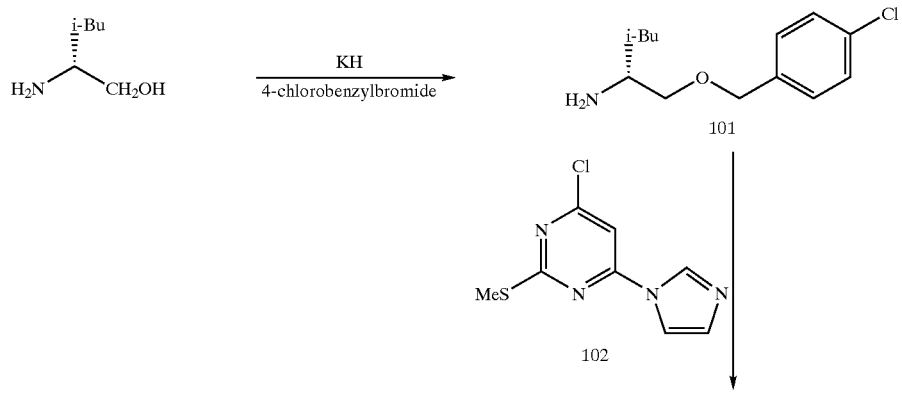

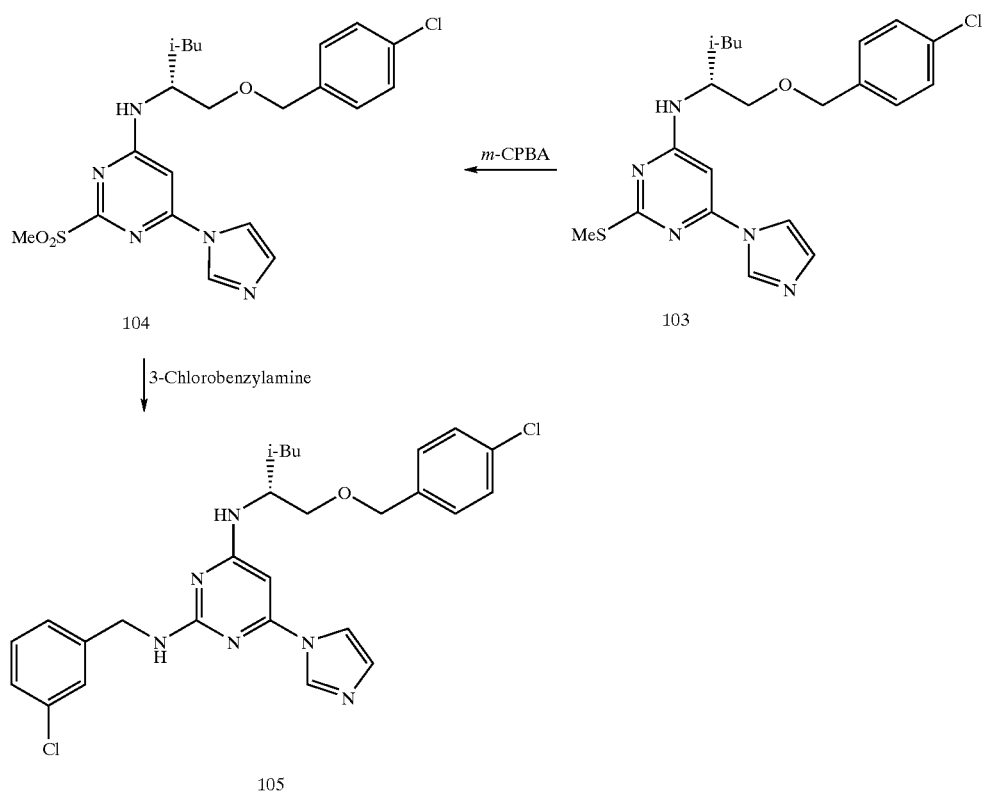

According to Scheme 13, a solution of (R)-leucinol (1.288 g, 11 mmol) in mL of THF at RT was added dropwise to a stirred suspension of potassium hydride (0.485 g, 12.1 mmol) in 25 mL of dry THF. After overnight stirring at RT, a solution of 4-chlorobenzylbromide (2.25 g, 11 mmol) in 5 mL of THF was added dropwise. The stirring was continued for additional 3 h. The solvent was evaporated and the residue was partitioned between water and ether. The ether layer was washed with brine, dried and the solvent was removed in vacuo to provide 2.1 g of ether 101.

A solution of 4-chloro-6-(1-imidazolyl)-2-methylthiopyrimidine (227 mg, 1 mmol), aminoether 101 (242 mg, 1 mmol) and Et$_3$N (101 mg, 1 mmol) in 4 mL of DMF was heated to 70° C. for 24 h. Aqueous work up and chromatography (silica gel, hexane:ethyl acetate, 1:1) provided 300 mg of thioether 103.

A solution of the thioether 103 (300 mg, 0.7 mmol) in 10 mL of CH$_2$Cl$_2$ was treated with m-CPBA (428 mg, 1.74 mmol) at 0° C. overnight. The precipitate was filtered and the filtrate was evaporated to obtain crude sulfone 104. No starting material or intermediate sulfoxide was detected by MS.

A solution of sulfone 104 (100 mg, 0.22 mmol) and 3-chlorobenzylamine (2 mmol) in 3 mL of n-butanol was refluxed for 24 h. Aqueous work up after removal of n-butanol, followed by chromatography (silica gel, ethyl acetate) gave 22 mg of 105, (M+H)$^+$: 525.2.

Scheme 14

-continued

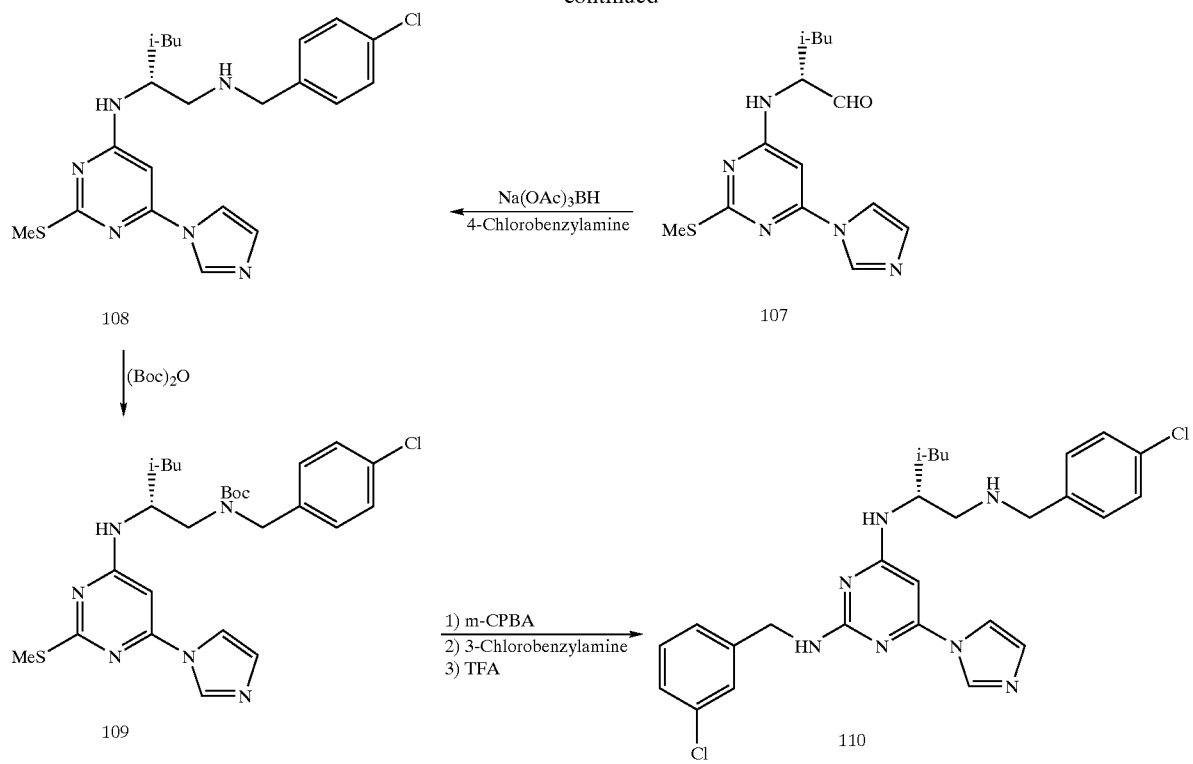

According to Scheme 14, a solution of 4-chloro-6-(1-imidazolyl)-2-methylthiopyrimidine (227 mg, 1 mmol), (R)-leucinol (117 mg, 1 mmol) and Et₃N (101 mg, 1 mmol) in 3 mL of DMF was heated to 70° C. for 24 h. Aqueous work up and chromatography (silica gel, hexane:ethyl acetate, 1:3) gave 290 mg of 106.

A solution of alcohol 106 (290 mg, 0.94 mmol) and Et₃N (303 mg, 3 mmol) in 5 mL of DMSO was treated with pyridine-sulfur trioxide complex (477 mg, 3 mmol) at RT overnight. Aqueous work up gave 280 mg of the crude aldehyde 107 which was used in the next step without purification.

A mixture of aldehyde 107 (280 mg, 0.91 mmol), Na(OAc)₃BH (290 mg, 1.37 mmol), 4-chlorobenzylamine (142 mg, 1 mmol) and HOAc (60 mg, 1 mmol) in 10 mL of dry 1,2-dichloroethane was stirred at RT overnight. Aqueous work up and chromatography (silica gel, CH₂Cl₂:methanol:NH₄OH, 95:5:0.5) gave 135 mg of 108.

A solution of amine 108 (130 mg, 0.3 mmol) and boc-anhydride (214 mg, 1 mmol) in 5 mL of THF was stirred at RT overnight. Aqueous work up after removal of the solvent, provided 60 mg of the Boc-protected amine 109.

A mixture of the Boc-protected amine 109 (60 mg, 0.11 mmol) and m-CPBA (83 mg, 0.33 mmol) in 20 mL of 1:1 CH₂Cl₂:phosphate buffer was stirred at 0° C. for 2 h and then kept in the refrigerator overnight. The methylene chloride layer was filtered and the solvent was removed to provide the crude sulfone. A solution of the sulfone in 5 mL of n-butanol containing 10 eq of 3-chlorobenzyl-amine was refluxed for 20 h. The solvent was removed in vacuo and the residue was treated with 2:1 CH₂Cl₂:TFA for two days. After removal of the solvent, the residue was taken in water and basified. The precipitated product was extracted into CH₂Cl₂. Evaporation of the CH₂Cl₂ layer gave 6 mg of 110, (M+H)⁺: 524.2.

Scheme 15

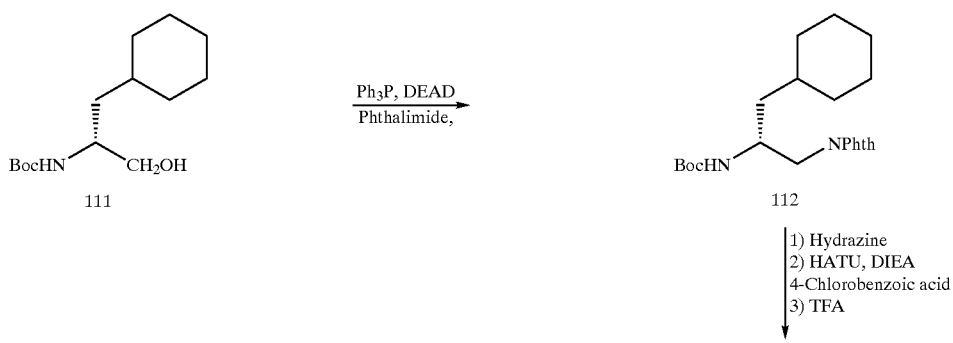

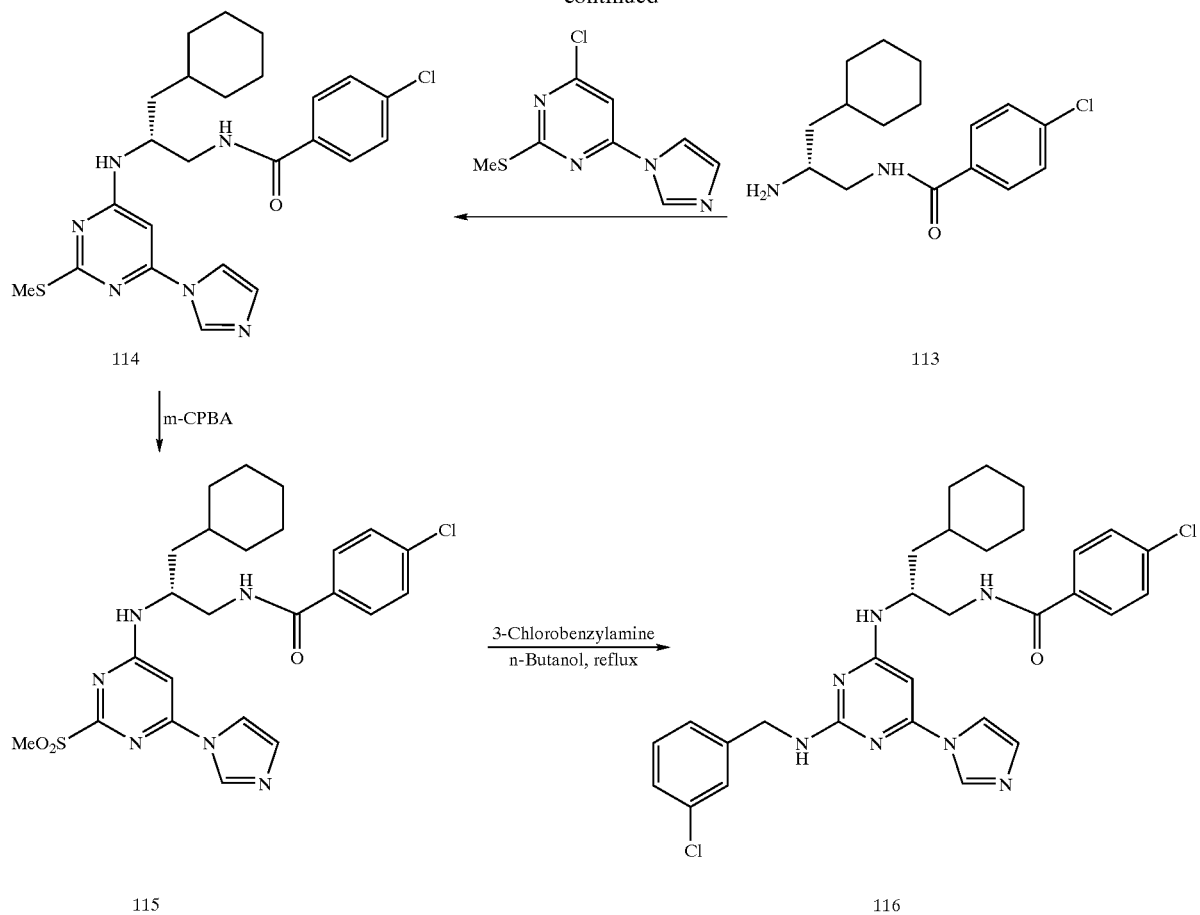

According to Scheme 15, a solution of Ph$_3$P (262 mg, 1 mmol) and phthalimide (147 mg, 1 mmol) in 3 mL of dry THF was treated with a solution of diethyl azodicarboxylate (174 mg, 1 mmol) in 2 mL of dry THF at RT. After stirring for 5 min, a solution of alcohol 111 (257 mg, 1 mmol) in 5 mL of dry THF was added and the stirring was continued for 3 days. The solvent was removed and the residue was chromatographed (silica gel, hexane:ethyl acetate, 4:1) to obtain 320 mg of phthalimide 112.

Three hundred twenty milligrams (0.83 mmol) of phthalimide 112 and 50 mg (1 mmol) of NH$_2$NH$_2$.H$_2$O in 5 mL of ethanol was refluxed for 2 h. The solvent was removed and the residue was partitioned between CH$_2$Cl$_2$ and 1N NaOH. Evaporation of the organic layer after drying provided the primary amine. The amine was coupled with 4-chlorobenzoic acid (130 mg, 0.83 mmol) using HATU (1 eq) in DMF containing 2 eq of DIEA. The amide was purified by chromatography (silica gel, hexane:ethyl acetate, 1:1), yield 200 mg. The boc group was removed by stirring in TFA:CH$_2$Cl$_2$ (1:2) at RT overnight to provide 113.

A solution of 4-chloro-6-(1-imidazolyl)-2-methylthiopyrimidine (227 mg, 1 mmol), TFA salt of amine 113 (220 mg, 1 mmol) and Et$_3$N (303 mg, 3 mmol) in 3 mL of DMF was heated to 80° C. overnight. Aqueous work up and chromatography (silica gel, hexane:ethyl acetate, 1:3) gave 130 mg of 114.

A solution of the thioether 114 (130 mg, 0.27 mmol) in 20 mL of CH$_2$Cl$_2$ was treated with m-CPBA (196 mg, 0.8 mmol) at 0° C. for 1 h, and then left in a refrigerator overnight. The reaction mixture was filtered and the crude sulfone 115 was isolated by evaporation of the filtrate.

A solution of sulfone 115 (130 mg, 0.25 mmol), 3-chlorobenzylamine (72 mg, 0.5 mmol) and Et$_3$N (50 mg, 0.5 mmol) in 4 mL of n-butanol was heated to reflux for 20 h. Aqueous work up and chromatography (silica gel, ethyl acetate:methanol, 99:1) gave 66 mg of 116, (M+H+): 578.2.

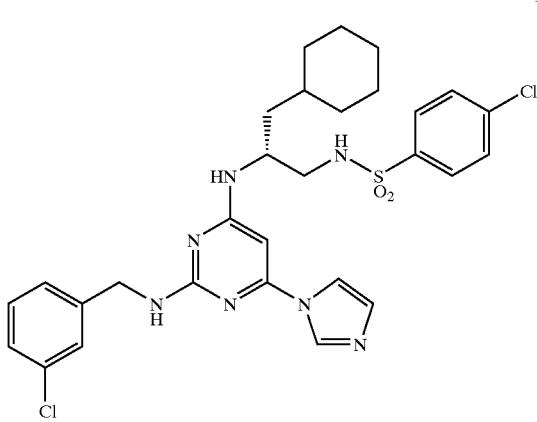

The corresponding sulfonamide 117 was prepared by a similar procedure to that of Scheme 15, using 4-chlorobenzenesulfonyl chloride in place of 4-chlorobenzoyl chloride, (M+H)$^+$: 614.2.

Compounds in which X, Y and Z are CH and Q is pyrrole are prepared as shown in Scheme 16.

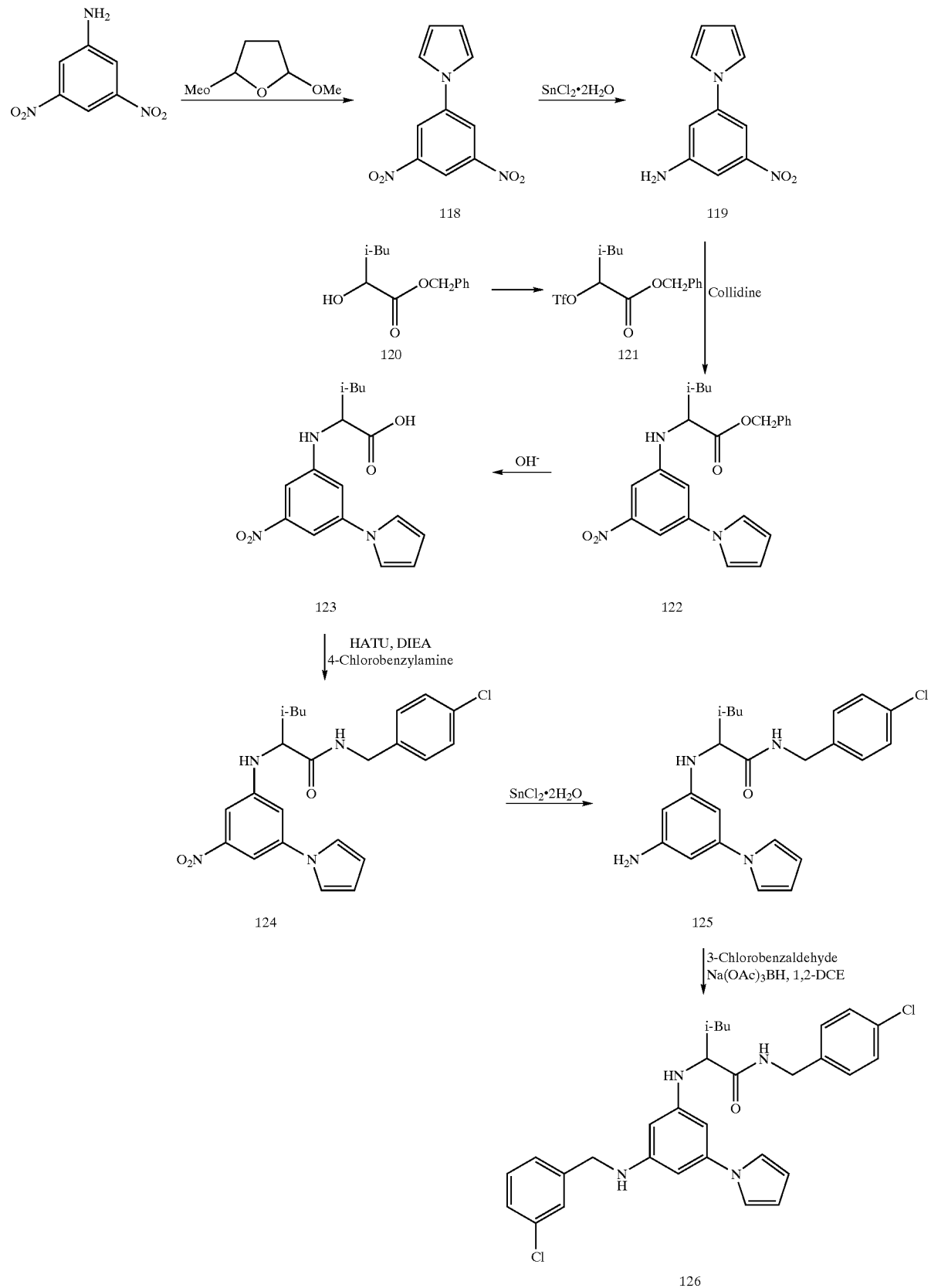
Scheme 16

According to Scheme 16, a solution of 3,5-dinitroaniline (1.83 g, 10 mmol) and 2,5-dimethoxytetrahydrofuran in 20 mL of HOAc was refluxed overnight. The reaction mixture was poured into water and extracted with EtOAc. The ethyl acetate layer was washed with water followed by aq NaHCO₃ and brine. After drying, the solvent was removed to provide 1.52 g of 1-(3,5-dinitrophenyl)pyrrole.

A mixture of 1-(3,5-dinitrophenyl)pyrrole (1.52 g, 6.52 mmol) and SnCl₂.2H₂O (4.4 g, 19.57 mmol) in 30 mL of ethyl acetate was stirred over weekend at RT. The solvent was removed and the residue was taken in water. The aqueous layer was basified with 1 N NaOH to dissolve the tin salts, and the product was extracted into ethyl acetate. Chromatography (silica gel, hexane:ethyl acetate, 4:1) of the crude product provided 440 mg of 1-(3-amino-5-nitrophenyl)pyrrole.

A solution of benzyl ester 120 (222 mg, 1 mmol), DIEA (129 mg, 1 mmol) and triflic anhydride (282 mg, 1 mmol) in 5 mL of dry CH₂Cl₂ was stirred at 0° C. for 1.5 h. TLC in hexane:ethyl acetate (4:1) indicated complete conversion of the starting material. The solvent was removed and the crude triflate 121 was used for the next step.

A solution of 1-(3-amino-5-nitrophenyl)pyrrole (203 mg, 1 mmol) and triflate 121 in 15 mL of 1,2-dichloroethane containing collidine (121 mg, 1 mmol) was refluxed for 24 h. Aqueous acidic work up, followed by chromatography (hexane:ethyl acetate, 4:1 gave 95 mg of 122.

The ester 122 (95 mg, 0.23 mmol) was treated 250 mg of NaOH in 5 mL of 95:5 methanol:water. After overnight stirring at RT, the solvent was removed and the residue was taken in water. The pH was adjusted to 3 and the precipitated acid was extracted into ethyl acetate. Evaporation of the ethyl acetate layer gave 57 mg of 123.

To a solution of carboxylic acid 123 (57 mg, 0.18 mmol) in 3 mL of dry DMF containing 2 eq of DIEA, 1 eq of HATU was added. After 5 min 1 eq of 4-chlorobenzyl amine was added and the stirring was continued overnight. The crude product 124 obtained after aqueous work up was used directly for the next step.

Amide 124 was reduced with SnCl₂.2H₂O (5 eq) in ethyl acetate as described earlier. The aniline 125 was purified by chromatography (silica gel, hexane:ethyl acetate, 1:1), yield 7 mg.

A mixture of aniline 125 (7 mg, 0.017 mmol), Na(Oac)₃BH (6 eq) and 3-chlorobenzaldehyde (6 eq) in 2 mL of 1,2-dichloroethane was stirred at RT overnight. Aqueous work up and chromatography (silica gel, hexane:ethyl acetate, 62:38) gave 3 mg 126, (M+H)⁺: 535.1.

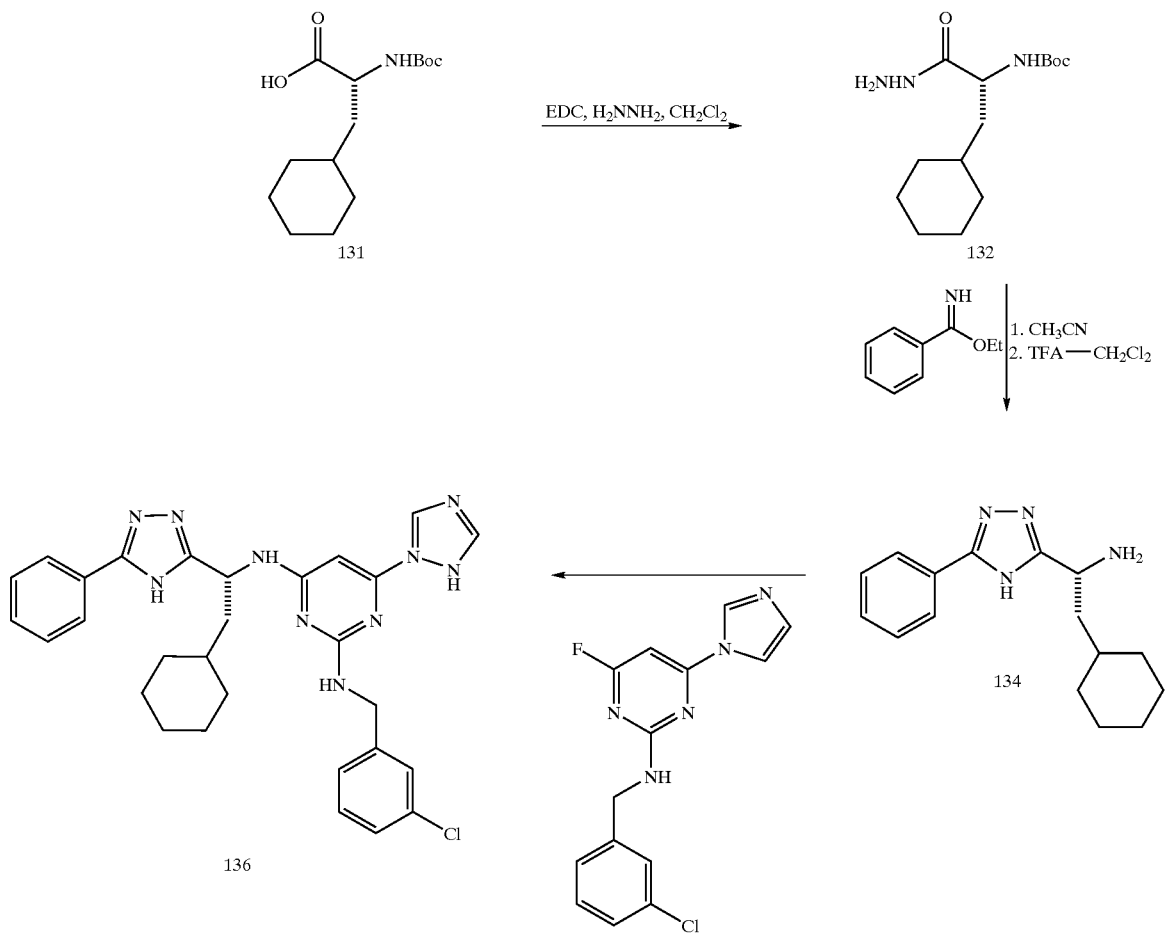

To a solution of N-BOC-cyclohexyl alanine (200 mg, 0.74 mmol) in 2 mL of dry methylenechloride was added dropwise hydrazine (0.1 mL, 0.89 mmol) and EDC (159 mg, 0.81 mmol) at 23° C. The reaction mixture was stirred for 48 h, then washed with NH₄Cl, water, and brine to give 150 mg of 132.

A solution of hydrazide 132 (72.4 mg, 0.254 mmol) and imidate 133 (52 mg, 0.28 mmol) in 2 mL of dry acetonitrile was stirred for 16 h at RT. TLC indicated complete absence of the starting material. Solvent was removed and the crude product was treated with TFA:methylenechloride, 1:1, and washed with 1 N NaOH, water and brine to give 16.2 mg of the triazole 134.

A solution of triazole 134 (16.2 mg, 0.06 mmol), fluoropyrimidine 68 (27.3 mg, 0.09 mmol) and iPr₂NEt (0.02 mL, 0.12 mmol) in 1 mL of dry nBuOH was refluxed for 16 h. Evaporation of the solvent, followed by aqueous work up and chromatography (silica gel, hexane:ethyl acetate:methanol, 4:4:1) gave 9.0 mg of the desired product 136.

Compounds of the invention in which A¹ is

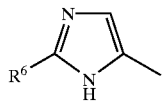

and in which A¹

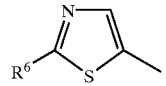

are synthesized as shown in Scheme 17. In both cases the Boc protecting group is cleaved with trifluoroacetic acid and the amine is reacted further as already described.

Scheme 18

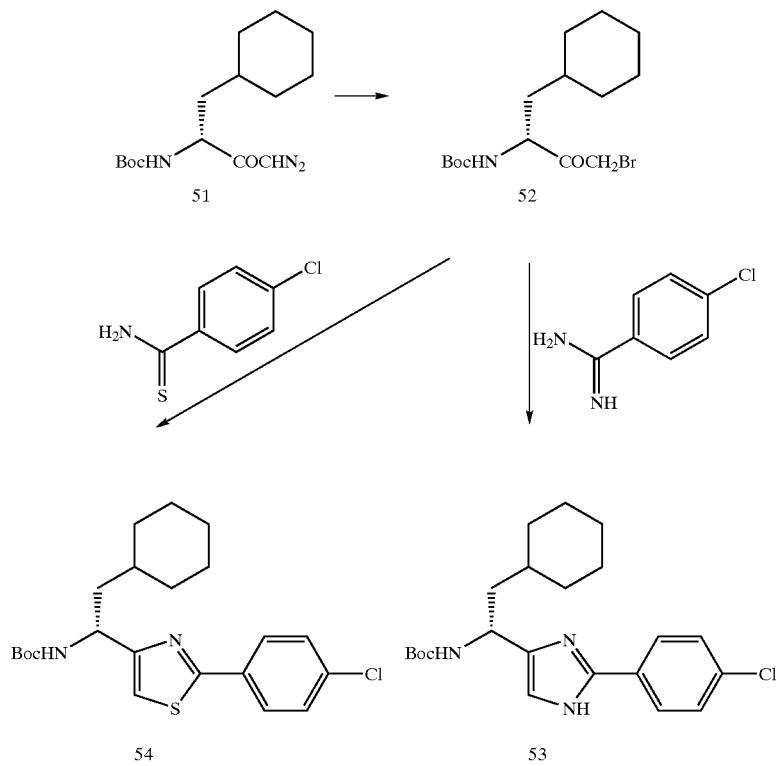

A solution of diazo ketone 51 (2.89 g, 9.78 mol.) in 60 mL of ether was cooled to −20° C. and 2 mL of 48% HBr (960 mg, 11.85 mol.) was added dropwise. After 35 minutes, an additional 0.5 mL of HBr (240 mg, 2.96 mol.) was added and the stirring was further continued for 25 min. TLC [hexane:ethyl acetate (4:1)] indicated complete absence of the starting material and appearance of the less polar α-bromoketone. Cold aqueous work-up and chromatography on silica gel with hexane:ethyl acetate (85:15) gave 2.7 g of the pure α-bromoketone 52. ¹H NMR (CDCl₃): 5.00–4.80 (m, 1H), 4.64–4.50 (m, 1H), 1,90–0.90 (m, 22H). The α-bromoketone is reacted with 4-chlorobenzamidine in refluxing chloroform to provide the imidazole 53 according to the method of Nagao et al. [*Heterocycles* 42, 517–523 (1996)]. The α-bromoketone is reacted with 4-chlorothiobenzamide in dioxane to provide the thiazole 54 according to the method of Nan'Ya et al. [*J. Heterocycl. Chem.* 32, 1299–1302 1995].

Scheme 19

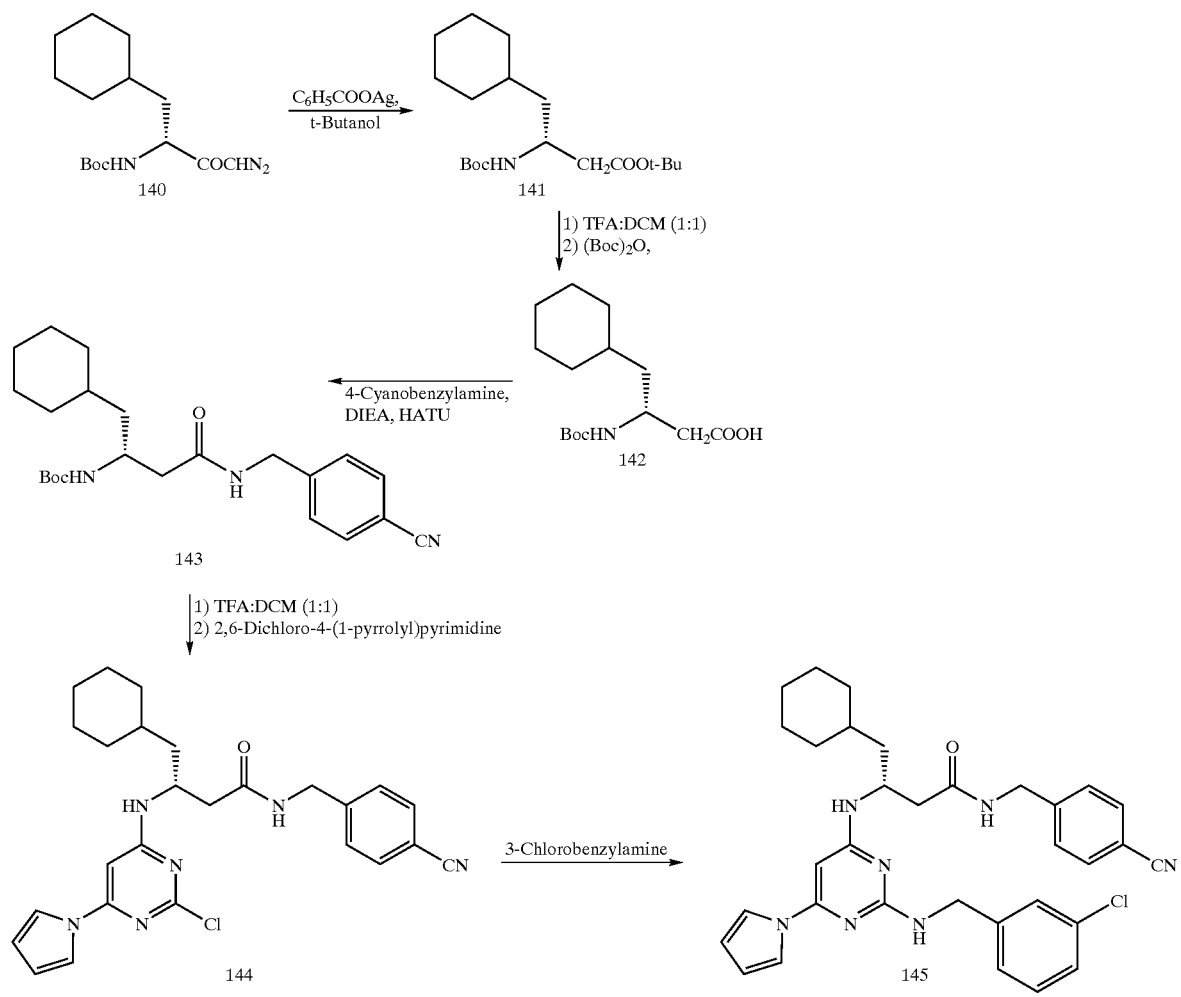

Scheme 19 illustrates the synthesis of an example in which m is 1. A solution of Boc-α-cyclohexyl-D-alanine (1.085 g, 4.0 mmol) and N-methylmorpholine (404 mg, 4.0 mmol) in 15 mL of dry THF was cooled to −10° C. and a solution of isobutyl chloroformate (544 mg, 4.0 mmol) in 5 mL of THF was added dropwise. After stirring for additional 10 min, an ethereal solution of diazomethane (ca. 9 mmol) was added slowly. After overnight stirring at RT, TLC indicated formation of diazoketone($R_f$≈0.4 in hexane:ethyl acetate 4:1). The excess diazomethane was destroyed by addition of aq HOAc and the solvent was evaporated in vacuo. The residue obtained was partitioned between ether and water. The ether layer was successively washed with aq $NaHCO_3$, water and brine. After drying ($MgSO_4$), the ether was evaporated to give the diazoketone 140 as a pale yellow oil.

The diazoketone was dissolved in 10 mL of t-butanol and the solution was brought to reflux under argon. A freshly prepared and filtered solution of silver benzoate (0.5 g, 2.18 mmol) in 3 mL of $Et_3N$ was added dropwise over 30 min via syringe. The reflux was continued for an additional 1 h. A small amount of decolorizing carbon was added and the reaction mixture was filtered through celite. After evaporation of the filtrate, the residue was chromatographed (silica, hexane:ethyl acetate (85:15)) to give 650 mg of R-t-butyl 3-(cyclohexylmethyl)-3-t-butoxycarbonylaminopropionate, 141 (M+H)$^+$: 342.0.

A solution of 141 (650 mg, 1.90 mmol)) in 10 mL of TFA:DCM (1:1) was stirred for 6 h at RT. The solvent was removed and the residue was treated with Boc-anhydride in dioxan-aq NaOH to give 486 mg of R-3-(cyclohexylmethyl)-3-t-butoxy carbonylamino-propionic acid, 142 (M−H)$^+$: 284.7.

A solution of 142 (284 mg, 1.0 mmol) and DIEA (258 mg, 2.0 mmol) in 5 mL of dry DMF was treated with HATU (380 mg, 1.0 mmol) at RT. After 5 min, 4-cyanobenzylamine (132 mg, 1.0 mmol) was added and the reaction mixture was stirred overnight at RT. Aqueous workup and chromatography (silica gel, hexane:ethyl acetate (1:3) gave 200 mg of the amide 143.

A solution of the amide 143 (200 mg, 0.5 mmol) in 10 mL of TFA:DCM (1:1) was stirred at RT for two days. The solvent was evaporated and the residue was taken in 5 mL of DMF containing DIEA (258 mg, 2.0 mmol) and 2,6-dichloro-4-(1-pyrrolyl)pyrimidine (107 mg, 0.5 mmol). After heating overnight at 80° C., the reaction mixture was diluted with water and the product was extracted into ethyl acetate. The solvent was removed and the residue was chromatographed (silica gel, hexane:ethyl acetate (1:3)) to give 50 mg of the 2-(1-pyrrolyl)pyrimidine derivative and 58 mg of the 4-(1-pyrrolyl)pyrimidine compound 144, (M+H)$^+$: 477.3

A solution of 144, (30 mg, 0.063 mmol) and 3-chlorobenzylamine (50 mg, 0.35 mmol) in 2 mL of n-butanol was refluxed overnight. The solvent was removed and the residue was purified by chromatography (silica gel, hexane:ethyl acetate (1:3)) to give 4 mg of 145, (M+H)$^+$: 582.3.

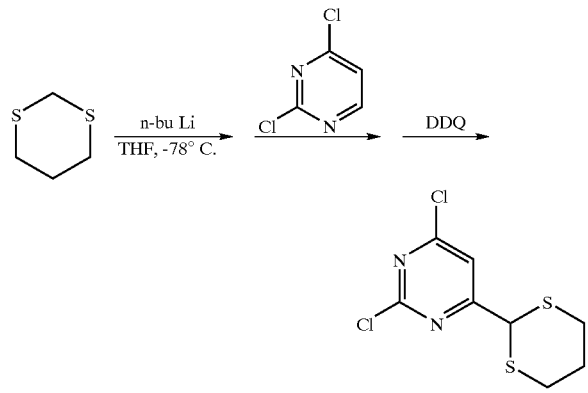

To 1,3-dithiane (6.2 g, 50.0 mmol) in 20 mL dry THF was added n-butyl lithium (2.5M, 22 mL, 55.0 mmol) dropwise while cooling to −78° C. After 30 minutes a solution of 2,4-dichloropyrimidine (10.0 g, 75 mmol) in 15 mL dry THF was added dropwise. After 30 minutes the mixture was warmed to 0° and DDQ (12.5 g, 55.0 mmol) was added and allowed to warm to room temperature. After 1 hour the mixture was concentrated and the resulting residue purified on a silica gel column, eluting with 3:7 EtOAc:hexanes to yield 2,4-dichloro-6-(2-dithianyl)pyrimidine as a light yellow oil (1.2 g, 5.5 mmol, 9%).

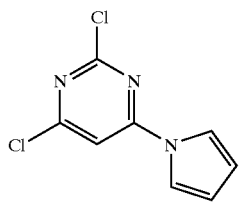

2,6-Dichloro-4-(1-pyrrolyl)pyrimidine was prepared as follows: A dry 500 mL round bottom flask (oven-heated/argon cooled), was charged with 2.97 g (74.34 mmol) of a 60% dispersion of sodium hydride in mineral oil. The flask was purged with argon, and 200 mL of hexane were quickly added. The mixture was purged again, and stirred for 5–10 minutes. The stirring was then stopped, and the sodium hydride was allowed to settle, at which point the hexane was quickly decanted off. The mixture was purged with argon again and the rinsing was repeated, to ensure the reaction is free from the mineral oil suspension. Next, 200 mL of dry THF were injected by syringe into the air-free mixture. The mixture was then cooled to 0° C., and connected to an oil-bubbler. Then 3.44 mL (49.60 mmol) of pyrrole were injected into the mixture by syringe (vigorous bubbling occurred as hydrogen evolved), and it was stirred for 1 hr. Finally, 10 g (54.52 mmol) of 2,4,6-trichloropyrimidine were injected quickly into the reaction mixture, and it was vigorously stirred overnight. The reaction mixture was diluted with 200 mL of ethyl acetate and washed with a solution of 14.5 g (75 mmol), of citric acid in 100 mL of water. The organic layer was extracted and dried with magnesium sulfate. The mixture was then concentrated down to give a brown, viscous material. The crude material was loaded relatively quickly onto a chromatographic column (25"×3"), which was filled with 11¼" silica gel. Elution was started at 40:1 hexane/ether for about 2 L, and then the concentration was increased to 35:1 hexane/ether for about 4 L. The best TLC system was 9:1 hexane/ether. With that system, the four product spots could be seen: the top spot was the regio-isomer with the pyrrole substituted on the 2-position of the pyrimidine, the second spot was unreacted pyrimidine, the third spot was the regioisomer with the pyrrole substituted at the 4-position (desired product), and the most polar spot was a bis-addition product. Most of the desired product was separated with the column (2.5 g), but the remaining mixture with the bis-product was recrystallized from hexane to give another 1.5 g. The total yield was 4 g (38%) of the white solid. $^1$H NMR in CDCl$_3$: a 2H triplet at 6.42 ppm (j=2.55 Hz), a 1H singlet at 7.16 ppm, and a 2H triplet at 7.48 ppm (J=2.55 Hz). In 9:1 hexane/ether, the R$_f$=0.37. This compound did not give a mass spec signal.

The corresponding 2,6-difluoro-4-(1-pyrrolyl)pyrimidine is made in analogous fashion from 2,4,6-trifluoropyrimidine. Both are useful as intermediates in the synthesis of B$_1$-BK antagonists of the invention. An improved synthesis of 2,6-dichloro-4-(1-pyrrolyl)pyrimidine proceeds from 4-amino-2,6-dichloropyrimidine. A mixture of 4-amino-2,6-dichloropyrimidine (5.0 g, 30.5 mmol) and 2,5-dimethoxytetrahydrofuran (4.03 g, 30.5 mmol) in 100 mL of HOAc was refluxed for 2 hours. The reaction mixture was cooled to RT and poured into large quantity of water. The crude product was extracted into ethyl acetate and the ethyl acetate layer was extracted successively with water, aqueous NaHCO$_3$ and brine. The organic layer was dried (MgSO$_4$) and the solvent was evaporated. The residue was purified by chromatography (silica gel, hexane:ethyl acetate (96:4) to provide 4.4 g (73%) of 2,6-dichloro-4-(1-pyrrolyl) pyrimidine. $^1$H NMR (CDCl$_3$): δ (ppm) 6.4 (s,2H), 7.15 (s, 1H), 7.5 (s, 2H).

As described above, both the dichloro and the difluoro-intermediates provide mixtures of regioisomers when reacted with nucleophiles (cf. 144 in Scheme 19). Although this is useful when both regioisomers are desired, the route shown in Scheme 20 below provides a regioselective synthesis. According to Scheme 20, 4-amino-6-chloro-2-methylthiopyrimidine 151 was reacted with 1 equivalent of 2,5-dimethoxytetrahydrofuran in refluxing acetic acid to provide 6-chloro-2-methylthio-4-(1-pyrrolyl)pyrimidine 152: $^1$H NMR (CDCl$_3$) δ 2.75 (s,3H), 6.55 (d,2H), 7.05 (s,1H), 7.65 (d,2H). The 6-chloro-2-methylthio-4-(1-pyrrolyl)pyrimidine 152 is either (a) oxidized with 2.2 equivalents of m-chloroperoxybenzoic acid in dichloromethane at 0° C. to provide 6-chloro-2-methylsulfonyl-4-(1-pyrrolyl)pyrimidine 153 or (b) reacted with 1 equivalent of the N-(p-cyanobenzyl)amide of cyclohexylalanine and 1 equivalent of diisopropylethylamine in DMF at 80° C. to provide the 2-methylthiopyrimidine 154. The oxidation and nucleophilic displacement steps are then reversed [i.e. 153 is reacted according to (b) or 154 is reacted according to (a)] to provide the 2-methylsulfonylpyrimidine 155, which is dissolved in n-butanol saturated with ethylamine and heated in a sealed tube to produce 156.

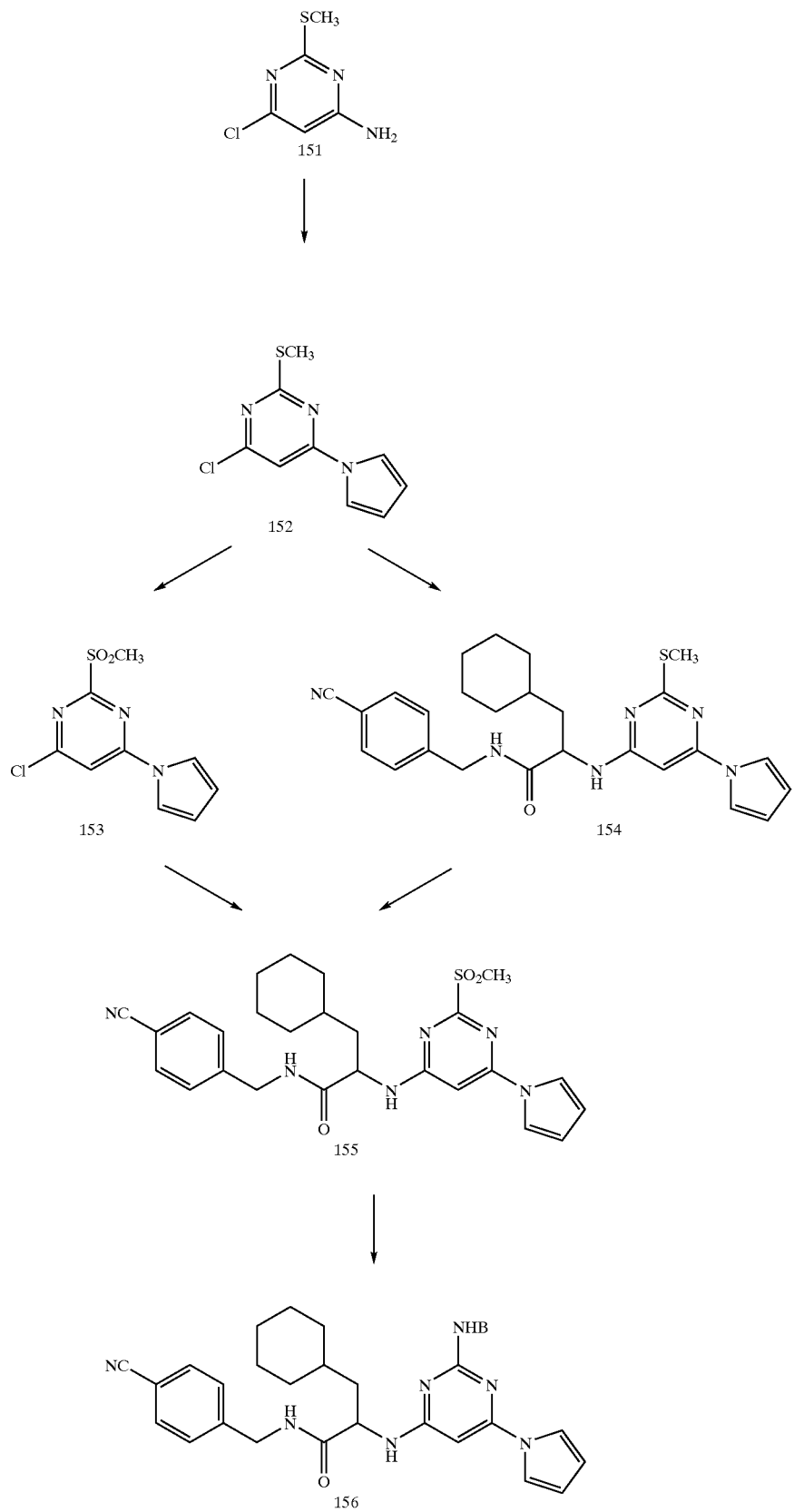

Compounds of formulae

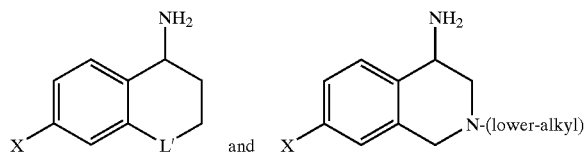

wherein X is —CN or halogen and L' is —O—, —CH$_2$— or —N(CH$_3$)— are useful intermediates for the preparation of compounds of preferred subgenera. Exemplary syntheses are shown below.

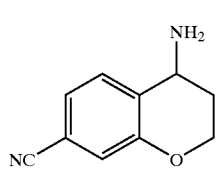

7-Cyano-4-chromanylamine was prepared as follows:

A dry, 250 mL round bottom flask was charged with 0.27 g (1.01 mmol) of triphenylphosphine, 0.73 g (11.15 mmol) of potassium cyanide, 0.22 g (3.38 mmol) of zinc dust, and 0.38 g (0.51 mmol) of bis(triphenylphosphine)nickel (II) bromide. The flask was then purged with argon, and an air-free solution of 3 g (10.14 mmol) of 7-(((trifluoromethyl)sulfonyl)oxy)-4-chromanone [Koch et al., *J. Org. Chem.* 59, 1216 (1994)] in 40 ml of dry acetonitrile was introduced by syringe. The solution was then heated at 60° C. for 3 hours, under argon. After cooling the solution to room temp, the solution was added to an equal volume of water. The organic layer was extracted out, and the aqueous layer was extracted several times with ethyl acetate and ether. The combined organic phase was dried over magnesium sulfate, filtered and evaporated. The crude mixture was chromatographed using a 20% ethyl acetate/hexane solvent system which yielded 1.3 g (76%) of 7-cyano-4-chromanone as a white solid.

A dry, 200 mL round bottom flask was charged with 0.85 g (4.83 mmol) of 7-(cyano)-4-chromanone, 3.72 g (48.30 mmol) of ammonium acetate, and 0.91 g (14.45 mmol) of sodium cyanoborohydride. The flask was then purged with argon, and 30 mL of dry methanol was added by syringe. The solution was stirred at room temp for 48 hours. Concentrated HCl was slowly added dropwise until pH<2 was reached. The methanol was then evaporated by rotovap, and 30 mL of water was added to the suspension, which was then washed 3 times with ethyl acetate. The pH was then brought to >10 by adding sodium hydroxide pellets to the stirring aqueous mixture. Saturated sodium chloride was added, and the mixture was then extracted several times with ether and ethyl acetate. The combined organic phase was dried over magnesium sulfate, filtered and evaporated to give 0.51 g (60%) of the desired 7-(cyano)-4-chromanylamine as a pale yellow oil.

Characterization: The $^1$H NMR in CDCl$_3$ (using a Varian Gemini 2000 model NMR coupled to a 300 Mz Oxford Magnet) gave the following signals: a broad 2H singlet at 1.6 ppm, a 2H multiplet from 1.8–2.2 ppm, a 1H triplet at 4.05 ppm (J=6 Mz), a 2H multiplet from 4.2–4.4 ppm, a 1H singlet at 7.1 ppm, a 2H doublet at 7.15 ppm (J=12 Mz), and a 2H doublet at 7.45 ppm (J=12 Mz).

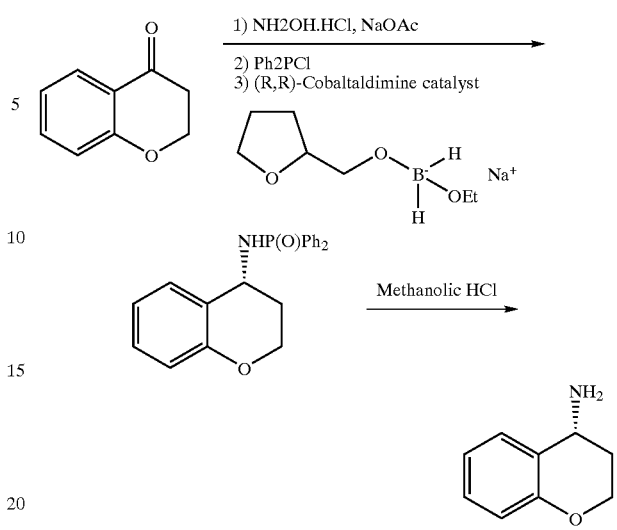

A mixture of 4-chromanone (5 g, 33.7 mmol), hydroxylamine hydrochloride (2.34 g, 33.7 mmol and NaOAc (2.766 g, 33.7 mmol) in 100 mL of ethanol was refluxed for 18 h. After cooling to RT, the solvent was removed and the residue was partitioned between water and EtOAc. The EtOAc layer was dried (MgSO$_4$), and the solvent was removed. The solid obtained was triturated with hexane and filtered to provide 4.1 g of 4-hydroxyiminochroman.

A solution of 4-hydroxyiminochroman (783 mg, 4.8 mmol) and triethylamine (484 mg, 4.8 mmol) in 120 mL of dry 1:1 DCM:hexane was cooled to −50° C. Chlorodiphenylphosphine (1.059 g, 4.8 mmol) was added via syringe and the mixture was allowed to stir at −50° C. for 2 h. The mixture was cooled to −78° C. and filtered quickly under N$_2$ in a glove bag. The filtrate was evaporated and the crude N-diphenylphosphinylimine was taken directly to the next step.

Formation of pre-modified borohydride: Under Ar atmosphere, in a pre-cooled flask at 0° C. were placed 290 mg of NaBH$_4$ (7.5 mmol), 50 mL of CHCl$_3$, and 0.44 mL of EtOH (7.5 mmol) and 10 mL of tetrahydrofurfuryl alcohol. The mixture was stirred for 3 h at 0° C.

Catalytic borohydride reduction: While maintaining solution of pre-modified borohydride at 0° C., its solution was slowly added to the solution of 37 mg of (1R,2R)-N,N'-Bis[3-oxo-2-(2,4,6-trimethylbenzoyl)butylidene]-1,2-diphenylethylenediaminato cobalt(II) (0.05 mmol, 1 mol %, TCI America) and the aforementioned phosphinylimine in 50 mL of CHCl$_3$. The stirring was continued for 4 h at 0° C. The reaction was quenched by addition of saturated NH$_4$Cl and extracted with ether. The organic layer was dried (MgSO$_4$) and the solvent was evaporated. The residue was purified by chromatography (silica, hexane:EtOAc, 1:3) to provide 300 mg of the diphenylphosphorylamine. (M+H)$^+$: 350.1.

The diphenylphosphorylamine (300 mg, 0.86 mmol) was dissolved in MeOH saturated with HCl gas and stirred overnight at RT. The solvent was removed and the residue was partitioned between water and ether. The aqueous layer was basified and the liberated amine was extracted into ether. The ether layer was evaporated after drying (K$_2$CO$_3$) to provide (R)-4-aminochroman. The stereochemistry was assigned based on the literature precedence (Sugi, K. D.; Nagata, T.; Mukaiyama, T. Chem. Lett. 1997, 493–494) and the optical purity was found to be >95% by chiral hplc. $^1$H NMR (CDCl$_3$): δ 1.75 (bs, 2H, NH$_2$), δ 1.95–2.05 (m, 1H, CH$_2$CH$_2$O), δ 2.30–2.40 (m, 1H, CH$_2$CH$_2$O), δ 4.2 (t, 1H, CHNH$_2$), δ 4.35–4.50 (m, 2H, CH$_2$O), δ 7.0 (d, 1H, ArH), δ 7.10 (t, 1H, ArH), δ 7.30 (t, 1H, ArH), δ 7.50 (t, 1H, ArH).

N-bromosuccinimide (12.9 g, 72.4 mmol) and a catalytic amount of benzoyl peroxide. The reaction was refluxed under stirring for 4 h and then filtered. Removed solvent Scheme 21

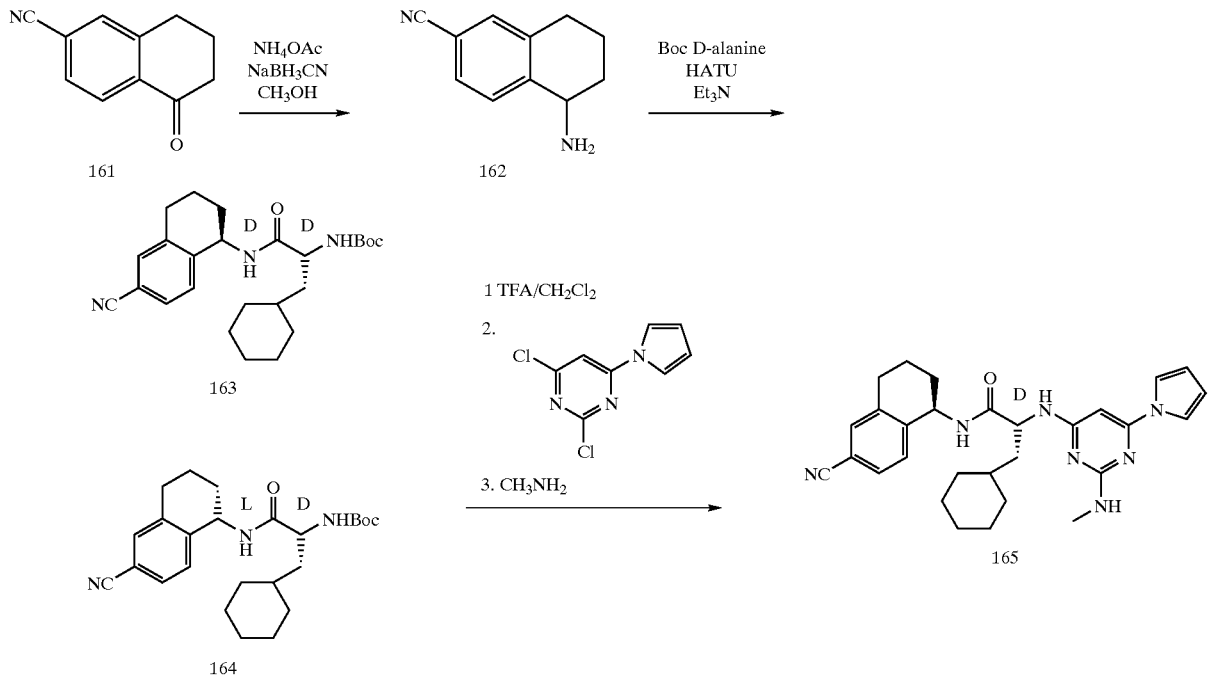

According to Scheme 21 NaCNBH$_3$ (264 mg, 4.2 mmol) was added to a mixture of 161 (340 mg, 1.99 mmol) [Almansa et al. *Synth. Commun.* 23, 2965 (1993)] and NH$_4$OAc (1.5 g, 19.9 mmol) in dry methanol (30 ml), and the reaction was stirred at room temperature for a week. Removed solvent under vacuum. The residue was separated by silica gel chromatography column with methanol/ammonium hydroxide/ethyl acetate (15:1:84) to give 290 mg (84%) of 7-cyano-1,2,3,4-tetrahydronaphthylene-1-amine (162). NMR (CDCl$_3$): δ 1.66–2.12 (4H, CH$_2$x2), 2.78 (2H, CH$_2$), 4.0 (1H, CH), 7.37 (1H, ArH), 7.44 (1H, ArH), 7.54 (1H, ArH).

To a solution of 7-cyano-1,2,3,4-tetrahydronaphthylene-1-amine (162) (290 mg, 1.69 mmol), and Et$_3$N (427 mg, 4.22 mmol) in DMF was added HATU (703 mg, 1.85 mmol) in one portion with stirring. The reaction was stirred at room temperature overnight, then solvent was removed in vacuo. Chromatographic purification with EtOAc/hexane (3:7) gave 145 mg (20%) of 163 and 151 mg (21%) of 164. The more polar diastereoisomer 163 was converted into final compound 165 as described earlier.

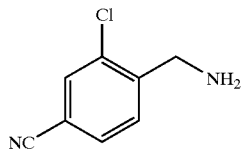

2-Chloro-4-cyanobenzylamine was prepared as follows: To a stirred solution of 2-chloro-4-cyanotoluene (10 g, 65.8 mmol) in dry carbon tetrachloride (150 ml) were added from filtrate in vacuo. The residue, 2-choro-4-cyanobenzyl bromide, was purified by chromatography with EtOAc/hexane.

To a stirred solution of 2-choro-4-cyanobenzyl bromide (6.9 g, 30.0 mmol) in DMF (150 ml), was added sodium azide (2.0 g, 30 mmol) The reaction was stirred overnight at room temperature, and then filtered. The DMF was removed from filtrate in vacuo. The residue was dissolved in EtOAc (300 ml), washed with water (200 ml×3), brine (200 ml×1), dried over sodium sulfate. Removed solvent in vacuo to give 5.8 g of raw 2-choro-4-cyanobenzyl azide.

To a solution of 2-choro-4-cyanobenzyl azide (5.8 g, 30.1 mmol) in THF/H$_2$O (3:1), was added triphenyl phosphine (12.3 g, 46.7 mmol). The reaction was stirred at room temperature overnight, then neutralized with 1N sodium hydroxide, extracted with ethyl acetate (150 ml×3). The organic layer was dried over sodium sulfate, and then solvent was removed in vacuo. The product was purified by silica-gel chromatography column with methanol/ammonia hydroxide/ethyl acetate (20:1:69) to give 4.5 g (90%) of 2-chloro-4-cyanobenzylamine. NMR (CDCl$_3$): δ 4.0 (s, 2H, CH$_2$), 7.58 (d, 2H, HAr), 7.62 (s, 1H, HAr)

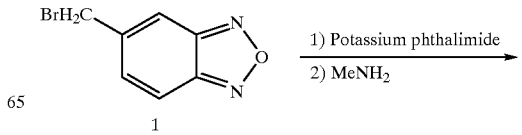

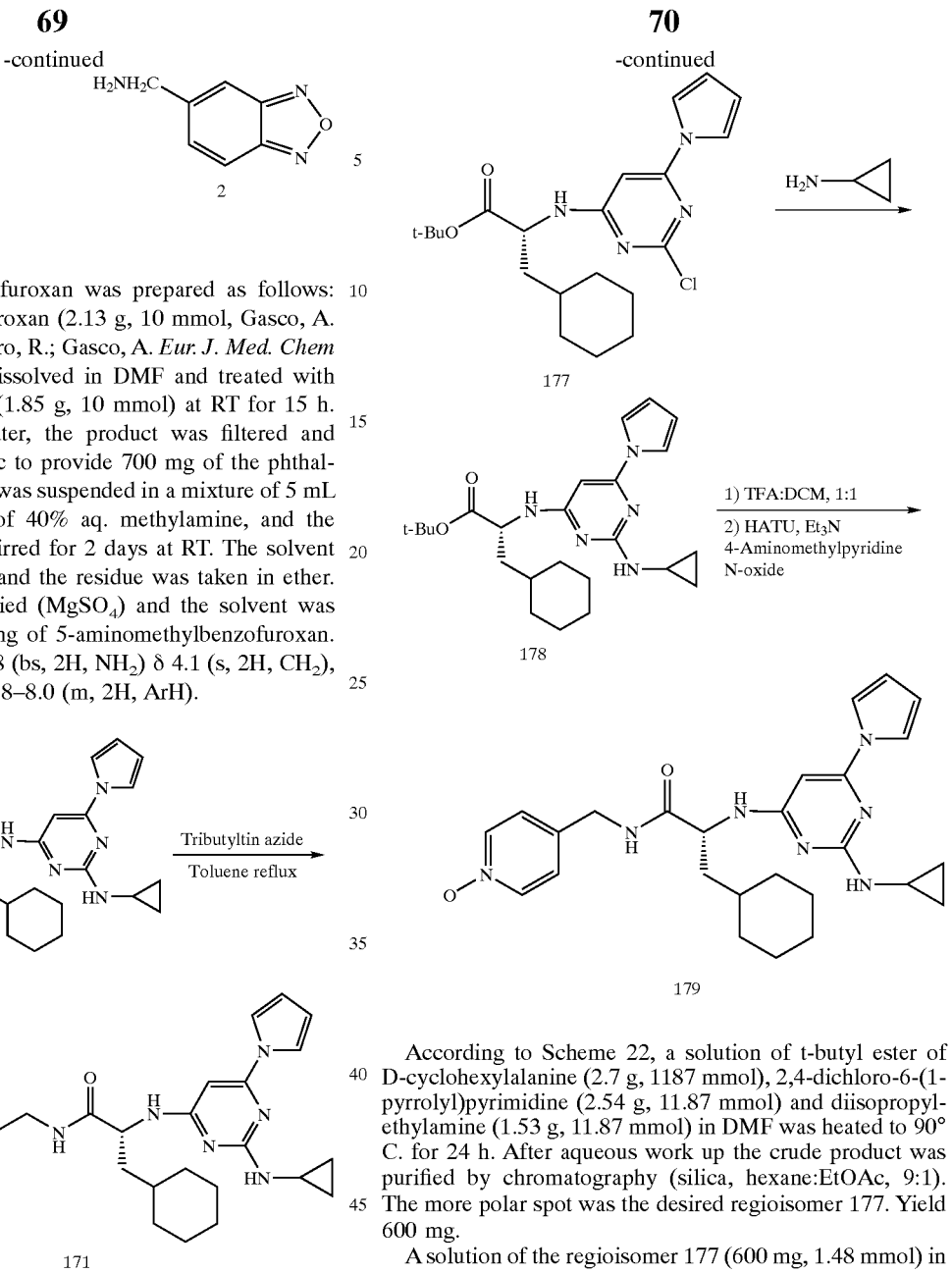

5-Aminomethylbenzofuroxan was prepared as follows: 5-Bromomethylbenzofuroxan (2.13 g, 10 mmol, Gasco, A. M.; Errnondi, G.; Fruttero, R.; Gasco, A. *Eur. J. Med. Chem* 1996, 31, 3–10) was dissolved in DMF and treated with potassium phthalimide (1.85 g, 10 mmol) at RT for 15 h. After diluting with water, the product was filtered and crystallized from EtOAc to provide 700 mg of the phthalimide. The phthalimide was suspended in a mixture of 5 mL of ethanol and 5 mL of 40% aq. methylamine, and the reaction mixture was stirred for 2 days at RT. The solvent was removed in vacuo and the residue was taken in ether. The ether layer was dried (MgSO$_4$) and the solvent was removed to yield 110 mg of 5-aminomethylbenzofuroxan. $^1$H NMR (CDCl$_3$): δ 1.8 (bs, 2H, NH$_2$) δ 4.1 (s, 2H, CH$_2$), δ 7.5 (d, 1H, ArH), δ 7.8–8.0 (m, 2H, ArH).

A solution of the nitrile 170 (100 mg, 0.2 mmol) and tributylstannyl azide (133 mg, 0.4 mmol) in toluene was refluxed for two days. The solvent was evaporated and the residue was treated with 6 N HCl overnight. After aqueous work up, the tetrazole 171 was purified by chromatography (silica, DCM:MeOH, 95:5). Yield: 35 mg (M+H)$^+$: 527.3

Scheme 22

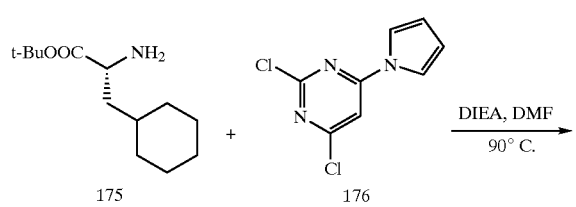

According to Scheme 22, a solution of t-butyl ester of D-cyclohexylalanine (2.7 g, 1187 mmol), 2,4-dichloro-6-(1-pyrrolyl)pyrimidine (2.54 g, 11.87 mmol) and diisopropylethylamine (1.53 g, 11.87 mmol) in DMF was heated to 90° C. for 24 h. After aqueous work up the crude product was purified by chromatography (silica, hexane:EtOAc, 9:1). The more polar spot was the desired regioisomer 177. Yield 600 mg.

A solution of the regioisomer 177 (600 mg, 1.48 mmol) in 10 mL of n-butanol containing 4 mL of cyclopropylamine was heated to 90° C. in a sealed tube overnight. The solvent was removed and the product 178 was purified by chromatography (silica, hexane:EtOAc, 9:1). Yield 486 mg. (M+H)$^+$: 426.3.

A solution of the t-butylester 178 (486 mg, 1.14 mmol) in 10 mL of 1:1 DCM:TFA was stirred overnight. The solvent was removed and the residue was taken in EtOAc. The EtOAc layer was washed several times with water and the solvent was removed in vacuo to provide 367 mg of the carboxylic acid. (M+H)$^+$: 370.8.

4-Aminomethylpyridine N-oxide dihydrochloride (200 mg, 1.01 mmol) was suspended in 3 mL of dry DMF and 200 mg of Et$_3$N (1.98 mmol) was added. The contents were stirred for 15 min. In the mean time, a solution of the carboxylic acid (100 mg, 0.27 mmol) from the previous step and Et$_3$N (300 mg, 2.97 mmol) in 5 mL of DMF was cooled in a ice bath and HATU (100 mg, 0.26 mmol) was added. After stirring for 3 min, aforementioned solution of 4-aminomethylpyridine N-oxide was added and the stirring was continued for 3 days. Aqueous work up and chromatography (silica, EtOAc:MeOH, 85:15) gave 19 mg of 179. (M+H)$^+$: 476.6.

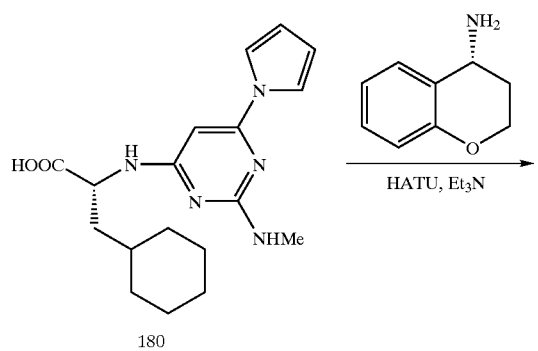

180

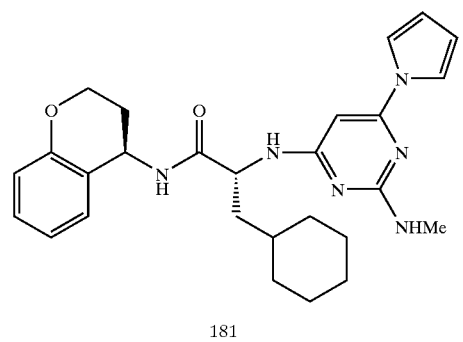

181

A solution of the carboxylic acid 180 (197 mg, 0.57 mmol), HATU (218 mg, 0.57 mmol) and Et$_3$N (172 mg, 1.70 mmol) in 5 mL of dry DMF was stirred for 5 minutes. Then a solution of (R)-4-aminochroman (81 mg, 0.54 mmol) in 2 mL of dry DMF was added and the contents were stirred overnight. After aqueous work up, the residue was purified by chromatography (silica, hexane:EtOAc, 1:1) to provide 32 mg of 181. (M+H)$^+$: 475.2.

Scheme 23

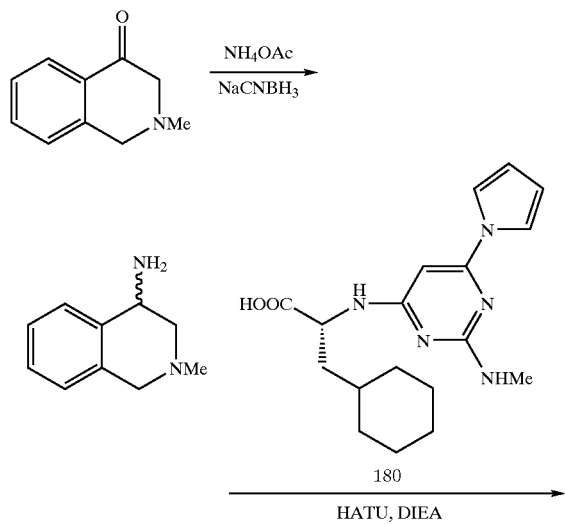

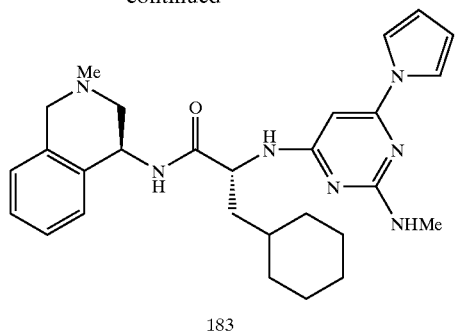

183

According to Scheme 23, a mixture of 2-methyl-2,3-dihydro-4-(1H)-isoquinolone (630 mg, 3.9 mmol, Nichols, D. E. et al.; WO9706799), ammonium acetate (3.0 g, 39 mmol) and NaCNBH$_3$ (491 mg, 7.8 mmol) in 25 mL of dry methanol was stirred for 2 days at RT. The solvent was removed and the residue was acidified to pH 2 to destroy the excess NaCNBH$_3$. After basification with aq Na$_2$CO$_3$ to pH 10, the product was extracted into ether. The ether layer was dried (K$_2$CO$_3$) and the solvent was evaporated to provide 330 mg of the racemic 4-amino-2-methyltetrahydroisoquinoline. $^1$H NMR (CDCl$_3$): δ 2.20 (bs, 2H, NH$_2$), δ 2.60 (s, 3H, NCH$_3$), δ 2.90 (d, 2H, CHCH$_2$N), δ 3.55 (d, 1H, ArCH$_2$N), δ 3.90 (d, 1H, ArCH$_2$N), δ 4.15 (t, 1H, ArCHN), δ 7.20–7.60 (m, 4H, ArH).

4-Amino-2-methyltetrahydroisoquinoline (320 mg, 1.97 mmol) was coupled with N-(2-methylamino-4-(1-pyrrolyl)-6-pyrimidinyl)-D-cyclohexylalanine (180)(237 mg, 0.69 mmol) using HATU as described earlier. After aqueous work up, the residue was purified by chromatography (silica, EtOAc). The diastereomer 183 with higher R$_f$ was assigned R-stereochemistry at the benzylic center based on its biological activity, yield: 78 mg, (M+H)$^+$: 488.2. The more polar isomer was assigned S-stereochemistry, yield: 71 mg, (M+H)$^+$: 488.1.

Scheme 24

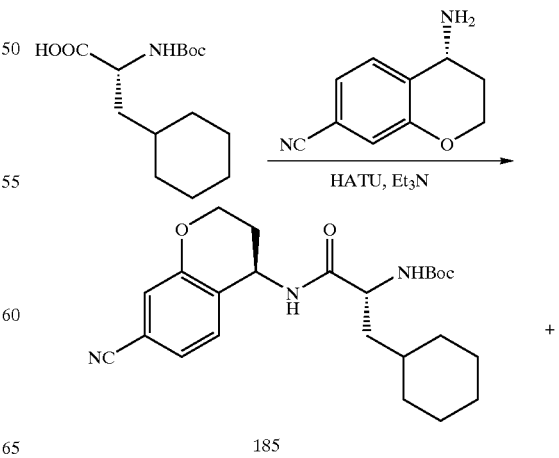

185

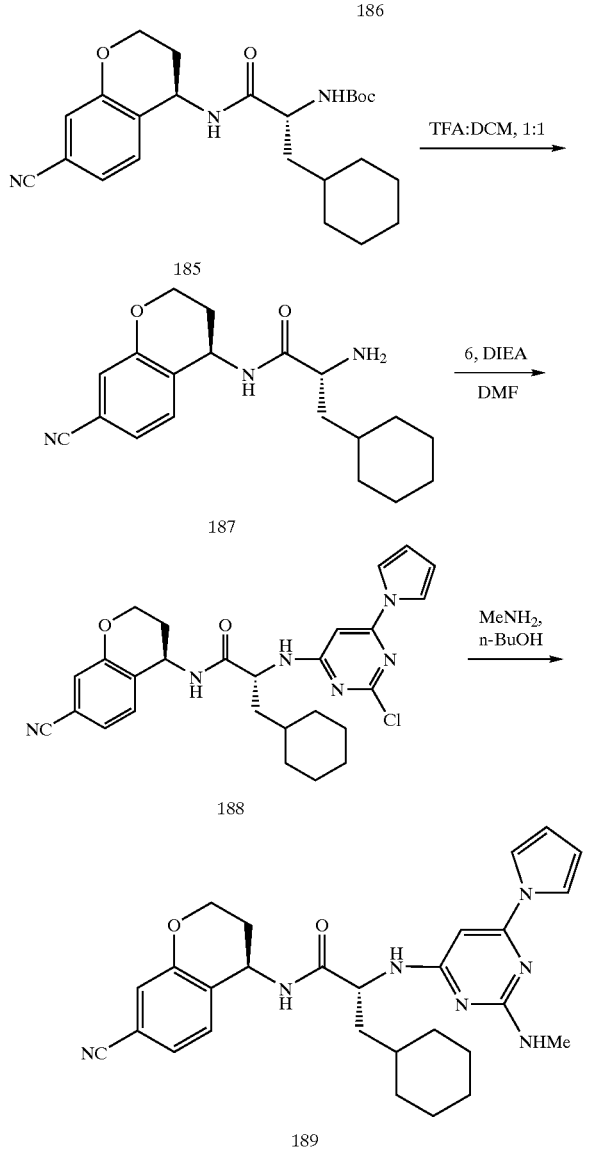

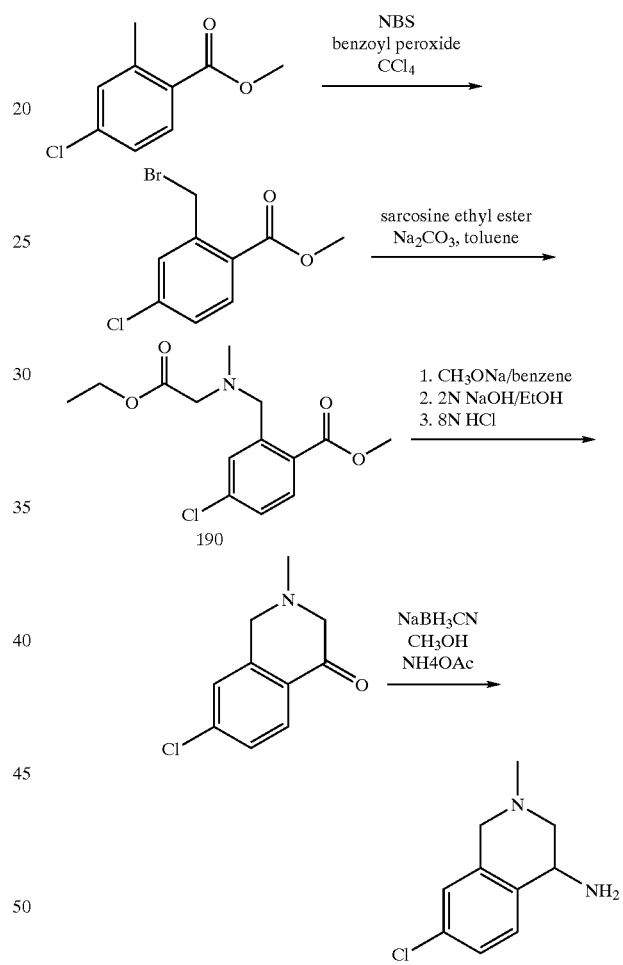

A mixture of amine 187 (270 mg, 0.82 mmol), DIEA (106 mg, 0.82 mmol) and 2,4-dichloro-6-(1-pyrrolyl)pyrimidine (175 mg, 0.82 mmol) in DMF was heated to 90° C. overnight. Aqueous work up and chromatography (silica, hexane:EtOAc, 1:1) provided 120 mg of the less polar regioisomer and 96 mg of the more polar desired regioisomer 188.

A solution of the more polar regioisomer 188 (58 mg, 0.11 mmol) in n-butanol was saturated with methylamine at −20° C. The solution was then heated to 90° C. in a sealed tube overnight. After cooling, the solvent was removed in vacuo and the residue was purified by chromatography (silica, hexane:EtOAc, 1:1) to provide 25 mg of 189. (M+H)⁺: 500.3.

Scheme 25

4-Amino-7-chloro-2-methyltetrahydroisoquinoline was prepared as shown above in Scheme 25: To a stirred solution of methyl 4-chloro-2-methylbenzoate (8.9 g, 48.2 mmol) in dry carbon tetrachloride (150 ml) were added N-bromosuccinimide (9.4 g, 53.0 mmol) and a catalytic amount of benzoyl peroxide. The reaction was refluxed under stirring for 12 h and then filtered. Removed solvent from filtrate in vacuo to give 12.0 g of the crude benzyl bromide. NMR (deuteriochloroform): δ 3.92 (s, 3H, CH₃), 4.92 (s, 2H, CH₂), 7.34 (d, 1H, ArH), 7.46 (s, 1H, ArH), 7.79 (d, 1H, ArH).

To a mixture of sarcosine ethyl ester hydrochloride (7.4 g, 63 mmol), sodium carbonate (8.2 g, 77.4 mmol), and toluene (300 ml) was added a solution of the benzyl bromide (12.0

According to Scheme 24, HATU (1.165 g, 3.07 mmol) was added at 0° C. to a solution of N-Boc-D-cyclohexylalanine (831 mg, 3.07 mmol) and Et₃N (620 mg, 6.14 mmol) in 15 mL of dry DMF. After stirring for 2 min, 7-cyano-4-chromanylamine (540 mg, 3.068 mmol) was added and the stirring was continued overnight. After aqueous work up and chromatography (silica, hexane:EtOAc, 70:30), 420 mg of the less polar diastereomer 186 (M+H⁺: 427.8), and 380 mg of the more polar diastereomermer 185 (M+H⁺: 427.8) were obtained. A solution of the more polar diastereomer 185 (380 mg, 0.89 mmol) was stirred in DCM:TFA (1:1) overnight at RT. Aqueous work up at basic pH provided 270 mg of the primary amine 187.

g, 45.5 mmol) in toluene at room temperature. The reaction was heated at 85° C. with stirring for 12 h, cooled to room temperature, and then filtered. The filtrate was collected and extracted with 3N HCl (150 ml×3). The aqueous layer was collected, basified with saturated $Na_2CO_3$ solution, and extracted with ether (150 ml×3). To remove the solvent from the organic solution give 8.4 g (61%) of 190. NMR ($CDCl_3$): δ 1.30 (m, 3H, $CH_3$), 2.38 (s, 3H, $CH_3$), 3.3 (s, 2H, $CH_2$), 3.86 (s, 3H, $CH_3$), 4.0 (S, 2H, $CH_2$), 4.18 (m, 2H, $CH_2$), 7.26 (D, 1H, ArH), 7.60 (s, 1H, ArH), 7.74 (D, 1H, ArH).

Freshly cut sodium (0.84 g, 36.3 mmol) was added to absolute methanol (30 ml) under argon. The reaction was refluxed until sodium metal disappeared. A solution of 190 (8.4 g, 27.9 mmol) in dry toluene (150 ml) was added slowly. The mixture was heated at reflux to remove extra methanol via a Dean Stark trap. Fresh dry toluene (150 ml) was added and refluxed for 2 h. After cooling, solvent was removed under vacuum. The remains dissolved in ethanol (150 ml) were treated with 2N NaOH (250 ml). It was refluxed for 1.5 h, cooled to room temperature, acidified with 8N HCl, and then refluxed for 2.5 h. The reaction mixture was cooled to room temperature, basified with 6N NaOH, extracted with methylene chloride (150 ml×3). The organic layer was dried over $Na_2SO_4$. The solvent was removed in vacuo. The residue was purified by chromatography with EtOAc/Hexane (1:1) to give 1.82 g (31%) of the isoquinolone. NMR ($CDCl_3$): δ 2.46 (s, 3H, $CH_3$), 3.3 (s, 2H, $CH_2$), 3.7 (s, 2H, $CH_2$), 7.22 (d, 1H, ArH), 7.3 (s, 1H, ArH), 7.96 (d, 1H, ArH).

To a mixture of compound tetrahydroisoquinolone (1.8 g, 9.3 mmol) and $NH_4OAc$ (7.1 g, 9.3 mmol) in dry methanol (80 ml) was added $NaCNBH_3$ (2.9 g, 46.4 mmol). The reaction was stirred at room temperature for 3 days. Removed solvent under vacuum. The residue was separated by silica gel chromatography column with methanol/ammonia hydroxide/ethyl acetate (20:1:79) to give 1.1 g (60%) of 4-Amino-7-chloro-2-methyltetrahydroisoquinoline. NMR ($CDCl_3$): δ 1.7 (2H, $CH_2$), 2.4 (3H, $CH_3$), 2.66 (2H, $CH_2$), 7.0(1H, ArH), 7.2 (1H, ArH), 7.28 (1H, ArH).

All of the compounds shown in the tables below have been examined by high resolution mass spectrometry and have provided $MH^+$ ions and fragments consistent with the structures shown.

Bioassays

Tissues are taken from New Zealand white rabbits (1.5–2.5 kg) and Duncan Hartley guinea pigs (250–350 g) of either sex, killed by stunning and exsanguination. Human umbilical cords are obtained after spontaneous delivery at term. The rabbit jugular vein (RbJV) and the guinea pig ileum (GPI), are two preparations containing $B_2$ receptors. The rabbit aorta (RbA) contains $B_1$ receptors, and the human umbilical vein (HUV) is a mixed preparation containing both $B_1$ and $B_2$ receptors. Helical strips of RbJV, treated with 1 μmol/L of captopril to avoid peptide degradation, are prepared according to Gaudreau et al. [*Can. J. Physical. Pharmacol.* 59, 371–379 (1981)] Helical strips of RbA devoid of endothelium are prepared according to Furchgott and Bhadrakom. [*J. Pharacol. Exp. Ther.* 108, 124–143 (1953)] Longitudinal segments of GPI are prepared with the procedure described by Rang [*Brit. J. Pharmacol.* 22, 356–365 (1964)]. Helical strips of HUV are prepared according to Gobeil et al. [*Brit. J. Pharmacol.* 118, 289–294 (1996)]. Unless otherwise indicated below, the tissues are suspended in 10-mL organ baths containing warm (37° C.), oxygenated (95% $O_2$–5% $CO_2$) Krebs solution of the following composition in mmol/L; NaCl: 118.1; KCl: 4.7; $CaCl_2 6H_2O$: 2.5; $KH_2PO_4$: 1.2; $MgSO_4 7H_2O$:1.18; $NAHCO_3$: 25.0 and D-Glucose: 5.5. The RbA are stretched with an initial tension of 2 g, whereas the RbJV and the GPI are loaded with 0.5 g. Changes of tension produced by the various agents are measured with Grass isometric transducers (model FT 03C, Grass Instrument Co., Quincy, Mass.). Myotropic contractions are displayed on a polygraph. Before testing the drugs, the tissues are allowed to equilibrate for 60–120 minutes, during which time the tissues are repeatedly washed and the tension readjusted every 15 min.

At the beginning of each experiment, a submaximal dose of bradykinin (BK) (9 mmol/L), is applied repeatedly on the RbJV, the GPI or the HUV to ensure that tissues responded with stable contractions. In the RbA, the $B_1$ preparation whose response has been shown to increase during the incubation in vitro, desArg$^9$ K (550 nmol/L) are applied 1, 3 and 6 h after the equilibration period, in order to monitor the progressive increase of sensitivity of the tissue which generally reaches the maximum after 3–6 h.

Repeated applications of a single and double concentration of BK (on RbJV, GPI and HUV) and of desArg$^9$BK (RbA and HUV) are made in the absence and in presence of the test compounds to evaluate their apparent affinities as antagonists, in terms of $pA_2$ ($-log_{10}$ of the molar concentration of antagonist that reduces the effect of a double concentration of agonist to that of a single one). The antagonists are applied 10 min before measuring the myotropic effects of either BK (the $B_2$ receptor agonist) or desArg$^9$BK (the $B_1$ receptor agonist). Pharmacological assays on the HUV (a mixed $B_1$ and $B_2$ receptor preparation) are done in presence of either HOE140 (400 mmol/L) (a potent $B_2$ receptor antagonist) or Lys[Leu$^8$]des Arg$^9$BK (1 μmol/L) (a potent $B_1$ receptor antagonist) (applied 10 min prior to the tested agents) to study the $B_1$ and the $B_2$ receptors, respectively. All kinin antagonists are initially applied to tissues at concentration of 10 μg/mL to measure their potential agonistic activities ($\alpha^E$) in comparison with BK (in the $B_2$ receptor preparations) or desArg$^9$BK (in the $B_1$ receptor preparations). The compounds of the present invention exhibit inhibition at very low concentrations only when tested in human or primate systems; thus the foregoing (and following) tests in rabbit and rodent tissues are useful only for demonstrating lack of undesired effects on other receptors than $B_1$ and in other tissues than human. In order to determine the potency of compounds of the invention, those tests that employ rabbit and rodent tissues are modified to employ human and primate tissues, as well known to persons in the art.

Streptozotocin has been extensively used to produce type I diabetes in animals. This experimental disease is characterized by a mild inflammatory reaction in the Langerhans islets. Male C57 L/$K_3$ mdb mice are injected with streptozotocin (40 mg/kg) for 5 consecutive days. The kinin $B_1$ receptor antagonists are injected subcutaneously to STZ mice at 300 μg/Kg bw twice a day and 500 μg/Kg per day, respectively. Treatment with antagonists is started 3 days after STZ and lasts for 10 days. Plasma glucose is determined by the glucose oxidase method, and urinary samples are assayed at 13 days for proteins, nitrites and kallikreins. Diabetic mice show hyperglycemia and increased diuresis, marked proteinuria and increased excretion of nitrites and kallikreins. $B_2$ receptor antagonists reduce water and protein excretion, compared to STZ group; STZ mice treated with $B_1$ receptor antagonists show normal glycemia and normalization of diuresis, protein, nitrite and kallikrein excretion.

The contractile response of the portal vein (a suitable preparation for $B_1$-BK studies) obtained from untreated 8-week old spontaneously hypertensive rats (SHR), is exaggerated and susceptible to enhanced capillary hydrostatic pressure and plasma leakage. Desendothelialized portal vein segments obtained from SHR are mounted in organ baths containing a Krebs solution for isometric contraction studies (baseline tension: 0.5 g). Test compounds are administered on portal vein segments obtained from normal rats and SHR, to establish dose-response curves.

Bradykinin $B_1$ receptor binding in human tissue is determined by the method of Levesque et al. [*Immunopharmacology* 29, 141–147 (1995); and *Immunopharmacology* 28, 1–7 (1994)]. Human embryonic fibroblast cells from the IMR-90 line (available from ATCC as CCL 186) are grown in minimal essential medium as described by Menke et al [*J. Biol. Chem.* 269, 21583–21586 (1994)]. After 24 hours, the culture medium is replaced with low serum media (0.4% fetal bovine serum) containing recombinant human IL-1β (0.25 mg/mL) and the cells are further incubated for 4–5 hours. The cells are harvested with trypsin and resuspended in Medium 11995-065 (Gibco, Gaithersburg, Md., USA) supplemented with L-glutamine, non-essential amino acids and 10% fetal bovine serum at $1.7 \times 10^6$ cells/mL. Thirty microliters of the cell suspension in a plate is mixed with 10 μL of straight buffer [1 L of Medium 199 (Gibco, Gaithersburg, Md., USA), 25 mL of HEPES buffer, 1 g bovine serum albumin 3 μM amastatin, 1 μM captopril and 1 μM phosphoramidon (Sigma, St. Louis, Mo., USA)] or 10 μL of buffer containing 5 to 50 μM $B_1$-BK antagonist and 10 μL of 11 μM $^3$H-desArg$^{10}$-kallidin. The plates are incubated at room temperature for about 1.5 hours. After incubation, each well is washed with 150 μL of ice-cold PBS at pH 2.4. The contents are transferred to a glass fiber plate that has been pretreated with polyethyleneimine and the plate is air dried. Scintillation fluid is added and the resulting solution is counted in a gamma counter for 10 minutes. Statistical analysis is performed on the saturation curves. Scatchard regression parameters are calculated from the mean saturation data using a computer program (Tallarida and Murray, 1987). The resulting $B_{max}$ and $K_d$ values and their respective SEM are compared in order to assess statistical differences using Student's t-test. The compounds of the invention exhibit Ki's below 10 μM. Specific examples of compounds which have been synthesized and tested are shown in Tables 1 and 2. Those compounds in Table 1 exhibited $K_i$'s of 1 to 500 nM; those in Table 2 exhibited $K_i$'s of 501 nM to 10 μM.

Potency and efficacy in human tissue are assessed as follows: Human umbilical cords are obtained within 24 hours following normal deliveries and are stored in physiological salt solution (PSS) at 4° C. The composition of the PSS is as follows: 118 mM NaCl, 4.6 mM KCl, 1.2 mM $KH_2PO_4$, 1.2 mM $MgSO_4$, 2.5 mM $CaCl_2$, 0.026 mM $CaNa_2EDTA$, 10 mM glucose, and 24.8 mM $NaHCO_3$. The umbilical vein is carefully dissected and placed in ice-cold, PSS, which is continuously aerated with 95% $O_2$/5% $CO_2$ to maintain pH at 7.4. Excess connective tissue is removed, and rings 2–3 mm in length are prepared. The rings are mounted between stainless steel wires in water-jacketed tissue baths for measuring contractile function. The rings are attached to a force-displacement transducer for measuring tension development. The baths contain 15 mL of oxygenated PSS maintained at 37° C.

After mounting, resting tension is adjusted to 1.0 g and the rings are equilibrated for 60 minutes before beginning the experiment. The tissue baths are rinsed with fresh PSS 30 min and 60 min after mounting the rings. Following each rinse, the resting tension is adjusted to 1.0 g. After the equilibration period, the rings are depolarized by adding increasing concentrations of KCl to the tissue bath until a maximum increase in tension is obtained. The bath is rinsed with fresh PSS, and the resting tension readjusted to 1.0 g. the response to KCl is repeated two additional times at 30-min intervals. The maximum increases in tension obtained following the second and third assessments of the response to KCl are averaged. The value is used to normalize the direct response to the test compound, and also the response to a reference bradykinin receptor agonist.

Evaluating an Antagonist Effect: After assessing the responses to KCl, the test compound is added to the tissue bath. Thirty minutes later, the following concentrations of desArg$^{10}$ Kallidin are added to the tissue bath: 0.01, 0.03, 0.1, 0.3, 1, 3, 10, 30, 100 nM. The response to each concentration of desArg$^{10}$ Kallidin is normalized as a percentage of the maximum constrictor response to KCl.

Evaluating a Direct Effect: After assessing the responses to KCl, the following concentrations of the test compound are added to the tissue bath: 1, 3, 10, 30, 100, 300, 1000, 3000 and 10000 nM. Alternatively, an equivalent volume of the vehicle used to solubilize the test compound is added to the tissue baths. Each new concentration is added to the bath after the response to the previous concentration has reached equilibrium. If no response is obtained, the next concentration of test compound is added to the bath 15 min after the previous concentration.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients, as discussed below. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of the invention or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Pharmaceutical formulations, particularly topical formulations, may additionally comprise steroidal anti-inflammatory drugs, which may include but are not limited to alclometasone dipropionate, amcinonide, beclamethasone dipropionate, betamethasone benzoate, betamethasone dipropionate, betamethasone valerate, budesonide, clobetasol propionate, clobetasone butyrate, desonide, desoxymethasone, diflorasone diacetate, diflucortolone valerate, flumethasone pivalate, fluclorolone acetonide, fluocinolone acetonide, fluocinonide, fluocortin butyl, fluocortolone preparations, fluprednidene acetate, flurandrenolone, halcinonide, hydrocortisone, hydrocortisone acetate, hydrocortisone butyrate, methylprednisolone acetate, mometasone furoate and triamcinolone acetonide.

Pharmaceutical formulations may also additionally comprise steroidal anti-inflammatory drugs for oral administration. These may include but are not limited to finasteride, betamethasone and hydrocortisone.

Alternatively or additionally, pharmaceutical formulations may additionally comprise nonsteroidal anti-inflammatory drugs (NSAIDS), which may include but are not limited to aminoarylcarboxylic acids (fenamic acid NSAIDs), arylacetic acids, arylbutyric acids such as fenbufen, arylpropionic acids (profens), pyrazoles such as epirizole, pyrazolones such as phenylbutazone, salicylic acids such as aspirin, oxicams and other compound classes that may be considered as NSAIDS including leucotriene antagonists. These formulations exhibit both the additive effects of the individual components and synergistic effects from blocking of multiple pathways in the pain and inflammation pathway.

Propionic acid NSAIDs are non-narcotic analgesics/ nonsteroidal antiinflammatory drugs having a free —CH(CH$_3$)COOH group, which optionally can be in the form of a pharmaceutically acceptable salt group, e.g., —CH(CH$_3$)COO$^-$Na$^+$. The propionic acid side chain is typically attached directly or via a carbonyl function to a ring system, preferably to an aromatic ring system. Exemplary propionic acid NSAIDS include: ibuprofen, indoprofen, ketoprofen, naproxen, benoxaprofen, flurbiprofen, fenoprofen, pirprofen, carpofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group. Profens, as well as NSAIDs from other classes, may exhibit optical isomerism. The invention contemplates the use of pure enantiomers and mixtures of enantiomers, including racemic mixtures, although the use of the substantially optically pure eutomer will generally be preferred.

Acetic acid NSAIDs are non-narcotic analgesics/ nonsteroidal antiinflammatory drugs having a free —CH$_2$COOH group (which optionally can be in the form of a pharmaceutically acceptable salt group, e.g. —CH$_2$COO$^-$Na$^+$, typically attached directly to a ring system, preferably to an aromatic or heteroaromatic ring system. Exemplary acetic acid NSAIDS include: ketorolac, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Fenamic acid NSAIDs are non-narcotic analgesics/ nonsteroidal antiinflammatory drugs having a substituted N-phenylanthranilic acid structure. Exemplary fenamic acid derivatives include mefenamic acid, meclofenamic acid, flufenamic acid, niflumic acid, and tolfenamic acid.

Biphenylcarboxylic acid NSAIDs are non-narcotic analgesics/nonsteroidal antiinflammatory drugs incorporating the basic structure of a biphenylcarboxylic acid. Exemplary biphenyl-carboxylic acid NSAIDs include diflunisal and flufenisal.

Oxicam NSAIDs are N-aryl derivatives of 4-hydroxyl-1,2-benzothiazine 1,1-dioxide-3-carboxamide. Exemplary oxicam NSAIDs are piroxicam, tenoxicam sudoxicam and isoxicam.

Pharmaceutical formulations may also include cyclooxygenase (COX) inhibitors (including arylpropionic acids such as ibuprofen and salicylic acids such as aspirin), selective cyclooxygenase-1 (COX-1) inhibitors or selective cyclo-oxygenase-2 (COX-2) inhibitors such as rofecoxib or celecoxib. These formulations also exhibit both the additive effects of the individual components and synergistic effects from blocking of multiple pathways in the pain and inflammation pathway.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia. It should be understood that in addition to the ingredients particularly mentioned above, the formulations of this invention may include other agents conventional in the art having regard to the type of formulation in question, for example those suitable for oral administration may include flavoring agents.

Preferred unit dosage formulations are those containing an effective dose, as hereinbelow recited, or an appropriate fraction thereof, of the active ingredient. The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

EXAMPLE 1

Aqueous Suspension for Injection

A suspending vehicle is prepared from the following materials:

| | |
|---|---|
| Polyethylene glycol 4000 | 30 gm. |
| Potassium chloride | 11.2 gm. |
| Polysorbate 80 | 2 gm. |
| Methylparaben | 0.2 gm. |
| Water for injection q.s. | 1000 mL. |

The parabens are added to a major portion of the water and are dissolved therein by stirring and heating to 65° C. The resulting solution is cooled to room temperature and the remainder of the ingredients are added and dissolved. The balance of the water to make up the required volume is then added and the solution sterilized by filtration. The sterile vehicle thus prepared is then mixed with 3 gm of $B_1$-BK inhibitor of the invention (e.g. compound 10), which has been previously reduced to a particle size less than about 10 microns and sterilized with ethylene oxide gas. This mixture may then be mixed, optionally, with 5 gm of an antiinflammatory (e.g. hydrocortisone), which has been previously reduced to a particle size less than about 10 microns and sterilized with ethylene oxide gas. The mixture is passed through a sterilized colloid mill and filled under aseptic conditions into sterile containers which are then sealed.

EXAMPLE 2

Water-washable Cream

The following ingredients are formulated:

| Ingredients | Percent w/w |
|---|---|
| Hydrocortisone acetate | 0.025 |
| Compound 10 | 0.025 |
| Mineral Oil | 6.0 |
| Petrolatum | 15.0 |
| Polyethylene glycol 1000 monocetyl ether | 1.8 |
| Cetostearyl alcohol | 7.2 |
| Chlorocresol | 0.1 |
| Distilled water to produce 100 parts by weight | |

The cortisone and $B_1$-BK antagonist 10 are ball-milled with a little mineral oil to a particle size of less than 5 microns. The water is heated to boiling, the chlorocresol added and the solution then cooled to 65° C. Then the petrolatum, cetostearyl alcohol and polyethylene glycol ether are mixed together while heating to 65° C. The milled steroid suspension is then added to the melt rinsing the container with mineral oil. The active ingredient oily phase thus prepared is added at 60° C. to the chlorocresol aqueous phase at 65° C. The mixture is stirred rapidly while cooling past the gelling point (40°–45° C.) and the stirring is continued at a speed sufficiently slow to permit the cream to set. The water-washable cream may be used in the treatment of dermatoses using either the open (without occlusion) or occlusive method of drug application. EXAMPLE 3

Topical Ointment

| | |
|---|---|
| Hydrocortisone acetate | 0.05 gm |
| Compound 10 | 1.00 gm. |
| Chloroxine | 1.00 gm. |
| Propylene Glycol | 7.00 gm. |
| Glyceryl monostearate with emulsifier | 5.00 gm. |
| White petrolatum q.s.a.d. | 100.00 gm. |

Heat the propylene glycol to 55° C. Add hydrocortisone acetate, compound 10, and chloroxine and mix well. Add the remaining ingredients and mix until melted. Remove from heat and mix slowly until cooled to 45° C., then homogenize.

EXAMPLE 4

Tablets

| Composition per tablet: | |
|---|---|
| compound 10 | 30 mg |
| Precipitated calcium carbonate | 50 mg |
| Corn Starch | 40 mg |
| Lactose | 73.4 mg |
| Hydroxypropylcellulose | 6 mg |
| Magnesium stearate | (0.05 mL) |
| Total | 200.0 mg |

Compound 10, precipitated calcium carbonate, corn starch, lactose and hydroxypropylcellulose are mixed together, water is added, and the mixture is kneaded, then dried in vacuum at 40° C. for 16 hours, ground in a mortar and passed through a 16-mesh sieve to give granules. To this is added magnesium stearate and the resultant mixture is made up into tablets each weighing 200 mg on a rotary tableting machine.

TABLE 1

| STRUCTURE | Identifier |
| --- | --- |
| 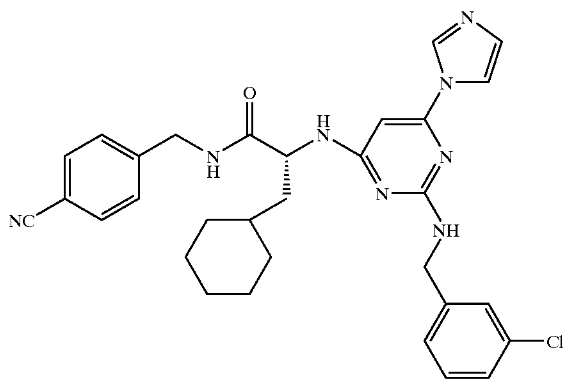 | 978163 |
| 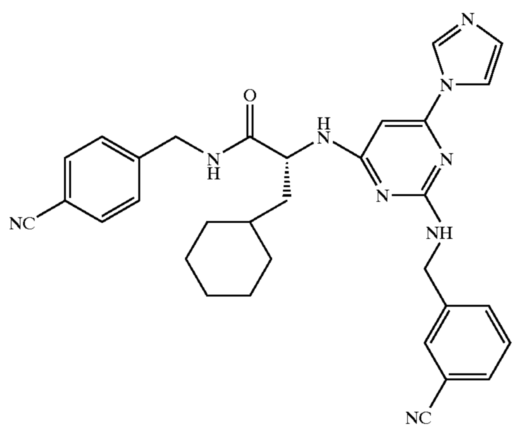 | 645199 |
| 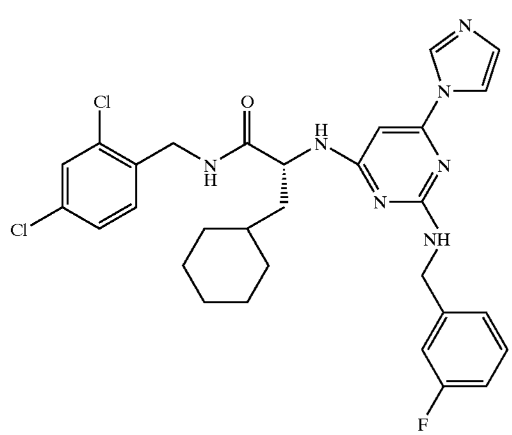 | 283326 |

TABLE 1-continued
| STRUCTURE | Identifier |
|---|---|
| 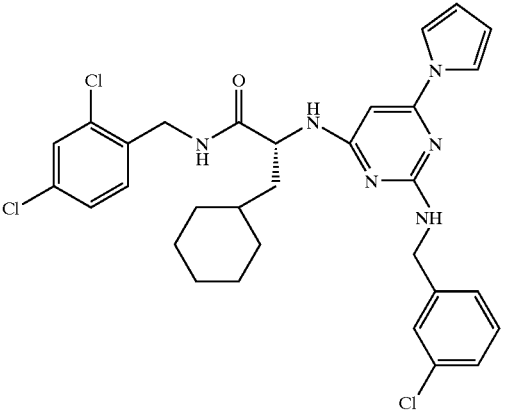 | 309799 |
| 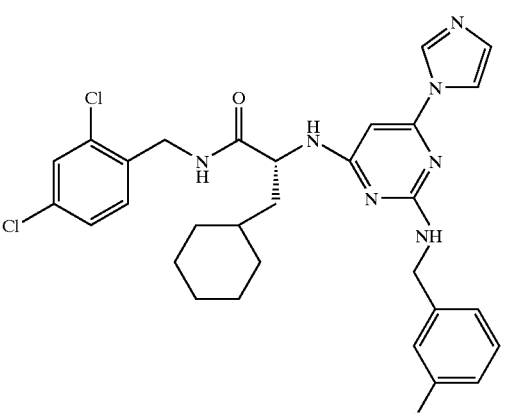 | 322835 |
| 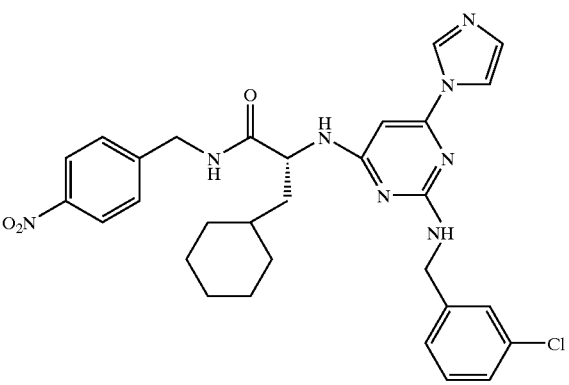 | 697855 |

TABLE 1-continued
| STRUCTURE | Identifier |
|---|---|
| 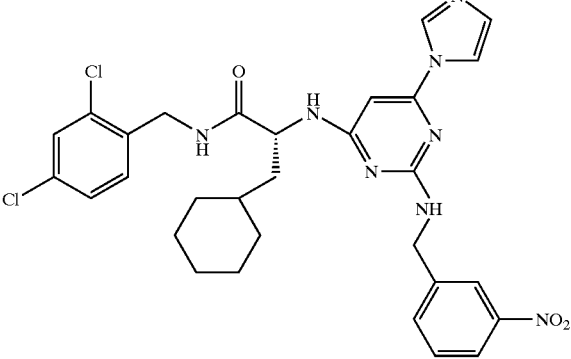 | 999865 |
| 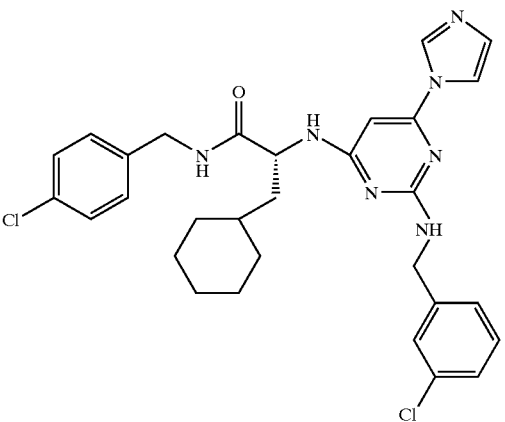 | 294578 |
| 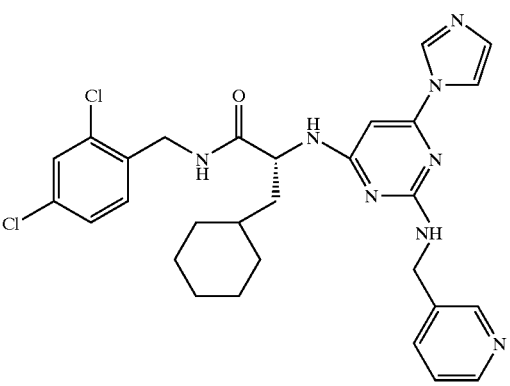 | 182337 |
| 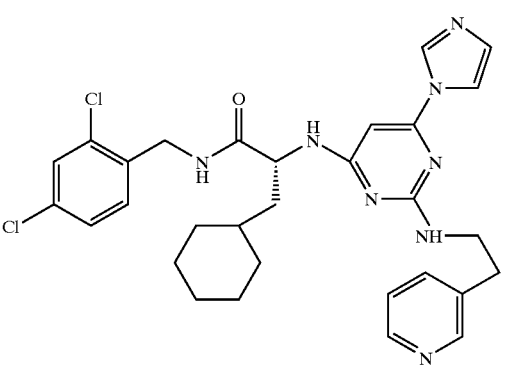 | 214748 |

TABLE 1-continued
| STRUCTURE | Identifier |
|---|---|
| 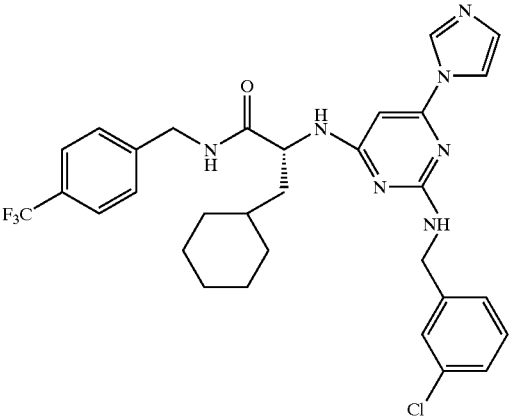 | 531746 |
| 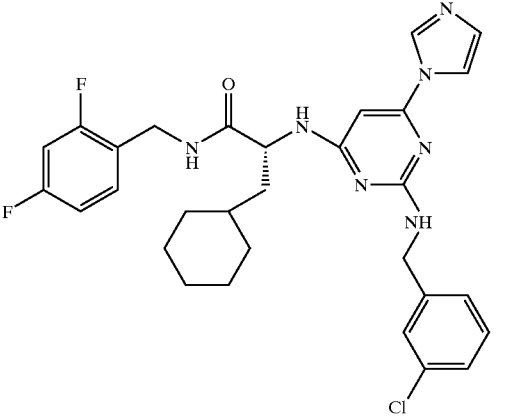 | 835218 |
| 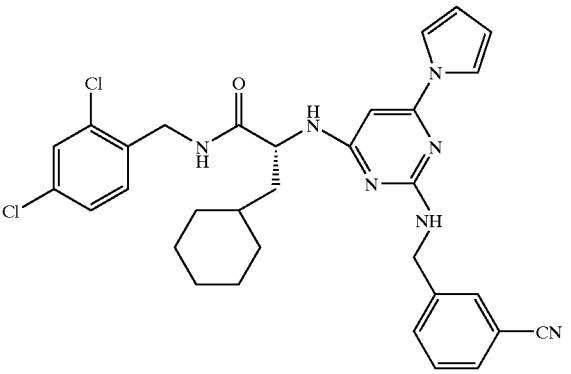 | 146684 |

TABLE 1-continued
| STRUCTURE | Identifier |
|---|---|
| 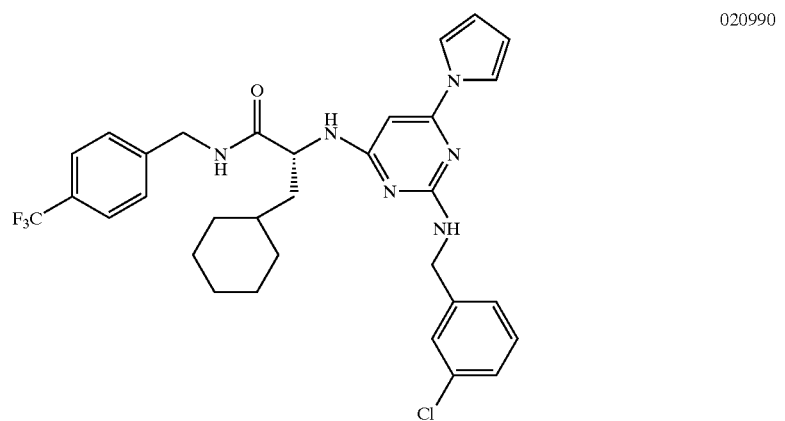 | 020990 |
| 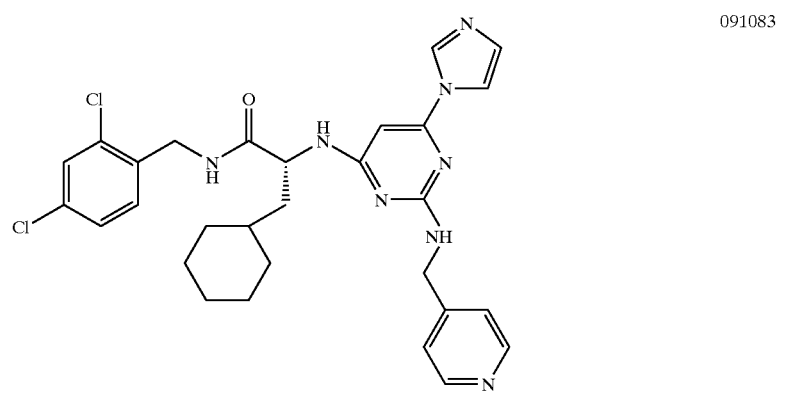 | 091083 |
| 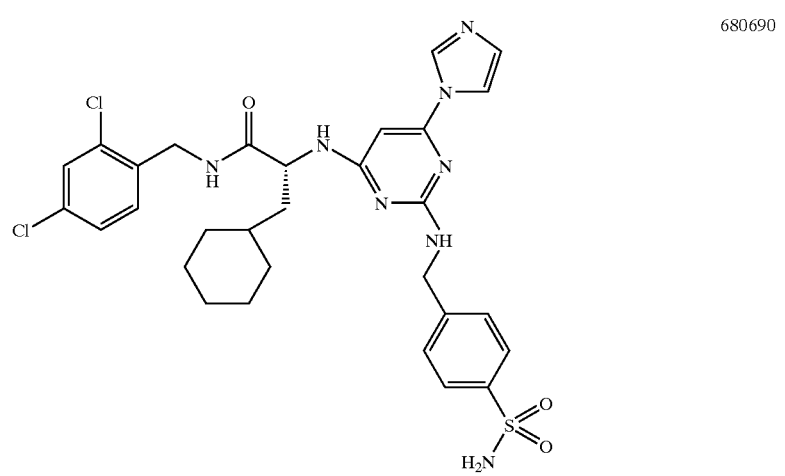 | 680690 |

TABLE 1-continued

| STRUCTURE | Identifier |
|---|---|
| 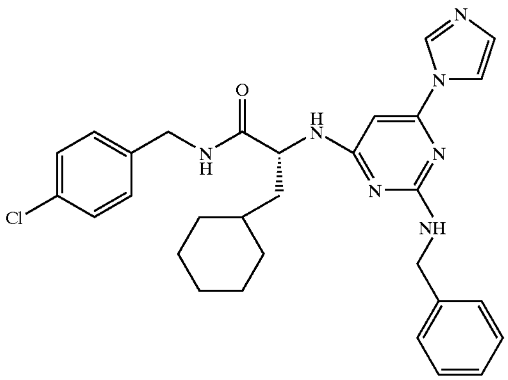 | 022238 |
| 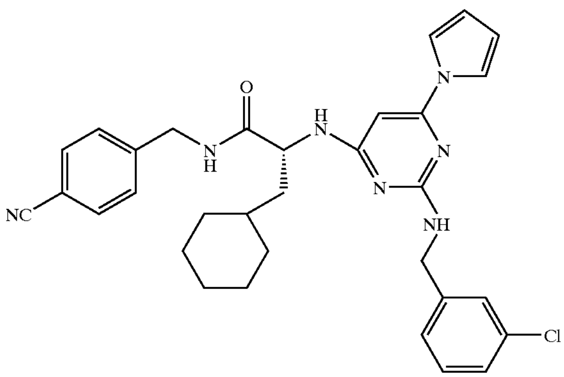 | 292412 |
| 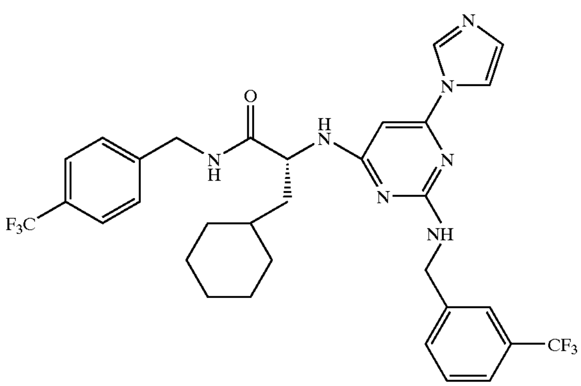 | 337677 |
| 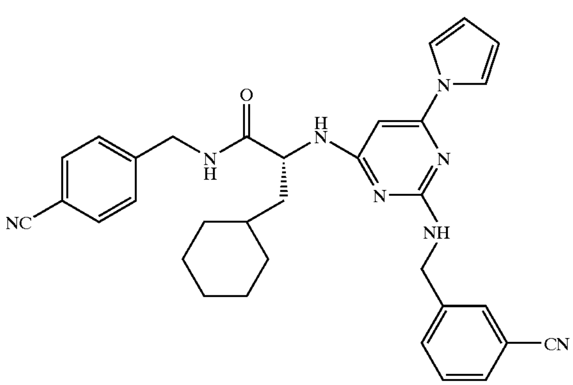 | 596668 |

TABLE 1-continued

| STRUCTURE | Identifier |
|---|---|
| 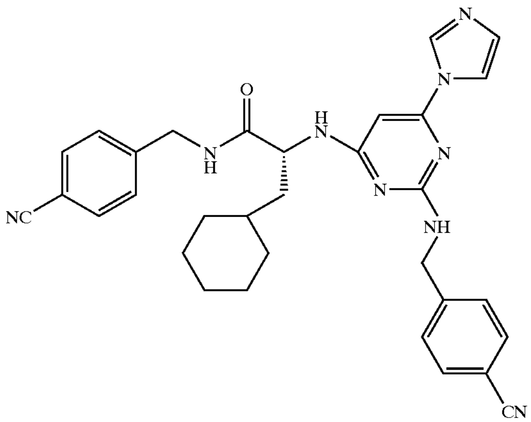 | 680800 |
| 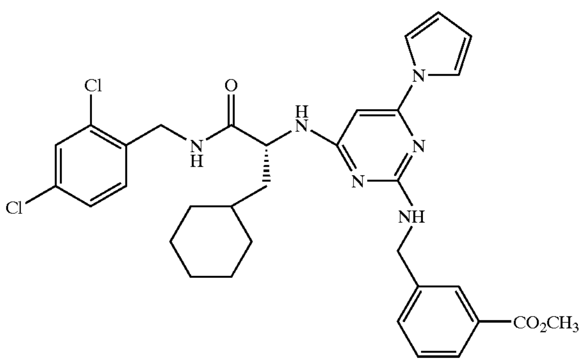 | 919044 |
| 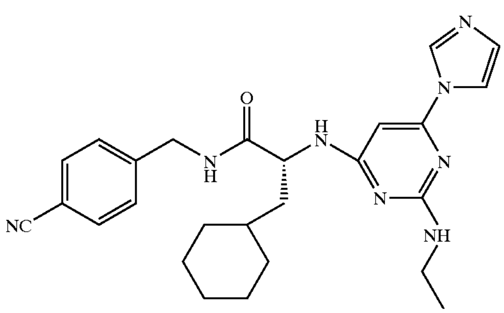 | 234134 |
| 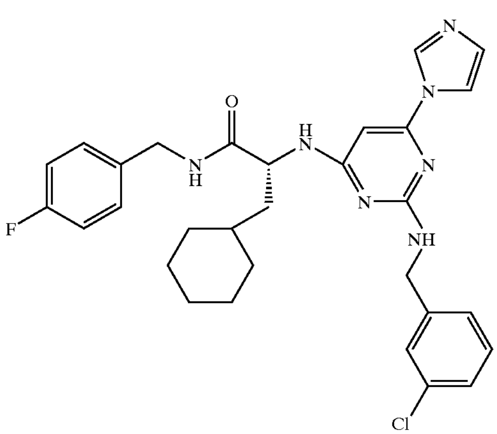 | 120005 |

TABLE 1-continued

| STRUCTURE | Identifier |
|---|---|
| 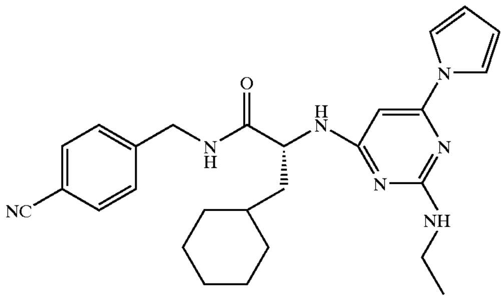 | 247664 |
| 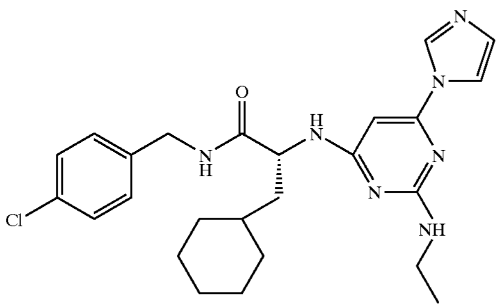 | 115870 |
| 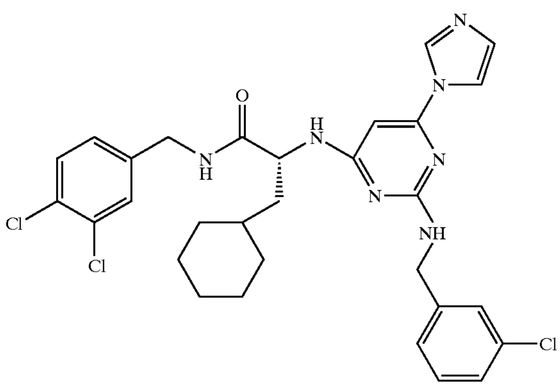 | 179617 |
| 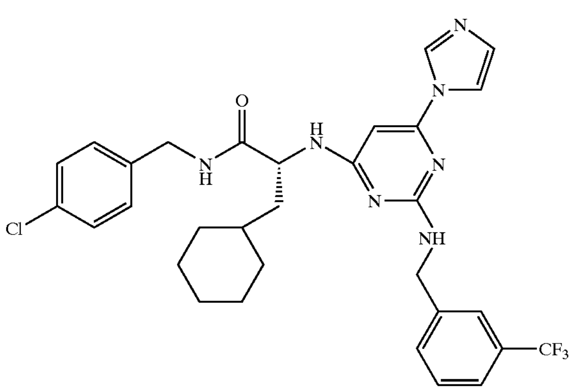 | 249564 |

TABLE 1-continued

| STRUCTURE | Identifier |
| --- | --- |
| 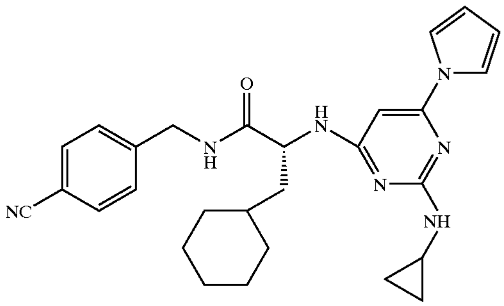 | 109900 |
| 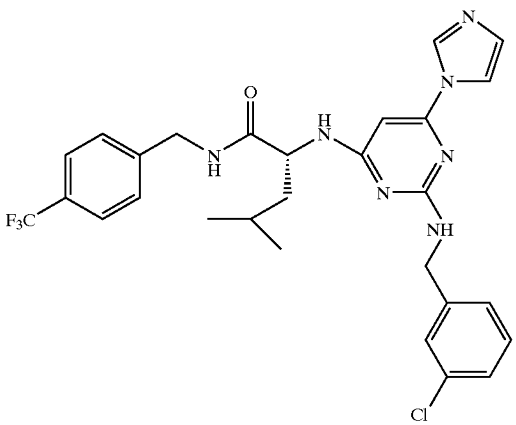 | 240885 |
| 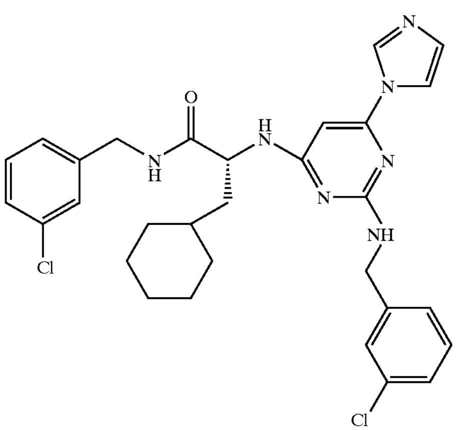 | 003493 |
| 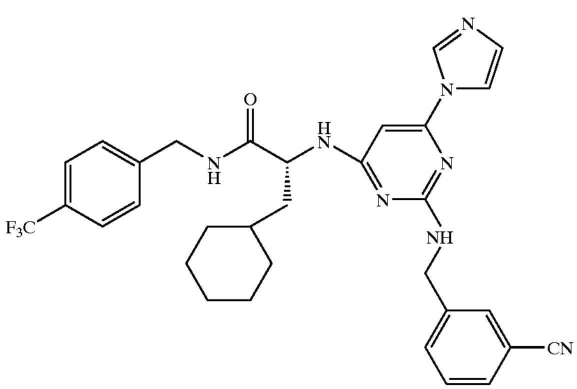 | 042066 |

TABLE 1-continued
| STRUCTURE | Identifier |
|---|---|
| 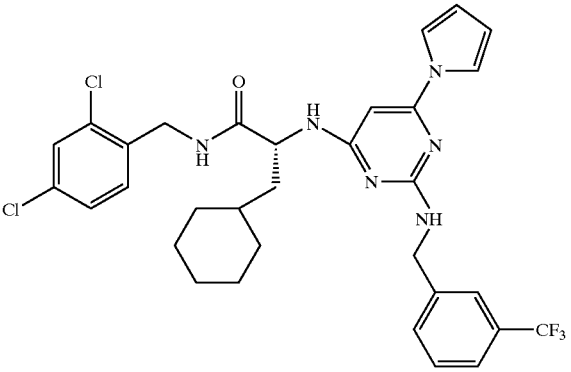 | 300801 |
| 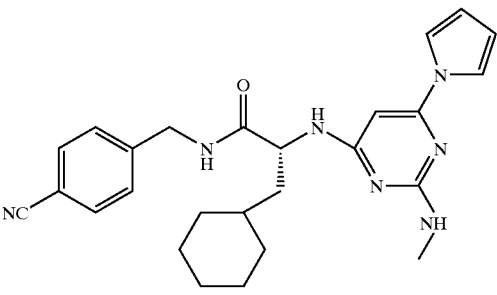 | 730438 |
| 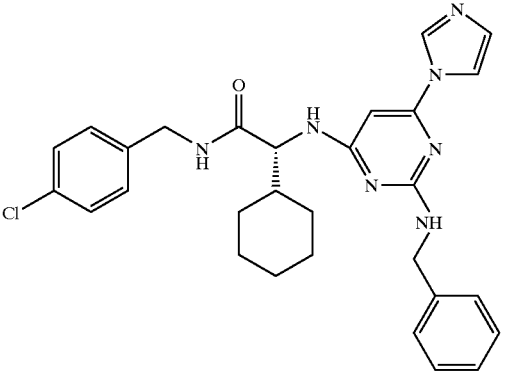 | 207077 |
| 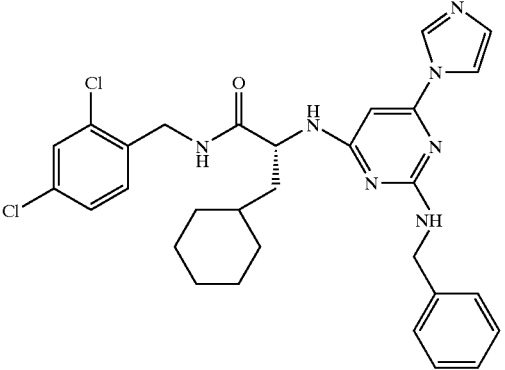 | 708899 |

TABLE 1-continued
| STRUCTURE | Identifier |
|---|---|
| 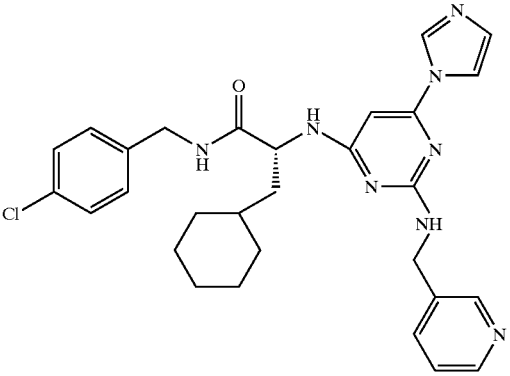 | 568105 |
| 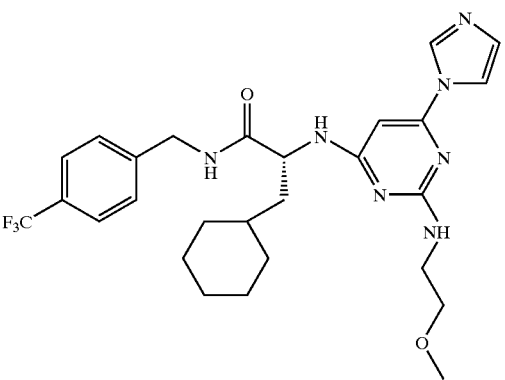 | 422025 |
| 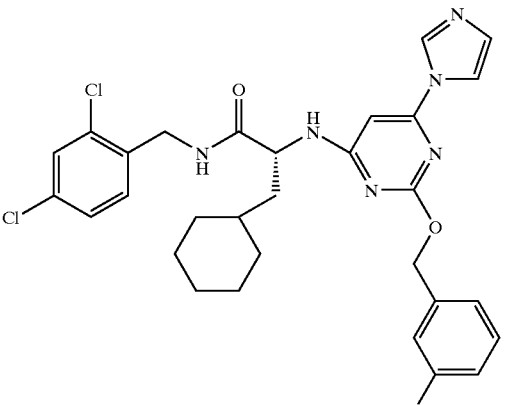 | 323150 |

TABLE 1-continued
| STRUCTURE | Identifier |
|---|---|
| 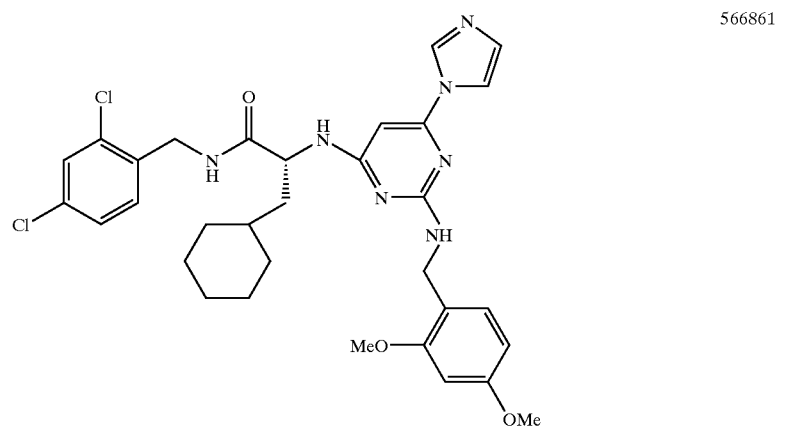 | 566861 |
| 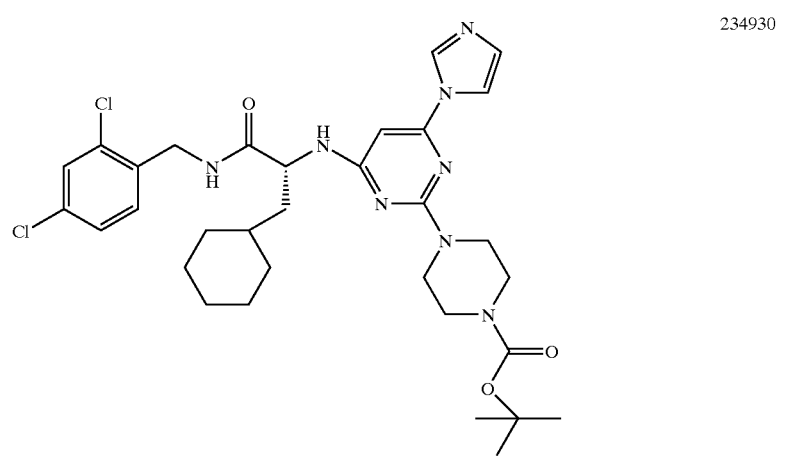 | 234930 |
| 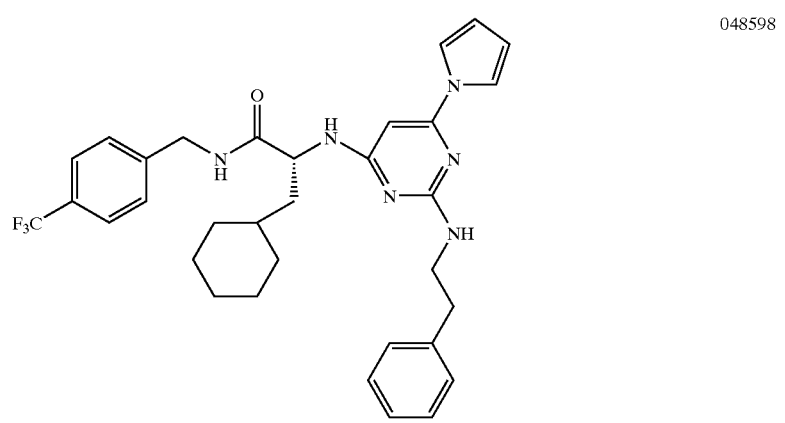 | 048598 |

TABLE 1-continued
| STRUCTURE | Identifier |
|---|---|
| 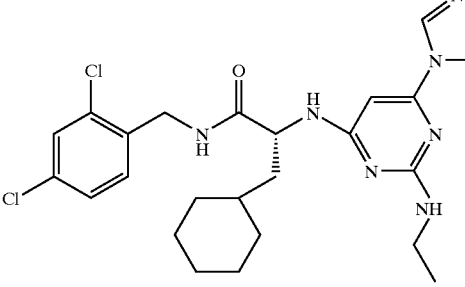 | 000753 |
| 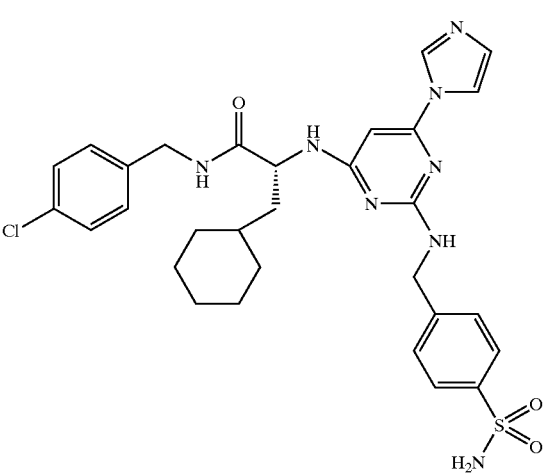 | 406301 |
| 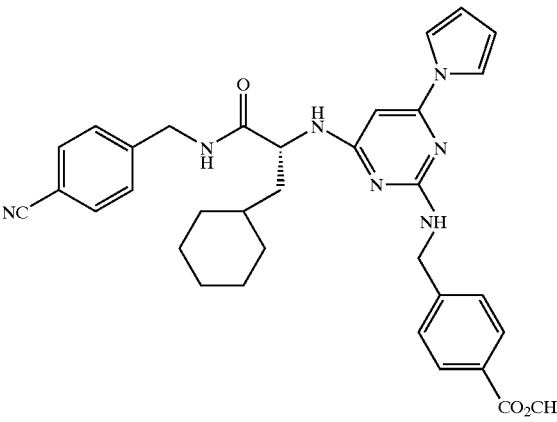 | 320650 |
| 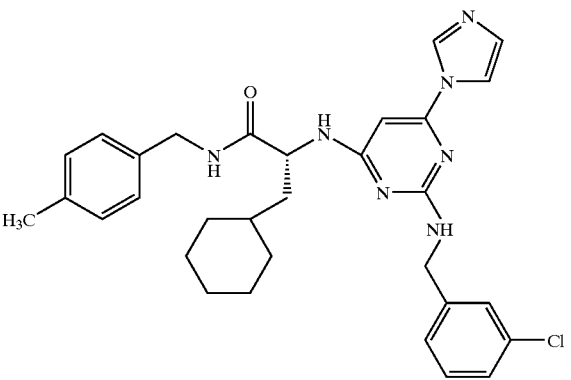 | 189058 |

TABLE 1-continued
| STRUCTURE | Identifier |
|---|---|
| 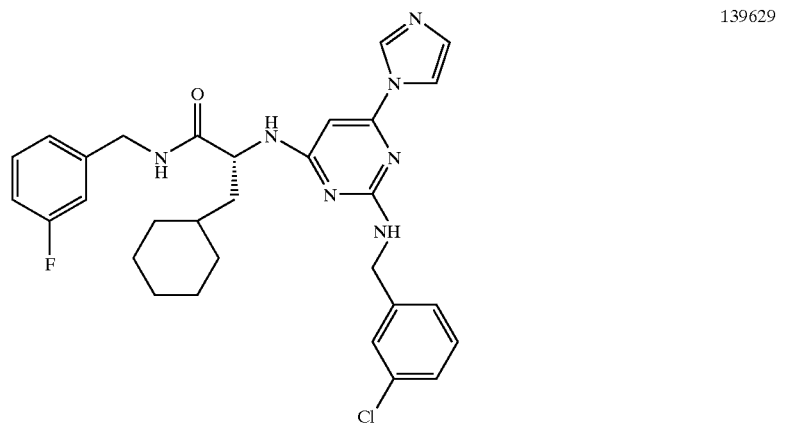 | 139629 |
| 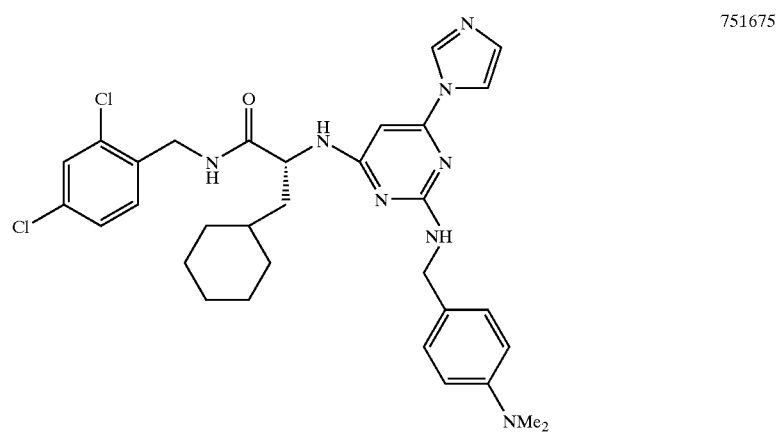 | 751675 |
| 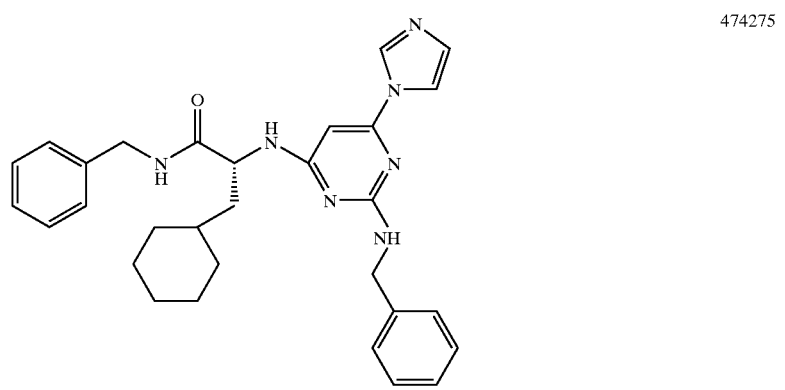 | 474275 |

TABLE 1-continued
| STRUCTURE | Identifier |
|---|---|
| 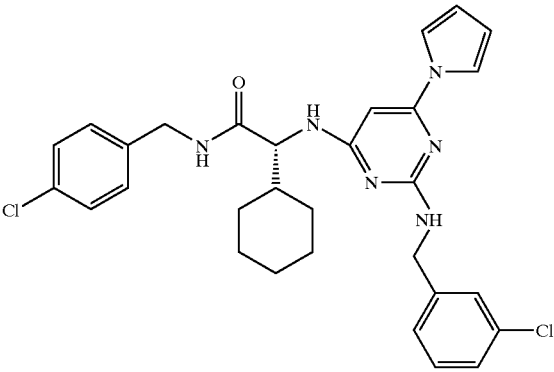 | 172231 |
| 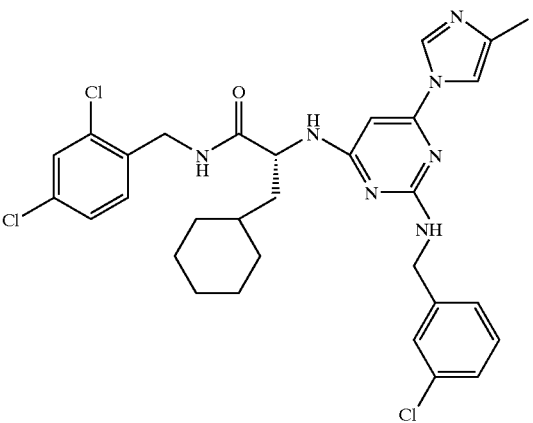 | 726261 |
| 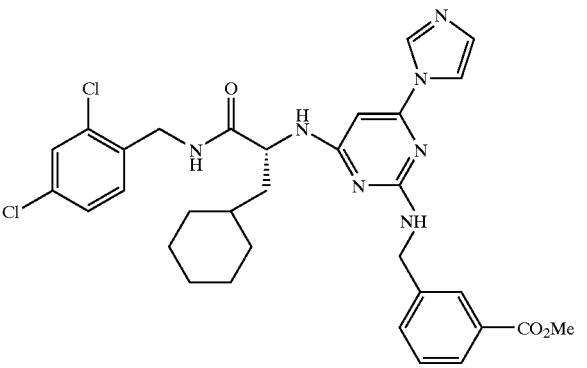 | 751597 |
| 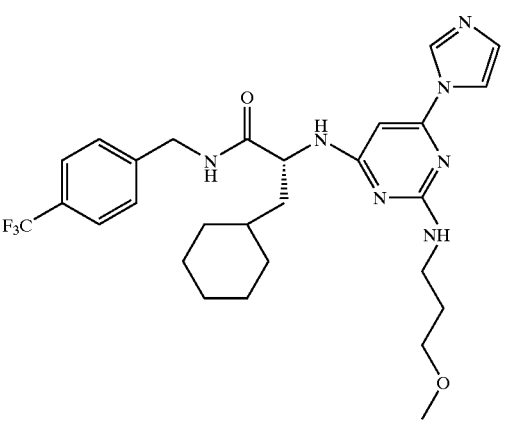 | 696705 |

TABLE 1-continued
| STRUCTURE | Identifier |
|---|---|
| 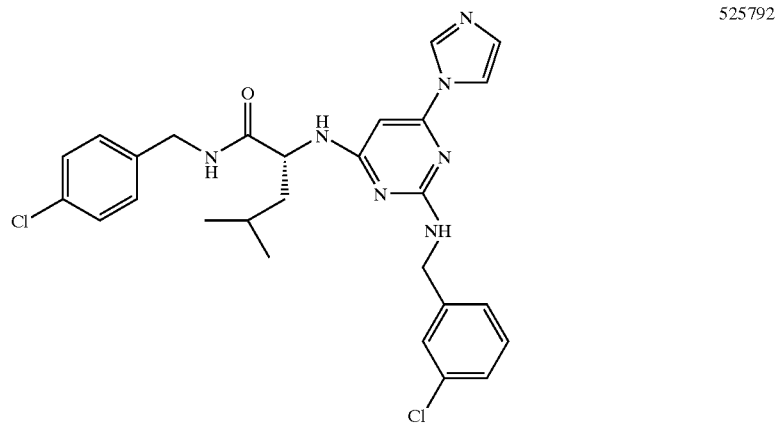 | 525792 |
| 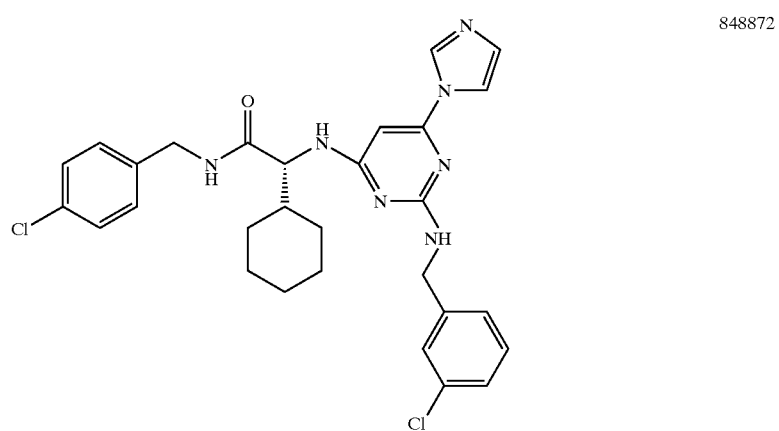 | 848872 |
| 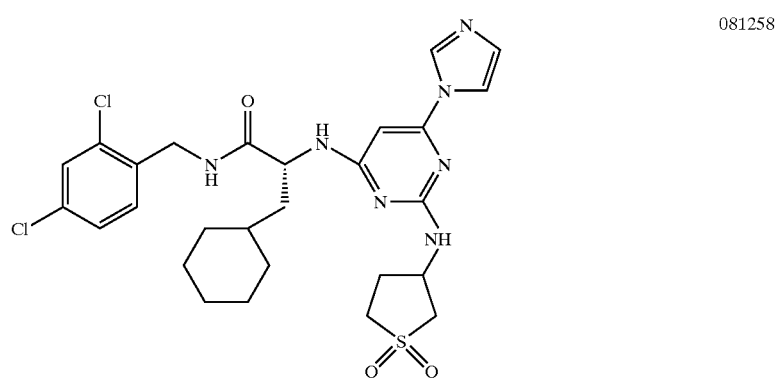 | 081258 |

TABLE 1-continued

| STRUCTURE | Identifier |
|---|---|
| 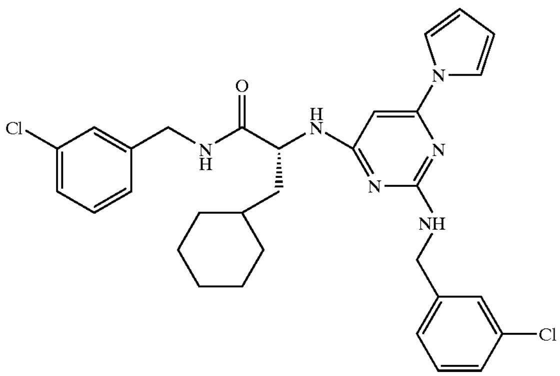 | 599337 |
| 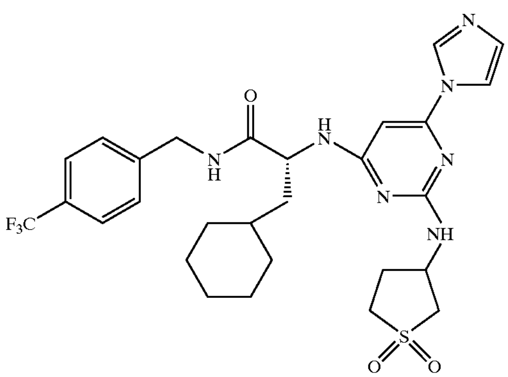 | 579244 |
| | 271260 840374 |
| 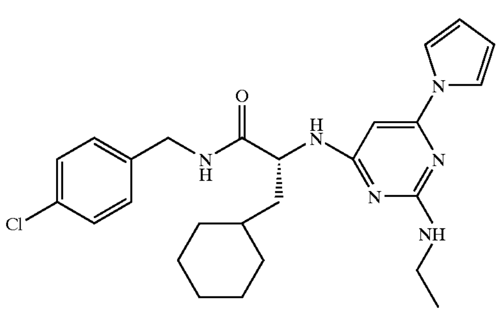 | 278223 |

TABLE 1-continued

| STRUCTURE | Identifier |
| --- | --- |
| 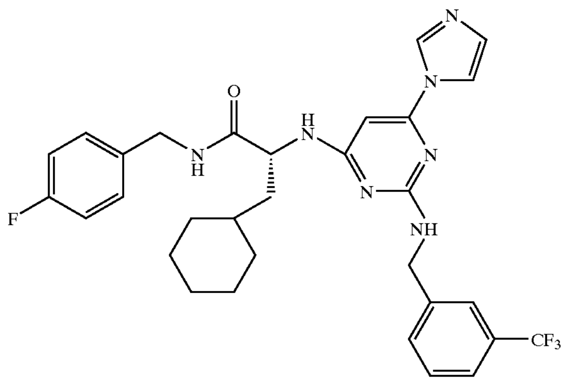 | 020166 |
| 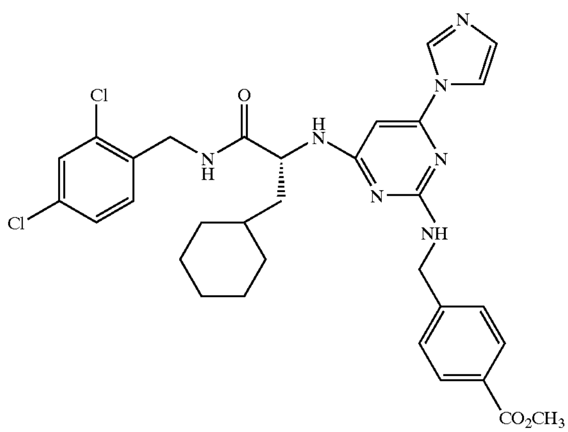 | 683298 |
| 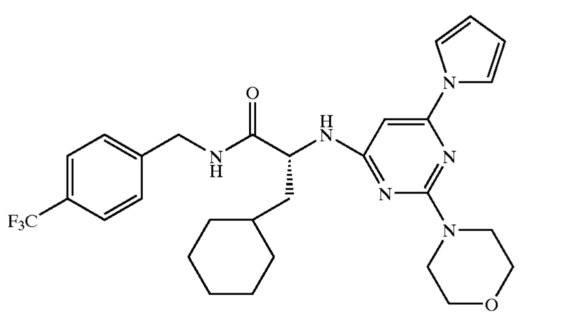 | 595832 |
| 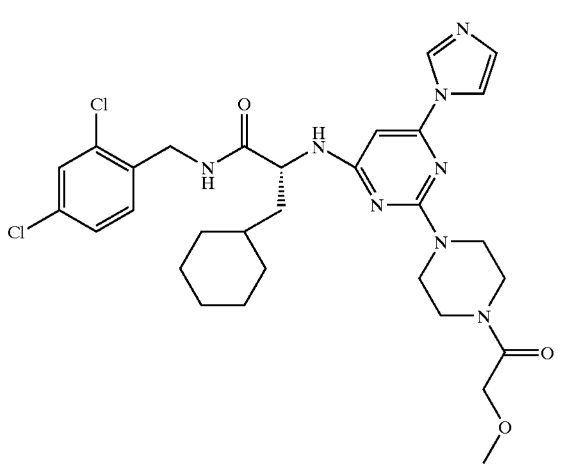 | 306362 |

TABLE 1-continued
| STRUCTURE | Identifier |
|---|---|
| 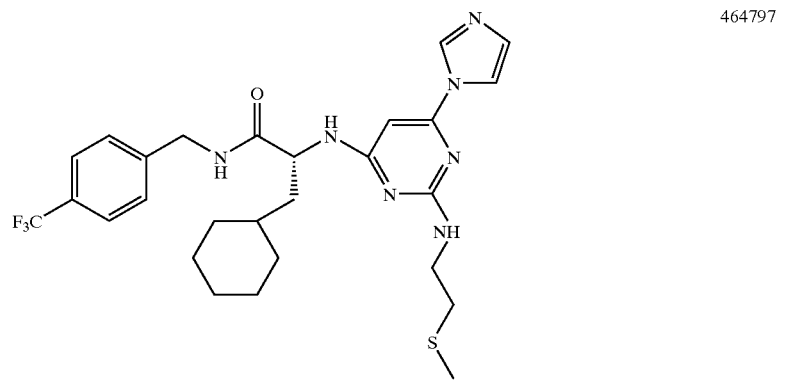 | 464797 |
| 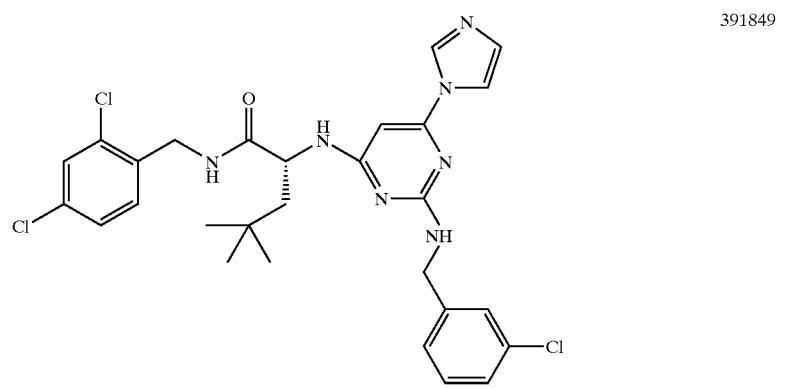 | 391849 |
| 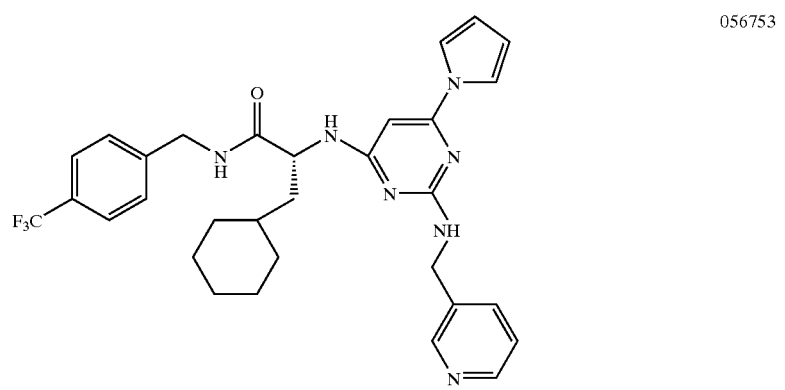 | 056753 |
| 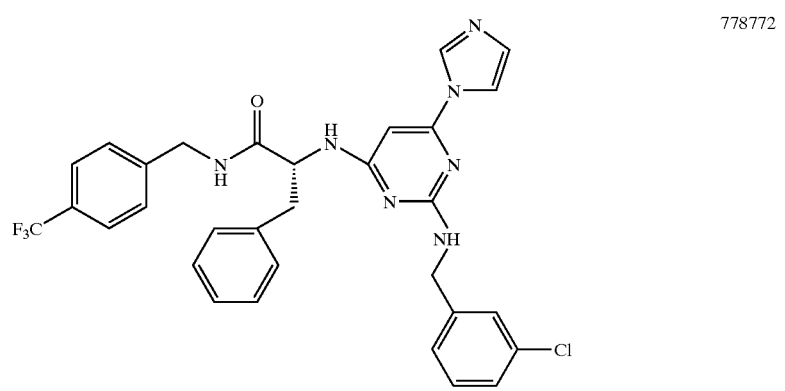 | 778772 |

TABLE 1-continued

| STRUCTURE | Identifier |
|---|---|
| 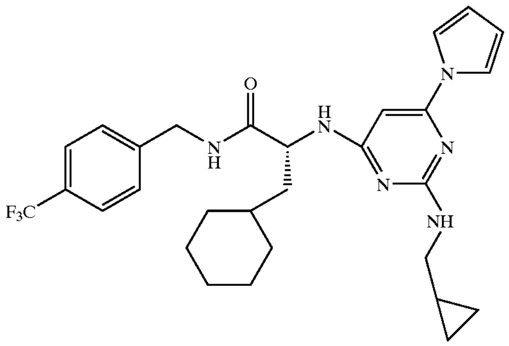 | 190226 |
| 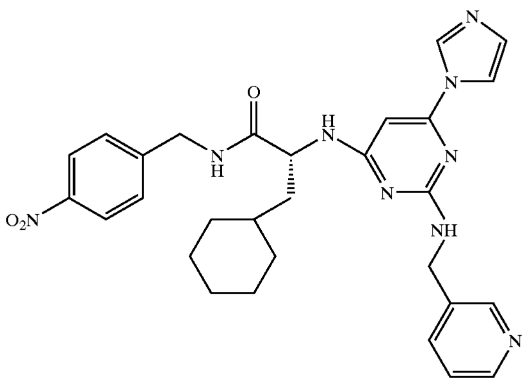 | 481412 |
| 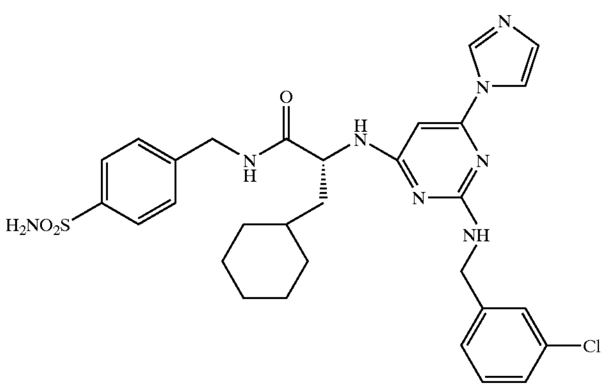 | 862426 |
| 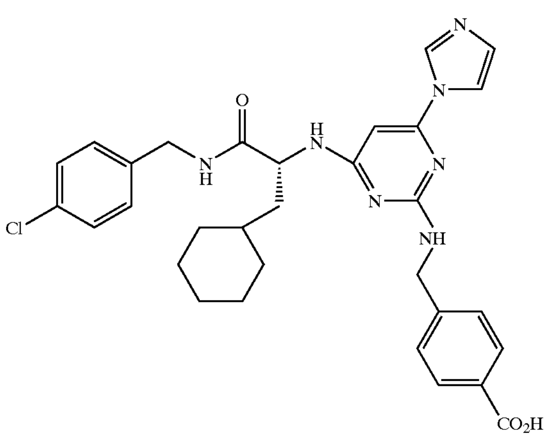 | 417305 |

TABLE 1-continued
| STRUCTURE | Identifier |
|---|---|
| 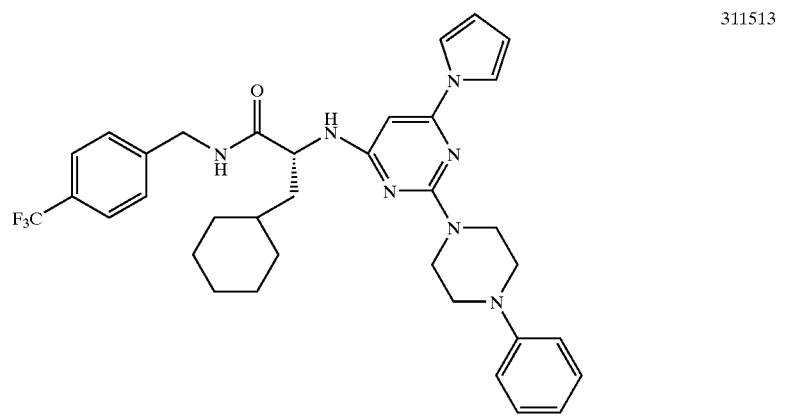 | 311513 |
| 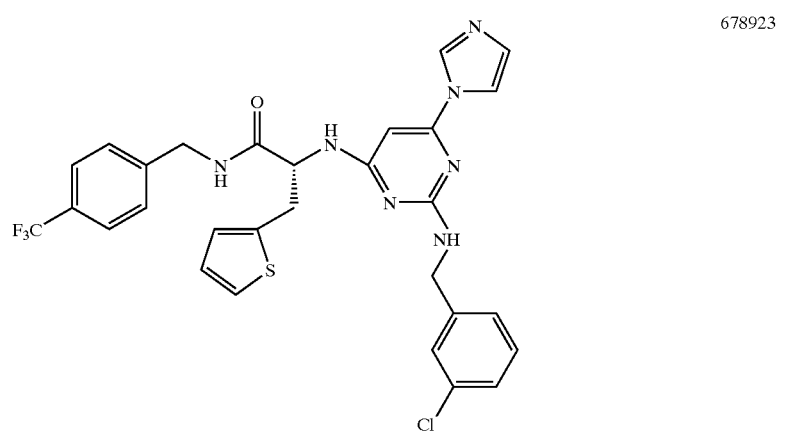 | 678923 |
| 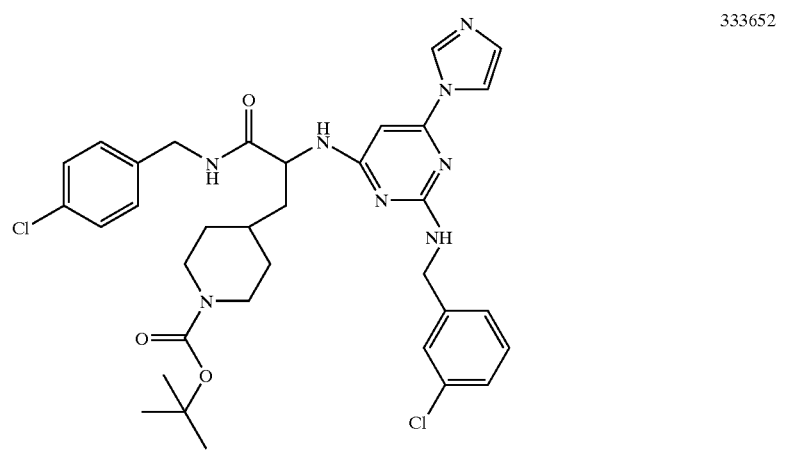 | 333652 |

TABLE 1-continued
| STRUCTURE | Identifier |
|---|---|
| 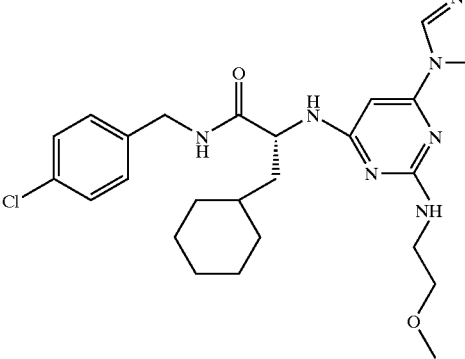 | 614669 |
| 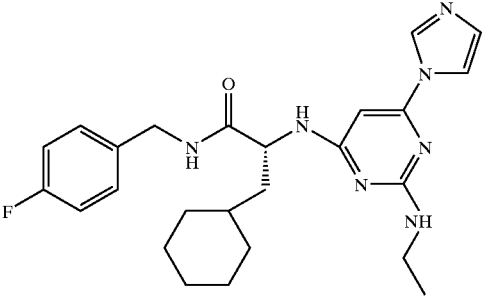 | 700597 |
| 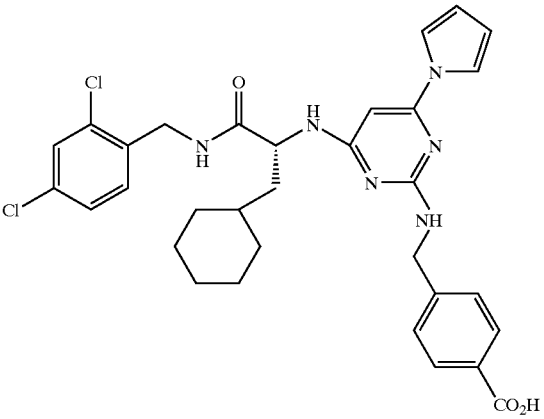 | 533089 |
| 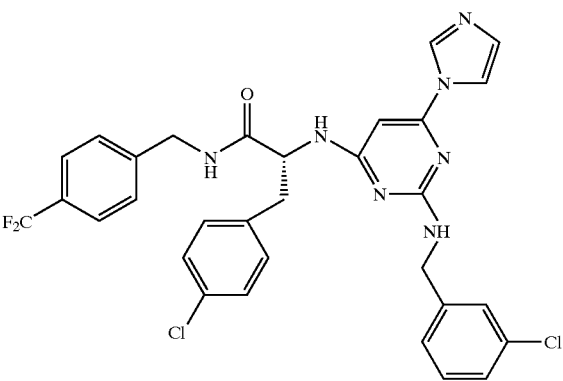 | 912433 |

TABLE 1-continued

| STRUCTURE | Identifier |
| --- | --- |
| 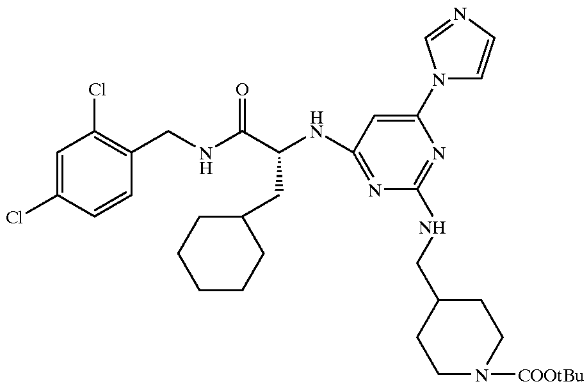 | 292686 |
| 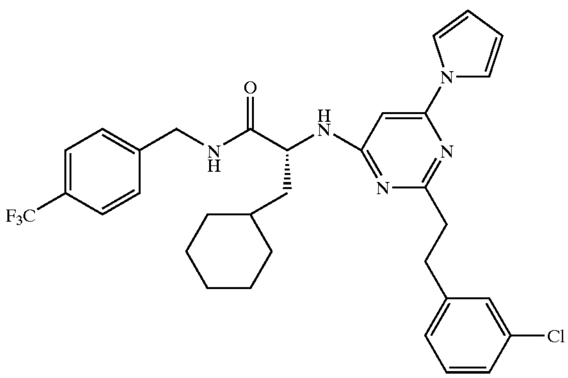 | 082240 |
| 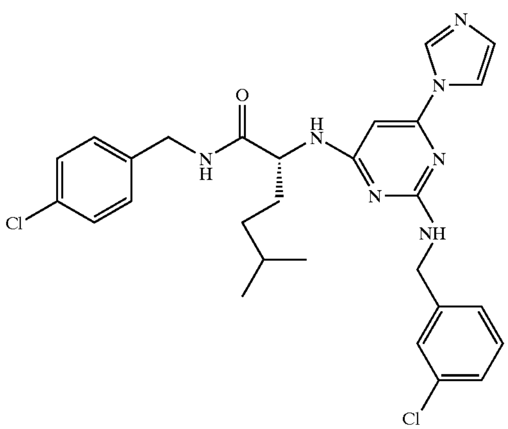 | 296547 |
| 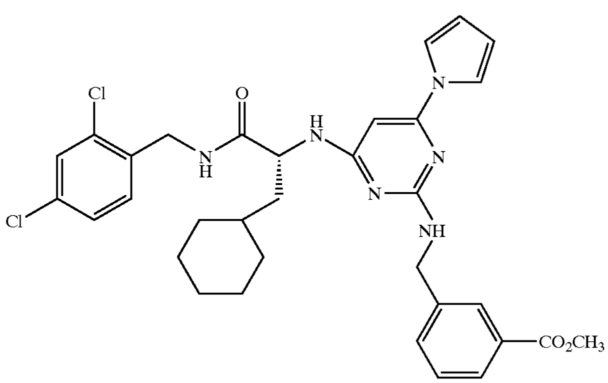 | 917474 |

TABLE 1-continued

| STRUCTURE | Identifier |
| --- | --- |
| 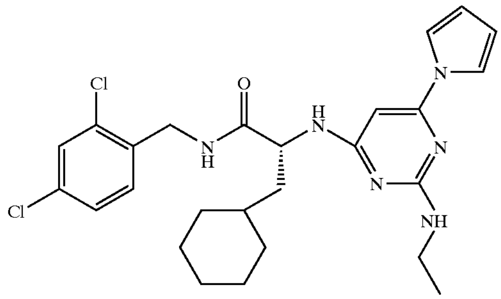 | 923768 |
| 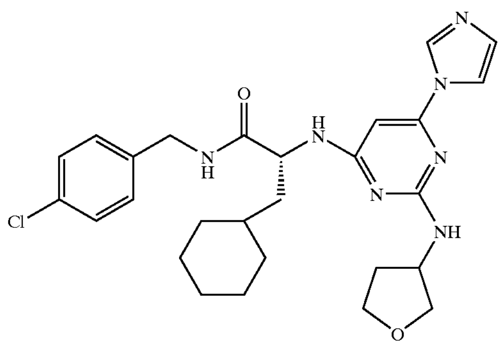 | 482006 |
| 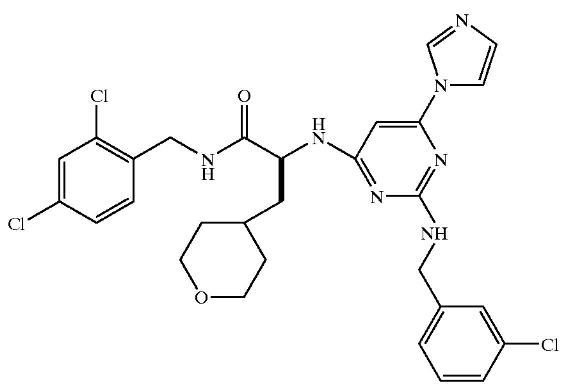 | 040264 |
| 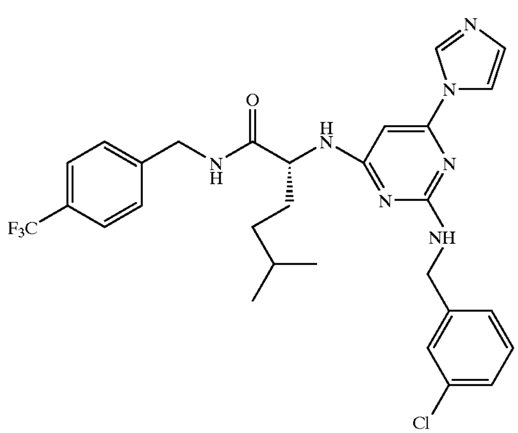 | 917511 |

TABLE 1-continued

| STRUCTURE | Identifier |
| --- | --- |
| 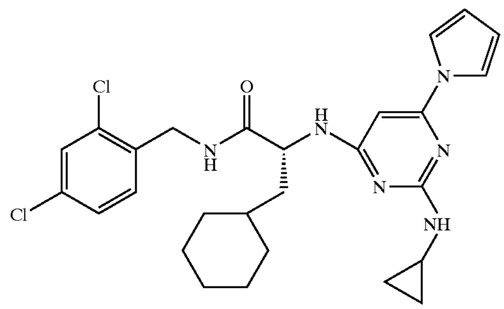 | 559426 |
| 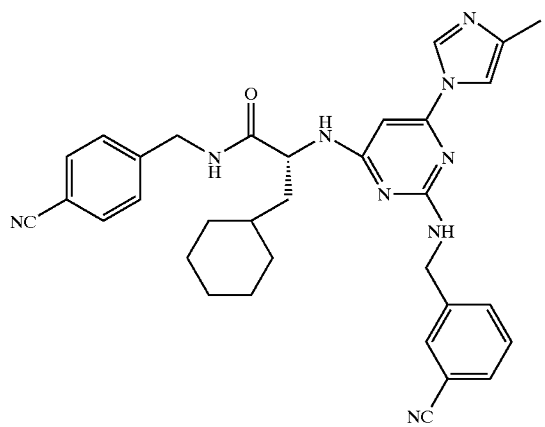 | 552742 |
| 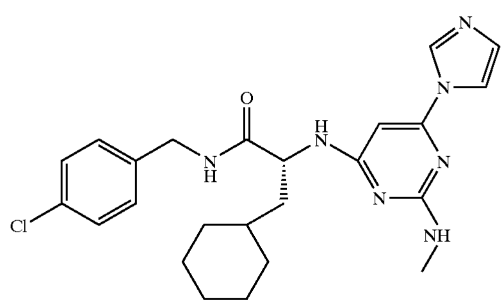 | 489595 |
| 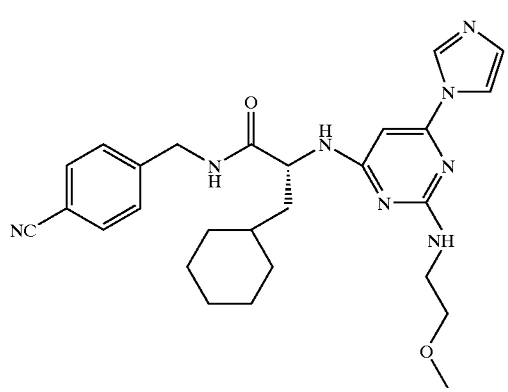 | 045950 |

TABLE 1-continued

| STRUCTURE | Identifier |
| --- | --- |
| 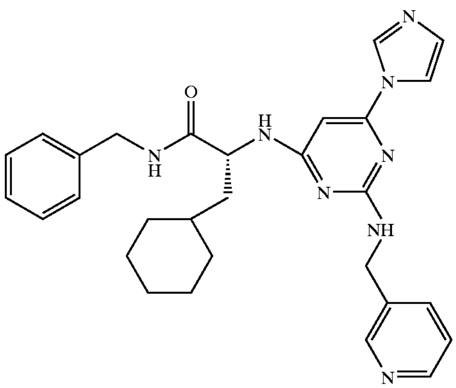 | 070576 |
| 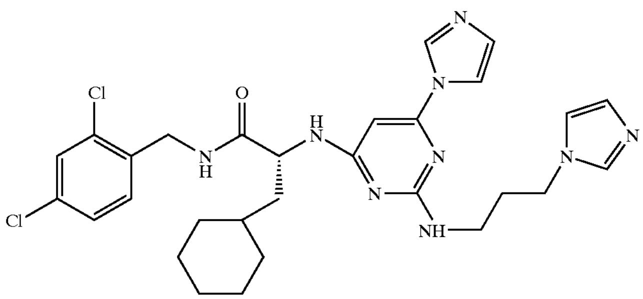 | 251669 |
| 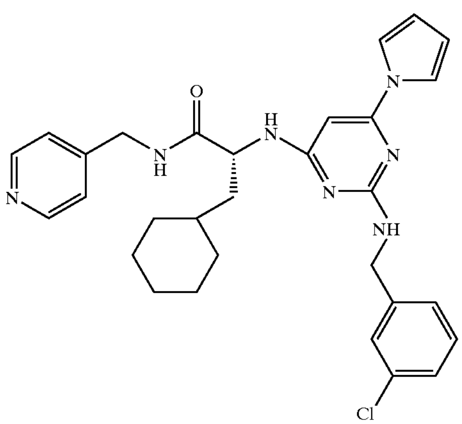 | 167032 |
| 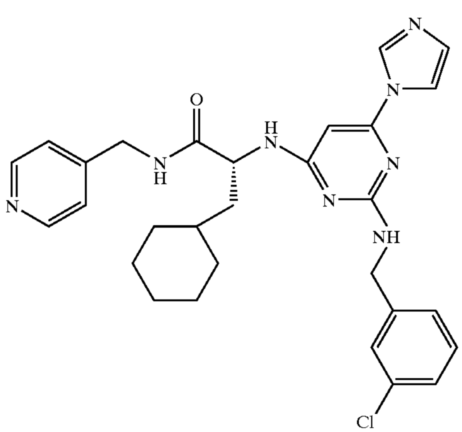 | 190237 |

TABLE 1-continued
| STRUCTURE | Identifier |
|---|---|
| 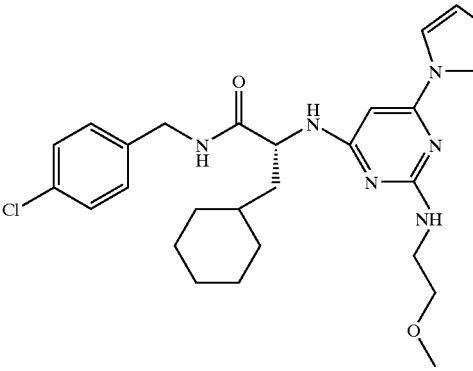 | 307763 |
| 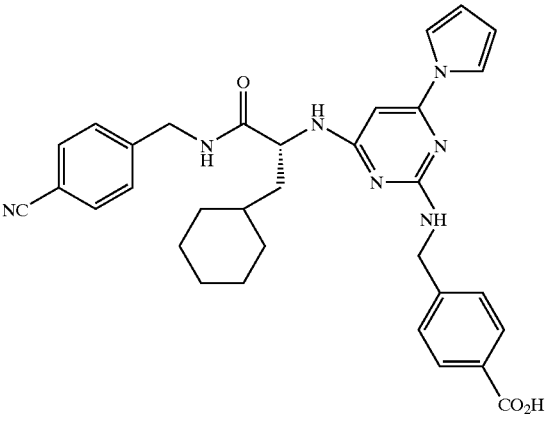 | 832836 |
| 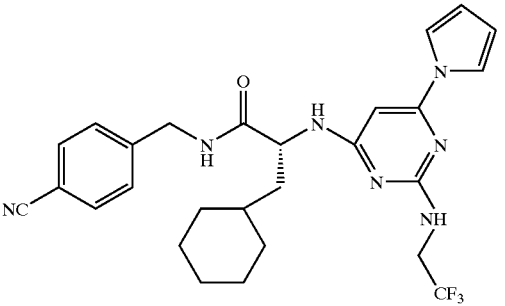 | 310187 |
| 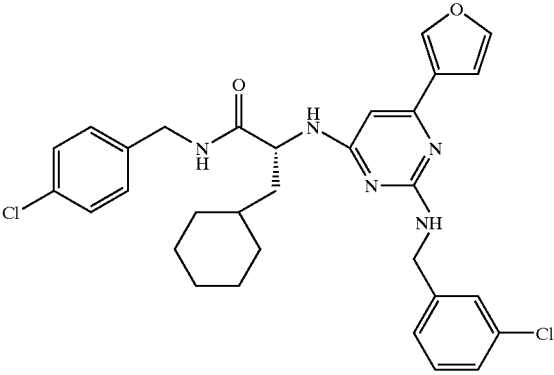 | 369774 |

TABLE 1-continued
| STRUCTURE | Identifier |
|---|---|
| 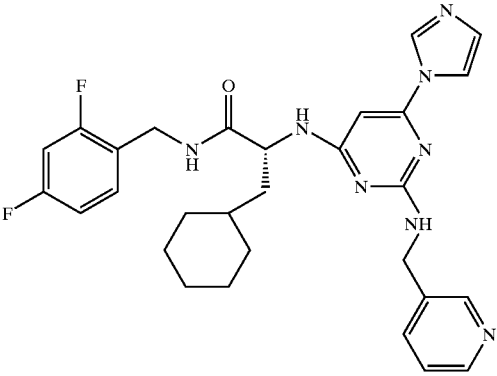 | 833980 |
| 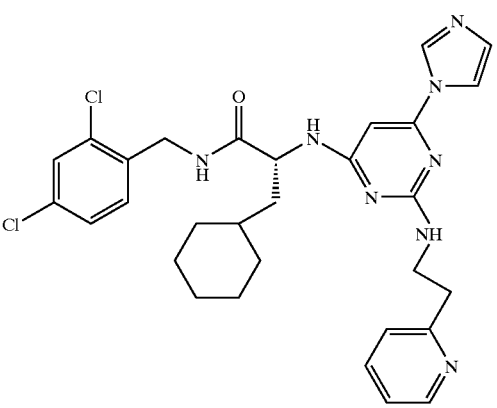 | 191099 |
| 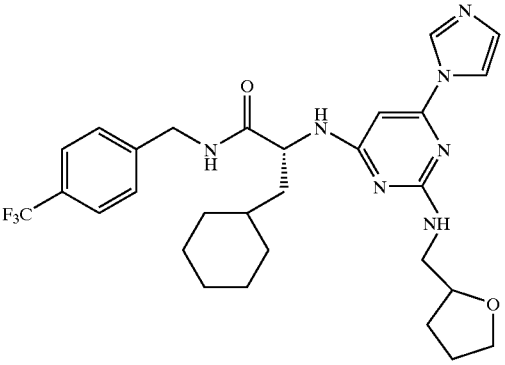 | 087621 |

TABLE 1-continued

| STRUCTURE | Identifier |
| --- | --- |
| 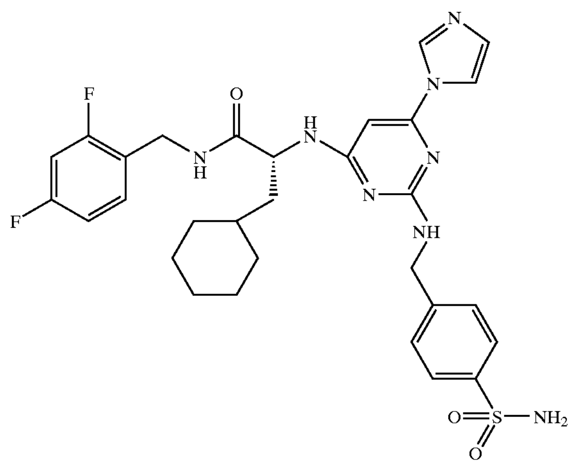 | 288176 |
| 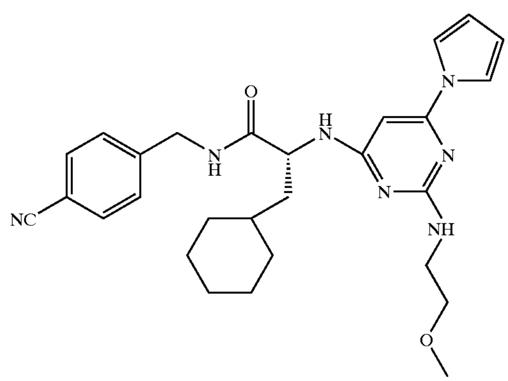 | 630450 |
| 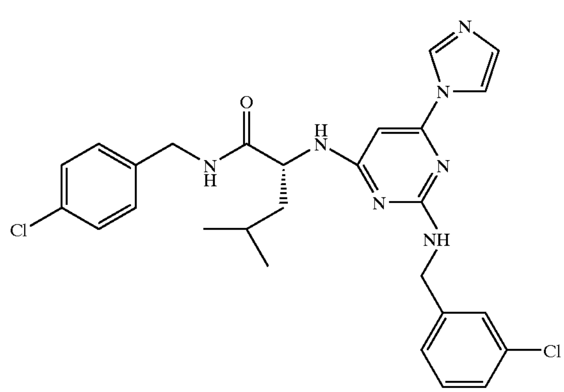 | 714119 |
| 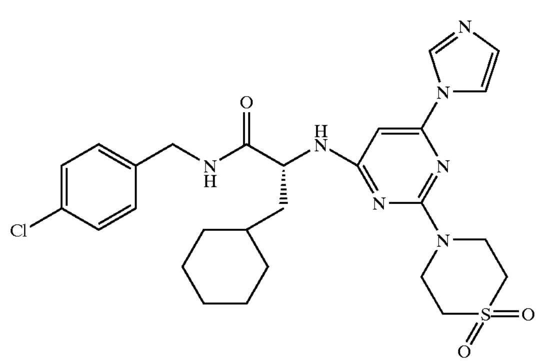 | 124640 |

TABLE 1-continued
| STRUCTURE | Identifier |
|---|---|
| 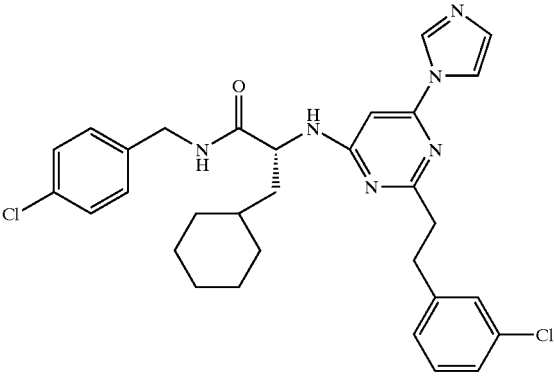 | 506593 |
| 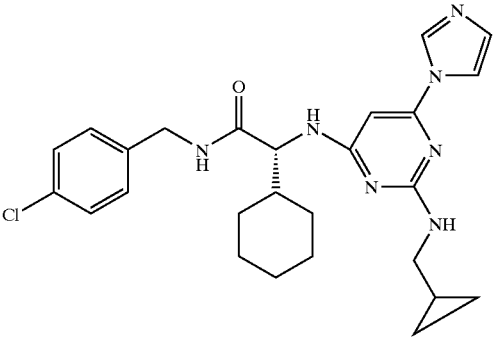 | 340407 |
| 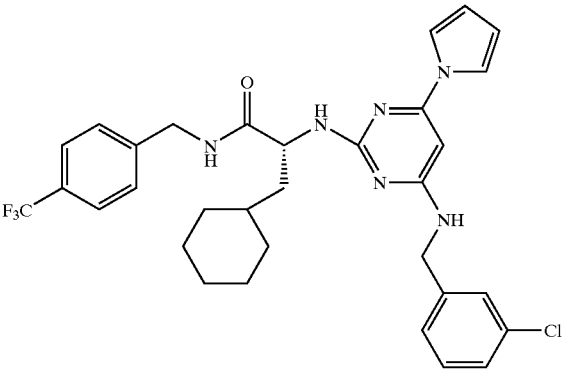 | 036412 |
| 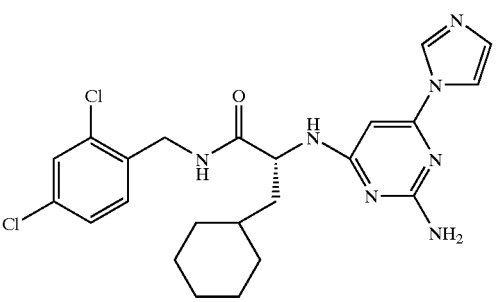 | 884068 |

TABLE 1-continued
| STRUCTURE | Identifier |
| --- | --- |
| 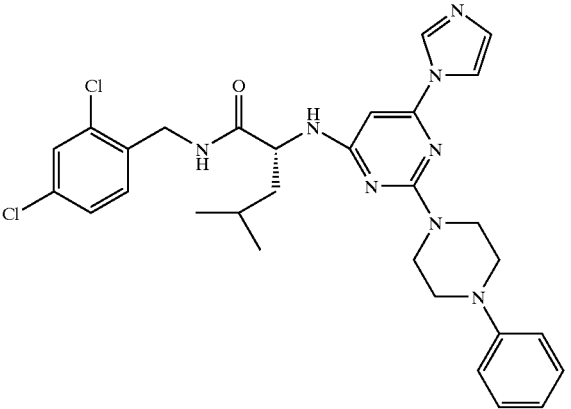 | 768710 |
| 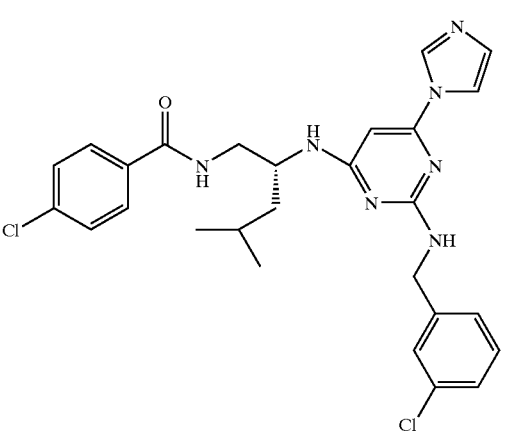 | 207224 |
| 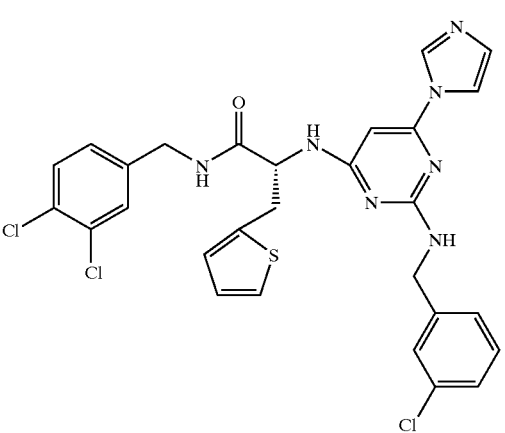 | 221378 |

TABLE 1-continued

| STRUCTURE | Identifier |
| --- | --- |
| 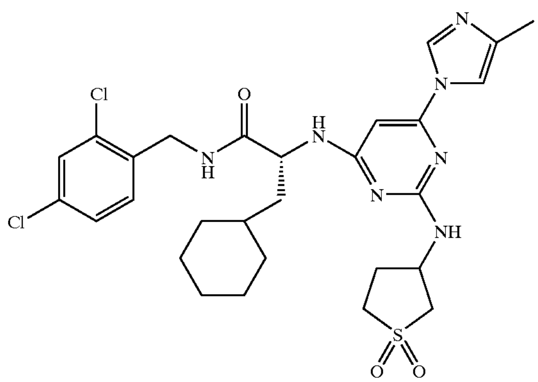 | 183701 |
| 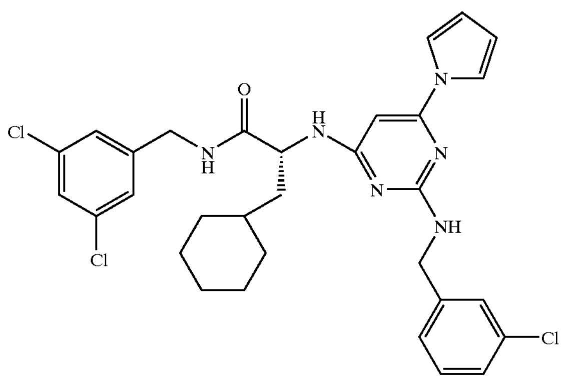 | 389573 |
| 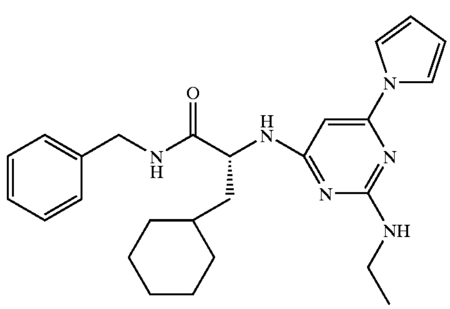 | 936359 |
| 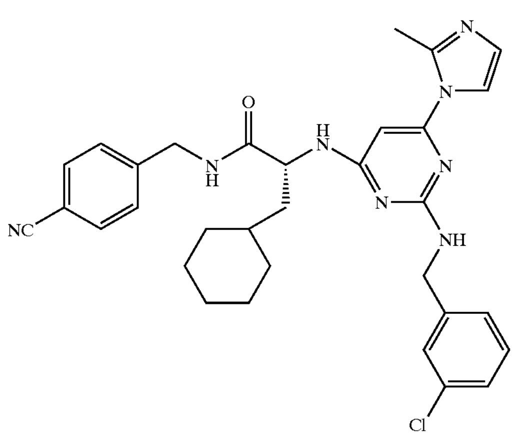 | 019738 |

TABLE 1-continued
| STRUCTURE | Identifier |
|---|---|
| 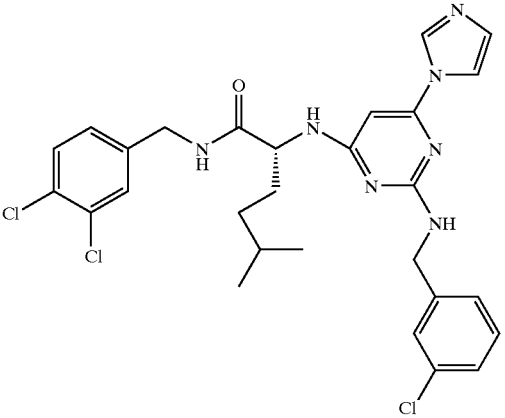 | 736433 |
| 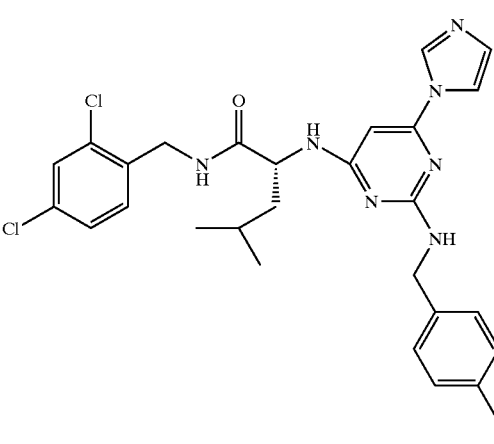 | 604361 |
| 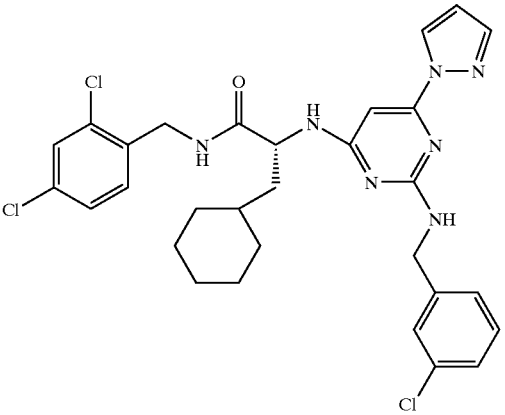 | 125906 |
| 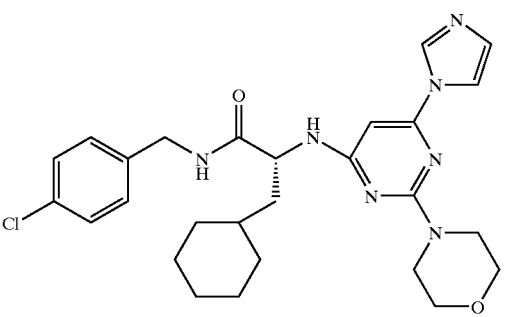 | 638954 |

TABLE 1-continued
| STRUCTURE | Identifier |
|---|---|
| 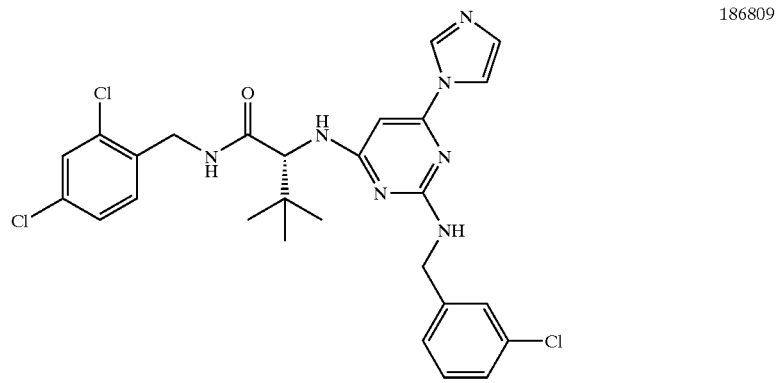 | 186809 |
| 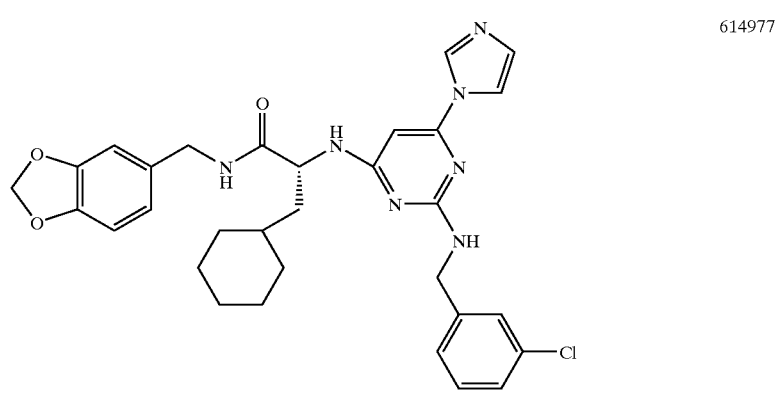 | 614977 |
| 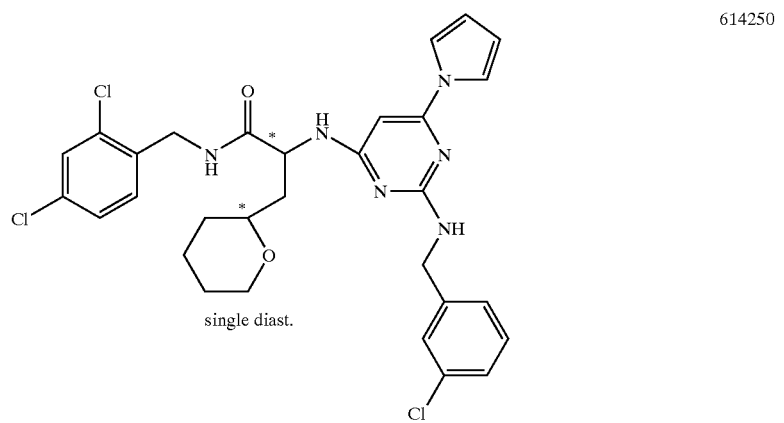 single diast. | 614250 |
| 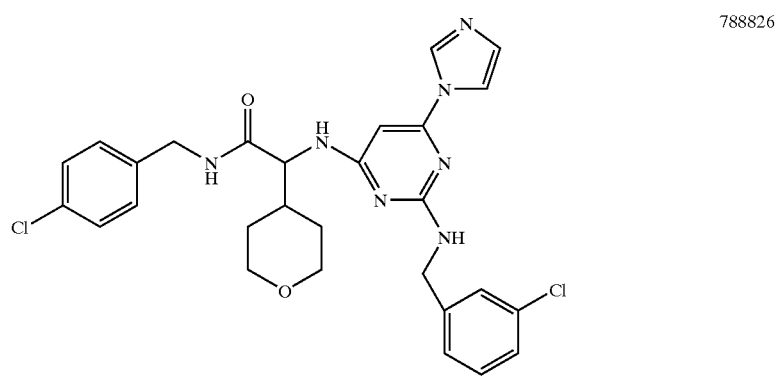 | 788826 |

TABLE 1-continued

| STRUCTURE | Identifier |
| --- | --- |
| 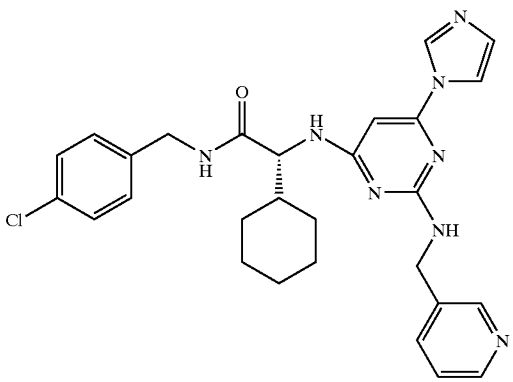 | 078208 |
| 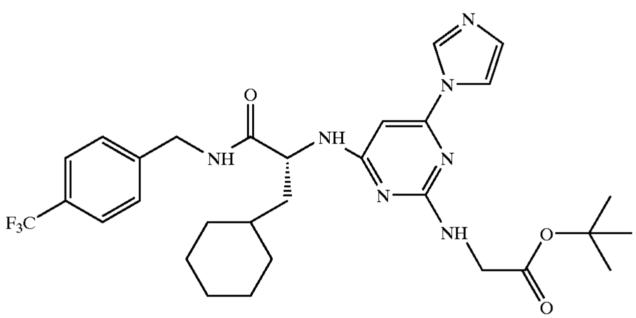 | 487103 |
| 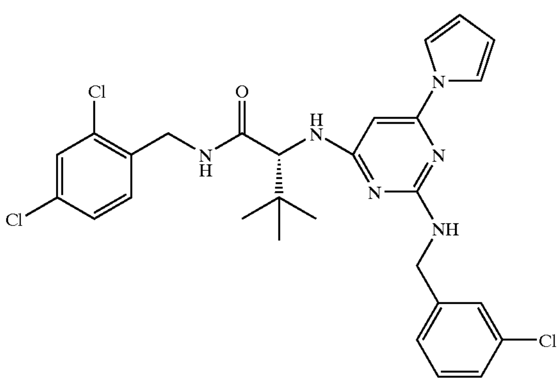 | 542442 |
| 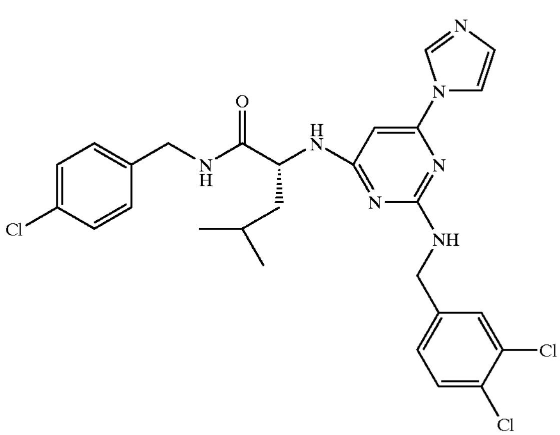 | 634762 |

TABLE 1-continued
| STRUCTURE | Identifier |
|---|---|
| 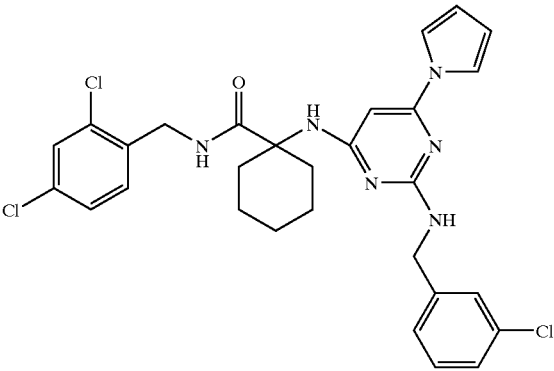 | 191433 |
| 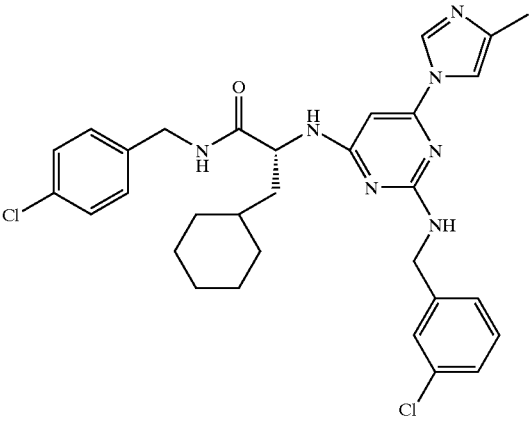 | 319591 |
| 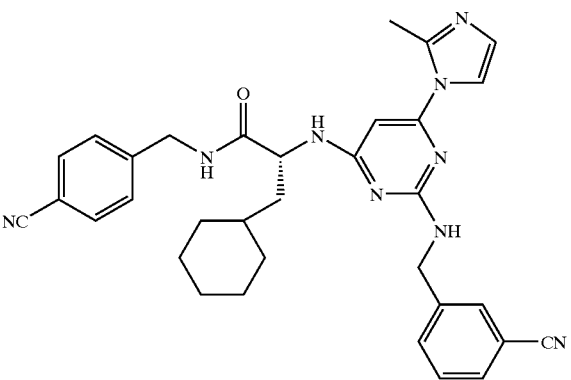 | 841733 |

TABLE 1-continued
| STRUCTURE | Identifier |
|---|---|
| 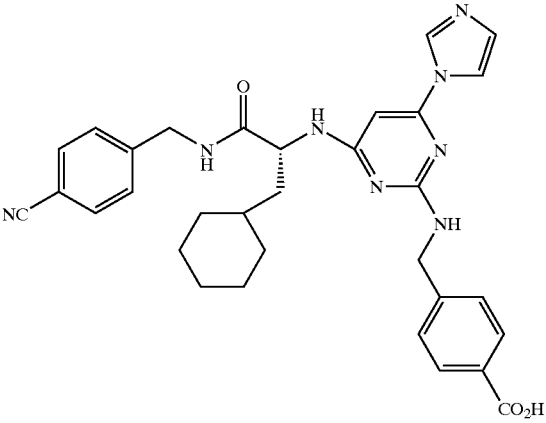 | 814072 |
| 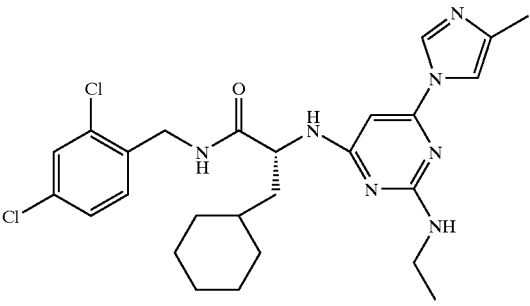 | 235566 |
| 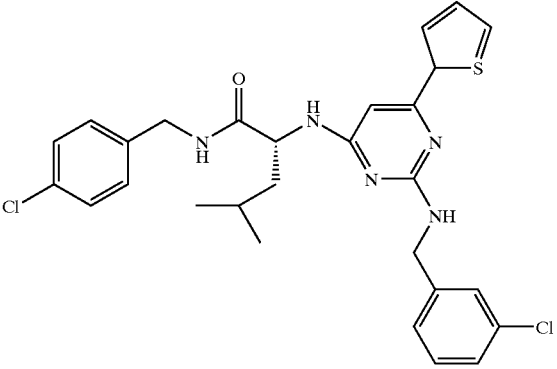 | 959191 |
| 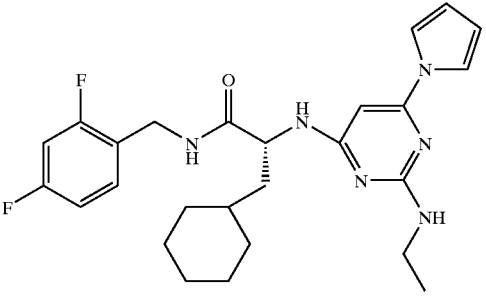 | 812971 |

TABLE 1-continued
| STRUCTURE | Identifier |
|---|---|
| 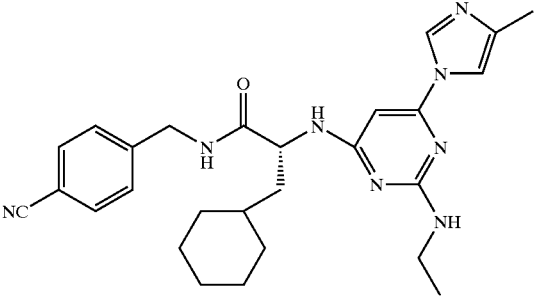 | 037353 |
| 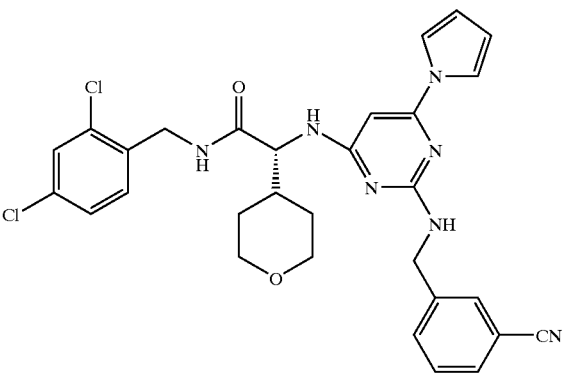 | 105995 |
| 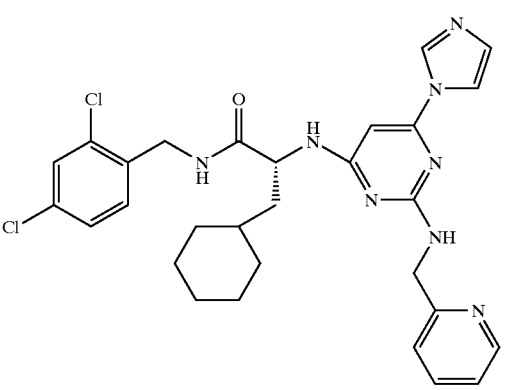 | 629668 |
| 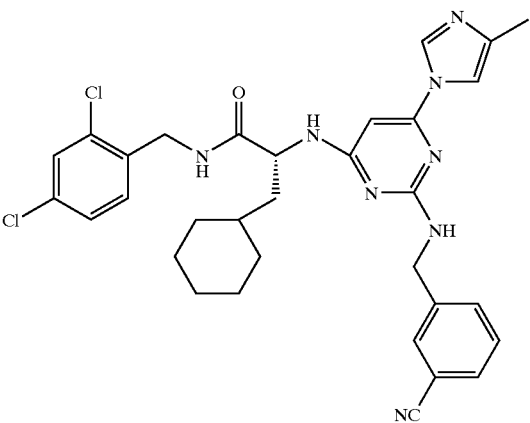 | 159661 |

TABLE 1-continued
| STRUCTURE | Identifier |
|---|---|
| 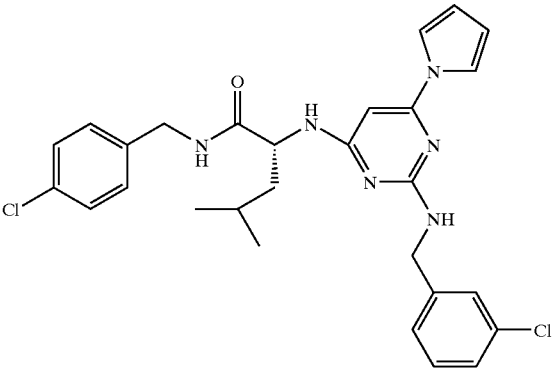 | 081752 |
| 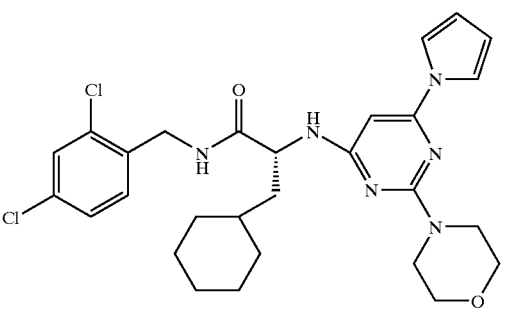 | 696652 |
| 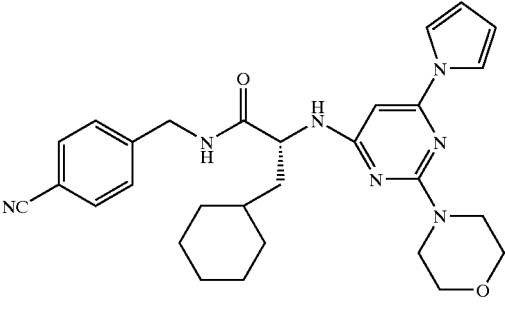 | 312958 |
| 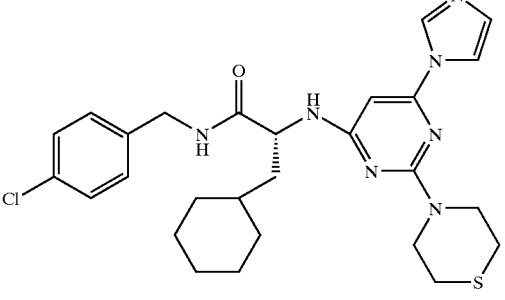 | 757098 |

TABLE 1-continued
| STRUCTURE | Identifier |
|---|---|
| 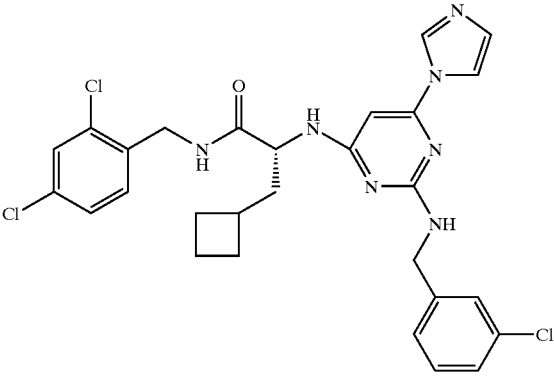 | 223929 |
| 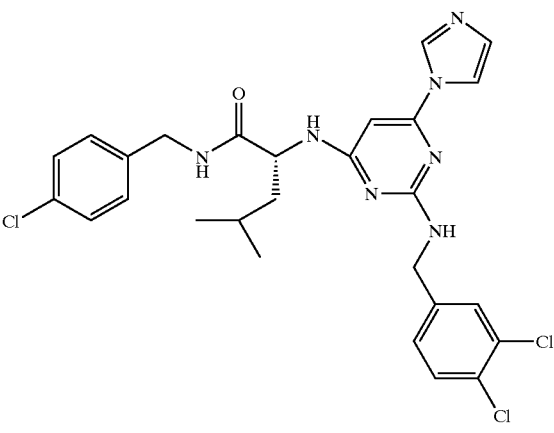 | 930464 |
| 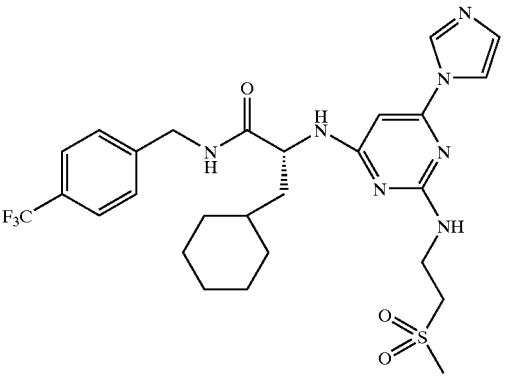 | 391100 |

TABLE 1-continued
| STRUCTURE | Identifier |
|---|---|
| 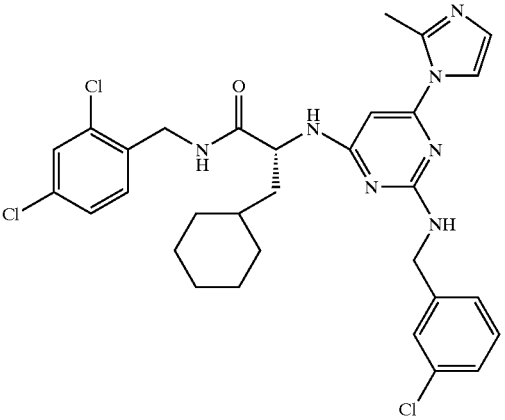 | 337128 |
| 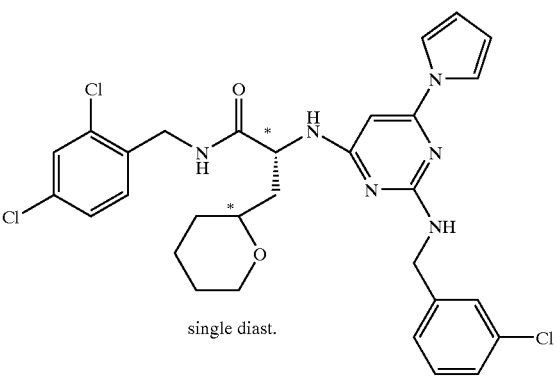 single diast. | 185383 |
| 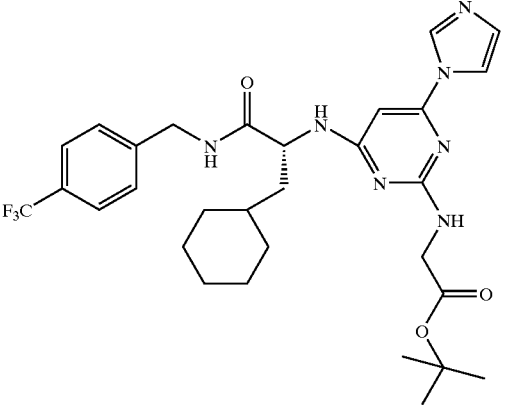 | 769887 |

TABLE 1-continued

| STRUCTURE | Identifier |
|---|---|
| 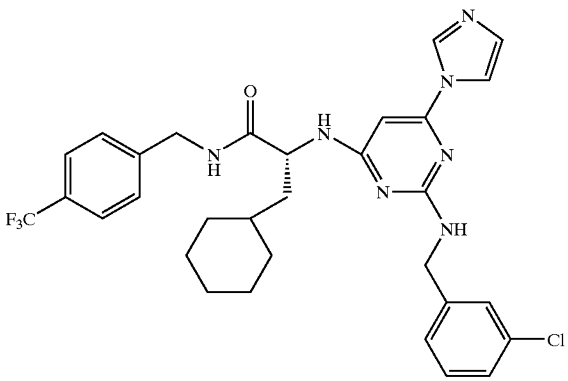 | 532528 |
| 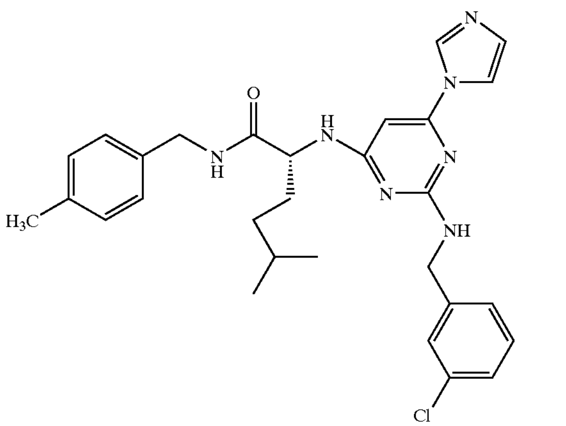 | 817699 |
| 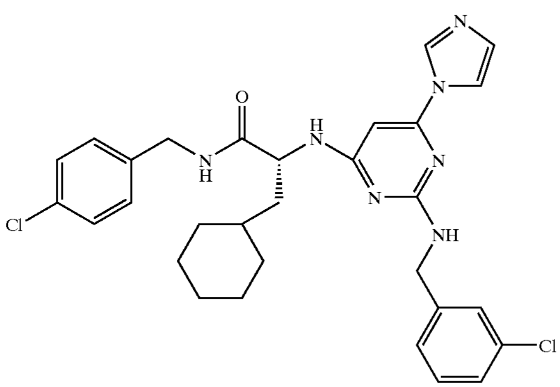 | 702309 |
| 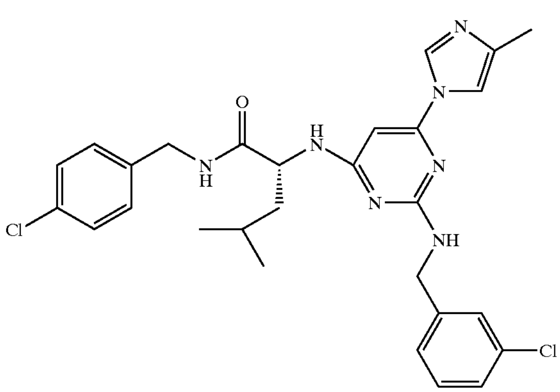 | 888316 |

TABLE 1-continued

| STRUCTURE | Identifier |
| --- | --- |
| 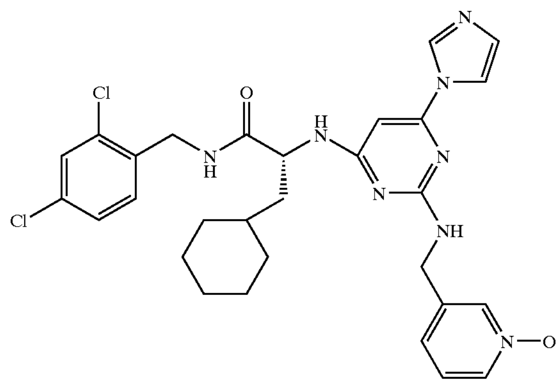 | 578730 |
| 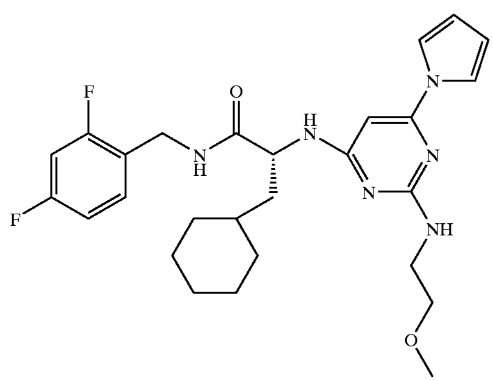 | 917717 |
| 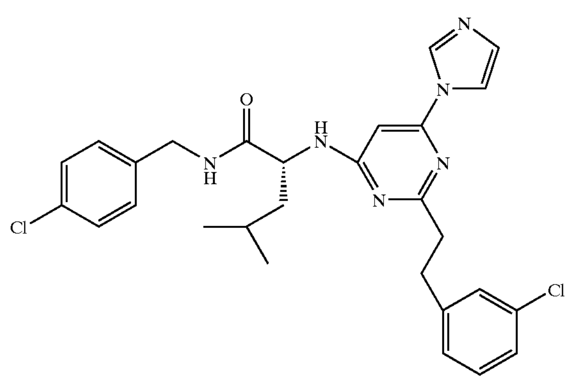 | 326011 |
| 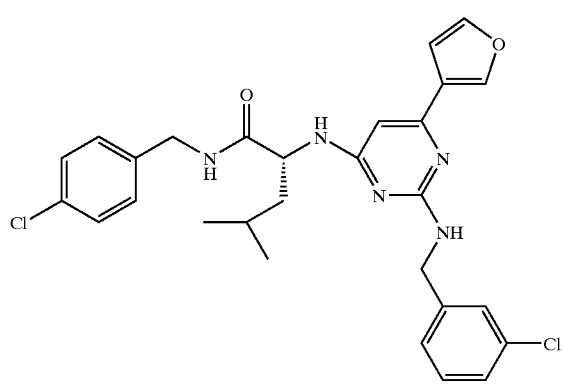 | 794377 |

TABLE 1-continued

| STRUCTURE | Identifier |
| --- | --- |
| 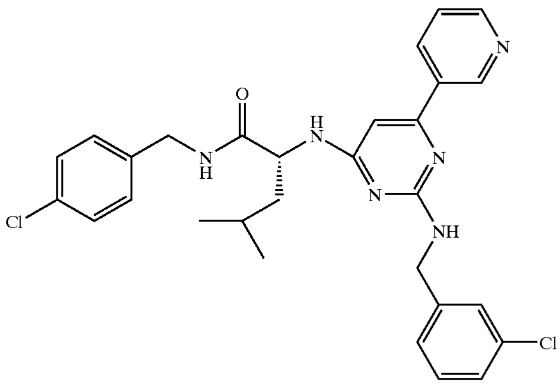 | 905178 |
| 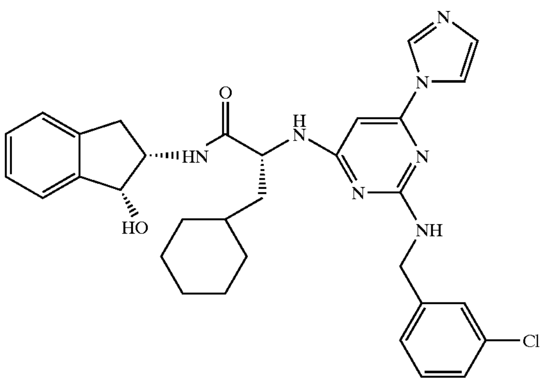 | 573817 |
| 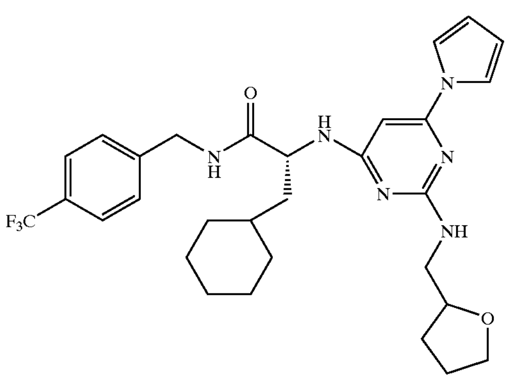 | 598738 |
| 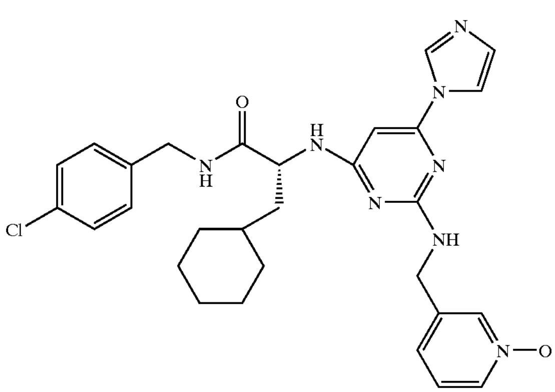 | 857482 |

TABLE 1-continued

| STRUCTURE | Identifier |
| --- | --- |
| 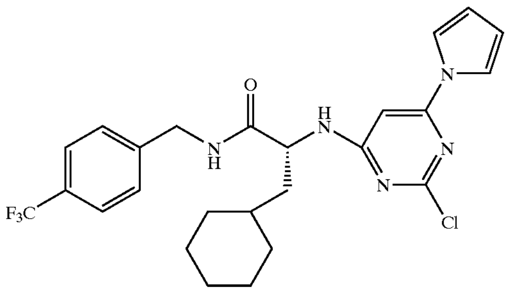 | 663495 |
| 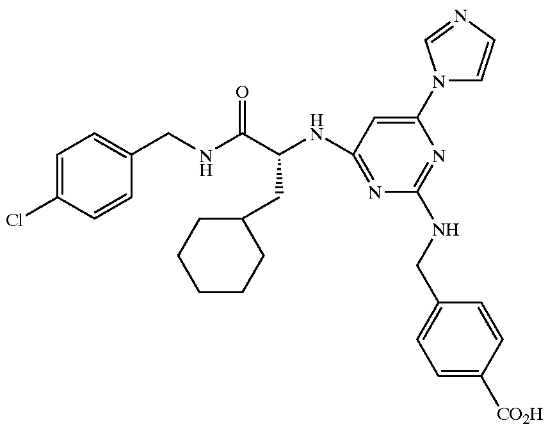 | 991312 |
| 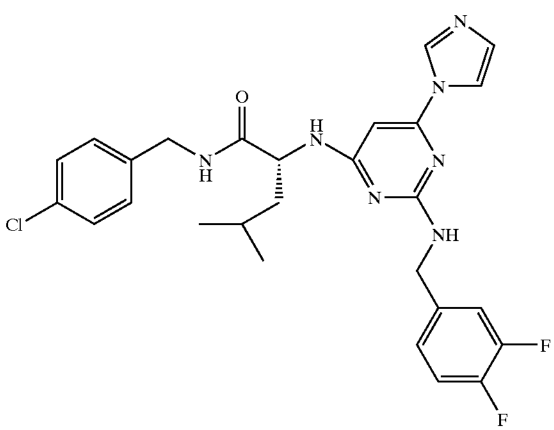 | 225992 |
| 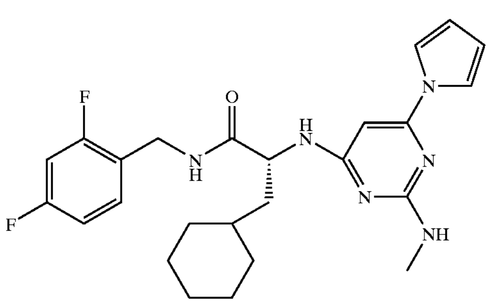 | 926424 |

TABLE 1-continued
| STRUCTURE | Identifier |
|---|---|
| 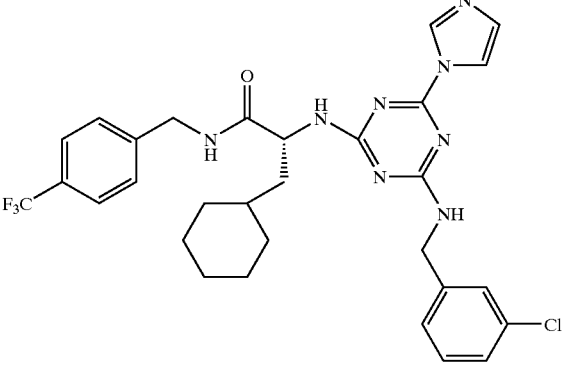 | 339394 |
| 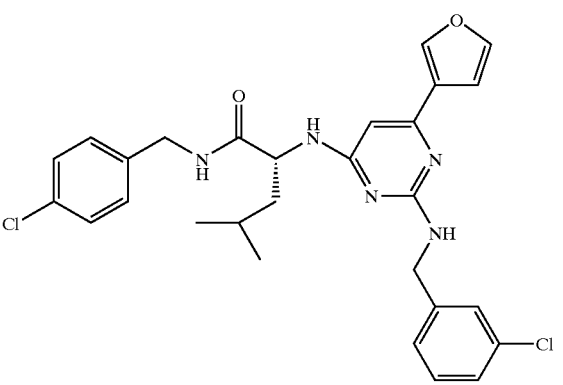 | 781549 |
| 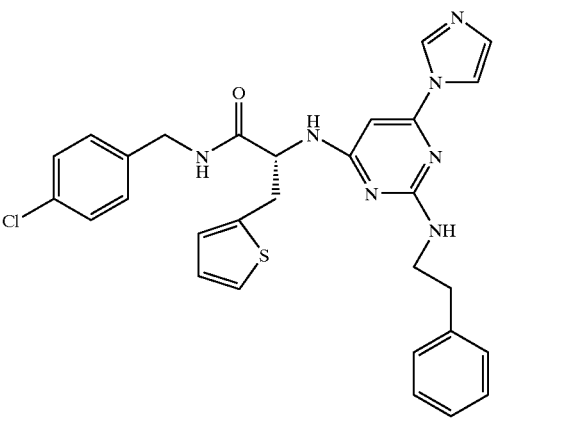 | 566540 |
| 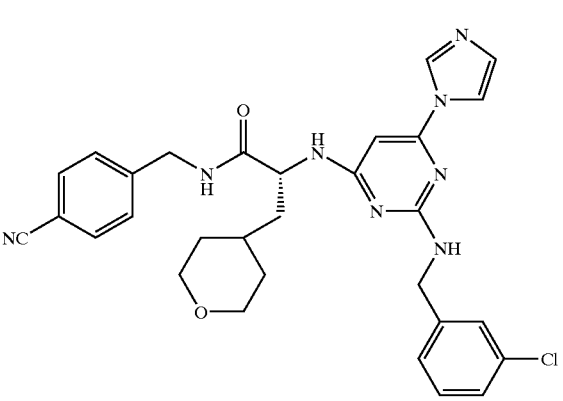 | 584062 |

TABLE 1-continued
| STRUCTURE | Identifier |
|---|---|
| 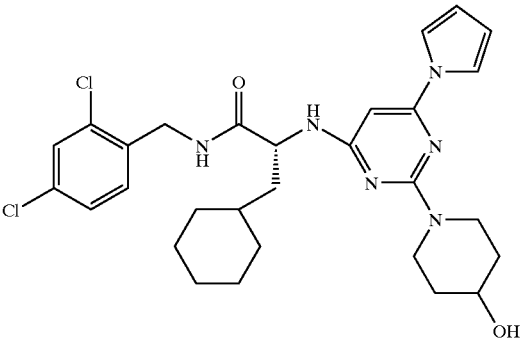 | 615004 |
| 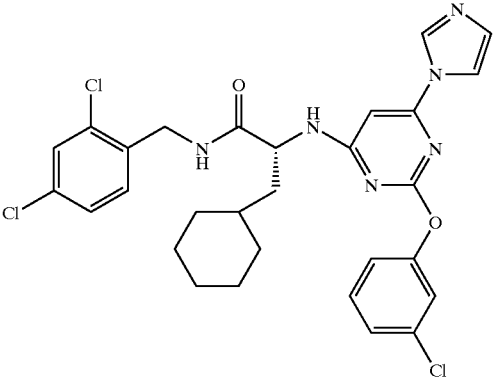 | 098519 |
| 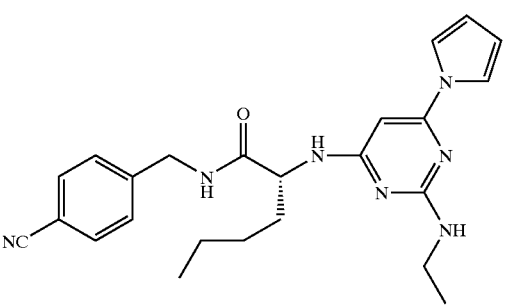 | 815097 |
| 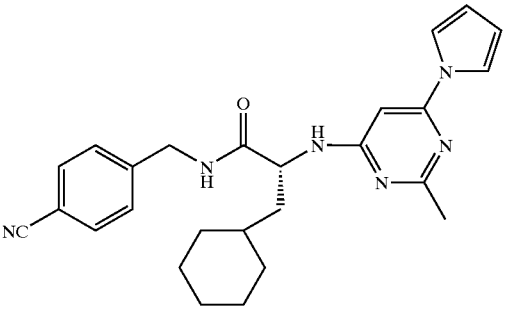 | 360639 |

TABLE 1-continued
| STRUCTURE | Identifier |
|---|---|
| 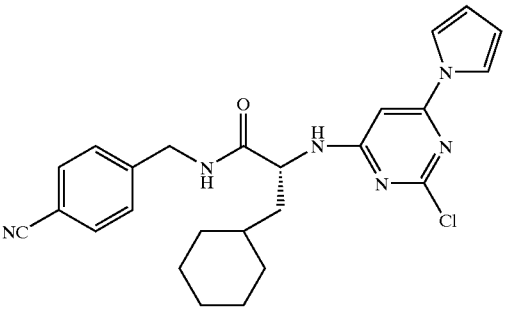 | 828037 |
| 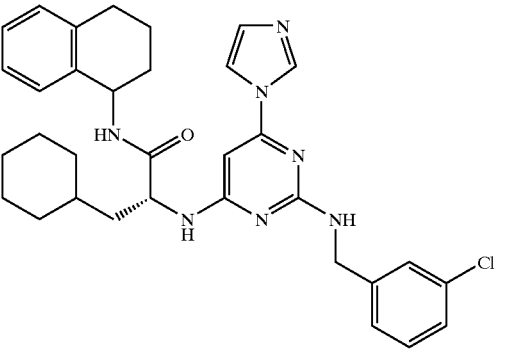 | 972282 |
| 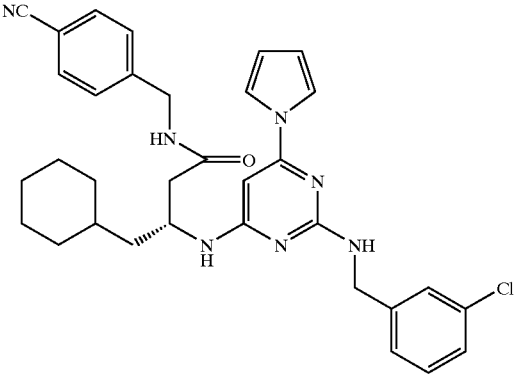 | 080030 |
| 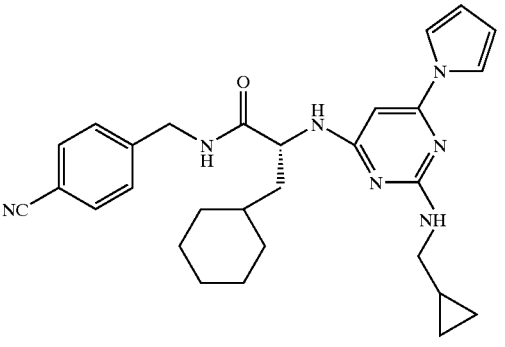 | 811358 |

TABLE 1-continued

| STRUCTURE | Identifier |
| --- | --- |
| 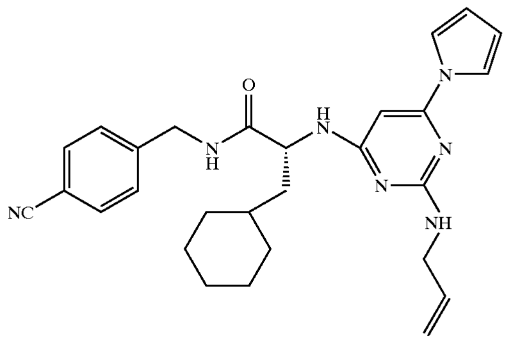 | 097881 |
| 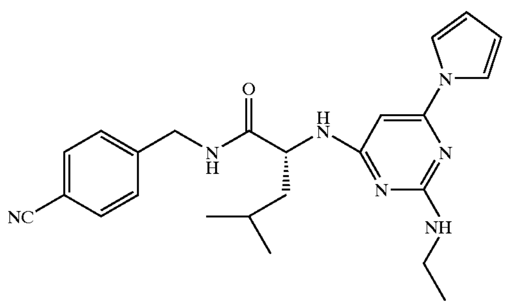 | 270821 |
| 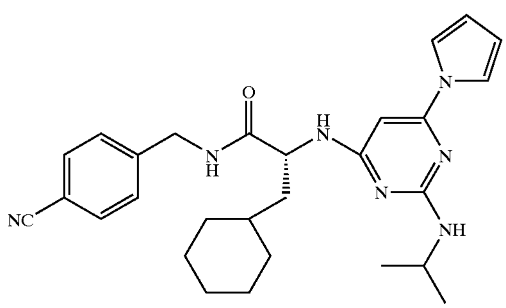 | 655480 |
| 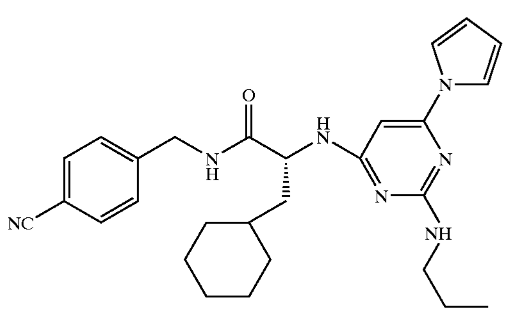 | 713653 |

TABLE 1-continued

| STRUCTURE | Identifier |
| --- | --- |
| 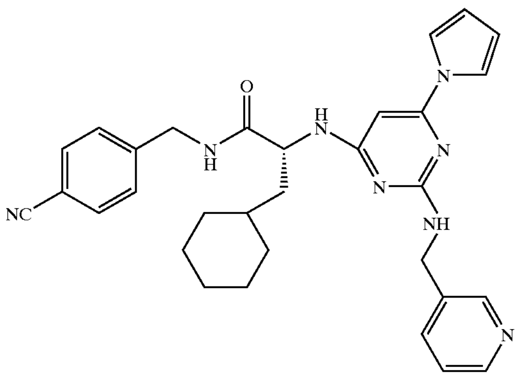 | 091950 |
| 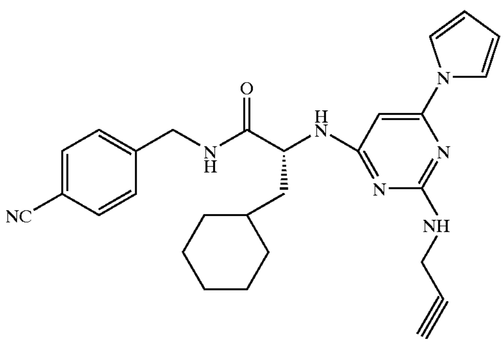 | 014922 |
| 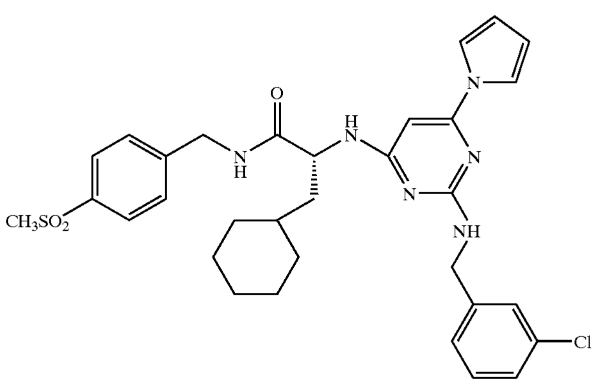 | 556200 |
| 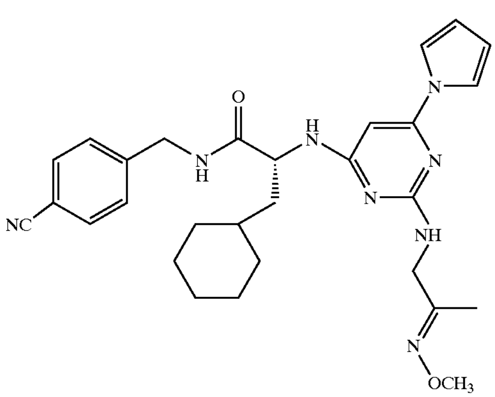 | 936852 |

TABLE 1-continued
| STRUCTURE | Identifier |
|---|---|
| 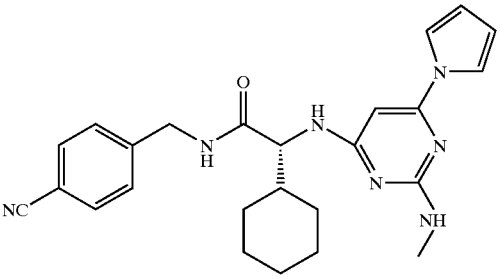 | 167307 |
| 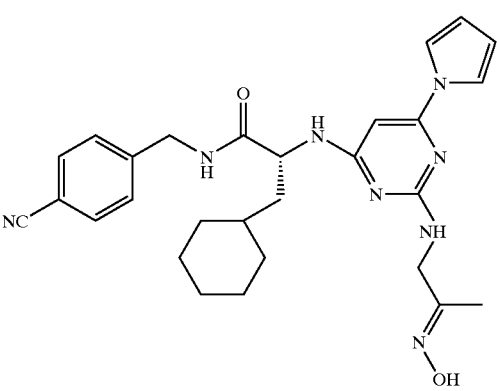 | 218245 |
| 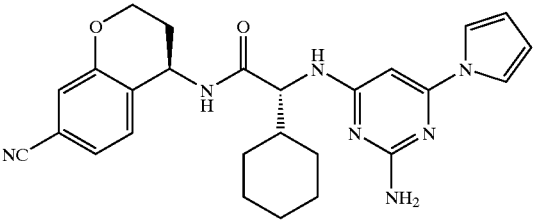 | 424569 |
| 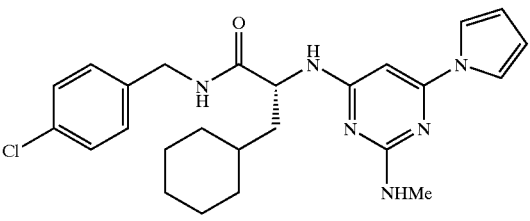 | 307763 |
| 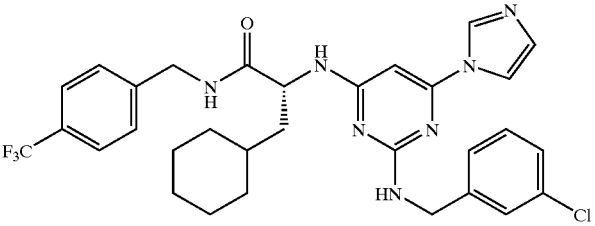 | 532528 |

TABLE 1-continued

| STRUCTURE | Identifier |
|---|---|
| 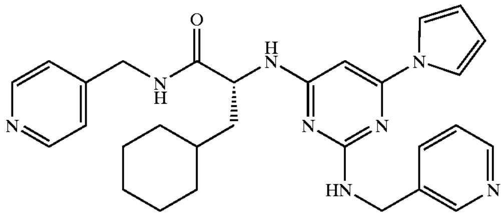 | 997039 |
| 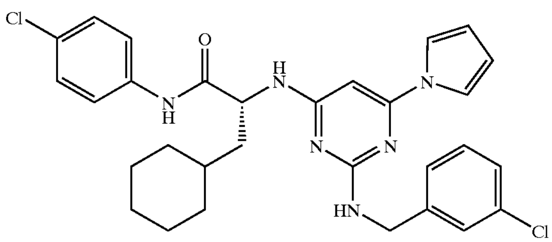 | 599337 |
| 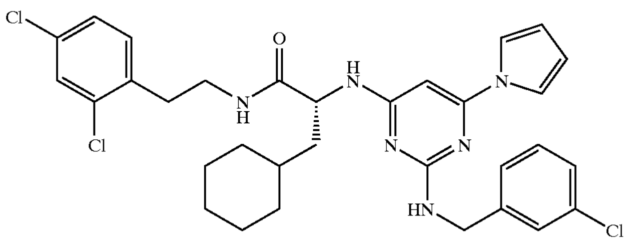 | 389573 |
| 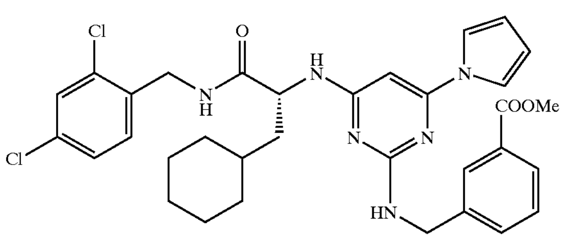 | 919044 |
| 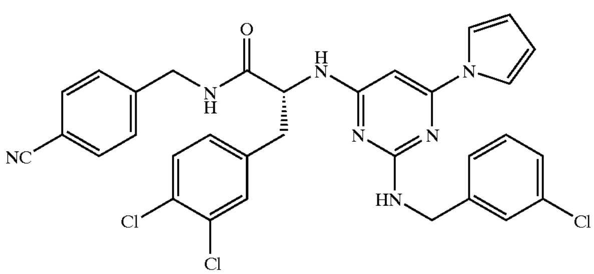 | 091217 |
| 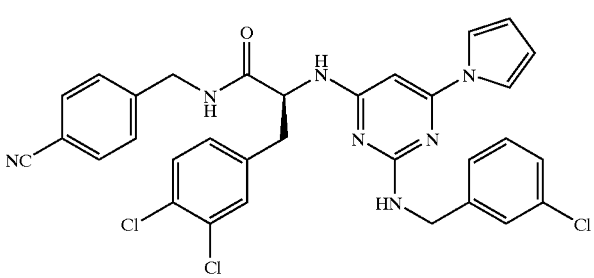 | 813326 |

TABLE 1-continued
| STRUCTURE | Identifier |
|---|---|
| 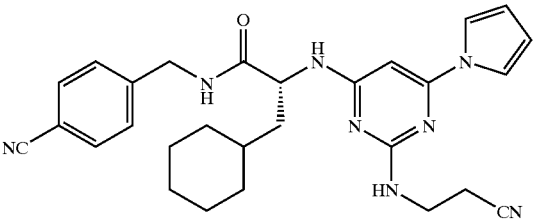 | 592843 |
| 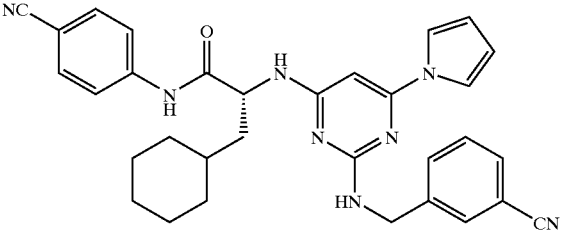 | 053116 |
| 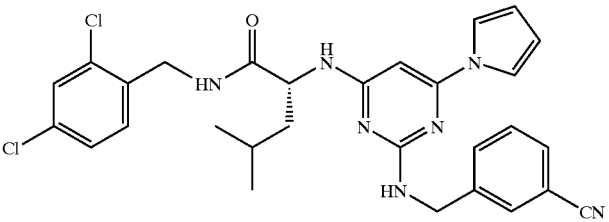 | 416383 |
| 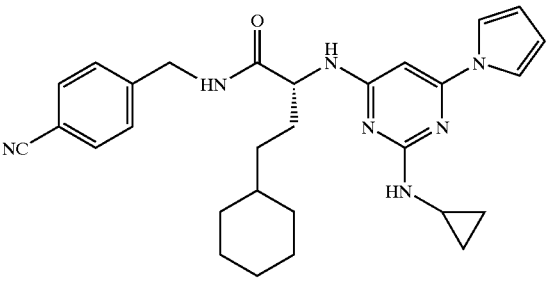 | 762112 |
| 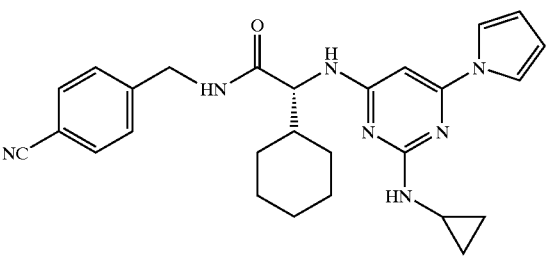 | 788965 |
| 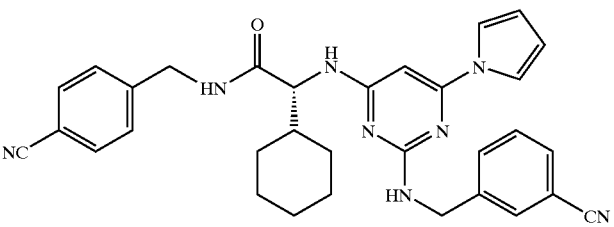 | 956568 |

TABLE 1-continued
| STRUCTURE | Identifier |
|---|---|
| 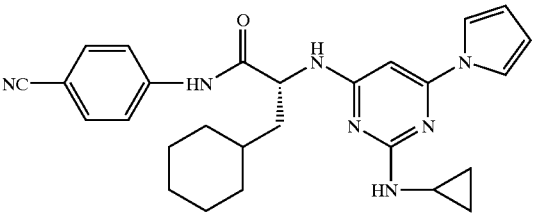 | 592995 |
| 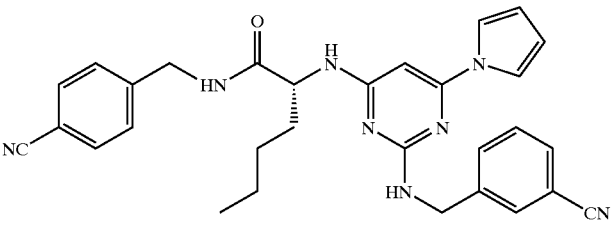 | 642706 |
| 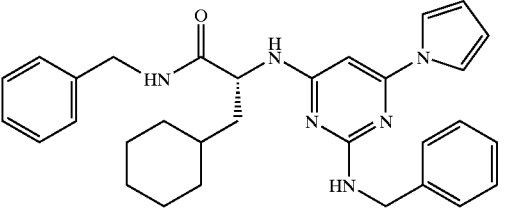 | 916924 |
| 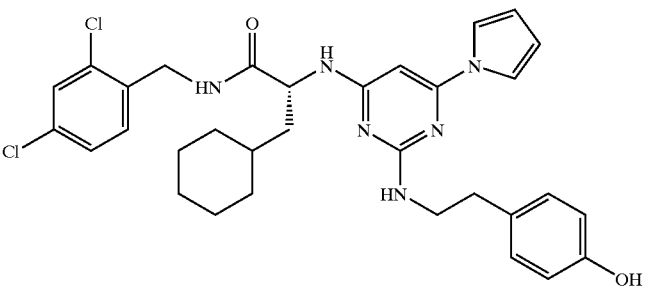 | 406896 |
| 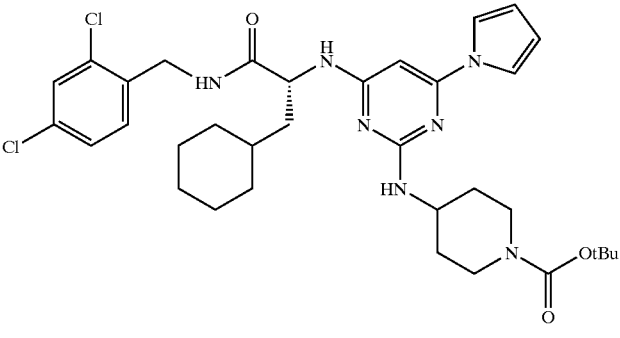 | 463621 |
| 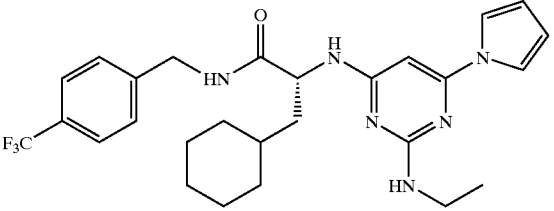 | 103379 |

TABLE 1-continued

| STRUCTURE | Identifier |
|---|---|
| 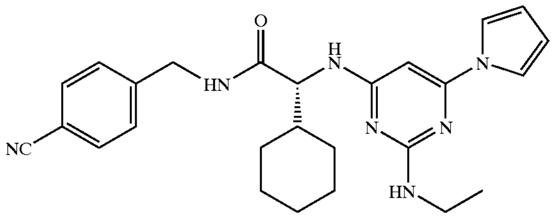 | 073408 |
| 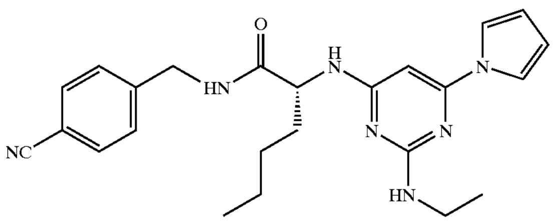 | 815097 |
| 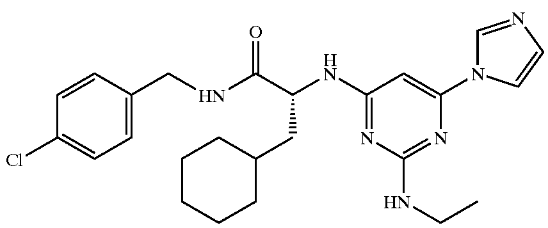 | 115870 |
| 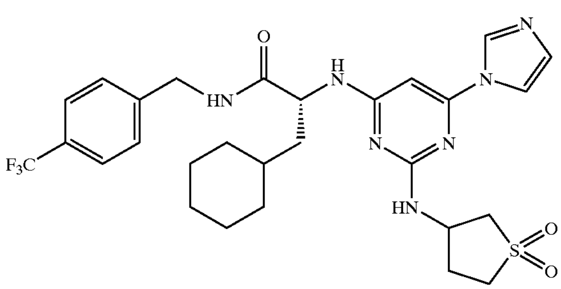 | 579244 |
| 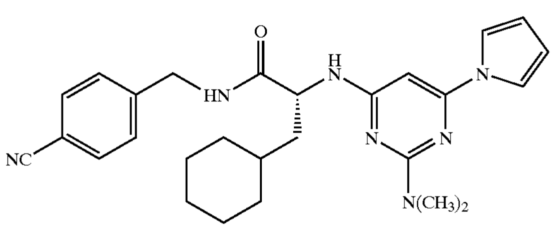 | 551184 |
| 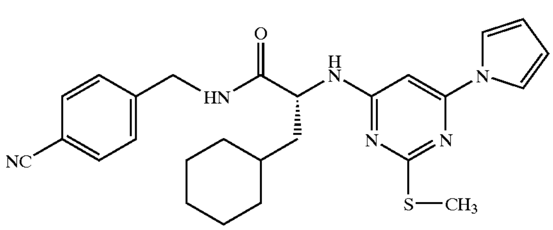 | 194859 |

TABLE 1-continued
| STRUCTURE | Identifier |
|---|---|
| 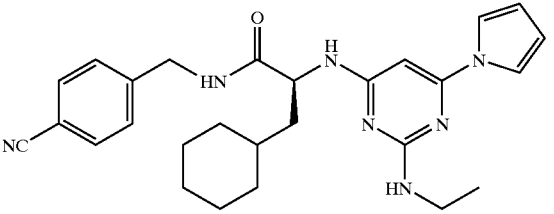 | 934834 |
| 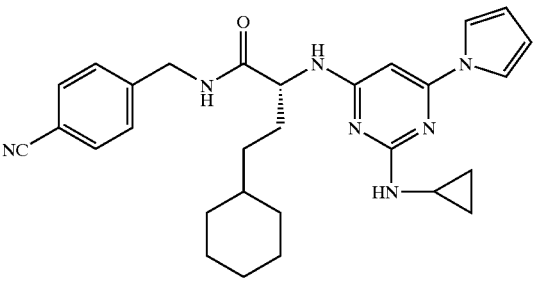 | 762112 |
| 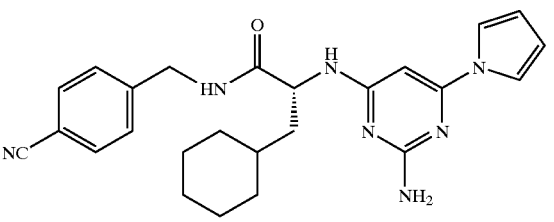 | 818697 |
| 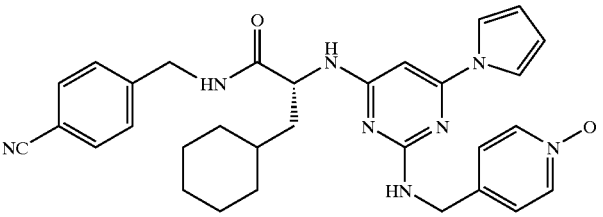 | 005195 |
| 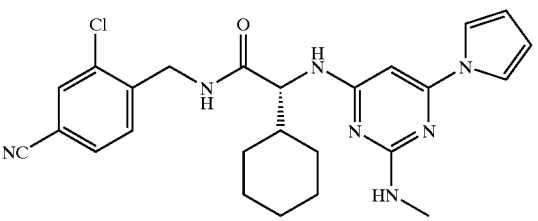 | 018412 |
| 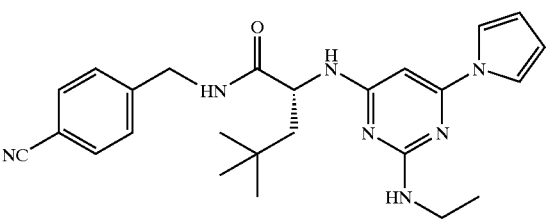 | 030876 |

TABLE 1-continued

| STRUCTURE | Identifier |
|---|---|
| 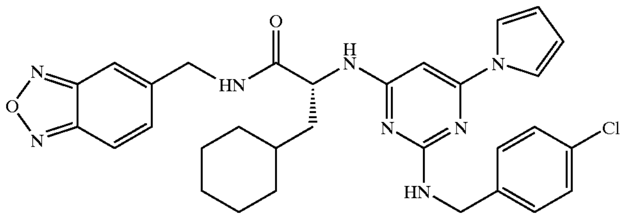 | 031155 |
| 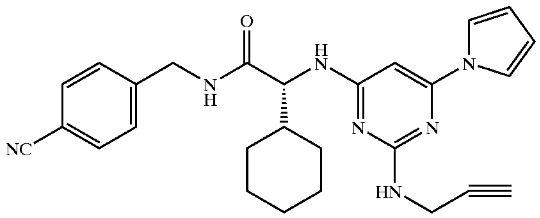 | 054101 |
| 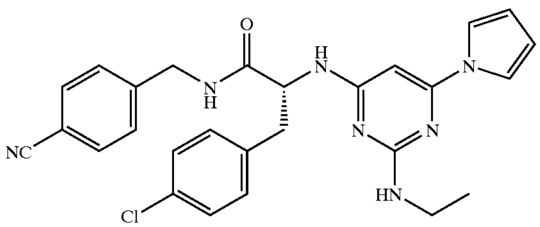 | 066361 |
| 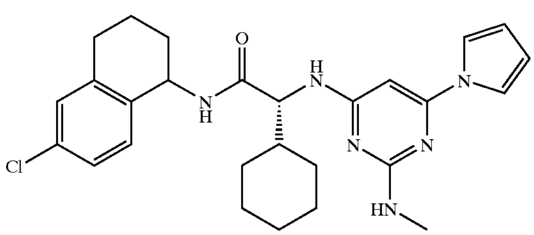 | 095564 |
| 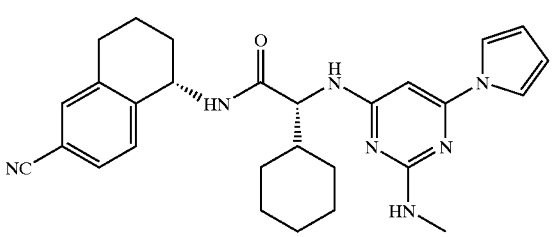 | 109718 |
| 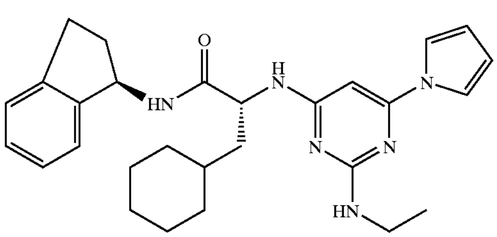 | 129311 |

TABLE 1-continued

| STRUCTURE | Identifier |
| --- | --- |
| 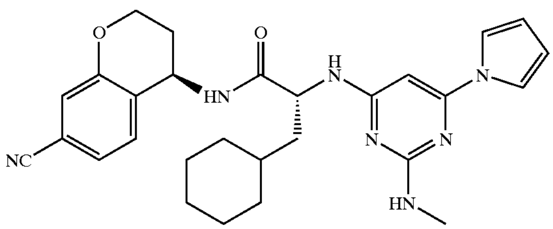 | 139299 |
| 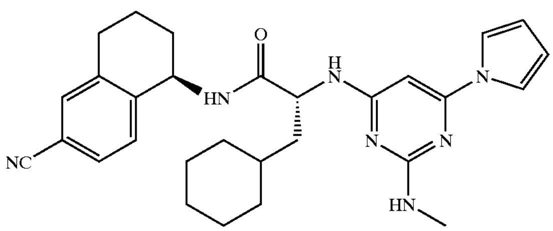 | 154213 |
| 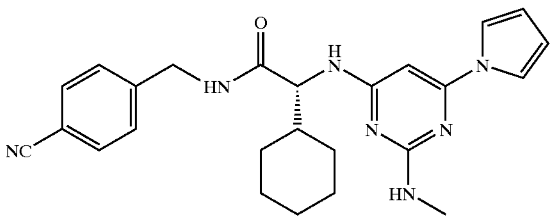 | 167307 |
| 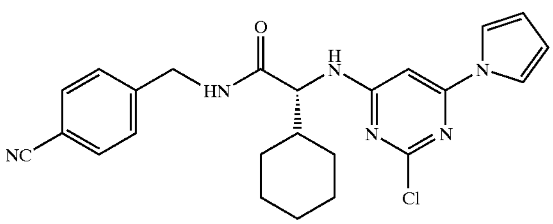 | 178323 |
| 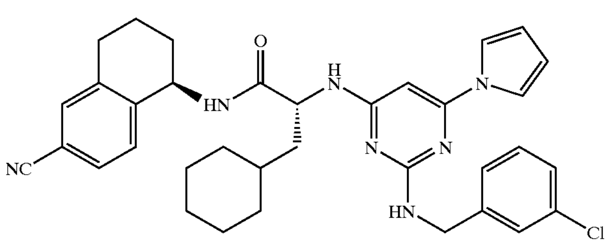 | 192258 |
| 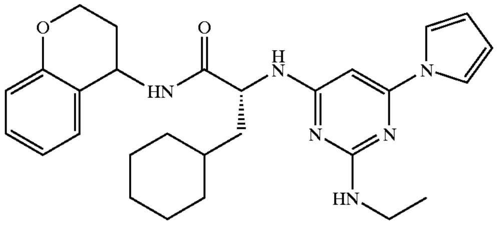 | 198950 |

TABLE 1-continued
| STRUCTURE | Identifier |
|---|---|
| 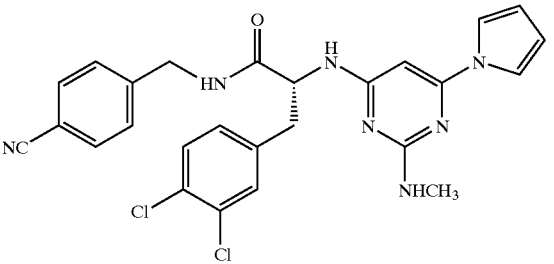 | 215301 |
| 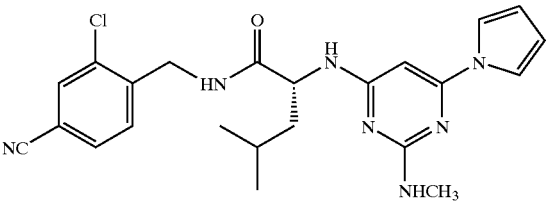 | 215318 |
| 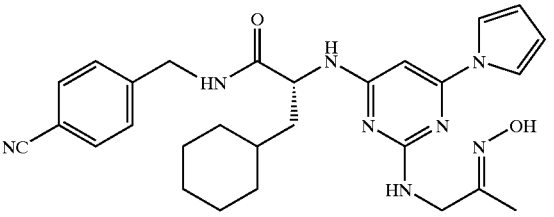 | 218245 |
| 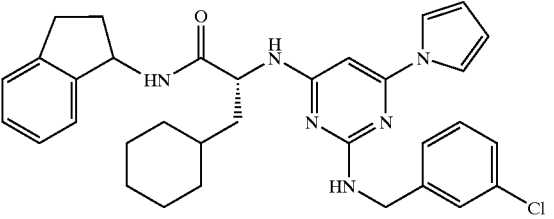 | 222477 |
| 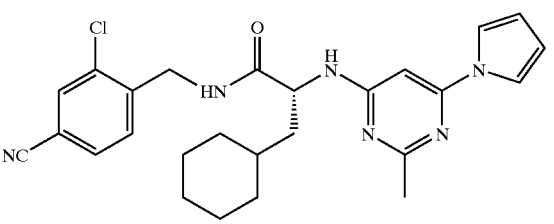 | 237360 |
| 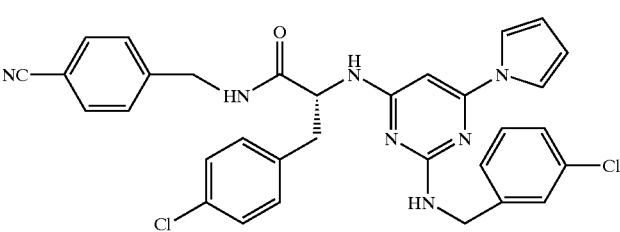 | 307742 |

TABLE 1-continued
| STRUCTURE | Identifier |
|---|---|
| 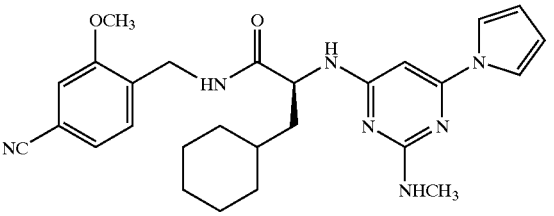 | 309001 |
| 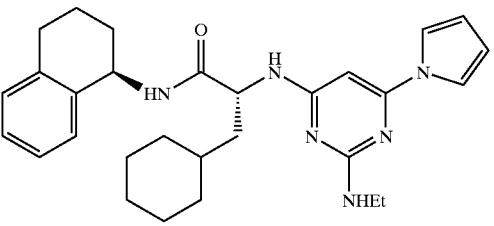 | 312972 |
| 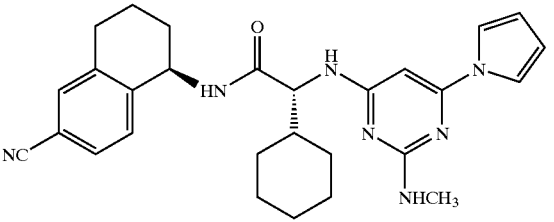 | 327891 |
| 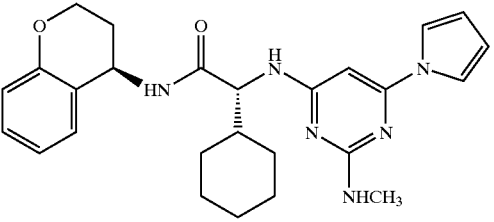 | 334878 |
| 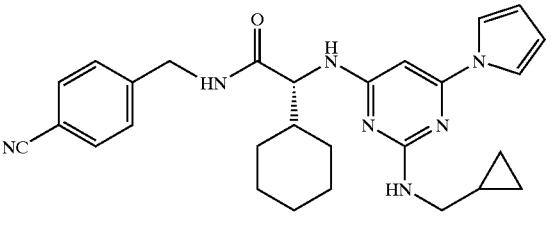 | 337854 |
| 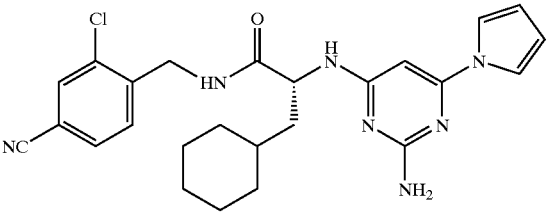 | 347952 |

TABLE 1-continued

| STRUCTURE | Identifier |
| --- | --- |
| 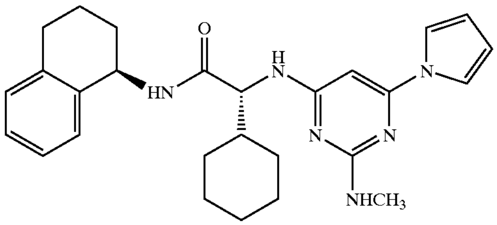 | 360912 |
| 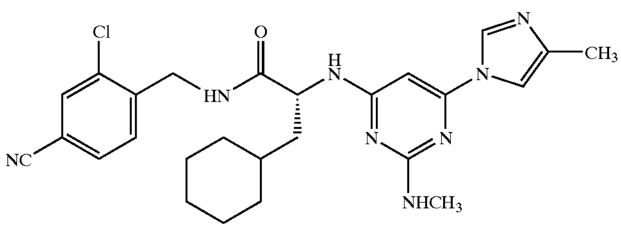 | 368057 |
| 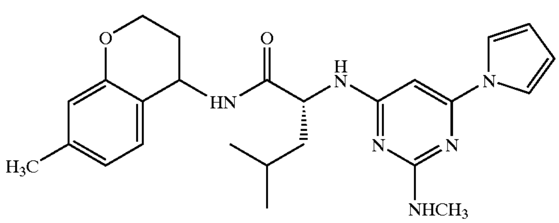 | 380712 |
| 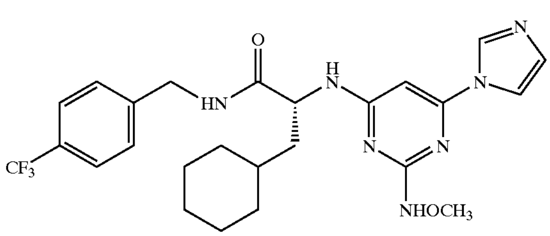 | 395117 |
| 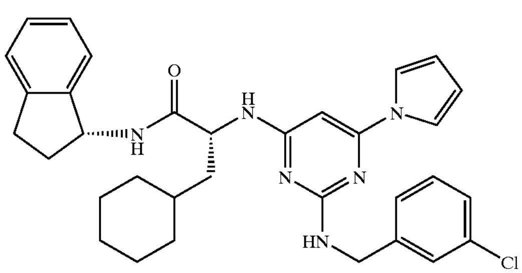 | 410204 |
| 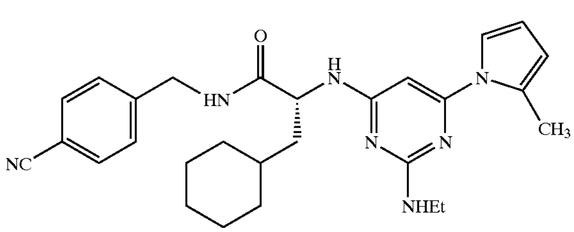 | 412904 |

TABLE 1-continued

| STRUCTURE | Identifier |
|---|---|
| 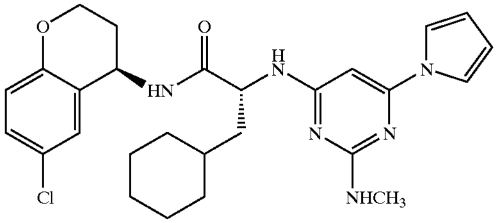 | 414904 |
| 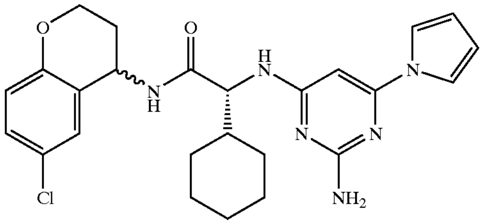 | 424569 |
| 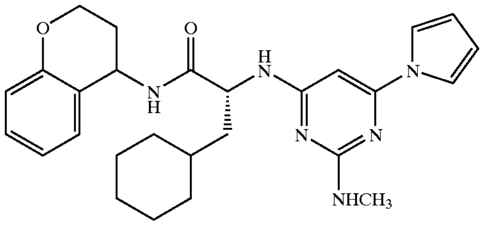 | 426754 |
| 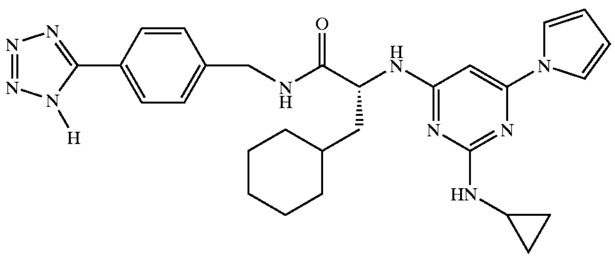 | 442350 |
| 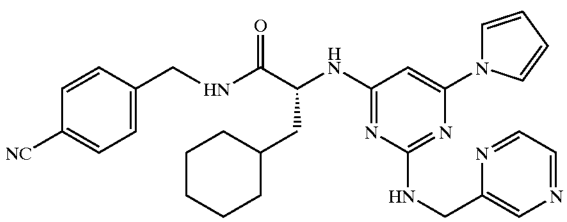 | 444713 |
| 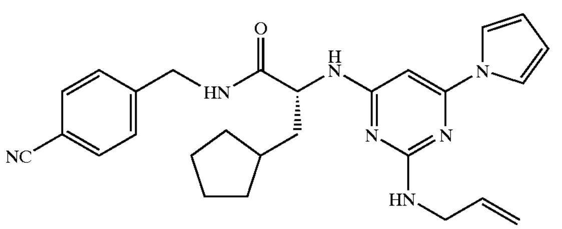 | 452881 |

TABLE 1-continued

| STRUCTURE | Identifier |
| --- | --- |
| 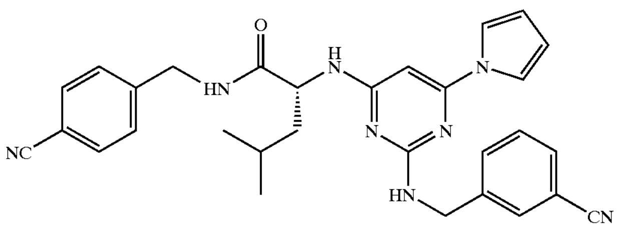 | 456816 |
| 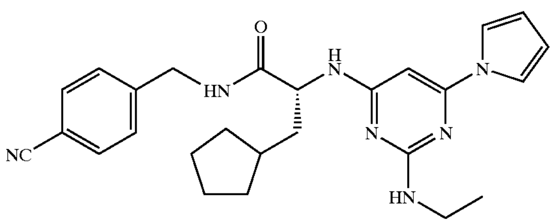 | 466502 |
| 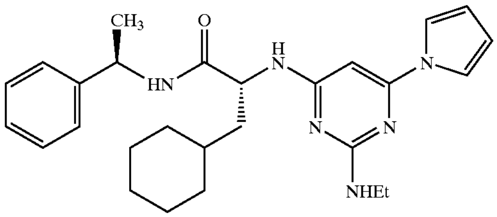 | 492190 |
| 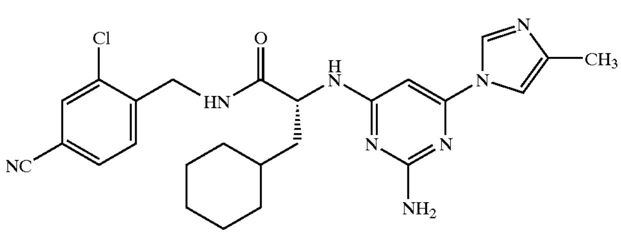 | 512937 |
| 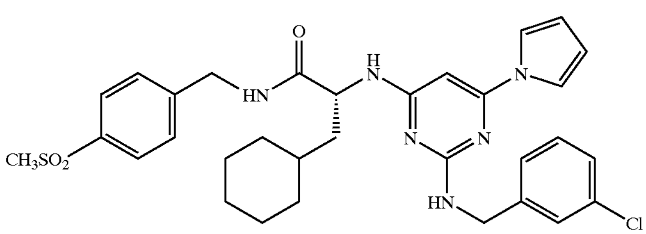 | 556200 |
| 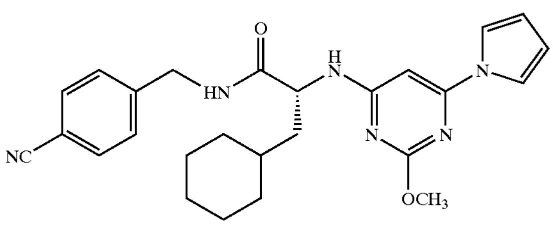 | 447846 |

TABLE 1-continued

| STRUCTURE | Identifier |
| --- | --- |
| 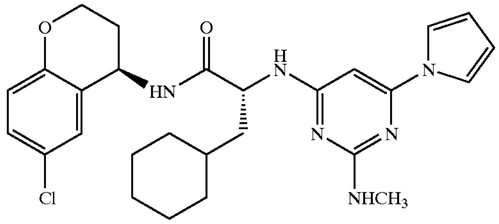 | 572620 |
| 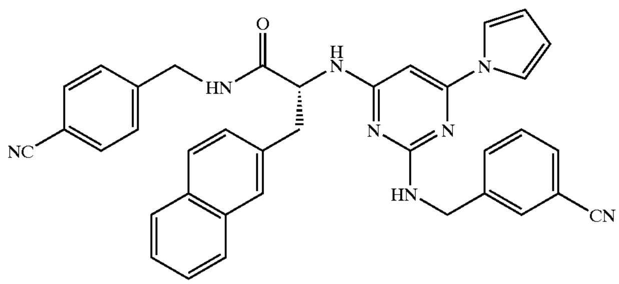 | 588712 |
| 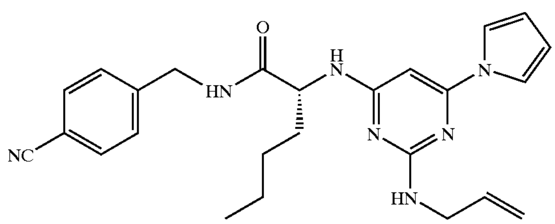 | 596982 |
| 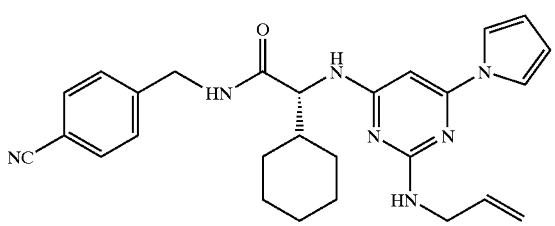 | 603364 |
| 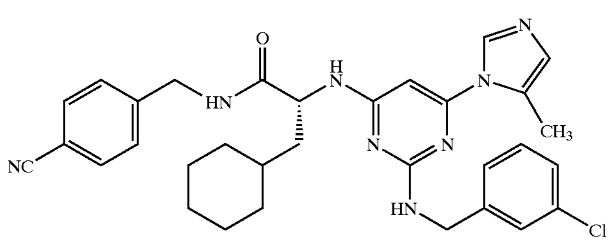 | 662666 |
| 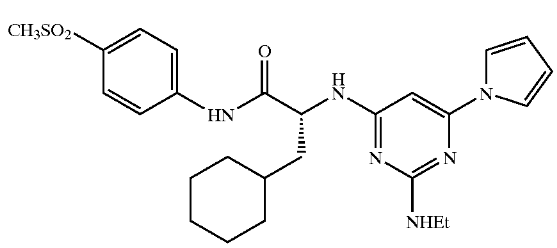 | 670583 |

TABLE 1-continued
| STRUCTURE | Identifier |
| --- | --- |
| 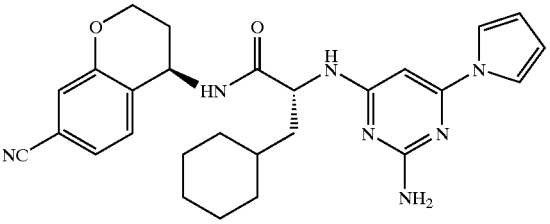 | 698545 |
| 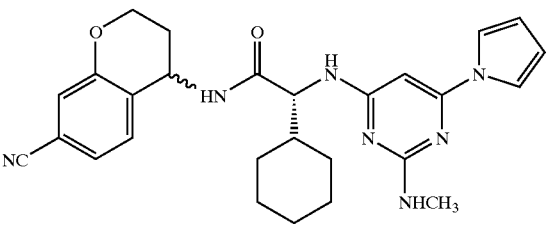 | 708752 |
| 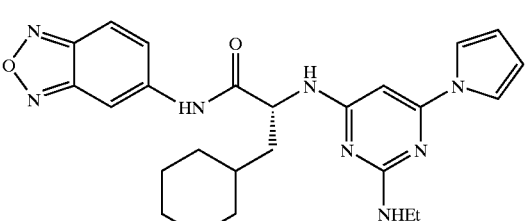 | 724612 |
| 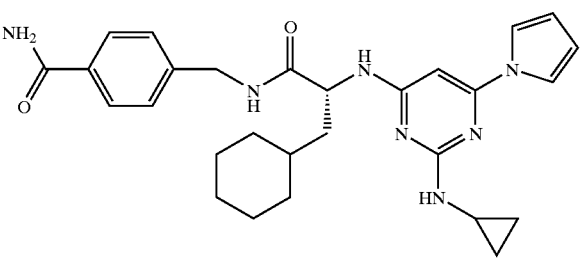 | 739750 |
| 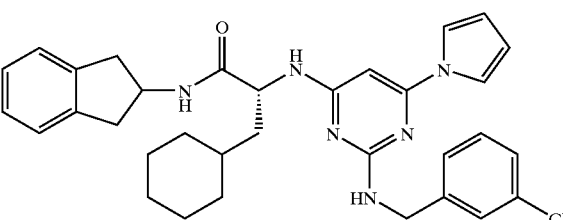 | 797241 |
| 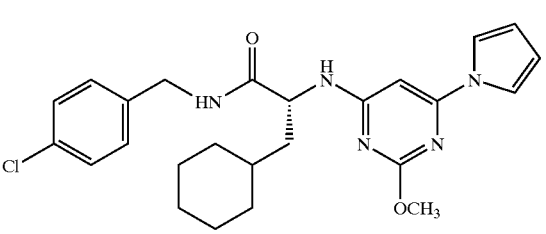 | 817552 |

TABLE 1-continued

| STRUCTURE | Identifier |
| --- | --- |
| 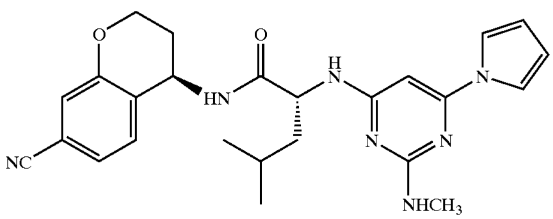 | 824754 |
| 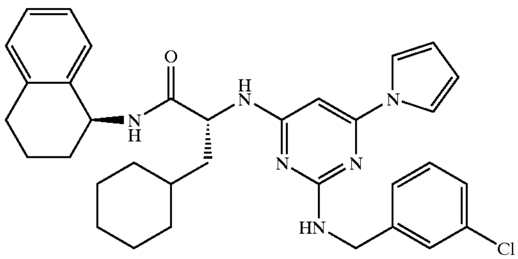 | 835714 |
| 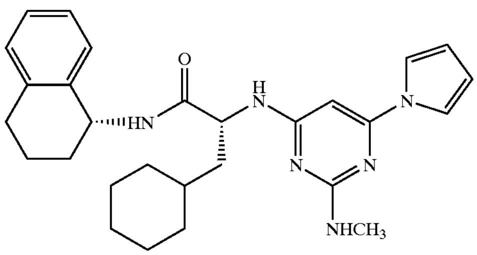 | 847939 |
| 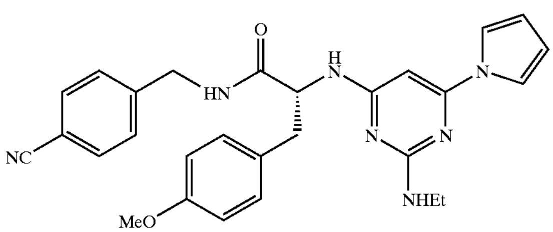 | 859657 |
| 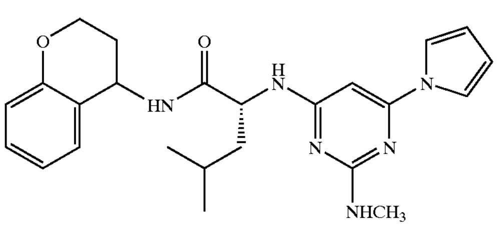 | 881196 |
| 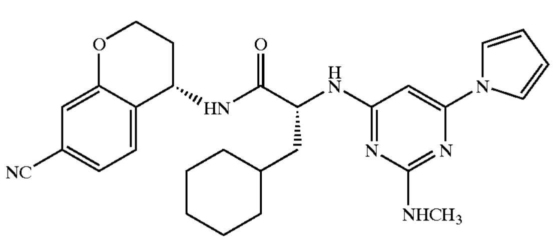 | 919420 |

TABLE 1-continued

| STRUCTURE | Identifier |
|---|---|
| 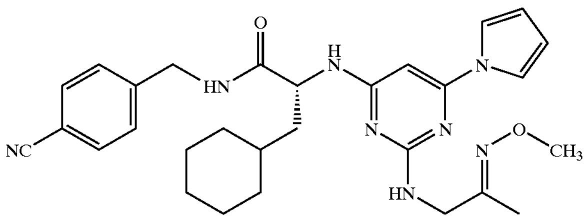 | 936852 |
| 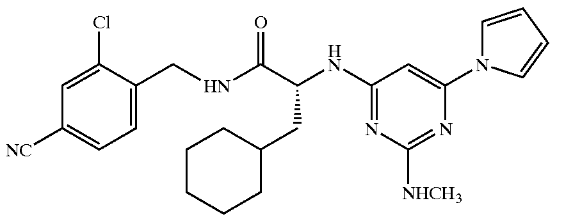 | 960142 |
| 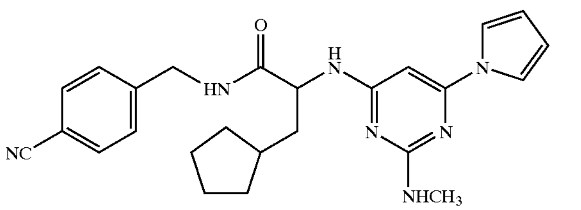 | 968882 |
| 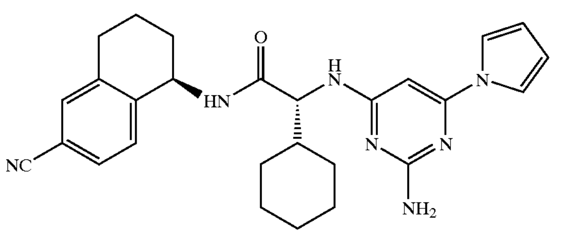 | 993416 |
| 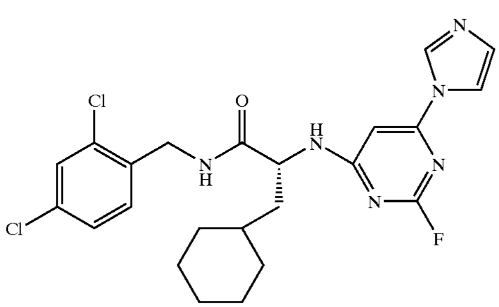 | 339883 |
| 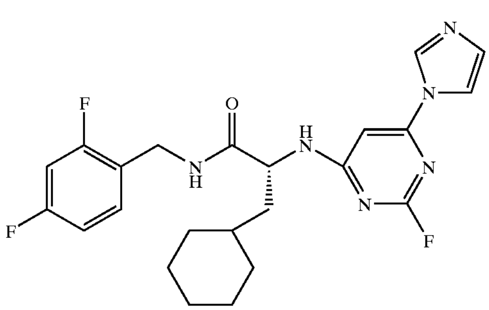 | 428825 |

TABLE 2

| STRUCTURE | Identifier |
|---|---|
| 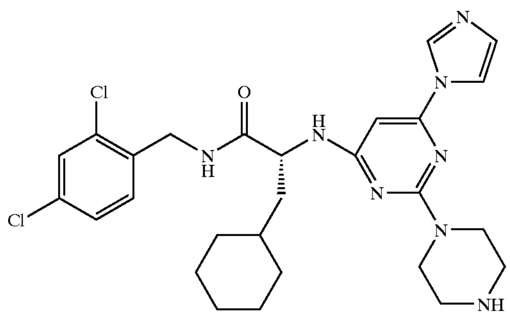 | 459868 |
| 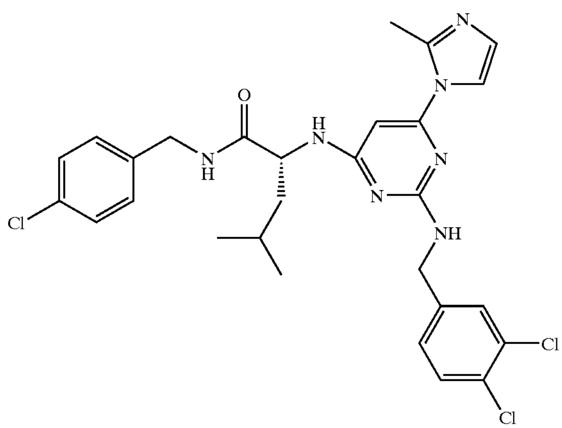 | 397897 |
| 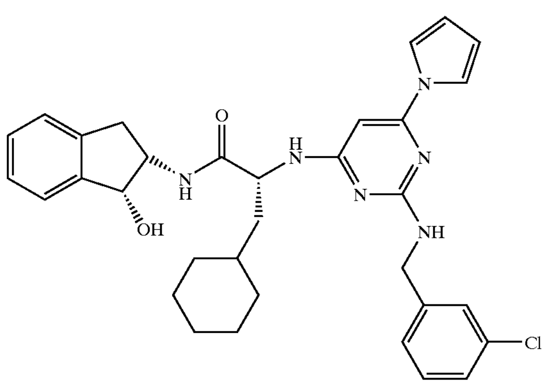 | 703779 |
| 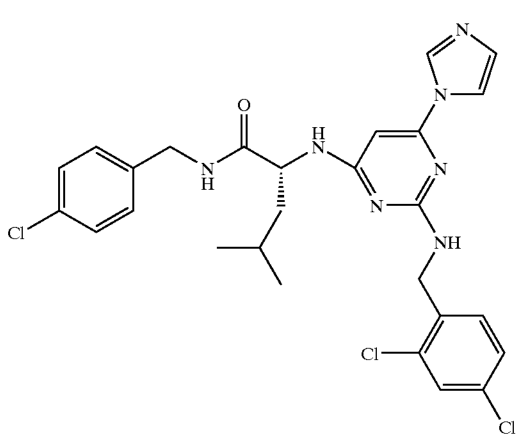 | 966132 |

TABLE 2-continued

| STRUCTURE | Identifier |
| --- | --- |
| 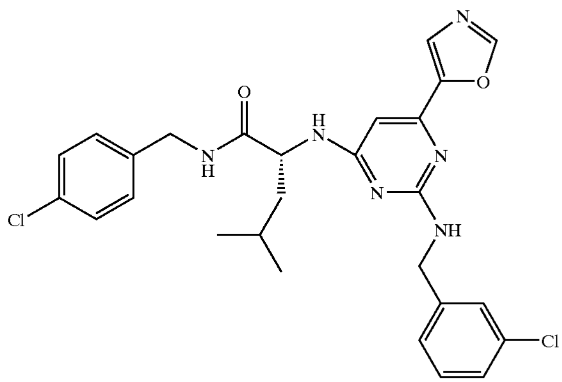 | 276572 |
| 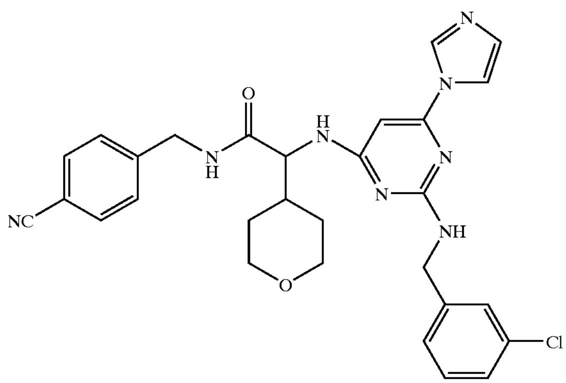 | 748623 |
| 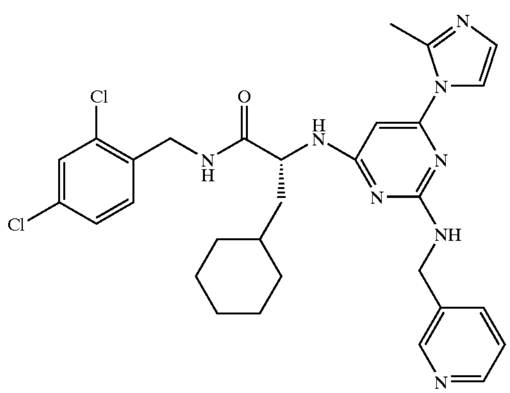 | 770799 |
| 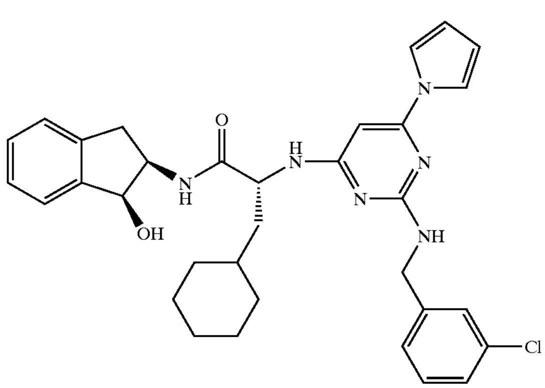 | 474269 |

TABLE 2-continued

| STRUCTURE | Identifier |
|---|---|
| 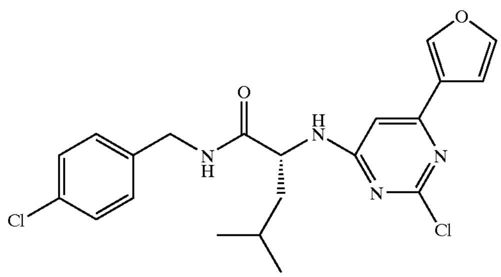 | 715066 |
| 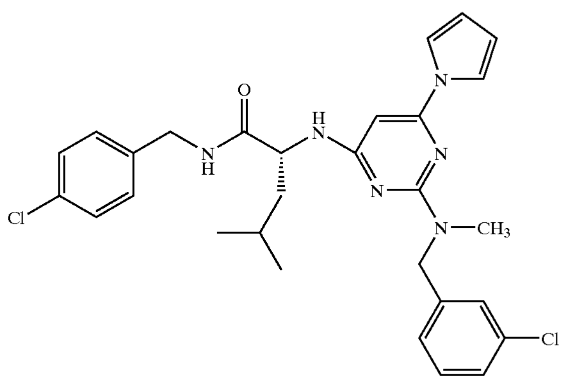 | 884607 |
| 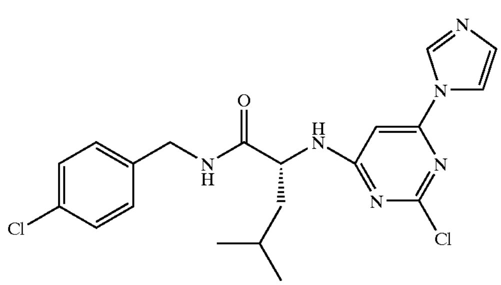 | 387845 |
| 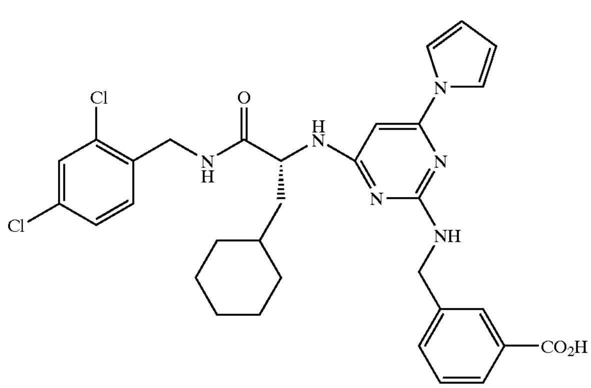 | 334057 |

TABLE 2-continued

| STRUCTURE | Identifier |
| --- | --- |
| 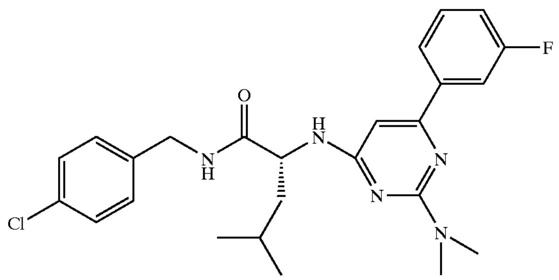 | 703736 |
| 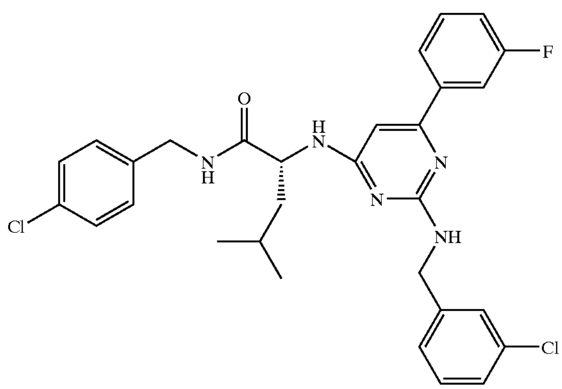 | 169968 |
| 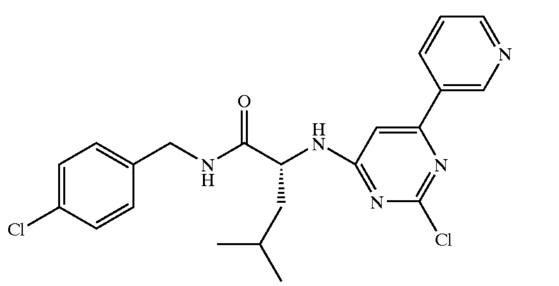 | 405907 |
| 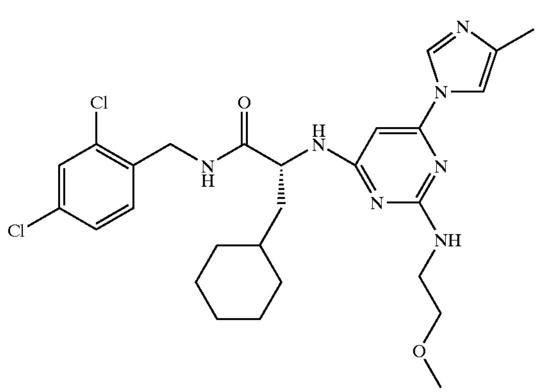 | 577561 |

TABLE 2-continued
| STRUCTURE | Identifier |
|---|---|
| 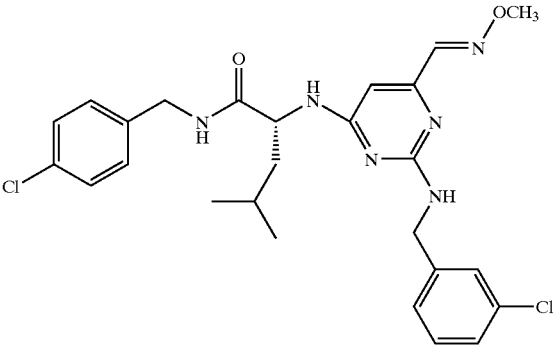 | 651408 |
| 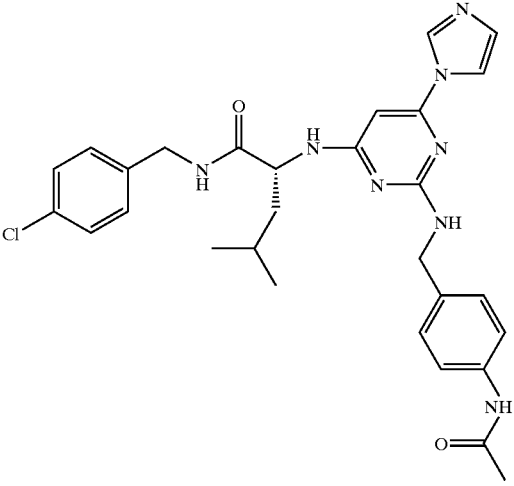 | 834615 |
| 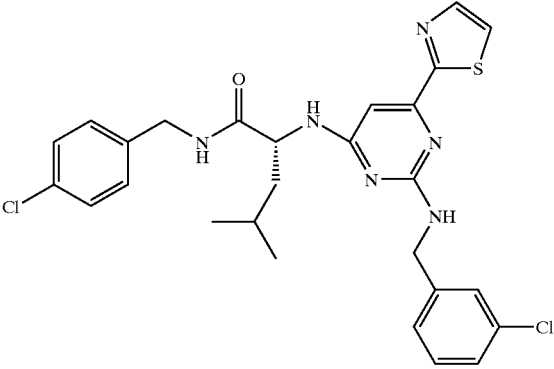 | 836641 |

TABLE 2-continued
| STRUCTURE | Identifier |
|---|---|
| 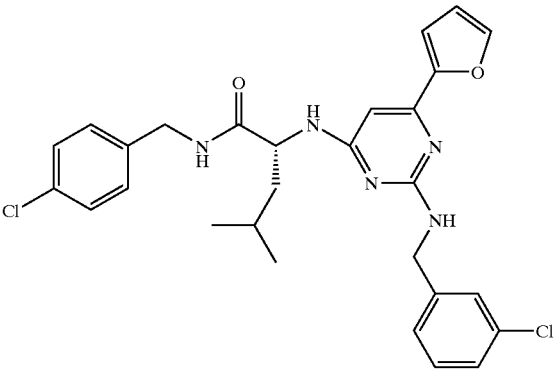 | 419551 |
| 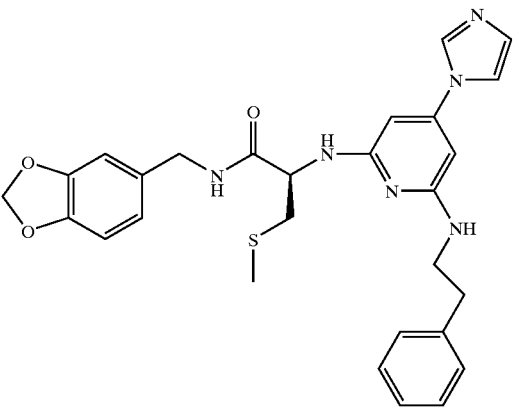 | 830601 |
| 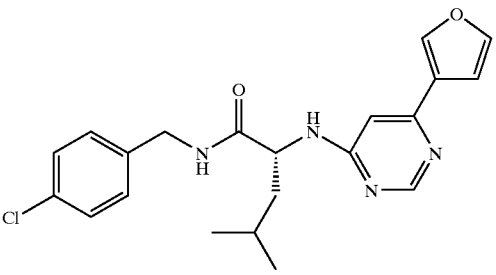 | 555804 |
| 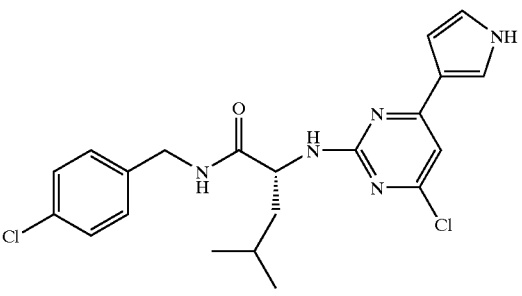 | 031557 |

TABLE 2-continued

| STRUCTURE | Identifier |
|---|---|
| 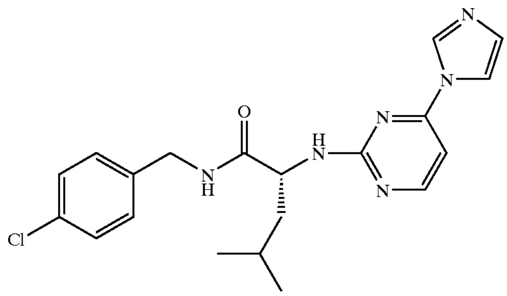 | 085311 |
| 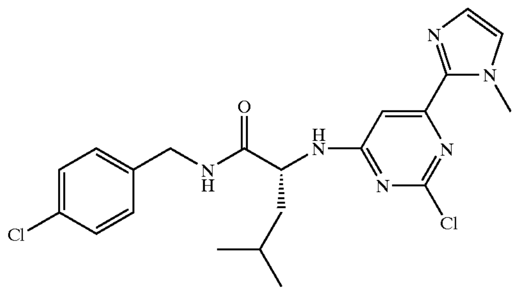 | 340085 |
| 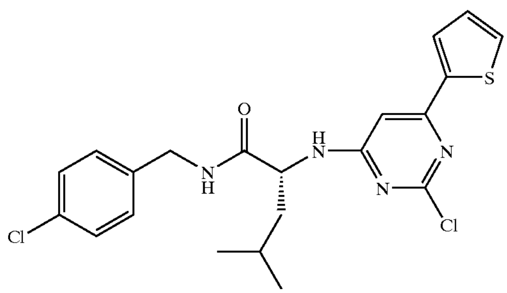 | 574878 |
| 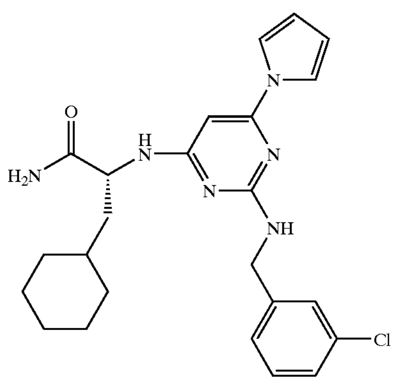 | 906426 |
| 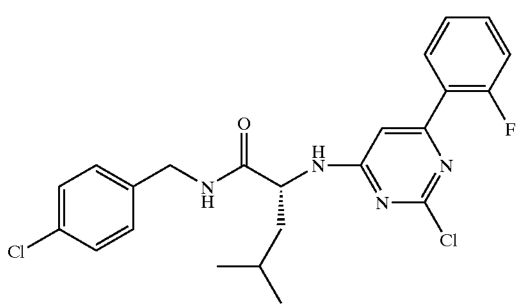 | 396104 |

TABLE 2-continued

| STRUCTURE | Identifier |
|---|---|
| 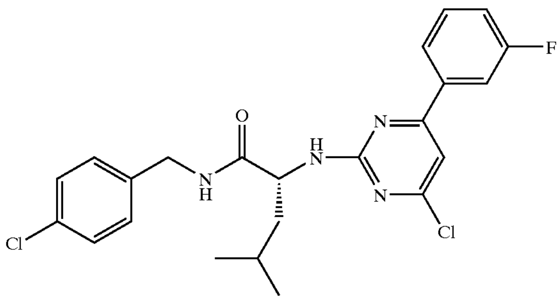 | 404682 |
| 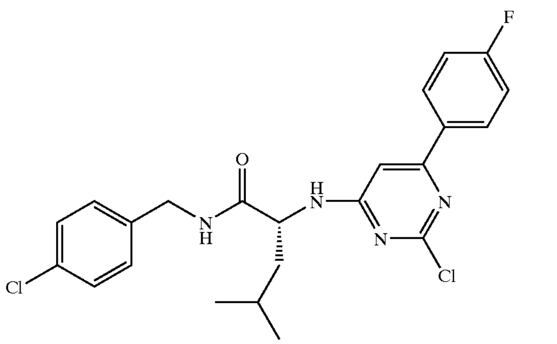 | 637763 |
| 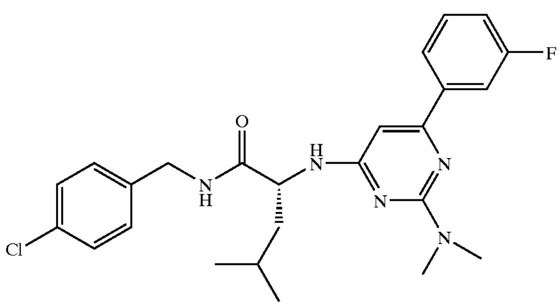 | 006801 |
| 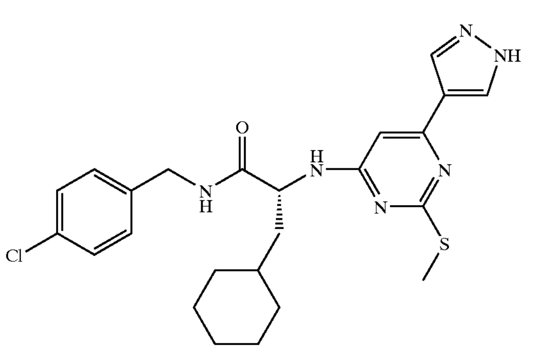 | 309888 |

TABLE 2-continued
| STRUCTURE | Identifier |
|---|---|
| 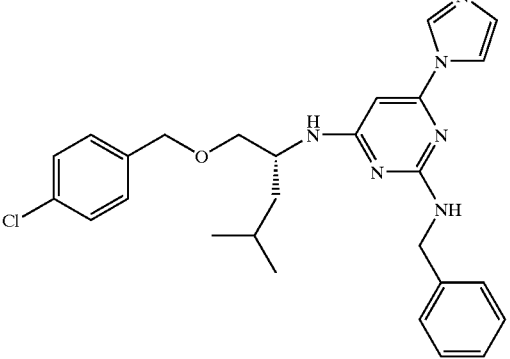 | 889134 |
| 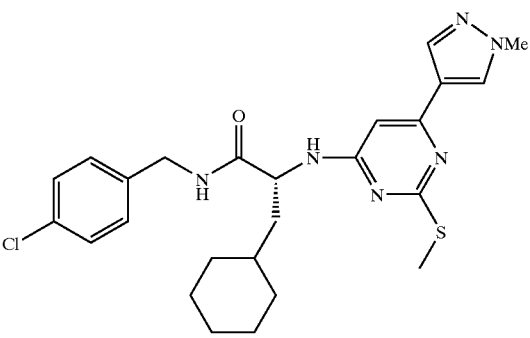 | 888340 |
| 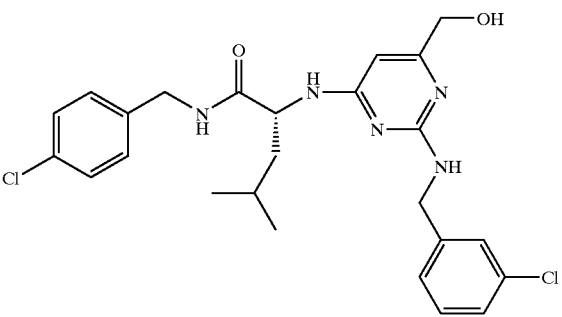 | 407599 |
| 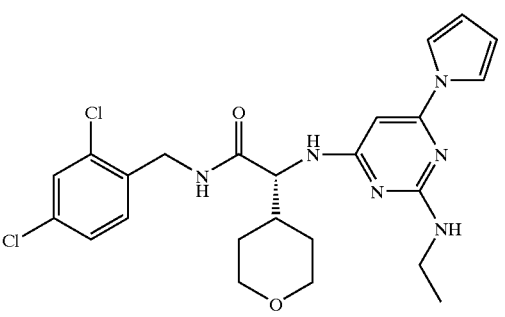 | 458001 |

TABLE 2-continued

| STRUCTURE | Identifier |
|---|---|
| 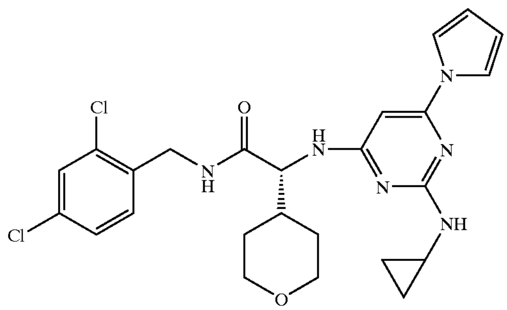 | 214357 |
| 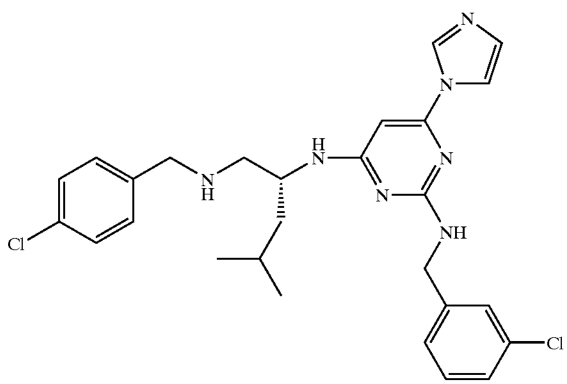 | 324675 |
| 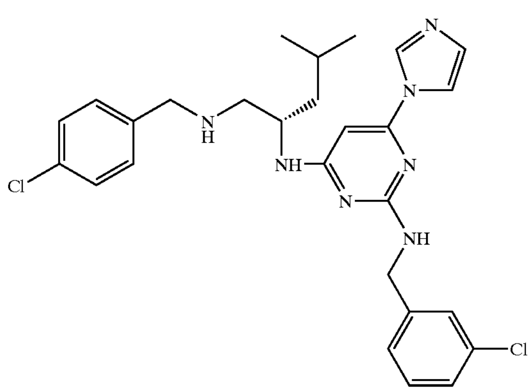 | 622414 |
| 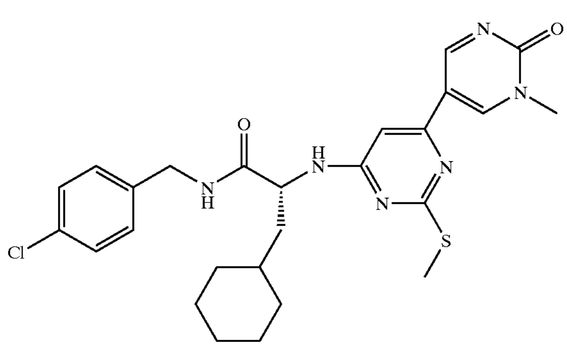 | 193177 |

TABLE 2-continued
| STRUCTURE | Identifier |
|---|---|
| 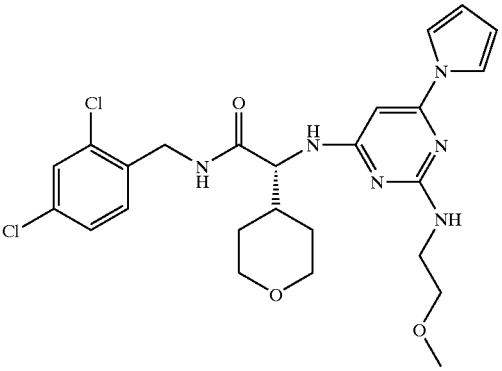 | 979425 |
| 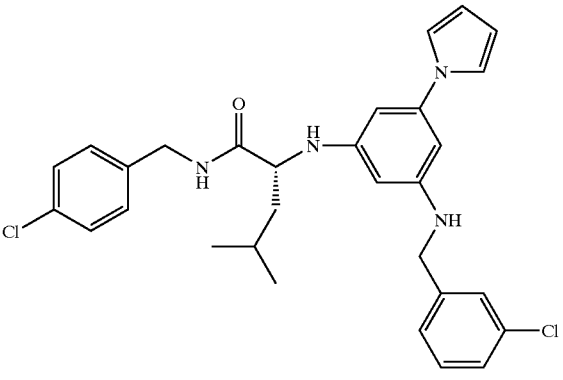 | 054066 |
| 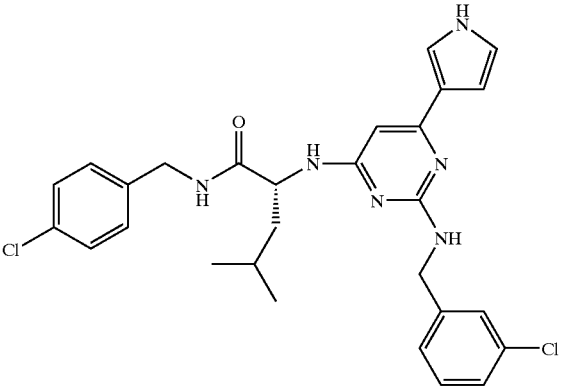 | 170440 |
| 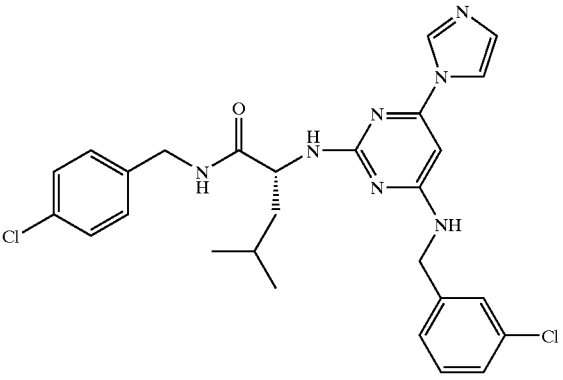 | 129647 |

TABLE 2-continued

| STRUCTURE | Identifier |
|---|---|
| 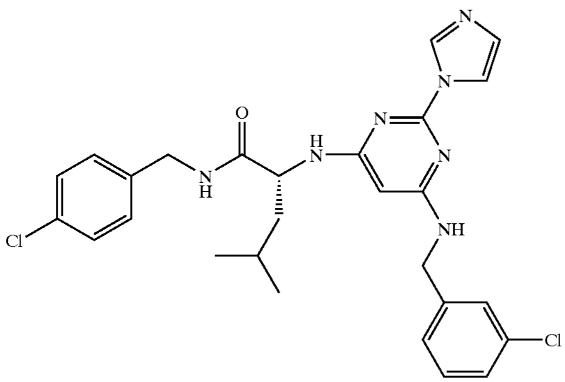 | 327168 |
| 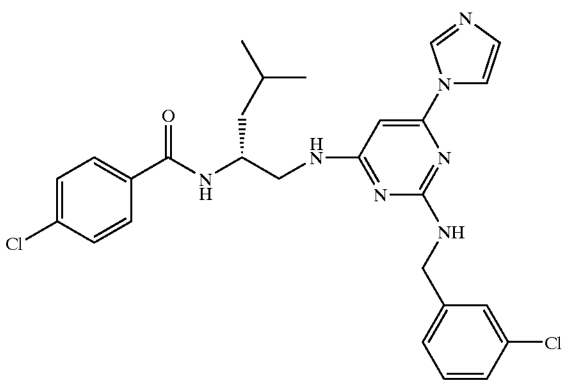 | 600629 |
| 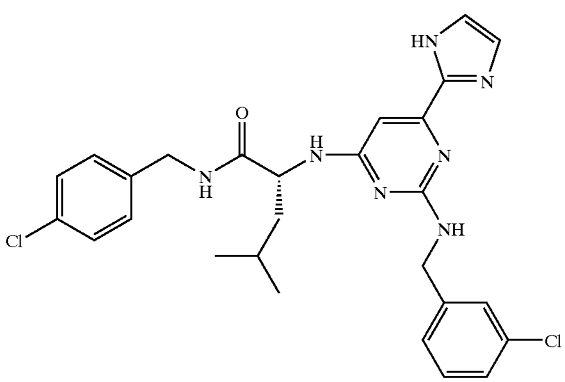 | 984213 |
| 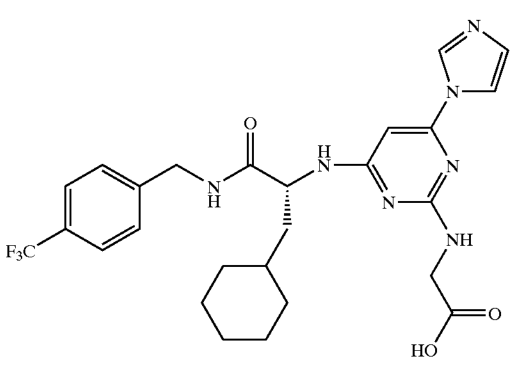 | 832914 |

TABLE 2-continued

| STRUCTURE | Identifier |
|---|---|
| 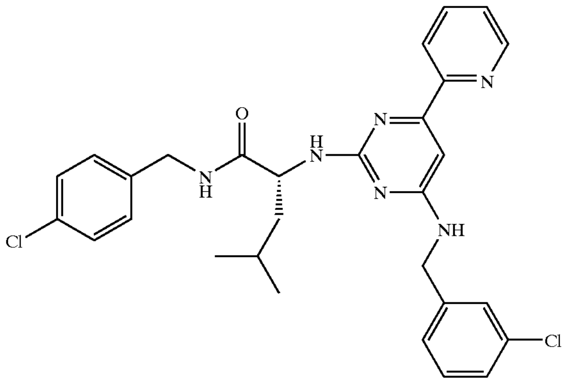 | 065864 |
| 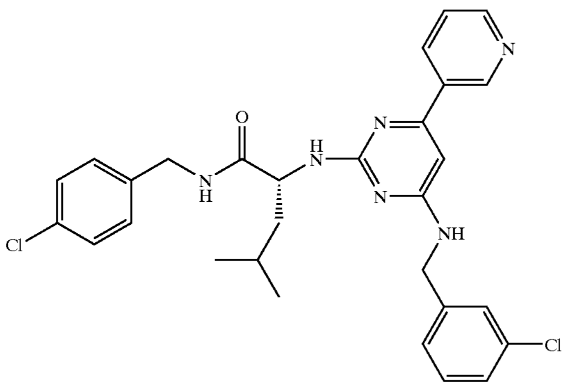 | 727448 |
| 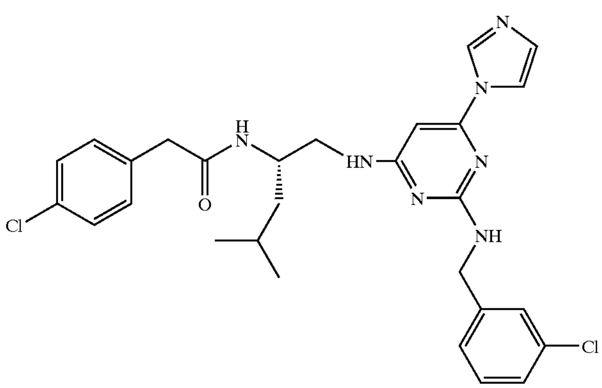 | 429933 |
| 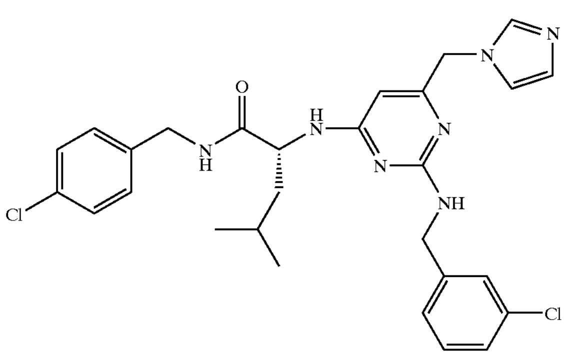 | 603335 |

TABLE 2-continued

| STRUCTURE | Identifier |
|---|---|
| 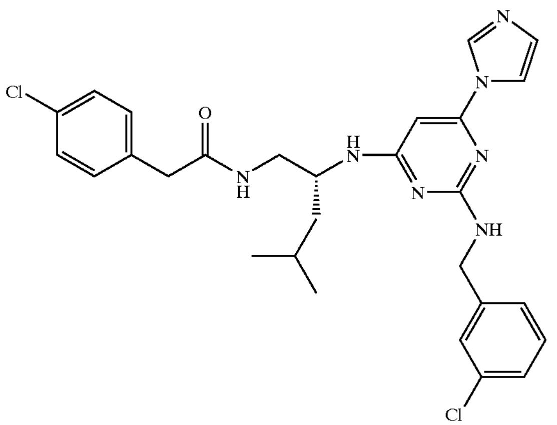 | 826751 |
| 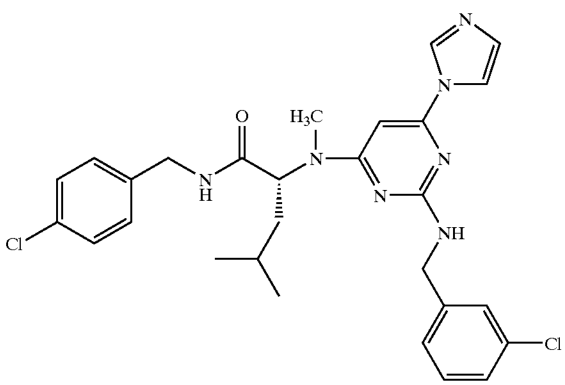 | 844156 |
| 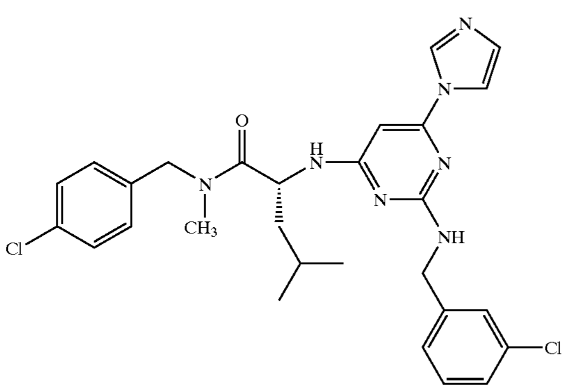 | 930501 |
| 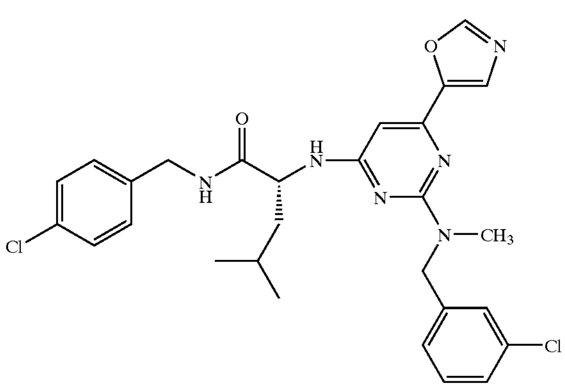 | 963106 |

TABLE 2-continued

| STRUCTURE | Identifier |
|---|---|
| 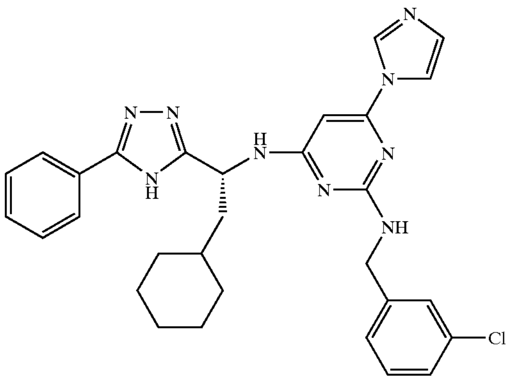 | 583734 |
| 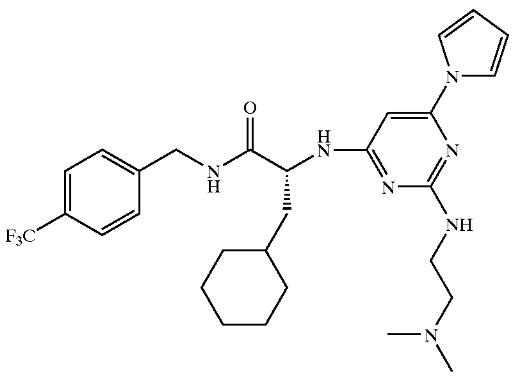 | 059809 |
| 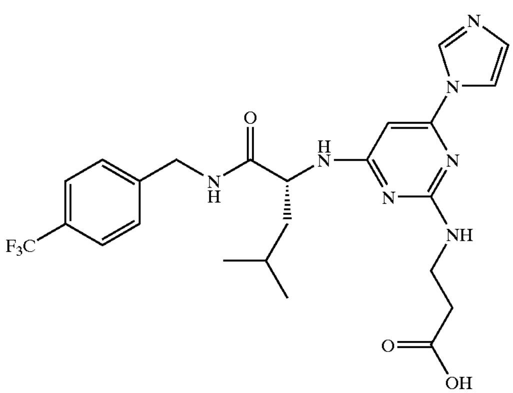 | 916267 |
| 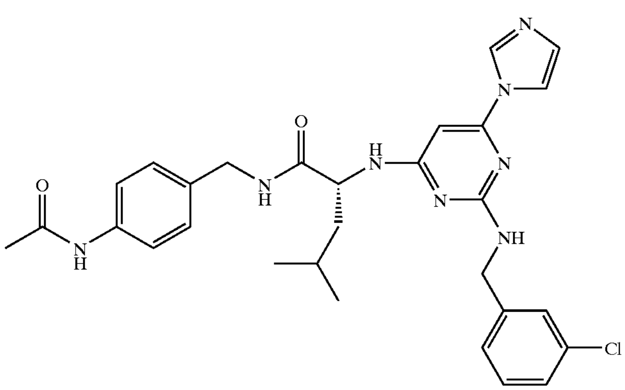 | 295459 |

TABLE 2-continued

| STRUCTURE | Identifier |
|---|---|
| 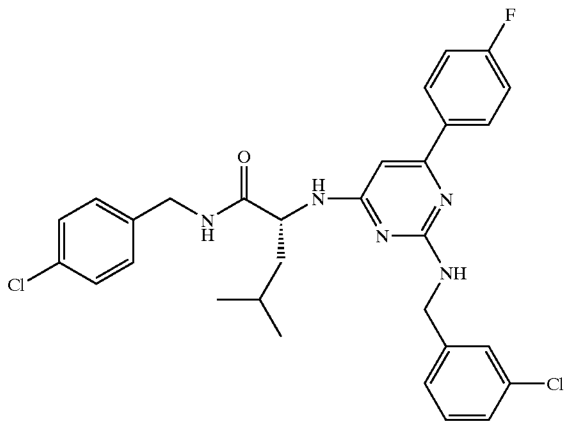 | 386842 |
| 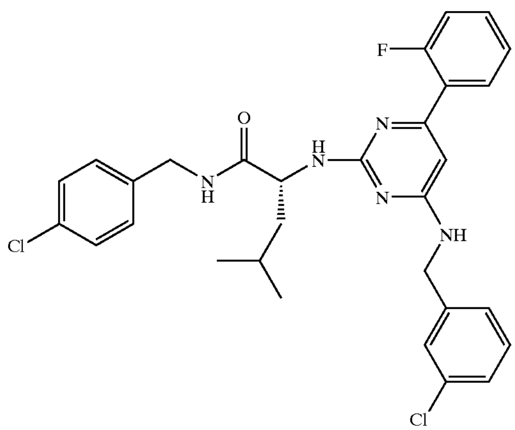 | 855317 |
| 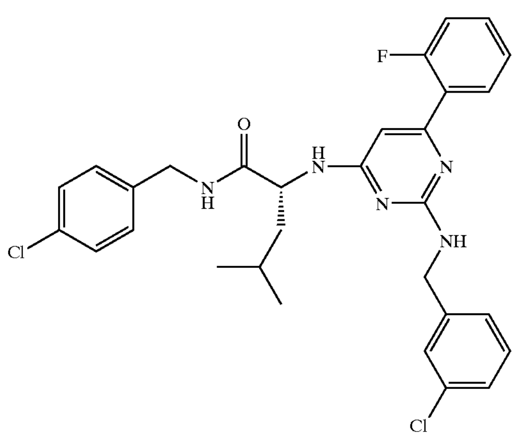 | 862111 |

TABLE 2-continued
| STRUCTURE | Identifier |
|---|---|
| 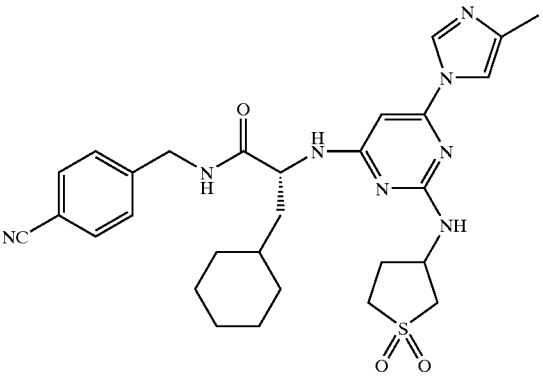 | 156360 |
| 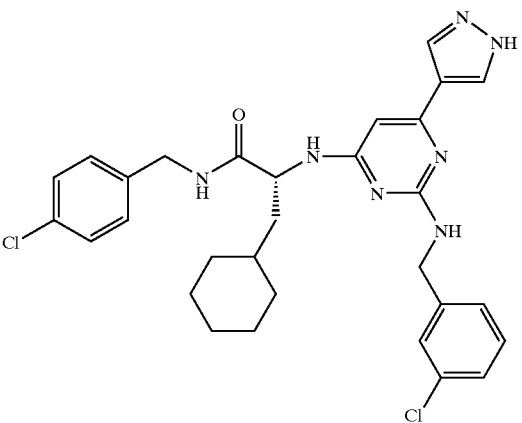 | 808880 |
| 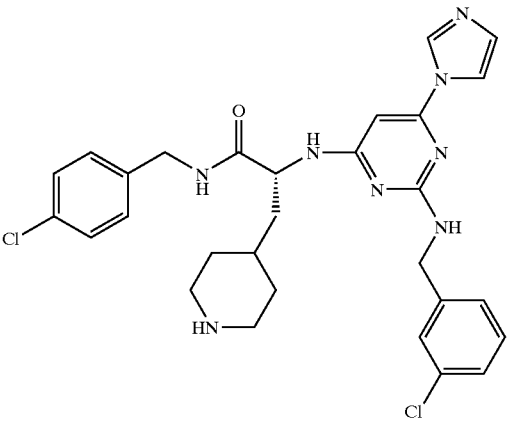 | 980203 |

TABLE 2-continued

| STRUCTURE | Identifier |
| --- | --- |
| 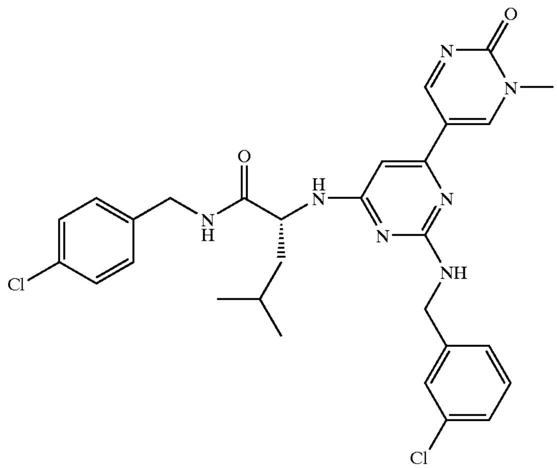 | 726338 |
| 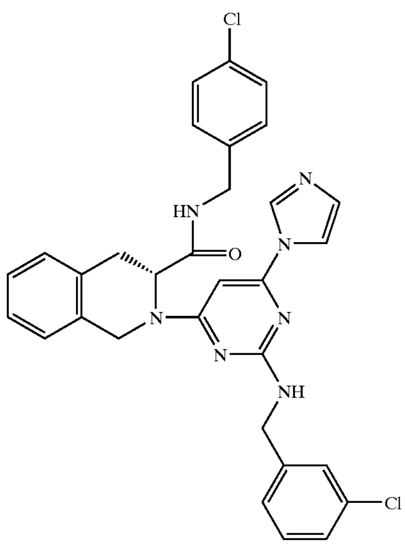 | 257040 |
| 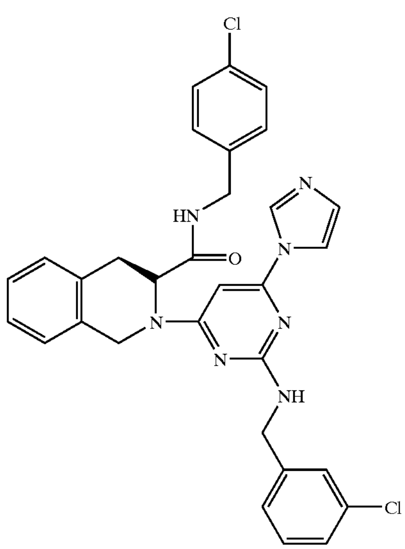 | 327989 |

TABLE 2-continued
| STRUCTURE | Identifier |
|---|---|
| 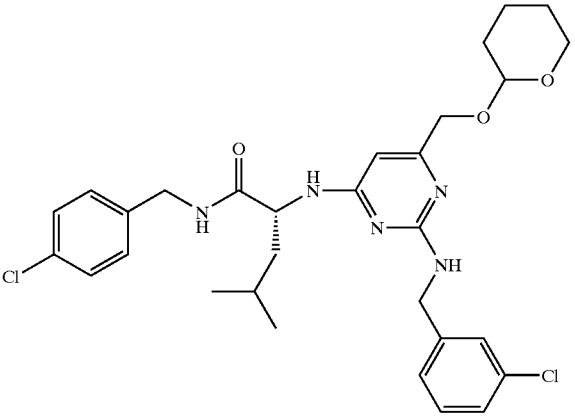 | 864091 |
| 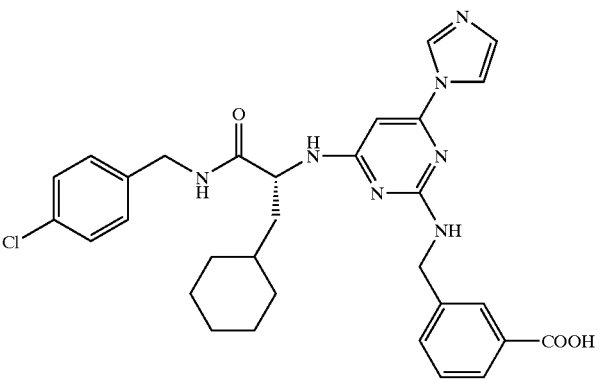 | 630878 |
| 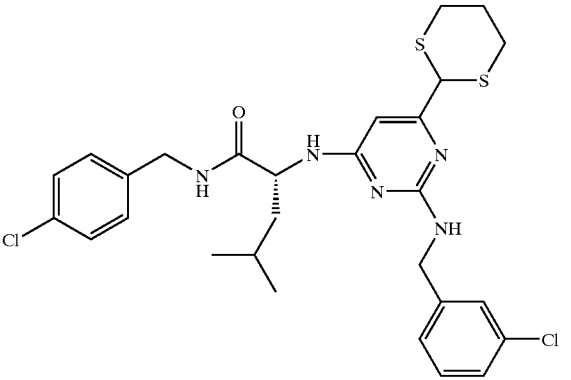 | 040296 |
| 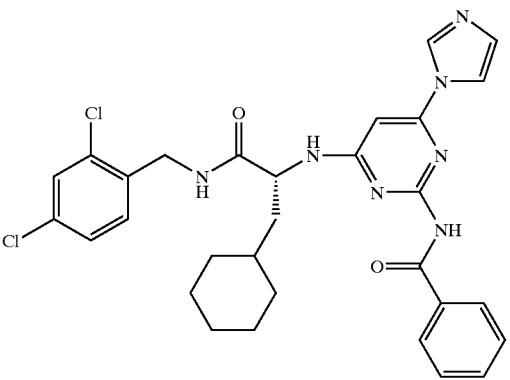 | 027665 |

TABLE 2-continued

| STRUCTURE | Identifier |
| --- | --- |
| 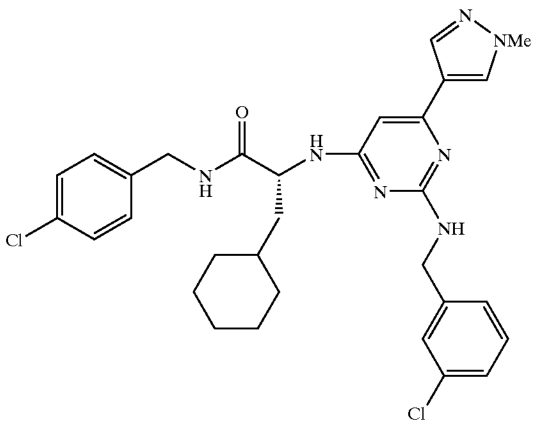 | 212579 |
| 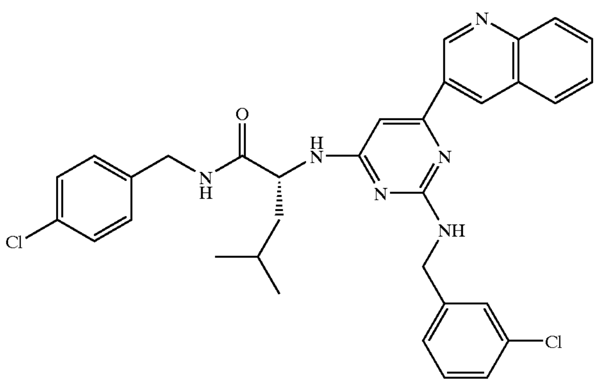 | 557004 |
| 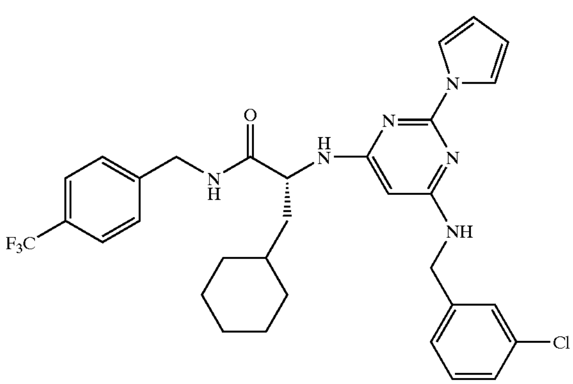 | 263415 |
| 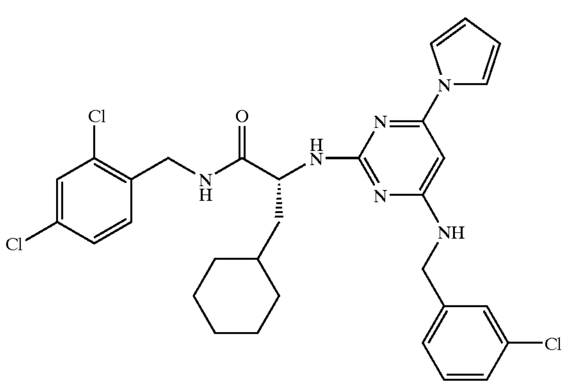 | 302927 |

TABLE 2-continued
| STRUCTURE | Identifier |
|---|---|
| 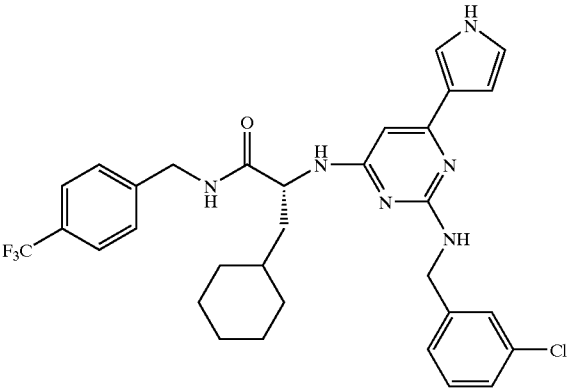 | 674216 |
| 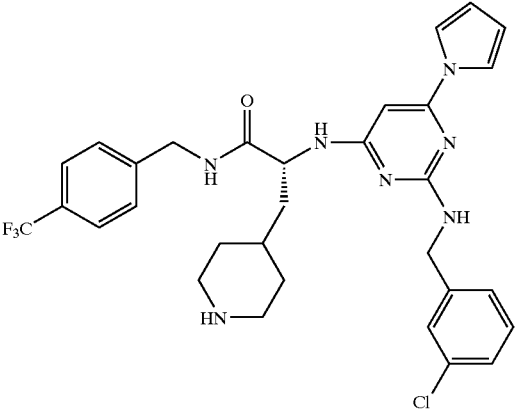 | 034480 |
| 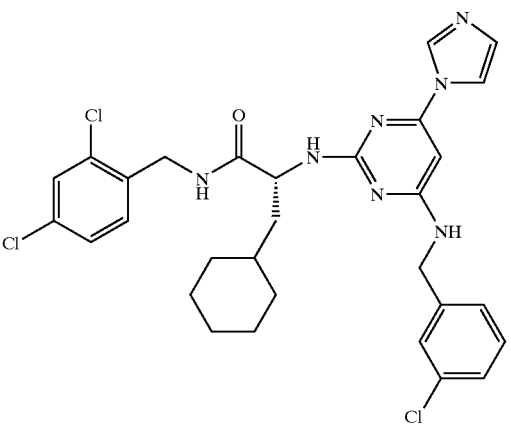 | 284784 |

TABLE 2-continued

| STRUCTURE | Identifier |
|---|---|
| 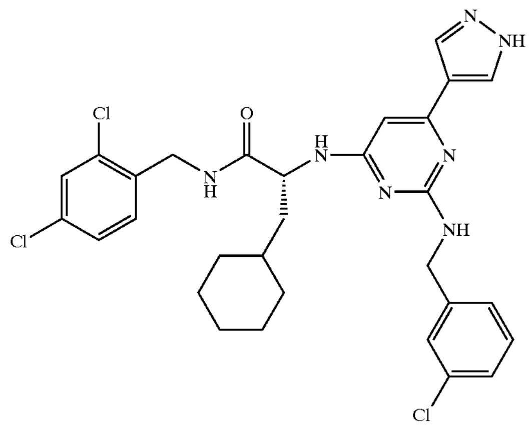 | 390534 |
| 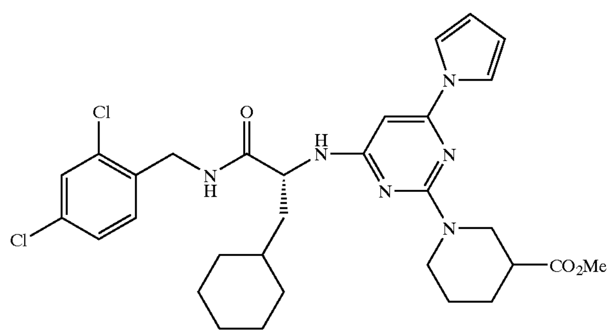 | 541410 |
| 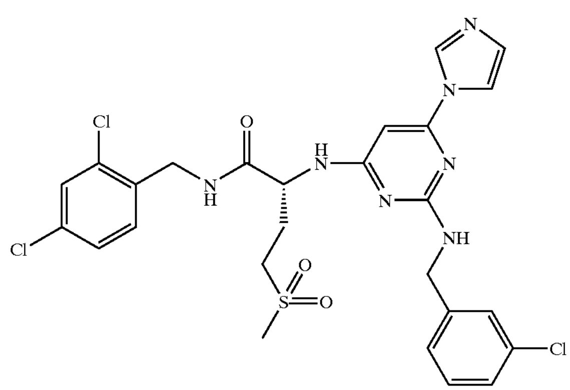 | 306344 |
| 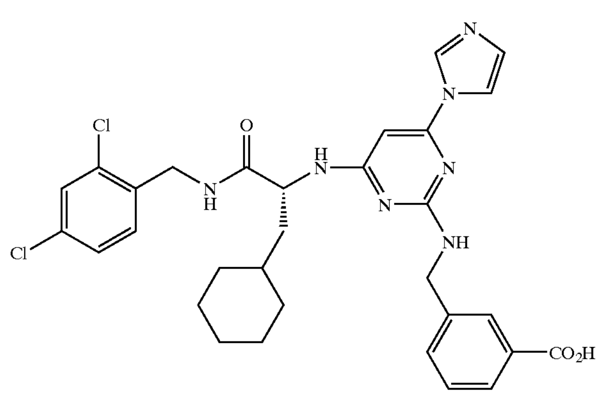 | 892732 |

TABLE 2-continued

| STRUCTURE | Identifier |
|---|---|
| 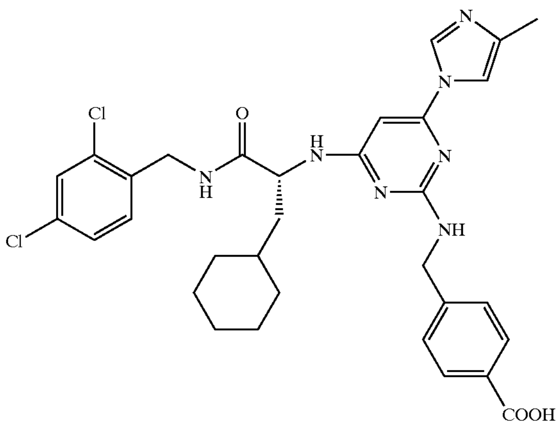 | 209284 |
| 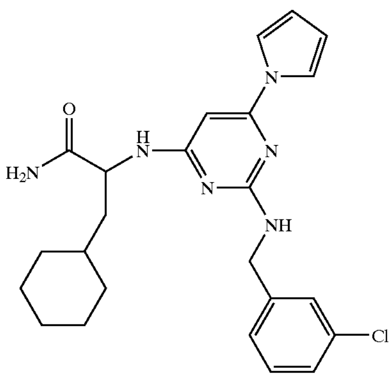 | 906426 |
| 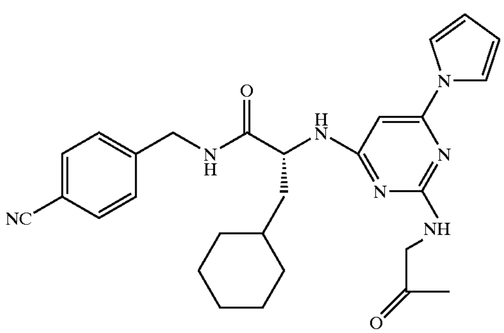 | 774868 |
| 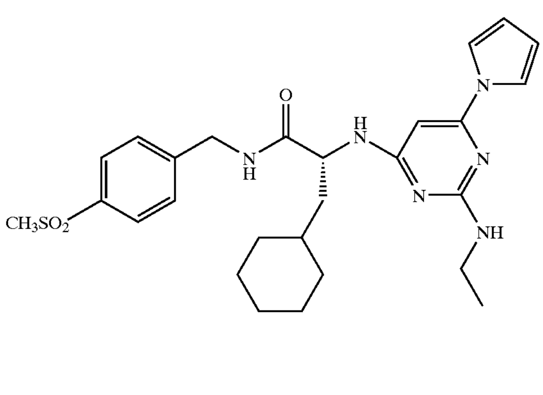 | 626899 |

TABLE 2-continued
| STRUCTURE | Identifier |
|---|---|
| 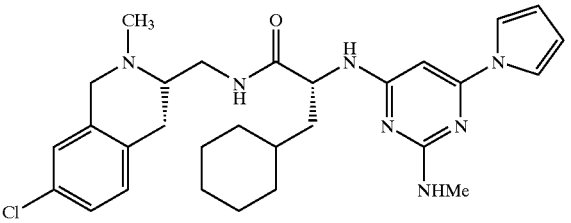 | 367587 |
| 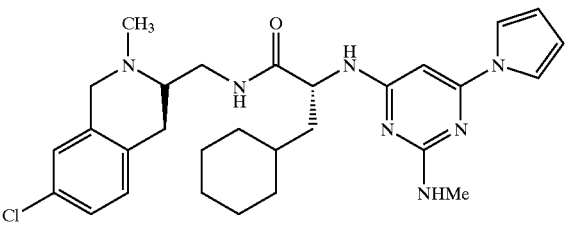 | 240936 |
| 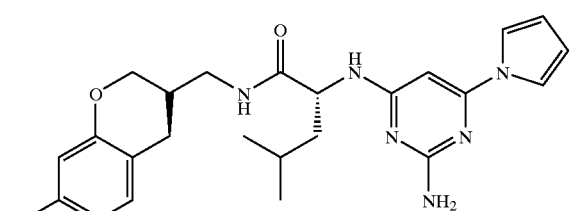 | 075438 |
| 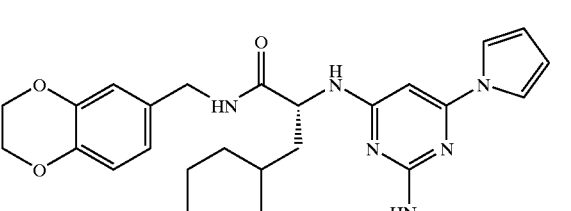 | 006518 |
| 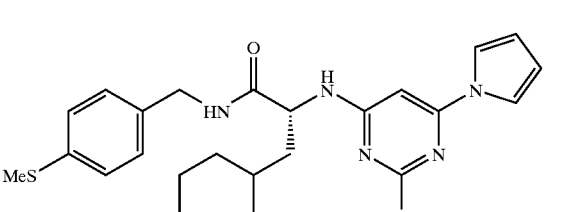 | 026511 |
| 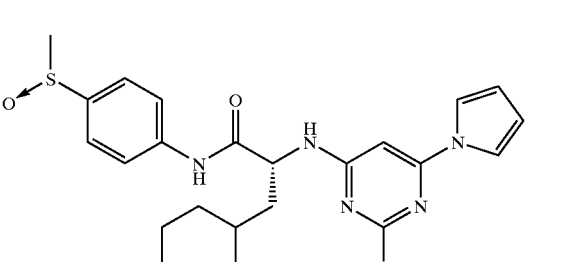 | 085374 |

TABLE 2-continued

| STRUCTURE | Identifier |
| --- | --- |
| 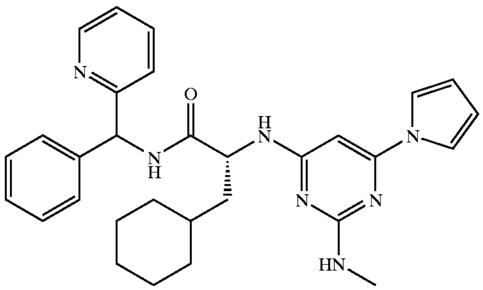 | 107571 |
| 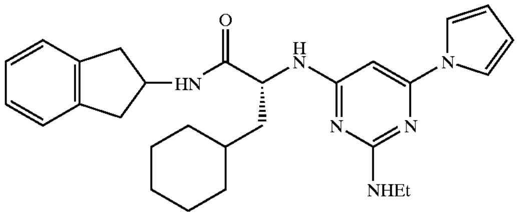 | 242518 |
| 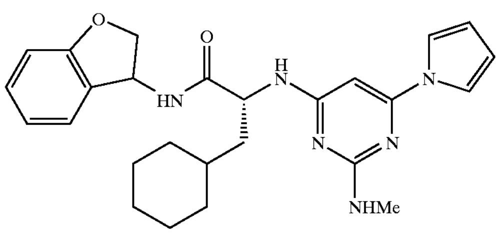 | 25037 |
| 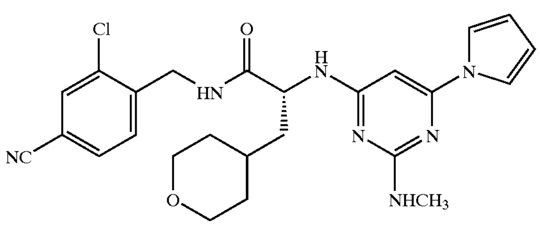 | 251559 |
| 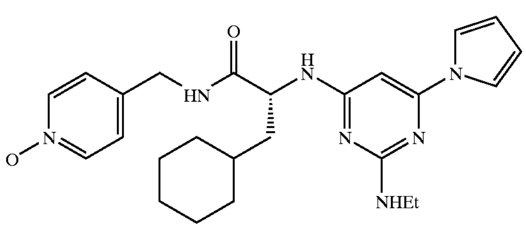 | 291582 |
| 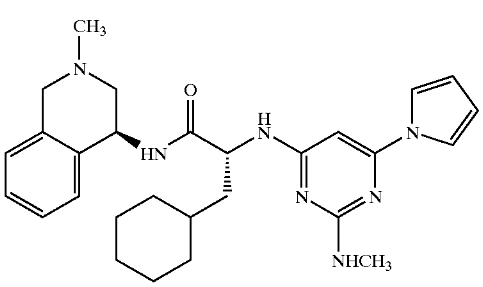 | 343424 |

TABLE 2-continued

| STRUCTURE | Identifier |
| --- | --- |
| 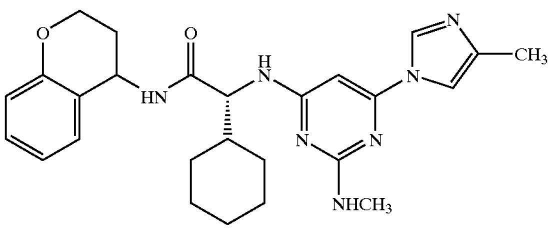 | 357720 |
| 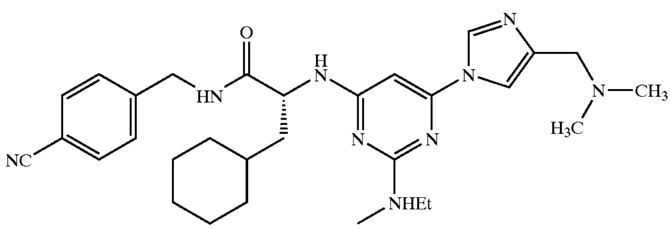 | 364637 |
| 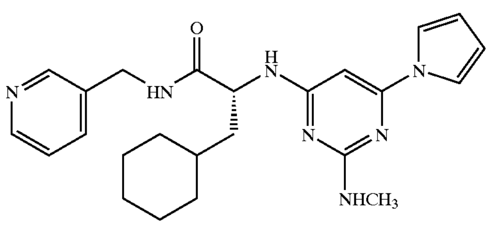 | 378606 |
| 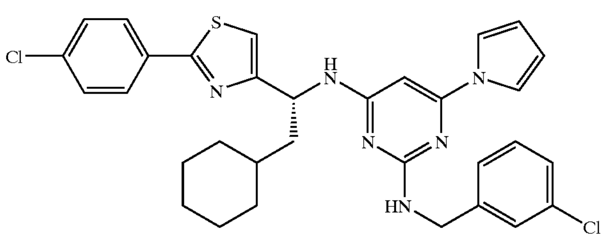 | 383670 |
| 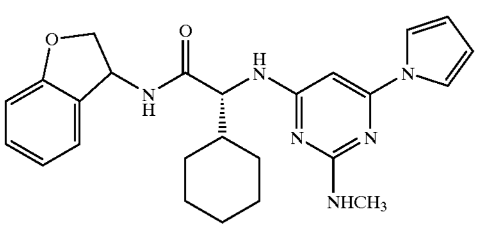 | 567456 |
| 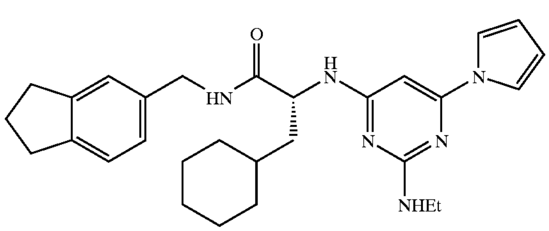 | 588918 |

TABLE 2-continued

| STRUCTURE | Identifier |
| --- | --- |
| 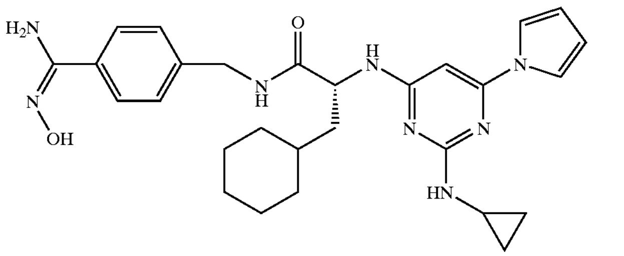 | 621206 |
| 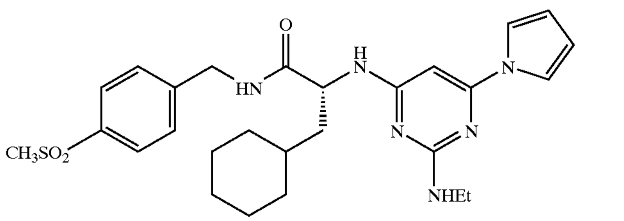 | 626899 |
| 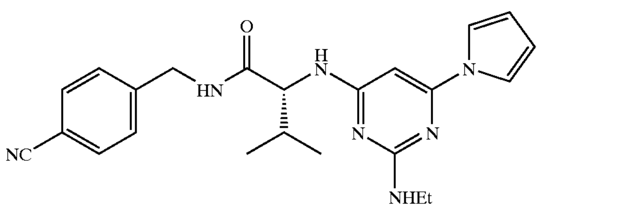 | 629441 |
| 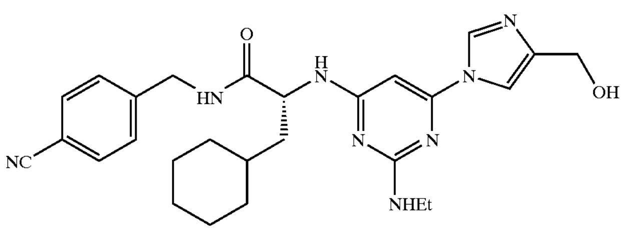 | 640538 |
| 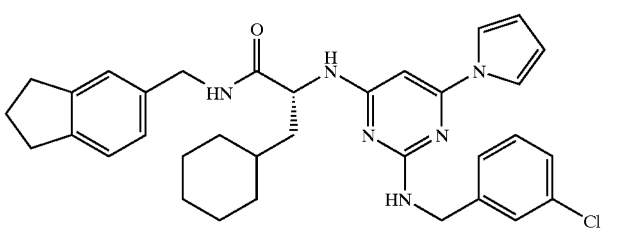 | 672975 |
| 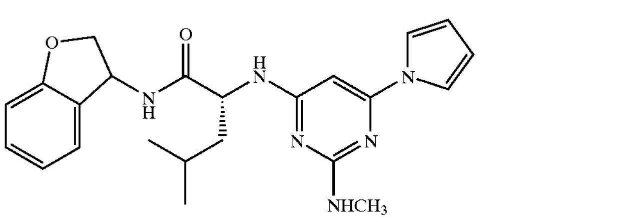 | 687899 |

TABLE 2-continued

| STRUCTURE | Identifier |
|---|---|
| 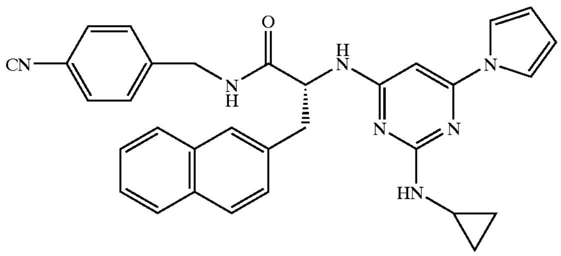 | 709833 |
| 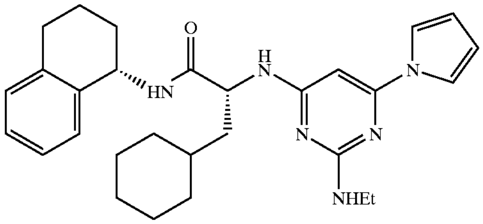 | 730697 |
| 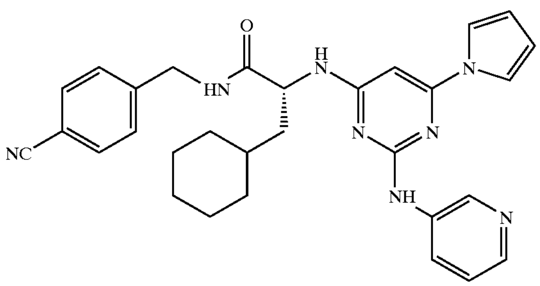 | 733184 |
| 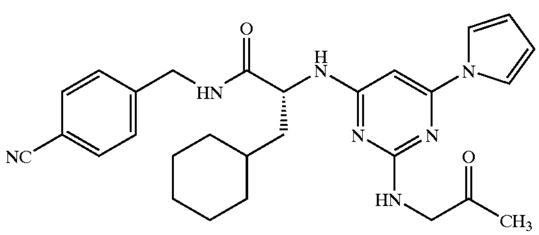 | 774868 |
| 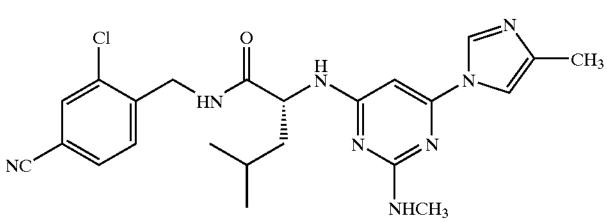 | 1828493 |
| 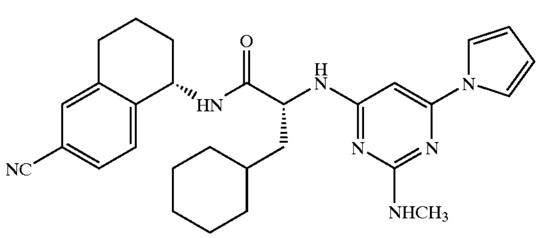 | 866399 |

TABLE 2-continued

| STRUCTURE | Identifier |
|---|---|
| 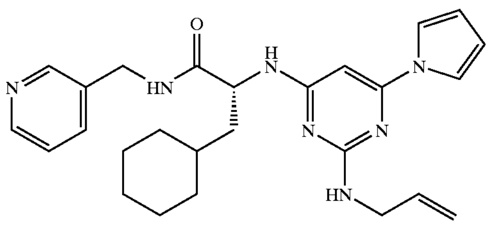 | 867894 |
| 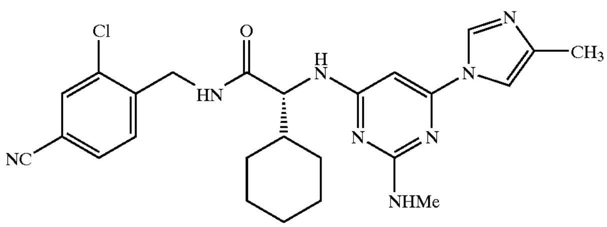 | 870562 |
| 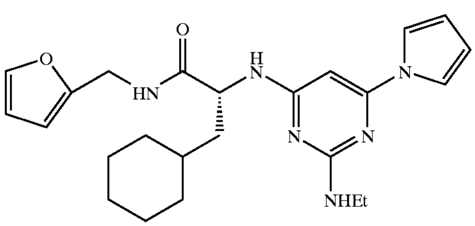 | 917930 |
| 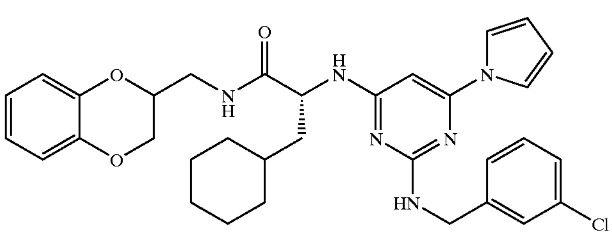 | 928221 |
| 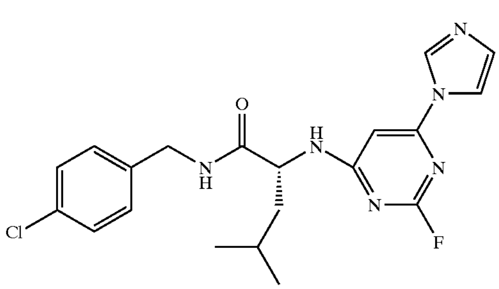 | 953837 |
| 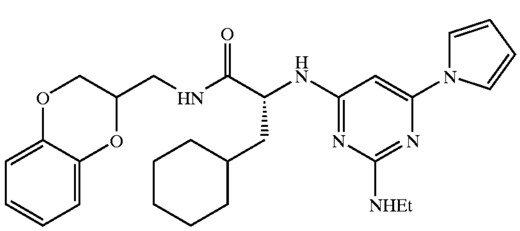 | 480759 |

What is claimed is:

1. A compound of formula

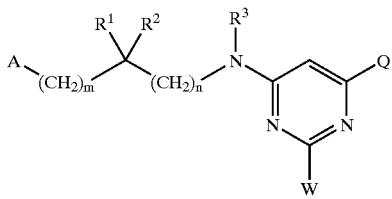

wherein:

A is $A^1$ or $A^2$;

$A^1$ is $R^4R^5N-C(O)-$,

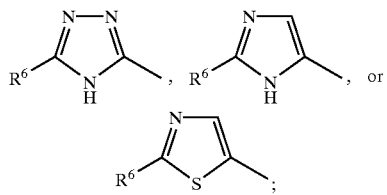

$A^2$ is chosen from $R^7C(O)NH-$, $R^7S(O)_2NH-$, $R^4NH-$, and $R^4O-$;

Q is chosen from imidazolyl, methylimidazolyl, pyrrolyl, methylpyrrolyl, pyrazolyl, methylpyrazolyl, hydroxymethylimidazolyl, (dimethylaminomethyl)imidazolyl, furanyl, methylfuranyl, thienyl, oxazolyl, thiazolyl, pyridinyl, quinolinyl, 1-methylpyrimidin-2-onyl, phenyl, fluorophenyl, hydroxymethyl, tetrahydropyranyloxymethyl, imidazolylmethyl, pyrrolylmethyl, $-CH=N-OCH_3$ and

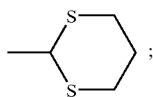

W is chosen from H, Cl, F, $R^8$, $C_1-C_4$-alkylaryl, $-OR^8$, $-SR^8$, $-NR^9R^{10}$ and $-NHC(O)R^{11}$, with the proviso that when Q is imidazolyl, W is not H, Cl, F or $R^8$;

$R^1$ is chosen from alkyl, cycloalkyl, alkenyl, $C_1-C_3$-alkylcycloalkyl, heterocyclyl, $C_1-C_3$-alkylheterocyclyl, aryl, $C_1-C_3$-alkylaryl, heteroaryl, $C_1-C_3$-alkylheteroaryl, ($C_1-C_3$-alkyloxy)alkyl, ($C_1-C_3$-alkyloxy)cycloalkyl, ($C_1-C_3$-alkylthio)alkyl, ($C_1-C_3$-alkylthio)cycloalkyl and ($C_1-C_3$-alkylsulfonyl)alkyl;

$R^2$ is H or $C_1-C_3$-alkyl, or $R^1$ and $R^2$ taken together form a 5- to 7-membered ring structure optionally containing O, S or $NR^{12}$;

$R^3$ is H or $C_1-C_6$-alkyl, or, when n is zero, $R^2$ and $R^3$ taken together may form a 6-membered ring, which may be fused to a six-membered saturated or aromatic carbocycle;

$R^4$ is chosen from H, aryl, heteroaryl, $C_1-C_4$-alkyl substituted with from one to three aryl or heteroaryl residues,

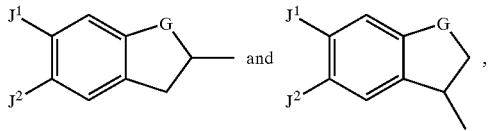

wherein $J^1$ and $J^2$ are independently chosen from H, F, Cl, CN, $NO_2$ and $CH_3$, and G is chosen from $-CH_2-$, $-CH_2CH_2-$, $-CH_2CH_2CH_2-$, $-OCH_2-$, $-CH_2O-$, $-CH_2CH_2O-$, $-OCH_2CH_2-$, $-O-$, $-N(\text{lower alkyl})-$, $-N(\text{lower alkyl})CH_2-$, $-CH_2N(\text{lower alkyl})-$, $-S-$, $-SO-$, $-SO_2-$, $-CH_2S-$, $-SCH_2-$, $-CH_2SO-$, $-SOCH_2-$, $-CH_2SO_2-$, and $-SO_2CH_2-$;

$R^5$ is H or $C_1-C_3$-alkyl, with the proviso that both $R^3$ and $R^5$ cannot be alkyl;

$R^6$ is aryl;

$R^7$ is aryl or $C_1-C_3$-alkylaryl;

$R^8$ is chosen from alkyl, aryl, heteroaryl, substituted alkyl, $C_1-C_4$-alkylaryl, $C_1-C_4$-alkylheterocyclyl and $C_1-C_4$-alkylheteroaryl;

$R^9$ is chosen from H, alkyl, alkenyl, substituted alkyl, cycloalkyl, aryl, alkoxy, heteroaryl, fluoroalkyl, $C_1-C_4$-alkylcycloalkyl, ($C_1-C_4$-alkoxy)alkyl, ($C_1-C_4$-alkoxycarbonyl)alkyl, ($C_1-C_4$-alkylthio)alkyl, heterocyclyl, $C_1-C_4$-alkylheterocyclyl, $C_1-C_4$-alkylaryl, and $C_1-C_4$-alkylheteroaryl;

$R^{10}$ is H or $C_1-C_3$-alkyl, or $R^9$ and $R^{10}$ taken together may form a 5- to 7-membered ring structure optionally containing O, S, SO, $SO_2$ or $NR^{12}$, said ring optionally substituted with $-OH$, $-CN$, $-COOH$ or $-COOCH_3$;

$R^{11}$ is aryl;

$R^{12}$ is chosen from H, $C_1-C_3$-alkyl, alkoxycarbonyl, methoxyacetyl and aryl;

m is zero or one; and n is zero or one, with the proviso that when A is $A^2$, m and n cannot both be zero.

2. A 4-pyrimidinamine according to claim 1 wherein:

Q is chosen from pyrrol-1-yl, imidazol-1-yl, furan-3-yl, 2-methylimidazol-1-yl and 4-methylimidazol-1-yl;

A is $R^4R^5N-C(O)-$;

W is Cl, $NHR^9$, $N(CH_3)R^9$, $OR^8$, $SR^8$, $R^8$, morpholin-4-yl;

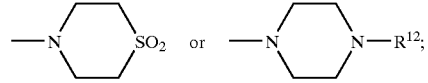

$R^1$ is chosen from alkyl, cycloalkyl, $C_1-C_3$-alkylaryl, $C_1-C_3$-alkylcycloalkyl, $C_1-C_3$-alkylheterocyclyl, $C_1-C_3$-alkylheteroaryl $R^2$, $R^3$ and $R^5$ are H;

$R^8$ is $C_1-C_4$-alkylaryl;

$R^9$ is chosen from hydrogen, alkyl, substituted alkyl, ($C_1-C_4$)-alkoxy, $C_1-C_4$-alkylcycloalkyl, $C_1-C_4$-alkylaryl, heterocyclyl, $C_1-C_4$-alkylheteroaryl, $C_1-C_4$-alkylheterocyclyl; and m and n are zero.

3. A 4-pyrimidinamine according to claim 2 wherein W is $NHR^9$ and $R^9$ is chosen from hydrogen; methyl; ethyl; 2,2,2-trifluoroethyl; allyl; cyclopropyl; 2-cyanoethyl; propargyl; methoxy; methoxyethyl; cyclopropyl; cyclopropylmethyl; (methylthio)ethyl; 3-methoxypropyl; 3-pyridyl; 2-(3-pyridyl)ethyl; 2-(2-pyridyl)ethyl; 3-pyridylmethyl; 4-pyridylmethyl; 4-pyridylmethyl-N-oxide; 2-pyridazinylmethyl; sulfolan-3-yl; 3-tetrahydrofuranyl; 2-tetrahydrofuranylmethyl; 3-(1-imidazolyl)propyl; 1-t-butoxycarbonyl-4-piperidinyl; 1-t-butoxycarbonyl-4-piperidinylmethyl; 2-(hydroxyimino)propyl; 2-(methoxyimino)propyl; 2-oxo-1-propyl; and

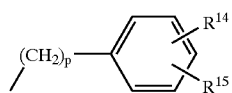

wherein $R^{14}$ is chosen from H, Cl, F, CN, $NO_2$, $SO_2NH_2$, $CF_3$, $COOCH_3$, $OCH_3$, OH, $SO_2CH_3$, $N(CH_3)_2$ and COOH;

$R^{15}$ is chosen from H, $OCH_3$ and Cl; and p is 1 or 2.

4. A 4-pyrimidinamine according to claim 2 wherein W is

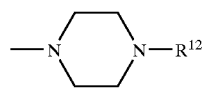

and $R^{12}$ is t-butoxycarbonyl, methoxyacetyl or phenyl.

5. A compound of formula

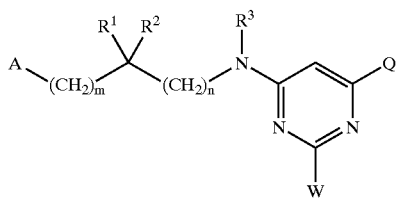

wherein:

A is

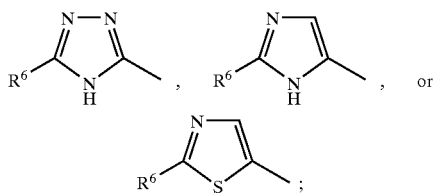

$R^1$ is chosen from n-butyl; cyclohexylmethyl; cyclopentylmethyl; 2-methylpropyl; 3-methyl-1-butyl; cyclohexyl; 2,2-dimethylpropyl; benzyl; 2-thienylmethyl; 1-t-butoxycarbonyl-4-piperidinyl; 4-chlorobenzyl; 2-pyranylmethyl; 4-pyranylmethyl; 4-pyranyl and 1,1-dimethylethyl;

$R^2$ and $R^3$ are H;

Q is imidazolyl or pyrrolyl;

$R^6$ is aryl;

$R^4$ is chosen from H, aryl, heteroaryl, $C_1$–$C_4$-alkyl substituted with from one to three aryl or heteroaryl residues,

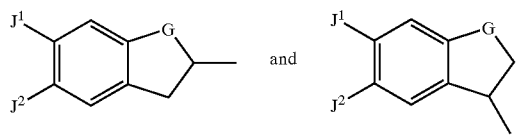

wherein $J^1$ and $J^2$ are independently chosen from H, F, Cl, CN, $NO_2$ and $CH_3$, and G is chosen from —$CH_2$—, —$CH_2CH_2$—, —$CH_2CH_2CH_2$—, —$OCH_2$—, —$CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—;

$R^7$ is aryl or $C_1$–$C_3$-alkylaryl;

W is $NHR^9$; and $R^9$ is alkyl, cycloalkyl or

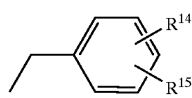

wherein $R^{14}$ is chosen from H, Cl, F, CN, $NO_2$, $SO_2NH_2$, $CF_3$, $COOCH_3$, $OCH_3$, $SO_2CH_3$, $N(CH_3)_2$ and COOH; and $R^{15}$ is chosen from H, $OCH_3$ and Cl;

m is zero or one; and n is zero or one, with the proviso that when A is chosen from $R^7C(O)NH$—, $R^7S(O)_2NH$—, $R^4NH$—, and $R^4O$—, m and n cannot both be zero.

6. A compound of formula

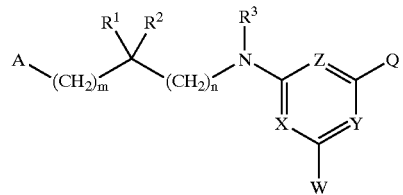

wherein:

two of X, Y and Z are N and the other of X, Y and Z is CH;

A is $R^4R^5N$—C(O)—;

Q is chosen from heteroaryl, aryl, —$CH_2R^{13}$, —CH=N—$OCH_3$ and

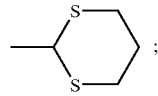

W is chosen from H, Cl, F, $R^8$, $C_1$–$C_4$-alkylaryl, —$OR^8$, —$SR^8$, —$NR^9R^{10}$ and —NHC(O)$R^{11}$, with the proviso that when Q is imidazolyl, W is not H, Cl, F or $R^8$;

$R^1$ is chosen from isopropyl; n-butyl; cyclohexylmethyl; cyclopentylmethyl; naphthylmethyl; cyclohexylethyl; 2-methylpropyl; 3-methyl-1-butyl; cyclohexyl; 2,2-dimethylpropyl; benzyl; 2-thienylmethyl; 1-t-butoxycarbonyl-4-piperidinyl; 4-methoxybenzyl; 4-chlorobenzyl; 3,4-dichlorobenzyl; 2-pyranylmethyl; 4-pyranylmethyl; 4-pyranyl and 1,1-dimethylethyl;

$R^2$, $R^3$ and $R^5$ are H;

$R^4$ is chosen from H, aryl, heteroaryl, $C_1$–$C_4$-alkyl substituted with from one to three aryl or heteroaryl residues,

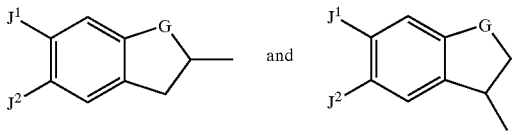 and wherein $J^1$ and $J^2$ are independently chosen from H, F, Cl, CN, $NO_2$ and $CH_3$, and G is chosen from —$CH_2$—, —$CH_2CH_2$—, —$CH_2CH_2CH_2$—, —$OCH_2$—, —$CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl, or $R^9$ and $R^{10}$ taken together may form a 5- to 7-membered ring structure optionally containing O, S, SO, $SO_2$ or $NR^{12}$, said ring optionally substituted with —OH, —CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and n is zero or one, with the proviso that when A is chosen from $R^7C(O)NH$—, $R^7S(O)_2NH$—, $R^4NH$—, and $R^4O$—, m and n cannot both be zero.

7. A pyrimidine according to claim 6 wherein:

$R^4$ is pyridinyl, pyridinylmethyl, tetrahydronaphthalenyl, indanylmethyl, furanylmethyl, substituted phenyl, or

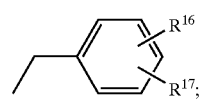

$R^{16}$ is chosen from H, Cl, F, CN, $NO_2$, $SO_2NH_2$, $CF_3$, $CH_3$, $COOCH_3$, $OCH_3$, $SO_2CH_3$, $SOCH_3$, $N(CH_3)_2$, tetrazol-5-yl, $CONH_2$, C(=NOH)$NH_2$ and COOH; and $R^{17}$ is chosen from H, $OCH_3$, F and Cl.

8. A pyrimidine according to claim 6 wherein $R^4$ is

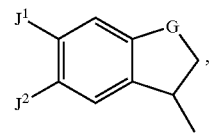

one of $J^1$ and $J^2$ is H and the other is H, Cl or CN and G is chosen from —$CH_2$—, —$CH_2CH_2$—, —$OCH_2$—, —O— and —$CH_2$N(lower alkyl)-.

9. A compound of formula

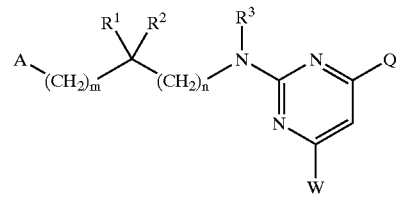

wherein:

A is $A^1$ or $A^2$;

$A^1$ is $R^4R^5N$—C(O)—,

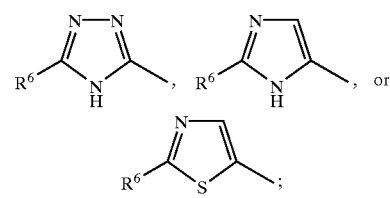

$A^2$ is chosen from $R^7C(O)NH$—, $R^7S(O)_2NH$—, $R^4NH$—, and $R^4O$—;

Q is chosen from heteroaryl, aryl, —$CH_2R^{13}$, —CH=N—$OCH_3$ and

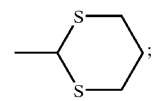

W is chosen from H, Cl, F, $R^8$, $C_1$–$C_4$-alkylaryl, —$OR^8$, —$SR^8$, —$NR^9R^{10}$ and —$NHC(O)R^{11}$, with the proviso that when Q is imidazolyl, W is not H, Cl, F or $R^8$;

$R^1$ is chosen from alkyl, cycloalkyl, alkenyl, $C_1$–$C_3$-alkylcycloalkyl, heterocyclyl, $C_1$–$C_3$-alkylheterocyclyl, aryl, $C_1$–$C_3$-alkylaryl, heteroaryl, $C_1$–$C_3$-alkylheteroaryl, ($C_1$–$C_3$-alkyloxy)alkyl, ($C_1$–$C_3$-alkyloxy)cycloalkyl, ($C_1$–$C_3$-alkylthio)alkyl, ($C_1$–$C_3$-alkylthio)cycloalkyl and ($C_1$–$C_3$-alkylsulfonyl)alkyl;

$R^2$ is H or $C_1$–$C_3$-alkyl, or $R^1$ and $R^2$ taken together form a 5- to 7-membered ring structure optionally containing O, S or $NR^{12}$;

$R^3$ is H or $C_1$–$C_6$-alkyl, or, when n is zero, $R^2$ and $R^3$ taken together may form a 6-membered ring, which may be fused to a six-membered saturated or aromatic carbocycle;

$R^4$ is chosen from H, aryl, heteroaryl, $C_1$–$C_4$-alkyl substituted with from one to three aryl or heteroaryl residues,

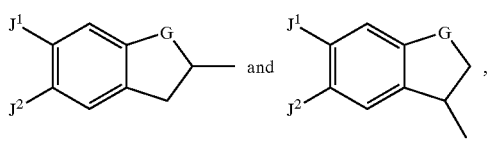 and wherein $J^1$ and $J^2$ are independently chosen from H, F, Cl, CN, $NO_2$ and $CH_3$, and G is chosen from —$CH_2$—, —$CH_2CH_2$—, —$CH_2CH_2CH_2$—, —$OCH_2$—, —$CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—;

$R^5$ is H or $C_1$–$C_3$-alkyl, with the proviso that both $R^3$ and $R^5$ cannot be alkyl;

$R^6$ is aryl;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl; or $R^9$ and $R^{10}$ taken together may form a 5- to 7-membered ring structure optionally containing O, S, SO, $SO_2$ or $NR^{12}$, said ring optionally substituted with —OH, CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and n is zero or one, with the proviso that when A is $A^2$, m and n cannot both be zero.

10. A 2-pyrimidinamine according to claim 9 wherein Q is chosen from imidazolyl, pyrrolyl, pyridinyl, fluorophenyl and 2-thienyl.

11. A 2-pyrimidinamine according to claim 10 wherein A is $R^4R^5$N—C(O)—;

W is H, Cl, $NHR^9$ or $OR^8$;

$R^1$ is chosen from alkyl and $C_1$–$C_3$-alkylcycloalkyl;

$R^2$, $R^3$ and $R^5$ are H;

$R^4$ is $C_1$–$C_4$-alkylaryl or $C_1$–$C_4$-alkylheteroaryl;

$R^8$ is $C_1$–$C_4$-alkylaryl;

$R^9$ is chosen from hydrogen, alkyl, fluoroalkyl, ($C_1$–$C_4$-alkoxy)alkyl, ($C_1$–$C_4$-alkylthio)alkyl, $C_1$–$C_4$-alkylcycloalkyl, $C_1$–$C_4$-alkylaryl, heterocyclyl, $C_1$–$C_4$-alkylheteroaryl, $C_1$–$C_4$-alkylheterocyclyl; and m and n are zero.

12. A 2-pyrimidinamine according to claim 11 wherein W is $NHR^9$ and $R^9$ is

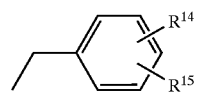

wherein $R^{14}$ is chosen from H, F, Cl, CN, $NO_2$, $SO_2NH_2$, $CF_3$, $COOCH_3$, $OCH_3$, $SO_2CH_3$, $N(CH_3)_2$ and COOH; and $R^{15}$ is chosen from H, $OCH_3$ and Cl.

13. A compound of formula

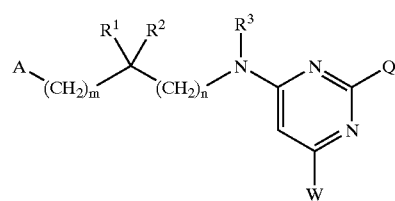

wherein:

A is $R^4R^5$N—(O)—;

Q is is chosen from imidazolyl and pyrrolyl;

W is $NHR^9$;

$R^1$ is chosen from cyclohexylmethyl; 2-methylpropyl and 3-methyl-1-butyl;

$R^2$, $R^3$ and $R^5$ are H;

$R^4$ and $R^9$ are benzyl or substituted benzyl;

m is zero; and n is zero.

14. A compound of formula

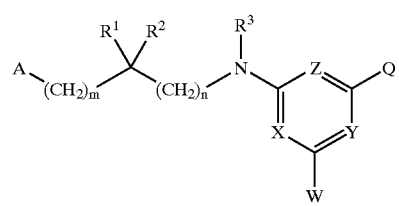

wherein:

two of X, Y and Z are N and the other of X, Y and Z is CH;

A is $A^1$ or $A^2$;

$A^1$ is $R^4R^5$N—C(O)—,

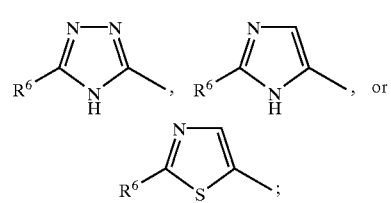

$A^2$ is chosen from $R^7$C(O)NH—, $R^7$S(O)$_2$NH—, $R^4$NH—, and $R^4$O—;

Q is chosen from heteroaryl, aryl, —$CH_2R^{13}$, —CH=N—$OCH_3$ and

283

[structure: 2-substituted 1,3-dithiane]

W is chosen from H, Cl, F, $R^8$, $C_1$–$C_4$-alkylaryl, —$OR^8$, —$SR^8$, —$NR^9R^{10}$ and —$NHC(O)R^{11}$, with the proviso that when Q is imidazolyl, W is not H, Cl, F or $R^8$;

$R^1$ is chosen from alkyl, cycloalkyl, alkenyl, $C_1$–$C_3$-alkylcycloalkyl, heterocyclyl, $C_1$–$C_3$-alkylheterocyclyl, aryl, $C_1$–$C_3$-alkylaryl, heteroaryl, $C_1$–$C_3$-alkylheteroaryl, ($C_1$–$C_3$-alkyloxy)alkyl, ($C_1$–$C_3$-alkyloxy)cycloalkyl, ($C_1$–$C_3$-alkylthio)alkyl, ($C_1$–$C_3$-alkylthio)cycloalkyl and ($C_1$–$C_3$-alkylsulfonyl)alkyl;

$R^2$ is H or $C_1$–$C_3$-alkyl, or $R^1$ and $R^2$ taken together form a 5- to 7-membered ring structure optionally containing O, S or $NR^{12}$;

$R^3$ is H or $C_1$–$C_6$-alkyl, or, when n is zero, $R^2$ and $R^3$ taken together may form a 6-membered ring, which may be fused to a six-membered saturated or aromatic carbocycle;

$R^4$ is

[structure: indane with $J^1$, $J^2$ substituents and G group]

having the R configuration at the carbon indicated with an asterisk, wherein $J^1$ and $J^2$ are independently chosen from H, F, Cl, CN, $NO_2$ and $CH_3$, and G is chosen from —$CH_2$—, —$CH_2CH_2$—, —$CH_2CH_2CH_2$—, —$OCH_2$—, —$CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—;

$R^5$ is H or $C_1$–$C_3$-alkyl, with the proviso that both $R^3$ and $R^5$ cannot be alkyl;

$R^6$ is aryl;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl; or $R^9$ and $R^{10}$ taken together may form a 5- to 7-membered ring structure optionally containing O, S, SO, $SO_2$ or $NR^{12}$, said ring optionally substituted with —OH, —CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and

284 n is zero or one, with the proviso that when A is $A^2$, m and n cannot both be zero.

15. A pyrimidine according to claim 9 wherein $R^4$ is

[structure: indane with $J^1$, $J^2$, G substituents]

having the R configuration at the carbon indicated with an asterisk.

16. A compound of formula

[structure: $A-(CH_2)_m-C(R^1)(R^2)-(CH_2)_n-N(R^3)-$pyrimidine with X, Y, Z, Q, W]

wherein:
two of X, Y and Z are N and the other of X, Y and Z is CH;
A is $A^1$ or $A^2$;
$A^1$ is $R^4R^5N$—C(O)—;

[structures: triazole with $R^6$, imidazole with $R^6$, or thiazole with $R^6$]

$A^2$ is chosen from $R^7C(O)NH$—, $R^7S(O)_2NH$—, $R^4NH$—, and $R^4O$—;

Q is chosen from aryl, —$CH_2R^{13}$, —CH=N—$OCH_3$ and

[structure: 2-substituted 1,3-dithiane]

heteroaryl other than 1-imidazolyl and 1-triazolyl;

W is chosen from H, Cl, F, $R^8$, $C_1$–$C_4$-alkylaryl, —$OR^8$, —$SR^8$, —$NR^9R^{10}$ and —$NHC(O)R^{11}$, with the proviso that when Q is imidazolyl, W is not H, Cl, F or $R^8$;

$R^1$ is chosen from alkyl, cycloalkyl, alkenyl, $C_1$–$C_3$-alkylcycloalkyl, heterocyclyl, $C_1$–$C_3$-alkylheterocyclyl, aryl, $C_1$–$C_3$-alkylaryl, heteroaryl, $C_1$–$C_3$-alkylheteroaryl, ($C_1$–$C_3$-alkyloxy)alkyl, ($C_1$–$C_3$-alkyloxy)cycloalkyl, ($C_1$–$C_3$-alkylthio)alkyl, ($C_1$–$C_3$-alkylthio)cycloalkyl and ($C_1$–$C_3$-alkylsulfonyl)alkyl;

$R^2$ is H or $C_1$–$C_3$-alkyl, or $R^1$ and $R^2$ taken together form a 5- to 7-membered ring structure optionally containing O, S or $NR^{12}$;

$R^3$ is H or $C_1$–$C_6$-alkyl, or, when n is zero, $R^2$ and $R^3$ taken together may form a 6-membered ring, which may be fused to a six-membered saturated or aromatic carbocycle;

$R^4$ is chosen from H, aryl, heteroaryl, $C_1$–$C_4$-alkyl substituted with from one to three aryl or heteroaryl residues,

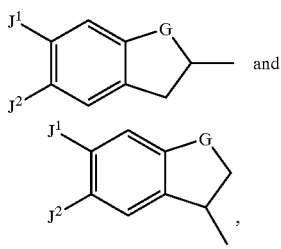

and wherein $J^1$ and $J^2$ are independently chosen from H, F, Cl, CN, $NO_2$ and $CH_3$, and G is chosen from —$CH_2$—, —$CH_2CH_2$—, —$CH_2CH_2CH_2$—, —$OCH_2$—, $CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—;

$R^5$ is H or $C_1$–$C_3$-alkyl, with the proviso that both $R^3$ and $R^5$ cannot be alkyl;

$R^6$ is aryl;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl, or $R^9$ and $R^{10}$ taken together may form a 5- to 7-membered ring structure optionally containing O, S, SO, $SO_2$ or $NR^{12}$, said ring optionally substituted with —OH, —CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and n is zero or one, with the proviso that when A is $A^2$, m and n cannot both be zero.

17. A 4-pyrimidinamine according to claim 16, wherein Z is CH, having the formula

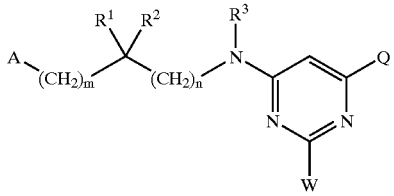

18. A 4-pyrimidinamine according to claim 17 wherein Q is chosen from methylimidazolyl, pyrrolyl, methylpyrrolyl, pyrazolyl, methylpyrazolyl, furanyl, methylfuranyl, thienyl, oxazolyl, thiazolyl, pyridinyl, quinolinyl, 1-methylpyrimidin-2-onyl, phenyl, fluorophenyl, hydroxymethyl, 2-imidazolyl, tetrahydropyranyloxymethyl, imidazolylmethyl, pyrrolylmethyl, —CH=N—$OCH_3$ and

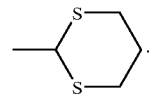

19. A 4-pyrimidinamine according to claim 18 wherein:

Q is chosen from pyrrol-1-yl, imidazol-1-yl, furan-3-yl, 2-methylimidazol-1-yl and 4-methylimidazol-1-yl;

A is $R^4R^5N$—C(O)—;

W is Cl, $NRH^9$, $N(CH_3)R^9$, $OR^8$, $SR^8$, $R^8$, morpholin-4-yl,

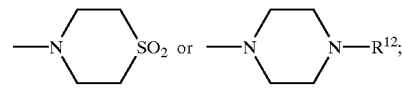

$R^1$ is chosen from alkyl, cycloalkyl, $C_1$–$C_3$-alkylaryl, $C_1$–$C_3$-alkylcycloalkyl, C—$C_3$-alkylheterocyclyl, $C_1$–$C_3$-alkylheteroaryl;

$R^2$, $R^3$ and $R^5$ are H;

$R^8$ is $C_1$–$C_4$-alkylaryl;

$R^9$ is chosen from hydrogen, alkyl, substituted alkyl, ($C_1$–$C_4$)-alkoxy, $C_1$–$C_4$-alkylcycloalkyl, $C_1$–$C_4$-alkylaryl, heterocyclyl, $C_1$–$C_4$-alkylheteroaryl, $C_1$–$C_4$-alkylheterocyclyl; and m and n are zero.

20. A 4-pyrimidinamine according to claim 19 wherein W is $NHR^9$ and $R^9$ is chosen from hydrogen; methyl; ethyl; 2,2,2-trifluoroethyl; allyl; cyclopropyl; 2-cyanoethyl; propargyl; methoxy; methoxyethyl; cyclopropyl; cyclopropylmethyl; (methylthio)ethyl; 3-methoxypropyl; 3-pyridyl; 2-(3-pyridyl)ethyl; 2-(2-pyridyl)ethyl; 3-pyridylmethyl; 4-pyridylmethyl; 4-pyridylmethyl-N-oxide; 2-pyridazinylmethyl; sulfolan-3-yl; 3-tetrahydrofuranyl; 2-tetrahydrofuranylmethyl; 3-(1-imidazolyl)propyl; 1-t-butoxycarbonyl-4-piperidinyl; 1-t-butoxycarbonyl-4-piperidinylmethyl; 2-(hydroxyimino)propyl; 2-(methoxyimino)propyl; 2-oxo-1-propyl; and

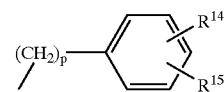

wherein $R^{14}$ is chosen from H, Cl, F, CN, $NO_2$, $SO_2NH_2$, $CF_3$, $COOCH_3$, $OCH_3$, OH, $SO_2CH_3$, $N(CH_3)_2$ and COOH;

$R^{15}$ is chosen from H, $OCH_3$ and Cl; and p is 1 or 2.

21. A 4-pyrimidinamine according to claim 19 wherein W is

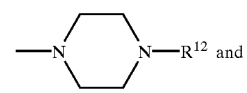

and $R^{12}$ is t-butoxycarbonyl, methoxyacetyl or phenyl.

22. A 4-pyrimidinamine according to claim 16 wherein Z is CH;

A is

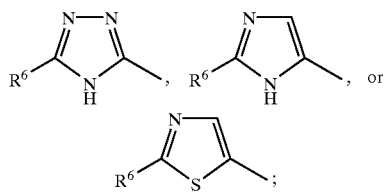

$R^1$ is chosen from n-butyl; cyclohexylmethyl; cyclopentylmethyl; 2-methylpropyl; 3-methyl-1-butyl; cyclohexyl; 2,2-dimethylpropyl; benzyl; 2-thienylmethyl; 1-t-butoxycarbonyl-4-piperidinyl; 4-chlorobenzyl; 2-pyranylmethyl; 4-pyranylmethyl; 4-pyranyl and 1,1-dimethylethyl;

$R^2$ and $R^3$ are H;

Q is pyrrolyl;

W is $NHR^9$; and $R^9$ is alkyl, cycloalkyl or

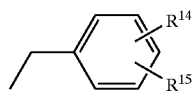

wherein $R^{14}$ is chosen from H, Cl, F, CN, $NO_2$, $SO_2NH_2$, $CF_3$, $COOCH_3$, $OCH_3$, $SO_2CH_3$, $N(CH_3)_2$ and COOH; and $R^{15}$ is chosen from H, $OCH_3$ and Cl.

23. A pyrimidine according to claim 16 wherein:

A is $R^4R^5N—C(O)—$;

$R^1$ is chosen from isopropyl; n-butyl; cyclohexylmethyl; cyclopentylmethyl; naphthylmethyl; cyclohexylethyl; 2-methylpropyl; 3-methyl-1-butyl; cyclohexyl; 2,2-dimethylpropyl; benzyl; 2-thienylmethyl; 1-t-butoxycarbonyl-4-piperidinyl; 4-methoxybenzyl; 4-chlorobenzyl; 3,4-dichlorobenzyl; 2-pyranylmethyl; 4-pyranylmethyl; 4-pyranyl and 1,1-dimethylethyl;

$R^2$, $R^3$ and $R^5$ are H;

$R^4$ is pyridinyl, pyridinylmethyl, indanylmethyl, furanylmethyl, tetrahydronaphthalenyl, substituted phenyl, or

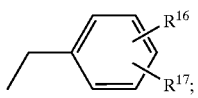

$R^{16}$ is chosen from H, Cl, F, CN, $NO_2$, $SO_2NH_2$, $CF_3$, $CH_3$, $COOCH_3$, $OCH_3$, $SO_2CH_3$, $N(CH_3)_2$ and COOH; and $R^{17}$ is chosen from H, $OCH_3$, F and Cl.

24. A pyrimidine according to claim 16 wherein $R^4$ is

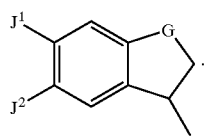

25. A pyrimidine according to claim 24, wherein one of $J^1$ and $J^2$ is H and the other is H, Cl or CN and G is chosen from $—CH_2—$, $—CH_2CH_2—$, $—OCH_2—$, $—O—$ and $—CH_2N$(lower alkyl)-.

26. A 2-pyrimidinamine according to claim 16, wherein Y is CH, having the formula

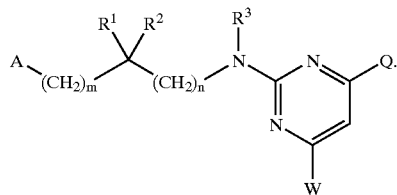

27. A 2-pyrimidinamine according to claim 26 wherein Q is chosen from pyrrolyl, pyridinyl, fluorophenyl and 2-thienyl.

28. A 2-pyrimidinamine according to claim 27 wherein

A is $R^4R^5N—C(O)—$;

W is H, Cl, $NHR^9$ or $OR^8$;

$R^1$ is chosen from alkyl and $C_1-C_3$-alkylcycloalkyl;

$R^2$, $R^3$ and $R^5$ are H;

$R^4$ is $C_1-C_4$-alkylaryl or $C_1-C_4$-alkylheteroaryl;

$R^8$ is $C_1-C_4$-alkylaryl;

$R^9$ is chosen from hydrogen, alkyl, fluoroalkyl, ($C_1-C_4$-alkoxy)alkyl, ($C_1-C_4$-alkylthio)alkyl, $C_1-C_4$-alkylcycloalkyl, $C_1-C_4$-alkylaryl, heterocyclyl, $C_1-C_4$-alkylheteroaryl, $C_1-C_4$-alkylheterocyclyl; and m and n are zero.

29. A 2-pyrimidinamine according to claim 28 wherein W is $NHR^9$ and $R^9$ is

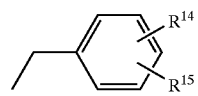

wherein $R^{14}$ is chosen from H, F, Cl, CN, $NO_2$, $SO_2NH_2$, $CF_3$, $COOCH_3$, $OCH_3$, $SO_2CH_3$, $N(CH_3)_2$ and COOH; and $R^{15}$ is chosen from H, $OCH_3$ and Cl.

30. A 2-pyrimidineamine according to claim 26 wherein $R^4$ is

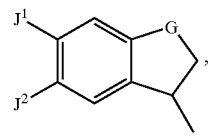

one of $J^1$ and $J^2$ is H and the other is H, Cl or CN and G is chosen from $—CH_2—$, $—CH_2CH_2—$, $—OCH_2—$, $—O—$ and $—CH_2N$(lower alkyl)-.

31. A 4-pyrimidinamine according to claim 16, wherein X is CH, having the formula

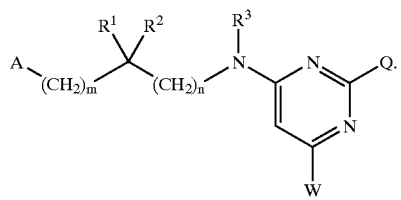

32. A 4-pyrimidinamine according to claim 31 wherein Q is pyrrolyl and m and n are zero.

33. A 4-pyrimidinamine according to claim 32 wherein:

A is R⁴R⁵N—C(O)—;

W is NHR⁹;

R¹ is chosen from cyclohexylmethyl; 2-methylpropyl and 3-methyl-1-butyl;

R², R³ and R⁵ are H; and

R⁴ and R⁹ are benzyl or substituted benzyl.

34. A 4-pyrimidineamine according to claim 31 wherein R⁴ is

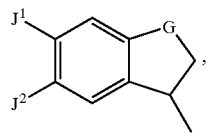

one of J¹ and J² is H and the other is H, Cl or CN and G is chosen from —CH₂—, —CH₂CH₂—, —OCH₂—, —O— and —CH₂N(lower alkyl)-.

35. A pharmaceutical composition comprising a pharmaceutically acceptable carrier and a compound according to any of claims 1, 6, 9, or 14.

36. A pharmaceutical composition according to claim 35 additionally comprising a steroidal or nonsteroidal antiinflammatory drug (NSAID).

37. A pharmaceutical composition according to claim 35 additionally comprising a cyclooxygenase inhibitor.

38. A pharmaceutical composition according to claim 35 additionally comprising a selective cyclooxygenase-2 inhibitor.

39. A pharmaceutical composition according to claim 35 additionally comprising a selective cyclooxygenase-1 inhibitor.

40. A pharmaceutical composition comprising a pharmaceutically acceptable carrier and a compound according to claim 16.

41. A pharmaceutical composition according to claim 40 additionally comprising a steroidal or nonsteroidal antiinflammatory drug (NSAID).

42. A pharmaceutical composition according to claim 40 additionally comprising a nonsteroidal antiinflammatory drug (NSAID).

43. A pharmaceutical composition according to claim 42 wherein said NSAID is chosen from arylpropionic acids, arylacetic acids, arylbutyric acids, fenamic acids, arylcarboxylic acids, pyrazoles, pyrazolones, salicylic acids; and oxicams.

44. A pharmaceutical composition according to claim 40 additionally comprising a cyclooxygenase inhibitor.

45. A pharmaceutical composition according to claim 44 wherein said cyclooxygenase inhibitor is ibuprofen or a salicylic acid derivative.

46. A pharmaceutical composition according to claim 40 additionally comprising a selective cyclooxygenase-2 inhibitor.

47. A pharmaceutical composition according to claim 46 wherein said selective cyclooxygenase-2 inhibitor is rofecoxib or celecoxib.

48. A pharmaceutical composition according to claim 40 additionally comprising a selective cyclooxygenase-I inhibitor.

49. A pharmaceutical composition according to claim 40 additionally comprising a steroidal antiinflammatory drug.

50. A pharmaceutical composition according to claim 49 wherein said steroidal antiinflammatory drug is chosen from finasteride, beclomethasone and hydrocortisone.

51. A method of treating vasculopathy comprising administering to a subject in need of such treatment a therapeutically effective amount of a compound of formula I

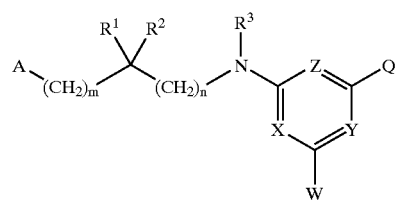

wherein:

two of X, Y and Z are N and the other of X, Y and Z is CH;

A is A¹ or A²;

A¹ is R⁴R⁵N—(O)—,

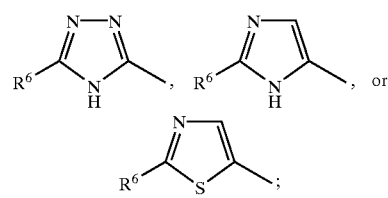

A² is chosen from R⁷C(O)NH—, R⁷S(O)₂NH—, R⁴NH—, and R⁴O—;

Q is chosen from heteroaryl, aryl, —CH₂R¹³, —CH=N—OCH₃ and

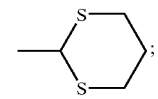

W is chosen from H, Cl, F, R⁸, C₁–C₄-alkylaryl, —OR⁸, —SR⁸, —NR⁹R¹⁰ and —NHC(O)R¹¹, with the proviso that when Q is imidazolyl, W is not H, Cl, F or R⁸;

R¹ is chosen from alkyl, cycloalkyl, alkenyl, C₁–C₃-alkylcycloalkyl, heterocyclyl, C₁–C₃-alkylheterocyclyl, aryl, C₁–C₃-alkylaryl, heteroaryl, C₁–C₃-alkylheteroaryl, (C₁–C₃-alkyloxy)alkyl, (C₁–C₃-alkyloxy)cycloalkyl, (C₁–C₃-alkylthio)alkyl, (C₁–C₃-alkylthio)cycloalkyl and (C₁–C₃-alkylsulfonyl)alkyl;

R² is H or C₁–C₃-alkyl, or R¹ and R² taken together form a 5- to 7-membered ring structure optionally containing O, S or NR¹²;

R³ is H or C₁–C₆-alkyl, or, when n is zero, R² and R³ taken together may form a 6-membered ring, which may be fused to a six-membered saturated or aromatic carbocycle;

R⁴ is chosen from H, aryl, heteroaryl, C₁–C₄-alkyl substituted with from one to three aryl or heteroaryl residues,

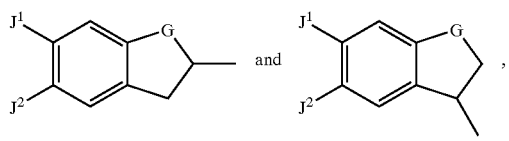 and wherein $J^1$ and $J^2$ are independently chosen from H, F, Cl, CN, $NO_2$ and $CH_3$, and G is chosen from $-CH_2-$, $-CH_2CH_2-$, $-CH_2CH_2CH_2-$, $-OCH_2-$, $-CH_2O-$, $-CH_2CH_2O-$, $-OCH_2CH_2-$, $-O-$, $-N(lower\ alkyl)-$, $-N(lower\ alkyl)CH_2-$, $-CH_2N(lower\ alkyl)-$, $-S-$, $-SO-$, $-SO_2-$, $-CH_2S-$, $-SCH_2-$, $-CH_2SO-$, $-SOCH_2-$, $-CH_2SO_2-$, and $-SO_2CH_2-$;

$R^5$ is H or $C_1-C_3$-alkyl, with the proviso that both $R^3$ and $R^5$ cannot be alkyl;

$R^6$ is aryl;

$R^7$ is aryl or $C_1-C_3$-alkylaryl;

$R^8$ is chosen from alkyl, aryl, heteroaryl, substituted alkyl, $C_1-C_4$-alkylaryl, $C_1-C_4$-alkylheterocyclyl and $C_1-C_4$-alkylheteroaryl;

$R^9$ is chosen from H, alkyl, alkenyl, substituted alkyl, cycloalkyl, aryl, alkoxy, heteroaryl, fluoroalkyl, $C_1-C_4$-alkylcycloalkyl, ($C_1-C_4$-alkoxy)alkyl, ($C_1-C_4$-alkoxycarbonyl)alkyl, ($C_1-C_4$-alkylthio)alkyl, heterocyclyl, $C_1-C_4$-alkylheterocyclyl, $C_1-C_4$-alkylaryl, and $C_1-C_4$-alkylheteroaryl;

$R^{10}$ is H or $C_1-C_3$-alkyl, or $R^9$ and $R^{10}$ taken together may form a 5- to 7-membered ring structure optionally containing O, S, SO, $SO_2$ or $NR^{12}$, said ring optionally substituted with $-OH$, $-CN$, $-COOH$ or $-COOCH_3$;

$R^{11}$ is aryl;

$R^{12}$ is chosen from H, $C_1-C_3$-alkyl, alkoxycarbonyl, methoxyacetyl and aryl;

$R^{13}$ is chosen from $-OH$, $-OTHP$, 1-imidazolyl, and 1-pyrrolyl;

m is zero or one; and n is zero or one, with the proviso that when A is $A^2$, m and n cannot both be zero.

52. The method according to claim 51 wherein said vasculopathy is diabetic vasculopathy.

53. The method according to claim 51 wherein said vasculopathy is hypertensive vasculopathy.

54. A method of treating asthma comprising administering to a subject in need of such treatment a therapeutically effective amount of a compound of formula I

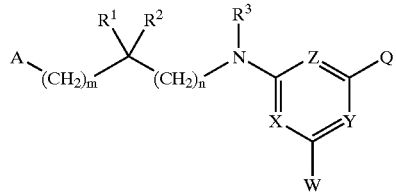

wherein:

two of X, Y and Z are N and the other of X, Y and Z is CH;

A is $A^1$ or $A^2$;

$A^1$ is $R^4R^5N-C(O)-$,

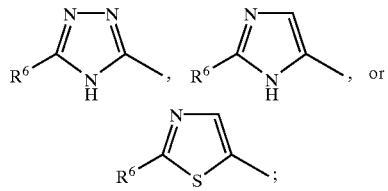

$A^2$ is chosen from $R^7C(O)NH-$, $R^7S(O)_2NH-$, $R^4NH-$, and $R^4O-$;

Q is chosen from heteroaryl, aryl, $-CH_2R^{13}$, $-CH=N-OCH_3$ and

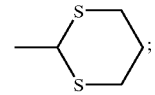

W is chosen from H, Cl, F, $R^8$, $C_1-C_4$-alkylaryl, $-OR^8$, $-SR^8$, $-NR^9R^{10}$ and $-NHC(O)R^{11}$, with the proviso that when Q is imidazolyl, W is not H, Cl, F or $R^8$;

$R^1$ is chosen from alkyl, cycloalkyl, alkenyl, $C_1-C_3$-alkylcycloalkyl, heterocyclyl, $C_1-C_3$-alkylheterocyclyl, aryl, $C_1-C_3$-alkylaryl, heteroaryl, $C_1-C_3$-alkylheteroaryl, ($C_1-C_3$-alkyloxy)alkyl, ($C_1-C_3$-alkyloxy)cycloalkyl, ($C_1-C_3$-alkylthio)alkyl, ($C_1-C_3$-alkylthio)cycloalkyl and ($C_1-C_3$-alkylsulfonyl)alkyl;

$R^2$ is H or $C_1-C_3$-alkyl, or $R^1$ and $R^2$ taken together form a 5- to 7-membered ring structure optionally containing O, S or $NR^{12}$;

$R^3$ is H or $C_1-C_6$-alkyl, or, when n is zero, $R^2$ and $R^3$ taken together may form a 6-membered ring, which may be fused to a six-membered saturated or aromatic carbocycle;

$R^4$ is chosen from H, aryl, heteroaryl, $C_1-C_4$-alkyl substituted with from one to three aryl or heteroaryl residues,

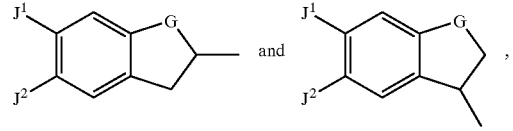 and wherein $J^1$ and $J^2$ are independently chosen from H, F, Cl, CN, $NO_2$ and $CH_3$, and G is chosen from $-CH_2-$, $-CH_2CH_2-$, $-CH_2CH_2CH_2-$, $-OCH_2-$, $-CH_2O-$, $-CH_2CH_2O-$, $-OCH_2CH_2-$, $-O-$, $-N(lower\ alkyl)-$, $-N(lower\ alkyl)CH_2-$, $-CH_2N(lower\ alkyl)-$, $-S-$, $-SO-$, $-SO_2-$, $-CH_2S-$, $-SCH_2-$, $-CH_2SO-$, $-SOCH_2-$, $-CH_2SO_2-$, and $-SO_2CH_2-$;

$R^5$ is H or $C_1-C_3$-alkyl, with the proviso that both $R^3$ and $R^5$ cannot be alkyl;

$R^6$ is aryl;

$R^7$ is aryl or $C_1-C_3$-alkylaryl;

$R^8$ is chosen from alkyl, aryl, heteroaryl, substituted alkyl, $C_1-C_4$-alkylaryl, $C_1-C_4$-alkylheterocyclyl and $C_1-C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl, or $R^9$ and $R^{10}$ taken together may form a 5- to 7-membered ring structure optionally containing O, S, SO, $SO_2$ or $NR^{12}$, said ring optionally substituted with —OH, —CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and n is zero or one, with the proviso that when A is $A^2$, m and n cannot both be zero.

55. A method of treating pain or hyperalgesia comprising administering to a subject in need of such treatment a therapeutically effective amount of a compound of formula I

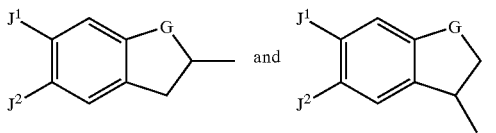

wherein:

two of X, Y and Z are N and the other of X, Y and Z is CH;

A is $A^1$ or $A^2$;

$A^1$ is $R^4R^5N$—C(O)—,

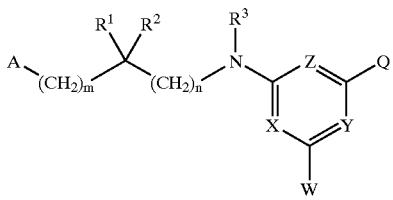

$A^2$ is chosen from $R^7C(O)NH$—, $R^7S(O)_2NH$—, $R^4NH$—, and $R^4O$—;

Q is chosen from heteroaryl, aryl, —$CH_2R^{13}$, —CH=N—$OCH_3$ and

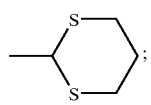

W is chosen from H, Cl, F, $R^8$, $C_1$–$C_4$-alkylaryl, —$OR^8$, —$SR^8$, —$NR^9R^{10}$ and —$NHC(O)R^{11}$, with the proviso that when Q is imidazolyl, W is not H, Cl, F or $R^8$;

$R^1$ is chosen from alkyl, cycloalkyl, alkenyl, $C_1$–$C_3$-alkylcycloalkyl, heterocyclyl, $C_1$–$C_3$-alkylheterocyclyl, aryl, $C_1$–$C_3$-alkylaryl, heteroaryl, $C_1$–$C_3$-alkylheteroaryl, ($C_1$–$C_3$-alkyloxy)alkyl, ($C_1$–$C_3$-alkyloxy)cycloalkyl, ($C_1$–$C_3$-alkylthio)alkyl, ($C_1$–$C_3$-alkylthio)cycloalkyl and ($C_1$–$C_3$-alkylsulfonyl)alkyl;

$R^2$ is H or $C_1$–$C_3$-alkyl, or $R^1$ and $R^2$ taken together form a 5- to 7-membered ring structure optionally containing O, S or $NR^{12}$;

$R^3$ is H or $C_1$–$C_6$-alkyl, or, when n is zero, $R^2$ and $R^3$ taken together may form a 6-membered ring, which may be fused to a six-membered saturated or aromatic carbocycle;

$R^4$ is chosen from H, aryl, heteroaryl, $C_1$–$C_4$-alkyl substituted with from one to three aryl or heteroaryl residues,

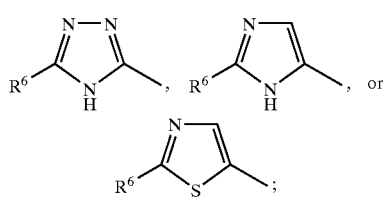

wherein $J^1$ and $J^2$ are independently chosen from H, F, Cl, CN, $NO_2$ and $CH_3$, and G is chosen from —$CH_2$—, —$CH_2CH_2$—, —$CH_2CH_2CH_2$—, —$OCH_2$—, —$CH_2O$—, —$CH_2CH_2O$—, —$OCH_2CH_2$—, —O—, —N(lower alkyl)-, —N(lower alkyl)$CH_2$—, —$CH_2$N(lower alkyl)-, —S—, —SO—, —$SO_2$—, —$CH_2S$—, —$SCH_2$—, —$CH_2SO$—, —$SOCH_2$—, —$CH_2SO_2$—, and —$SO_2CH_2$—;

$R^5$ is H or $C_1$–$C_3$-alkyl, with the proviso that both $R^3$ and $R^5$ cannot be alkyl;

$R^6$ is aryl;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, ($C_1$–$C_4$-alkoxy)alkyl, ($C_1$–$C_4$-alkoxycarbonyl)alkyl, ($C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl; or $R^9$ and $R^{10}$ taken together may form a 5- to 7-membered ring structure optionally containing O, S, SO, $SO_2$ or $NR^{12}$, said ring optionally substituted with —OH, —CN, —COOH or —$COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from —OH, —OTHP, 1-imidazolyl, and 1-pyrrolyl;

m is zero or one; and n is zero or one, with the proviso that when A is $A^2$, m and n cannot both be zero.

56. The method according to claim 55 wherein said pain is chronic pain, pain associated with inflammation or dental pain.

57. The method of treating pain or hyperalgesia according to claim 55 additionally comprising administering a steroidal or nonsteroidal antiinflammatory drug (NSAID).

58. The method of treating pain or hyperalgesia according to claim 57 wherein an NSAID is administered.

59. The method of treating pain or hyperalgesia according to claim 55 additionally comprising administering a cyclooxygenase inhibitor.

60. The method of treating pain or hyperalgesia according to claim 59 wherein said cyclooxygenase inhibitor is a selective cyclooxygenase-2 inhibitor.

61. The method of treating pain or hyperalgesia according to claim 59 wherein said cyclooxygenase inhibitor is a selective cyclooxygenase-1 inhibitor.

62. A method of treating post-capillary resistance or diabetic symptoms associated with insulitis comprising administering to a subject in need of such treatment a therapeutically effective amount of a compound of formula I

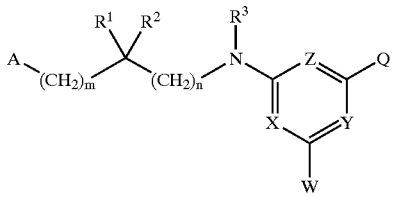

wherein:
two of X, Y and Z are N and the other of X, Y and Z is CH;
A is $A^1$ or $A^2$;
$A^1$ is $R^4R^5N\text{—}(O)\text{—}$,

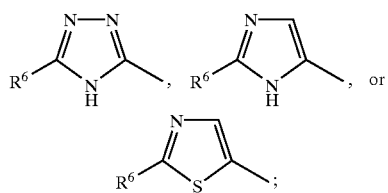

$A^2$ is chosen from $R^7C(O)NH\text{—}$, $R^7S(O)_2NH\text{—}$, $R^4NH\text{—}$, and $R^4O\text{—}$;
Q is chosen from heteroaryl, aryl, $\text{—}CH_2R^{13}$, $\text{—}CH\text{=}N\text{—}OCH_3$ and

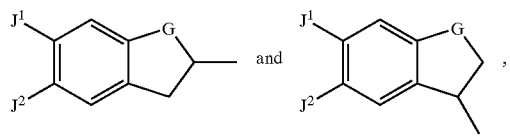

W is chosen from H, Cl, F, $R^8$, $C_1\text{–}C_4$-alkylaryl, $\text{—}OR^8$, $\text{—}SR^8$, $\text{—}NR^9R^{10}$ and $\text{—}NHC(O)R^{11}$, with the proviso that when Q is imidazolyl, W is not H, Cl, F or $R^8$;
$R^1$ is chosen from alkyl, cycloalkyl, alkenyl, $C_1\text{–}C_3$-alkylcycloalkyl, heterocyclyl, $C_1\text{–}C_3$-alkylheterocyclyl, aryl, $C_1\text{–}C_3$-alkylaryl, heteroaryl, $C_1\text{–}C_3$-alkylheteroaryl, $(C_1\text{–}C_3$-alkyloxy)alkyl, $(C_1\text{–}C_3$-alkyloxy)cycloalkyl, $(C_1\text{–}C_3$-alkylthio)alkyl, $(C_1\text{–}C_3$-alkylthio)cycloalkyl and $(C_1\text{–}C_3$-alkylsulfonyl)alkyl;
$R^2$ is H or $C_1\text{–}C_3$-alkyl, or $R^1$ and $R^2$ taken together form a 5- to 7-membered ring structure optionally containing O, S or $NR^{12}$;
$R^3$ is H or $C_1\text{–}C_6$-alkyl, or, when n is zero, $R^2$ and $R^3$ taken together may form a 6-membered ring, which may be fused to a six-membered saturated or aromatic carbocycle;
$R^4$ is chosen from H, aryl, heteroaryl, $C_1\text{–}C_4$-alkyl substituted with from one to three aryl or heteroaryl residues,

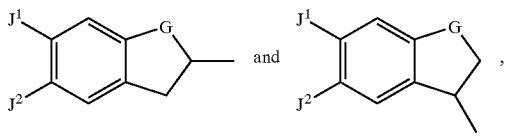

wherein $J^1$ and $J^2$ are independently chosen from H, F, Cl, CN, $NO_2$ and $CH_3$ and G is chosen from $\text{—}CH_2\text{—}$, $\text{—}CH_2CH_2\text{—}$, $\text{—}CH_2CH_2CH_2\text{—}$, $\text{—}OCH_2\text{—}$, $\text{—}CH_2O\text{—}$, $\text{—}CH_2CH_2O\text{—}$, $\text{—}OCH_2CH_2\text{—}$, $\text{—}O\text{—}$, $\text{—}N(\text{lower alkyl})\text{-}$, $\text{—}N(\text{lower alkyl})CH_2\text{—}$, $\text{—}CH_2N(\text{lower alkyl})\text{-}$, $\text{—}S\text{—}$, $\text{—}SO\text{—}$, $\text{—}SO_2\text{—}$, $\text{—}CH_2S\text{—}$, $\text{—}SCH_2\text{—}$, $\text{—}CH_2SO\text{—}$, $\text{—}SOCH_2\text{—}$, $\text{—}CH_2SO_2\text{—}$, and $\text{—}SO_2CH_2\text{—}$;
$R^5$ is H or $C_1\text{–}C_3$-alkyl, with the proviso that both $R^3$ and $R^5$ cannot be alkyl;
$R^6$ is aryl;
$R^7$ is aryl or $C_1\text{–}C_3$-alkylaryl;
$R^8$ is chosen from alkyl, aryl, heteroaryl, substituted alkyl, $C_1\text{–}C_4$-alkylaryl, $C_1\text{–}C_4$-alkylheterocyclyl and $C_1\text{–}C_4$-alkylheteroaryl;
$R^9$ is chosen from H, alkyl, alkenyl, substituted alkyl, cycloalkyl, aryl, alkoxy, heteroaryl, fluoroalkyl, $C_1\text{–}C_4$-alkylcycloalkyl, $(C_1\text{–}C_4$-alkoxy)alkyl, $(C_1\text{–}C_4$-alkoxycarbonyl)alkyl, $(C_1\text{–}C_4$-alkylthio)alkyl, heterocyclyl, $C_1\text{–}C_4$-alkylheterocyclyl, $C_1\text{–}C_4$-alkylaryl, and $C_1\text{–}C_4$-alkylheteroaryl;
$R^{10}$ is H or $C_1\text{–}C_3$-alkyl; or
$R^9$ and $R^{10}$ taken together may form a 5- to 7-membered ring structure optionally containing O, S, SO, $SO_2$ or $NR^{12}$, said ring optionally substituted with $\text{—}OH$, $\text{—}CN$, $\text{—}COOH$ or $\text{—}COOCH_3$;
$R^{11}$ is aryl;
$R^{12}$ is chosen from H, $C_1\text{–}C_3$-alkyl, alkoxycarbonyl, methoxyacetyl and aryl;
$R^{13}$ is chosen from $\text{—}OH$, $\text{—}OTHP$, 1-imidazolyl, and 1-pyrrolyl;
m is zero or one; and
n is zero or one, with the proviso that when A is $A^2$, m and n cannot both be zero.

63. The method according to claim 62 wherein said diabetic symptoms associated with insulitis comprise hyperglycemia, diuresis, proteinuria and increased nitrile and kallikrein urinary excretion.

64. A method of treating edema comprising administering to a subject in need of such treatment a therapeutically effective amount of a compound of formula I

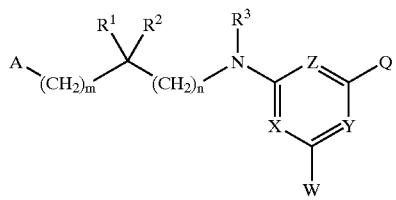

wherein:
two of X, Y and Z are N and the other of X, Y and Z is CH;
A is $A^1$ or $A^2$;

$A^1$ is $R^4R^5N—C(O)—$,

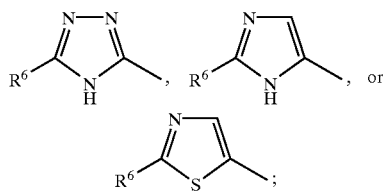, or

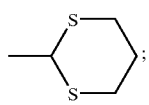;

$A^2$ is chosen from $R^7C(O)NH—$, $R^7S(O)_2NH—$, $R^4NH—$, and $R^4O—$;

Q is chosen from heteroaryl, aryl, $—CH_2R^{13}$, $—CH=N—OCH_3$ and

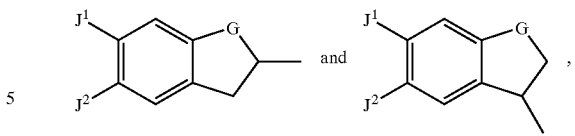

and wherein $J^1$ and $J^2$ are independently chosen from H, F, Cl, CN, $NO_2$ and $CH_3$, and G is chosen from $—CH_2—$, $—CH_2CH_2—$, $—CH_2CH_2CH_2—$, $—OCH_2—$, $—CH_2O—$, $—CH_2CH_2O—$, $—OCH_2CH_2—$, $—O—$, $—N(lower\ alkyl)-$, $—N(lower\ alkyl)CH_2—$, $—CH_2N(lower\ alkyl)-$, $—S—$, $—SO—$, $—SO_2—$, $—CH_2S—$, $—SCH_2—$, $—CH_2SO—$, $—SOCH_2—$, $—CH_2SO_2—$, and $—SO_2CH_2—$;

W is chosen from H, Cl, F, $R^8$, $C_1$–$C_4$-alkylaryl, $—OR^8$, $—SR^8$, $—NR^9R^{10}$ and $—NHC(O)R^{11}$, with the proviso that when Q is imidazolyl, W is not H, Cl, F or $R^8$;

$R^1$ is chosen from alkyl, cycloalkyl, alkenyl, $C_1$–$C_3$-alkylcycloalkyl, heterocyclyl, $C_1$–$C_3$-alkylheterocyclyl, aryl, $C_1$–$C_3$-alkylaryl, heteroaryl, $C_1$–$C_3$-alkylheteroaryl, $(C_1$–$C_3$-alkyloxy)alkyl, $(C_1$–$C_3$-alkyloxy)cycloalkyl, $(C_1$–$C_3$-alkylthio)alkyl, $(C_1$–$C_3$-alkylthio)cycloalkyl and $(C_1$–$C_3$-alkylsulfonyl)alkyl;

$R^2$ is H or $C_1$–$C_3$-alkyl, or $R^1$ and $R^2$ taken together form a 5- to 7-membered ring structure optionally containing O, S or $NR^{12}$;

$R^3$ is H or $C_1$–$C_6$-alkyl, or, when n is zero, $R^2$ and $R^3$ taken together may form a 6-membered ring, which may be fused to a six-membered saturated or aromatic carbocycle;

$R^4$ is chosen from H, aryl, heteroaryl, $C_1$–$C_4$-alkyl substituted with from one to three aryl or heteroaryl residues, $R^5$ is H or $C_1$–$C_3$-alkyl, with the proviso that both $R^3$ and $R^5$ cannot be alkyl;

$R^6$ is aryl;

$R^7$ is aryl or $C_1$–$C_3$-alkylaryl;

$R^8$ is chosen from alkyl, aryl, heteroaryl, substituted alkyl, $C_1$–$C_4$-alkylaryl, $C_1$–$C_4$-alkylheterocyclyl and $C_1$–$C_4$-alkylheteroaryl;

$R^9$ is chosen from H, alkyl, alkenyl, substituted alkyl, cycloalkyl, aryl, alkoxy, heteroaryl, fluoroalkyl, $C_1$–$C_4$-alkylcycloalkyl, $(C_1$–$C_4$-alkoxy)alkyl, $(C_1$–$C_4$-alkoxycarbonyl)alkyl, $(C_1$–$C_4$-alkylthio)alkyl, heterocyclyl, $C_1$–$C_4$-alkylheterocyclyl, $C_1$–$C_4$-alkylaryl, and $C_1$–$C_4$-alkylheteroaryl;

$R^{10}$ is H or $C_1$–$C_3$-alkyl; or $R^9$ and $R^{10}$ taken together may form a 5- to 7-membered ring structure optionally containing O, S, SO, $SO_2$ or $NR^{12}$, said ring optionally substituted with $—OH$, $—CN$, $—COOH$ or $—COOCH_3$;

$R^{11}$ is aryl;

$R^{12}$ is chosen from H, $C_1$–$C_3$-alkyl, alkoxycarbonyl, methoxyacetyl and aryl;

$R^{13}$ is chosen from $—OH$, $—OTHP$, 1-imidazolyl, and 1-pyrrolyl;

m is zero or one; and n is zero or one, with the proviso that when A is $A^2$, m and n cannot both be zero.

* * * * *

UNITED STATES PATENT AND TRADEMARK OFFICE
CERTIFICATE OF CORRECTION

PATENT NO. : 6,919,347 B2
DATED : July 19, 2005
INVENTOR(S) : Ohlmeyer et al.

It is certified that error appears in the above-identified patent and that said Letters Patent is hereby corrected as shown below:

Column 282,
Line 26, delete "A is $R^4R^5N-(O)-$;" and insert -- A is $R^4R^5N-C(O)-$; --.

Column 283,
Lines 26 thru 32, structure, delete current structure and replace with
-- 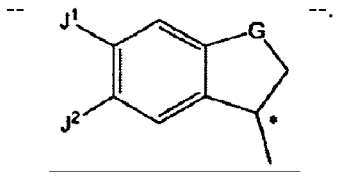 --.

Column 284,
Lines 5 thru 10, structure, delete current structure and replace with
-- 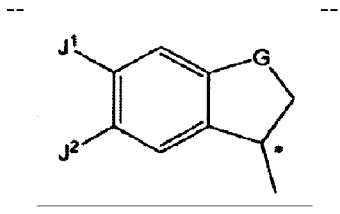 --.

Line 28, delete "$A^1$ is $R^4R^5N-C(O)-$;" and insert -- $A^1$ is $R^4R^5N-C(O)-$, --.

Column 286,
Line 21, delete "$C-C_3$" in the second instance and insert -- $C_1-C_3$ --.

Column 288,
Lines 3 thru 10, structure, delete current structure which has a "." after the letter "Q", and replace with
-- 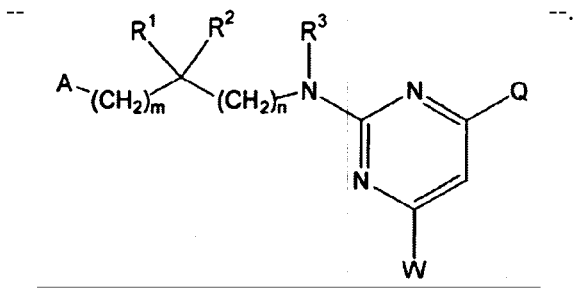 --.

UNITED STATES PATENT AND TRADEMARK OFFICE
CERTIFICATE OF CORRECTION

PATENT NO.   : 6,919,347 B2
DATED        : July 19, 2005
INVENTOR(S)  : Ohlmeyer et al.

It is certified that error appears in the above-identified patent and that said Letters Patent is hereby corrected as shown below:

Column 288 (cont'd),
Lines 57 thru 64, structure, delete current structure which has a "." after the letter "Q", and replace with

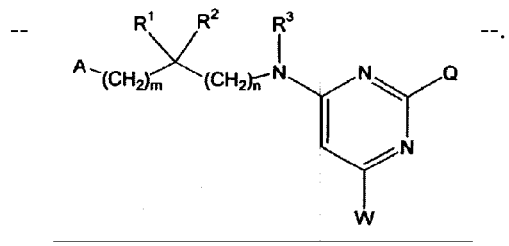

Column 295,
Lines 41-48, delete current structure and replace with

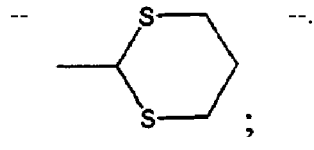

Signed and Sealed this

Eighth Day of November, 2005

JON W. DUDAS
*Director of the United States Patent and Trademark Office*